US007465456B2

(12) United States Patent
Hoffmann et al.

(10) Patent No.: US 7,465,456 B2
(45) Date of Patent: Dec. 16, 2008

(54) MULTI PLASMID SYSTEM FOR THE PRODUCTION OF INFLUENZA VIRUS

(75) Inventors: Erich Hoffmann, Memphis, TN (US); Hong Jin, Cupertino, CA (US); Bin Lu, Los Altos, CA (US); Gregory Duke, Redwood City, CA (US); George Kemble, Saratoga, CA (US); Zhongying Chen, Cupertino, CA (US)

(73) Assignee: MedImmune, LLC, Gaithersburg, MD (US)

( * ) Notice: Subject to any disclaimer, the term of this patent is extended or adjusted under 35 U.S.C. 154(b) by 0 days.

(21) Appl. No.: 11/133,345

(22) Filed: May 20, 2005

(65) Prior Publication Data

US 2005/0266026 A1 Dec. 1, 2005

Related U.S. Application Data

(63) Continuation-in-part of application No. 11/018,624, filed on Dec. 22, 2004.

(60) Provisional application No. 60/657,372, filed on Mar. 2, 2005, provisional application No. 60/643,278, filed on Jan. 13, 2005, provisional application No. 60/578,962, filed on Jun. 12, 2004.

(51) Int. Cl.
*A61K 39/145* (2006.01)
*C12Q 1/70* (2006.01)
*C12P 19/34* (2006.01)

(52) U.S. Cl. ....................... 424/209.1; 435/5; 435/91.1; 424/206.1

(58) Field of Classification Search ....................... None
See application file for complete search history.

(56) References Cited

U.S. PATENT DOCUMENTS

| | | | |
|---|---|---|---|
| 3,992,522 | A | 11/1976 | Chanock |
| 4,071,618 | A | 1/1978 | Konobe |
| 4,634,666 | A | 1/1987 | Engelman et al. |
| 4,659,569 | A | 4/1987 | Mitsuhashi |
| 5,166,057 | A | 11/1992 | Palese et al. |
| 5,690,937 | A | 11/1997 | Parkin |
| 5,716,821 | A | 2/1998 | Wertz |
| 5,789,229 | A | 8/1998 | Wertz |
| 5,820,871 | A | 10/1998 | Palese |
| 5,840,520 | A | 11/1998 | Clarke |
| 5,854,037 | A | 12/1998 | Palese |
| 5,922,326 | A | 7/1999 | Murphy |
| 6,033,886 | A | 3/2000 | Conzelmann |
| 6,090,391 | A | 7/2000 | Parkin |
| 6,146,642 | A | 11/2000 | Garcia-Sastre |
| 6,146,873 | A | 11/2000 | Kistner |
| 6,168,943 | B1 | 1/2001 | Rose |
| 7,037,707 | B2 | 5/2006 | Webster et al. |
| 2002/0119445 | A1 | 8/2002 | Parkin |
| 2002/0164770 | A1 | 11/2002 | Hoffmann |
| 2003/0035814 | A1 | 2/2003 | Kawaoka |
| 2003/0147916 | A1 | 8/2003 | Ferko |
| 2004/0029251 | A1 | 2/2004 | Hoffman |
| 2004/0137013 | A1 | 7/2004 | Katinger |
| 2005/0042229 | A1 | 2/2005 | Yang |
| 2005/0266026 | A1 | 12/2005 | Hoffmann |

FOREIGN PATENT DOCUMENTS

| | | |
|---|---|---|
| EP | 0 702 085 | 3/1996 |
| EP | 0 863 202 | 9/1998 |
| EP | 0 864 645 | 9/1998 |
| EP | 0 780 475 | 6/1999 |
| EP | 1826269 A1 | 8/2007 |
| WO | WO-91-03552 | 3/1991 |
| WO | WO-93-21306 | 10/1993 |
| WO | WO-96-10632 | 4/1996 |
| WO | WO-96-34625 | 11/1996 |
| WO | WO-97-06270 | 2/1997 |
| WO | WO-97-12032 | 4/1997 |
| WO | WO-98-02530 | 1/1998 |
| WO | WO-98-13501 | 4/1998 |
| WO | WO-98-53078 | 11/1998 |
| WO | WO-99-02657 | 1/1999 |
| WO | WO-99-15672 | 4/1999 |
| WO | WO-00-53786 | 9/2000 |
| WO | WO-00-60050 | 10/2000 |

OTHER PUBLICATIONS

Flandorfer et al., Chimeric Influenza A Viruses with a Functional Influenza B Virus Neuraminidase or Hemagglutinin 2003, Journal of Virology, vol. 77, No. 17, pp. 9116-9123.*

Martin et al., Studies of the Binding Properties of Influenza Hemagglutinin Receptor-Site Mutants 1998, Virology, vol. 241, pp. 101-111.*

Nakajima et al., Restriction of Amino Acid Change in Influenza A Virus H3HA: Comparison of Amino Acid Changes Observed in Nature and In Vitro 2003, Journal of Virology, vol. 77, No. 18, pp. 10088-10098.*

Xu et al. Influenza A/Hong Kong/8/68 virus (H3N2) Neuraminidase sequence. Sequence accession # AAB06964, GI # 1517824. Sequence submitted to CDC on Dec. 8, 1995. [Retrived Nov. 2, 2006], Retrived from the Internet:<URL:http://www.ncbi.nlm.nih.gov/entrez/viewer.fcgi?db=protein&val=1517824>.*

(Continued)

*Primary Examiner*—Bruce Campell
*Assistant Examiner*—Benjamin P Blumel

(57) ABSTRACT

Vectors and methods for the production of influenza viruses suitable as recombinant influenza vaccines in cell culture are provided. Bi-directional expression vectors for use in a multi-plasmid influenza virus expression system are provided. Additionally, the invention provides methods of producing influenza viruses with enhanced ability to replicate in embryonated chicken eggs and/or cells (e.g., Vero and/or MDCK) and further provides influenza viruses with enhanced replication characteristics. A method of producing a cold adapted (ca) influenza virus that replicates efficiently at, e.g., 25° C. (and immunogenic compositions comprising the same) is also provided.

10 Claims, 71 Drawing Sheets

OTHER PUBLICATIONS

Xu et al., Genetic Variation in Neuraminidase Genes of Influenza A (H3N2) Viruses, 1996, Virology, vol. 224, pp. 175-183, especially pp. 175, 179, table 1 and figure 3.*
Hilleman M., Vaccines in historic evolution and perspective: a narrative of vaccine discoveries, 2000, Vaccine, vol. 18, pp. 1436-1447.*
Wang et al., Extensive Heterogenity in the Hemagglutinin of Egg-Grown Influenza Viruses from Different Patients, 1989, Virology, vol. 171, pp. 275-279.*
Giudice et al., An MF59-adjuvanted inactivated influenza vaccine containing A/Panama/1999 (H3N2) induced broader serological protection against hetervariant influenza virus strain A/Fujian/2002 than a subunit and a split influenza vaccine, 2006, Vaccine, vol. 24, pp. 3063-3065.*
Hardy et al., Egg Fluids and Cells of the Chorioallantoic Membrane of Embryonated Chicken Eggs Can Select Different Variants of Influenza A (H3N2) Viruses, 1995, Virology, vol. 211, pp. 302-306.*
Lugotsev et al., Mutational pattern of influenza B viruses adapted to high growth replication in embryonated eggs, 2005, Virus Research, vol. 109, pp. 149-157.*
Rocha et al., Comparison of 10 influenza A (H1N1 and H3N2) haemagglutinin sequences obtained directly from clinical specimens to those of MDCK cell- and egg-grown viruses, 1993, Journal of General Virology, vol. 74, pp. 2513-2518.*
Banerjee and Barik, 1992, "Gene expression of vesicular stomatitis virus genome RNA", Virology. 188):417-28.
Baron and Barrett, 1997, "Rescue of Rinderpest Virus from Cloned cDNA", J. Virol. 71:1265-1271.
Beare et al., 1975, "Trials in Man with Live Recombinants Made from A/PR/8/34 (H0 N1) and Wild H3 N2 Influenza Viruses", Lancet 729-732.
Boyer et al., 1994, "Infectious transcripts and cDNA clones of RNA viruses", Virology. 198:415-26.
Brigden and Elliott, 1996, "Rescue of a Segmented Negative-Strand RNA Virus Entirely from Cloned Complementary DNAS", Proc. Natl. Acad. Sci. USA 93:15400-15404.
Buchholz et al., 1999 "Generation of Bovine Resp. Syncytial Virus (BRSV) from cDNA: BRSV NS2 Is Not Essential for Virus Replication in Tissue Culture . . . " J. Virol. 73:251-259.
Bukreyev et al., 1996, "Recovery of infectious respiratory syncytial virus expressing an additional, foreign gene", J Virol. 70(10):6634-41.
Castrucci et al., 1995, "Reverse genetics system. for generation of an influenza A virus mutant containing a deletion of the carboxyl-terminal M2 . . . ", J Virol. 69(5):2725-28.
Chen et al., 1999, "Influenza A virus NS1 protein targets poly (A)-binding protein II of the cellular 3'-end processing machinery", EMBO 18: 2273-2283.
Clarke et al., 2000, "Rescue of mumps virus from cDNAJ", J Virol. 74 (10):4831-38.
Collins et al., 1991, "Rescue of Synthetic Analogs of Respiratory Syncytial Virus Genomic RNA and Effect of Truncations.", Proc. Natl. Acad. Sci. USA 88:9663-9667.
Collins et al., 1995, "Production of infectious human respiratory syncytial virus from cloned cDNA confirms an essential role . . . " PNAS 92: 11563-1567.
Collins et al., 1996, "Parainfluenza Viruses", Fields Virology, Lippincott-Raven Publishers, Phila., pp. 1205-1241.
Conzelmann, 1996, "Genetic manipulation of non-segmented negative-strand RNA viruses", J Gen Virol. 77 (Pt 3):381-89.
Conzelmann et al., 1998, "Nonsegmented negative-strand RNA viruses: genetics and manipulation of viral genomes", Annu Rev Genet. 32:123-62.
Conzelmann et al., 1996, "Genetic engineering of animal RNA viruses", Trends Microbiol. 4(10):386-93.
Conzelmann et al., 1994, "Rescue of synthetic genomic RNA analogs of rabies virus by plasmid-encoded proteins", J Virol. 68(2):713-19.
De la Luna et al., 1993, "Influenza virus naked RNA can be expressed upon transfection into cells co-expressing the three subunits . . . " J. Gen. Virol. 74: 535-39.
De La Luna et al., 1995, "Influenza virus NS1 Protein Enhances the Rate of Translation Initiation of Viral mRNAs", J. of Virol. 69: 2427-2433.
De and Banerjee, 1985, "Requirements and Functions of Vesicular Stomatitis Virus L and NS Proteins in the Transcription . . . ", Biochem. & Biophys. Res. Commun. 126:40-49.
De and Banerjee, 1993, "Rescue of synthetic analogs of genome RNA of human parainfluenza virus type 3", Virology, 96:344-48.
De and Banerjee, 1994, "Reverse genetics of negative strand RNA viruses," Indian J Biochem & Biophys. 31:367-76.
Dimock et al., 1993, "Rescue of synthetic analogs of genomic RNA and replicative-intermed. RNA of human parainfluenza virus type 3,", J Virol. 67(5):2772-78.
Dreher et al., 1984, "Mutant Viral RNAs Synthesized in vitro Show Altered Aminoacylation and Replicase Template Activities", Nature 311:171-175.
Dreher and Hall, 1988, "Mutational Analysis of the Sequence and Structural Requirements in Brome Mosiac Virus RNA for Minus Strand Promoter Activity", J. Mol. Biol. 201:31-40.
Dunn et al., 1995, "Transcription of a recombinant bunyavirus RNA template by transiently expressed bunyavirus protiens", Virology, 211:133-43.
Durbin et al., 1997, "Recovery of infectious Human Parainfluenza Virus Type 3 from cDNA", Virol. 235:323-332.
Elliot et al., 1997, Abstract # 96 10.sup.th International conference on Negative Strand Viruses.
Elliott et al., 1991, "Some highlights of virus research in 1990", J Gen Virol. 72:1761-79, Review.
Emerson and Yu, 1975, "Both NS and L Proteins are Required for in vitro RNA Syntheis by Vosicular Stomatitis Virus", J. Virol. 15:1348-1356.
Enami and Palese, 1991, "Highly-Efficiency Formation of Influenza Virus Transfectants", J. Virol. 65:2711-2713.
Enami et al., 1991, "An influenza virus containing nine different RNA segments", Virology. 185:291-98.
Fahey and Schooley, 1992, "Status of Immune-Based Therapies in HIV Infection and AIDS", Clin. Exp. Immunol. 88:1-5.
Fortes et al., 1994, "Influenza virus NS1 protein inhibits pre-mRNA splicing and blocks mRNA nucleocytoplasmic transport", EMBO J. 13: 704-712.
Garcia-Sastre A, Palese P, 1993. "Genetic manipulation of negative-strand RNA virus genomes", Annu Rev Microbiol. 47:765-90.
Garcin et al., 1995, "A highly recombinogenic system for the recovery of infectious sendai paramyzovirus from cDNA: generation of a novel . . . " EMBO J. 14: 6087-6094.
Goto et al., 1997, "Mutations Affecting the Sensitivity of the Influenza Virus Neuraminidase to 4-Guanidino-2,4-Dideoxy-2,3 Dehydro-N-Acetyineuraminic Acid", Virol. 238:265-27.
Grosfeld et al., 1995, "RNA replication by respiratory syncytial virus (RSV) is directed by the N., P., and L proteins: transcription . . . " J. Virol. 69(9):5677-86.
Hatada and Fukudo, 1992, "Binding of influenza A virus NS1 protein to dsRNA in vitro", J. of Gen. Virol. 73: 3325-3329.
He et al., 1997, "Recovery of Infectious SV5 from Cloned DNA and Expression of a Foreign Gene", Virol. 237:249-260.
Hoffman and Banerjee, 1997. "An Infectious Clone of Human Parainfluenza Virus Type 3", J. Virol. 71:4272-4277.
Huang et al., 1990, "Determination of Influenza virus proteins required for genome replication", J Virol. 64(11):5669-73.
Kaplan et al., 1985. "In vitro Synthesis of Infectious Poliovirus RNA", Proc. Natl. Acad. Sci. USA 82: 8424-8428.
Kato et al., 1996, "Initiation of Sendai Virus Multiplication from Transfected cDNA or RNA with Negative or Positive Sense", Genes to Cells 1:569-579.
Kimura et al., 1993, "An in vivo study of the replication origin in the influenza virus complementary RNA", J Biochem (Tokyo) 113:88-92.
Kimura et al., 1992, "Transcription of a recombinant influenza virus RNA in cells that can express the influenza virus RNA polymerase . . . ", J Gen Virol. 73:1321-28.
Kobayashi et al., 1992, Reconstitution of influenza virus RNA polymerase from three subunits expressed using recombinant baculovirus system. Virus Res. 22:235-45.

Konarska et al., 1990, "Structure of RNAs replicated by the DNA-dependent T7 RNA polymerase", Cell. 63(3):609-18.
Krystal et al., 1986, "Expression of the Three Influenza Virus Polymerase Proteins in a Single Cell Allows Growth . . . ", Proc. Natl. Acad. Sci. USA 83:2709-2713.
Kunkel, 1985, "Rapid and Efficient Site-Specific Mutagenesis without Phenotypic Selection", Proc. Natl. Acad. Sci. USA 82:468-492.
Lamb et al., 1996, Fundamental Virology 3.sup.rd ed. Chapters 20 and 21.
Lawson et al., 1995, "Recombinant vesicular stomatitis viruses from DNA", Proc Natl Acad Sci U S A.92:4477-81.
Levis et al., 1986, "Deletion Mapping of Sindbis Virus DI RNAs Derived from cDNAs Defines the Sequences Essential for Replication and Packaging", Cell 44:137-145.
Luytjes et al., 1989, "Amplification, Expression, and Packaging of a Foreign Gene by Influenza Virus", Cell 59:1107-1113.
Mena et al., 1994, "Synthesis of biologically active influenza virus core proteins using a vaccinia virus-T7 RNA polymerase expression system", J Gen Virol. 75:2109-14.
Mena et al., 1996, "Rescue of a Synthetic Chloramphenicol Acetyltransferase RNA into Influenza Virus-Like Particles Obtained fr. Recombinant Plasmids", J. Virol. 70: 5016-5024.
Moyer et al., 1991, "Assembly and transcription of synthetic vesicular stomatitis virus nucleocapsids", J Virol. 65(5):2170-88.
Muster et al., 1991, "An influenza A virus containing influenza B virus 5' and 3' noncoding regions on the neuraminidase gene . . . ", Proc Natl Acad Sci USA 88:5177-81.
Naito and Ishihama, 1976, "Function and Structure of RNA Polymerase from Vesicular Stomatitis Virus", J. Biol. Chem. 251:4307-4314.
Nara et al., 1987, "Simple, Rapid, Quantitative, Syncytium-Forming Microassay for the Detection of Human Immunodeficiency . . . ", AIDS Res. Hum. Retroviruses 3:283-302.
Nemeroff et al., 1998, "Influenza Virus NS1 Protein Interacts with the Cellular 30 kDa Subunit of CPSF and Inhibits 3' End Formation . . . ", Mol. Cell 1:991-1000.
Neumann et al., 1994, "RNA Polymerase I-Mediated Expression of Influenza Viral RNA Molecules", Virol. 202:477-479.
Palese et al., 1996, "Negative-Strand RNA Viruses: Genetic Engineering and Applications", Proc. Natl. Acad. Sci. USA 93,11354-11358.
Park et al., 1991, "Rescue of a Foreign Gene by Sendai Virus", Proc. Natl. Acad. Sci. USA 88:5537-5541.
Pattnaik et al., 1991, "Cells that express all five proteins of vesicular stomatitis virus from cloned cDNAs support replication . . . " Proc Natl Acad Sci USA 88:1379-83.
Peeters et al., 1999, "Rescue of Newcastle Disease Virus from Cloned cDNA: Evidence that Cleavability of the Fusion Protein . . . ", J. Virol. 73:5001-5009.
Pekosz et al., 1999, "Reverse genetics of negative-strand RNA viruses: closing the circle", Proc Natl Acad Sci USA. 96(16):8804-16.
Percy et al., 1994, "Expression of a foreign protein by influenza A virus", J Virol 68(7):4486-92.
Pleschka et al., 1996, "A Plasmid-Based Reverse Genetics System for Influenza A Virus", J. Virol. 70:4188-4192.
Qui et.al., 1995. "The influenza virus NS1 protein binds to a specific region in human U6 snRNA and inhibits U6-U2 and U6-U4 snRNA . . . ", RNA Society 1:304-16.
Zhang et al., "Persistence of four related human munodeficiency virus subtypes during the course of zidovudine therapy . . . ", J. Virol. 1994 68: 425-432.
Racaniello et al., 1981. "Cloned Poliovirus Complementary DNA is Infectious in Mammalian Cells", Science 214:916-919.
Radecke et al., 1995, "Rescue of measles viruses from cloned DNA", EMBO J. 14(23)5773-84.
Roberts and Rose, 1998, "Recovery of Negative-Strand RNA Viruses from Plasmid DNAs: a Positive Approach Revitalizes a Negative Field", Virol. 247:1-6.
Rose 1996, "Positive Strands to the Rescue Again: A Segmented Negative-Strand RNA Virus Derived from Cloned . . . ",PNAS USA 94:14998-15000.
Schlesinger, 1995. "RNA viruses as vectors for the expression of heterologous proteins", Mol Biotechnol. 3:155-65.
Schnell et al., 1994, "Infectious Rabies Viruses from Cloned cDNA", EMBO J. 13:4195-4203.
Seong et al., 1992, "A new method for reconstituting influenza polymerase and RNA in vitro: a study of the promoter elements for cRNA . . . ", Virology 186:247-60.
Sidhu et al., 1995, "Rescue of synthetic measles virus minireplicons: measles genomic termini direct efficient expression . . . ", Virology. 208(2):800-07.
Szewczyk et al., 1988, "Purification, Thioredoxin Renaturation, and Reconstituted Activity of the Three Subunits of the Influenza . . . ", Proc. Natl. Acad. Sci. USA 85:7907-7911.
Yamanaka et al., 1991, "In vivo analysis of the promoter structure of the influenza virus RNA genome using a transfection system . . . ," Proc Natl Acad Sci USA 88: 5369-5373.
Belshe, 1995 "A Review of Attenuation of Influenza Viruses by Genetic manipulation", American Journal of Respiratory And Critical Care Medicine 152:S72-S75.
Brandt et al., 2001, "Molecular Determinants of Virulence, Cell Tropsim, and Pathogenic Phenotype of Infectious Bursal Disease Virus", Journal of Virology 75(24):11974-11982.
Qiu et. al., 1994, "The influenza virus NS1 protein is a poly(A)-binding protein that inhibits nuclear export of mRNAs containing poly(A)", J Virol. 68(4):2425-32.
Maassab, "Adaptation and growth characteristics of influenza virus at 25 degrees C", Nature, 213:612-614 (1967).
Furminger, "Vaccine Production", Textbook of Influenza, pp. 324-332; (1996).
Subbarao et al., "The Attenuation Phenotype Conferred by the M Gene of the Influenza A/Ann Arbor/6/60 Cold-Adapted Virus (H2N2) on the . . ." Virus Res., 25:37-50; (1992).
Snyder et al., "Four Viral Genes Idependently Contribute to Attenuation of Live Influenza A/Ann Arbor/6/60 (H2N2) Cold-Adapted . . . ", J. Virol., 62:488-95; (1988).
Parkin et al., "Temperature Sensitive Mutants of Influenza A Virus Generated by Reverse Genetics . . . ", Virus Res., 46:31-44; (1996).
Parkin N. et al., "Genetically Engineered Live Atenuated Influenza A Virus Vaccine Candidates", J. Virol., pp. 2772-2778; (1997).
Murphy & Coelingh, "Principles Uderlying the Development and Use of Live Attenuated Cold-Adapted Influenza A and B Virus Vaccines", Viral Immunol, 15:295-323; (2002).
Merten et al., "Production of influenza virus in Cell Cultures for Vaccine Preparation", Novel Strategies in Design and Production of Vaccines, pp. 141-151; (1996).
Maassab et al., "Evaluation of a Cold-Recombinant Influenza Virus Vaccine in Ferrets", J. of Infectious Diseases, 146:780-790; (1982).
Hoffman et al., "Eight-Plasmid Resue System for Influenza A Virus", International Congress Series, 1219:1007-1013; (2001).
Hoffman et al., "Eight-Plasmid System for Rapid Generation Generation of Influenza Virus Vaccines", Vaccine, 20:3165-3170; (2002).
Herlocher et al., "Sequence Comparisons of A/AA/6/60 Influenza Viruses: Mutations Which May Contribute to Attenuation", Virus Research, 42:11-25; (1996).
Hoffman et al., "Ambisense" Approach for the Generation of Influenza A Virus: vRNA and mRNA Synthesis from One Template, Virology, 267:310-317; (2000).
Radecke et al., "Reverse Genetics Meets the Nonsegmented Negative-Strand RNA Viruses", Medical Virology, vol. 7: 49-63 (1997).
Katinger et al., "Attenuated Influenza Virus as a Vector for Mucosal Immunization against HIV-1", Vaccines, pp. 315-319, (1997).
Neumann, et al., "Genetic Engineering of Influenza and Other Negative-Strand RNA Viruses Containing Segmented Genomes," Advances in Virus Research, 1999; 53: 265-300.
Taylor et al., 1990, "Newcastle Disease Virus Fusion Protein Expressed in a Fowlpox Virus Recombinant Confers Protection in Chickens", J. Virol. 64:1441-1450.
Ward et al., 1988, "Direct Measurement of the Poliovirus RNA Polymerase Error Frequency in Vitro", J. Virol. 62:558-562.
Whelan et al., 1995, "Efficient recovery of infectious vesicular stomatitis virus entirely from cDNA clones", Proc.Natl.Acad.Sci. USA 92:8388-8392.

Yu et al., 1995, "Functional cDNA clones of the human respiratory syncytial (RS) virus N, P, and L proteins support replication . . . ", J Virol. 69(4):2412-19.
Yusoff et al., 1987, "Nucleotide Sequence Analysis of the L Gene of Newcastle Disease Virus: Homologies with Sendi and Vesicular Stomatitis.", Nucleic Acids Res. 15:3961-76.
Zaghouani et al., 1991, "Induction of antibodies to the envelope protein of the human immunodeficiency virus by immunization . . . ", Proc. Natl. Acad Sci. USA 88:5645-5649.
Zaghouni et al., 1992, "Cells Expressing an H Chain to Gene Carrying a Viral T Cell Epitope Are Lysed by Specific Cytolytic T Cells", J. Immunol. 148:3604-3609.
Zhang and Air, 1994, "Expressing of Functional Influenza Virus A Polymerase Proteins and Template from Cloned cDNAs . . . ", Biochem. & Biophys. Res. Commun. 200:95-101.
Zobel et al., 1993, "RNA polymerase I catalysed transcription of insert viral cDNA", Nucleic Acids Res. 21(16):3607-14.
Enami et al., 1990, "Introduction of Site Specific Mutations into the Genome of Influenza Virus", Proc Natl Acad Sci USA 87: 3802-3805.
Govorkova, E.A., et al., "African Green Monkey Kidney (Vero) Cells Provide an Alternative Host Cells . . . ", J. of Virology, Am. Soc. for Microbiology, Aug. 1996, 70(8):5519-5524.
Guan, Yi, et al., "Molecular Characterization of H9N2 Influenza Viruses: Were They The Donors of the "Internal". . . ?", Proc. Natl. Acad. Sci., U.S.A. Aug. 1999, 96:9363-9367.
Erich Hoffman et al., 2002, "Rescue of Influenza B virus from eight plasmids", PNAS 99: 11411-11416.
Hoffmann; 1997, "Generation of an RNA-Polymerase Vector Syst. for the Select. Mutagenesis . . . ," Inaugural Dissertation of Sch. of Nat. Sciences, Justus Liebig U. Gieben.
Cox, et al.; "Identification of Sequence Changes in the Cold-Adapted, Live Attenuated Influenza Vaccine Strain, A/Ann Arbor/6/60 (H2N2)," Virology, 1988; 167: 554-567.
Belshe et al. 1998 , "The efficacy of live attenuated, cold-adapted, trivalent, intranasal influenza virus vaccine in children ," N Engl J Med 338:1405-12.
Boyce et al., 2000, "Safety and immunogenicity of adjuvanted sub-unit influenza vaccines administered intranasally to healthy adults", Vaccine 19:217-26.
Edwards et al., 1994, "A randomized controlled trial of cold adapted and inactivated vaccines for the prevention of influenza A disease", J Infect Dis 169:68-76.
Hoffmann et al."Universal primer set for the full-length amplification of all influenza A viruses." Arch Virol. Dec. 2001;146(12):2275-89).
Li et al., 1999, "Recombinant influenza A virus vaccines for the pathogenic human A/Hong Kong/97 (H5N1) viruses," J. of Infectious Diseases, 179:1132-8.
Nichol et al. 1999, "Effectiveness of live, attenuated intranasal influenza virus vaccine in healthy, working adults: a randomized controlled trial", JAMA 282:137-44.
Hoffmann et al.,2000, "Unidirectional RNA polymerase I-polymerase II transcription system for the generation of influenza A virus . . . ", J.I of Gen. Virology 81:2843-2847.
Hoffmann et al., 2000, "A DNA transfection system for generation of influenza A virus from eight plasmids", PNAS 97(11):6108-6113.
Subbarao et al., 1995, "Sequential addition of temperature-sensitive missense mutations into the PB2 gene of influenza A . . . ", J. of Virology 69(10):5969-5977.
Fodor et al., 1999, "Rescue of Influenza A Virus from Recombinant DNA", J. of Virology 73(11):9679-9682.
Neumann et al.. 1999, "Generation of influenza A viruses entirely from cloned cDNAs", PNAS 96(16):9345-9350.
Egorov et al., 1998, "Transfectant Influenza A Viruses with Long Deletions in the NS1 Protein Grow Efficiently in Vero Cells", J. of Virology 72(8):6437-6441.
Enami et al., 2000, "Characterization of Influenza Virus NS1 Protein by Using a Novel Helper-Virus Free Reverse Genetic System", J. of Virology 74(12):5556-5561.
Schickli et al., 2001, "Plasmid-only rescue of influenza A virus vaccine candidates", Philos Trans Society of London Ser B 356:1965-1973.
Basler et al., 1999, "Mutations of Neuraminidase Cysteine Residues Yields Temperature-Sensitive Influenza Viruses", J. of Virology 73(10):8095-8103.
Webby et al., 2004, "Responsiveness to a pandemic alert: use of reverse genetics for rapid development of influenza vaccines", Lancet 363:1099-1103.
Wareing, J.M., et al, 2001, "Immunogenic and Isotype-Specific Responses to Russian and US Cold-Adapted Influenza A Vaccine Donor . . . ", J. of Medical Virology 65:171-177.
Subbarao, Kanta et al., 2003, "Evaluation of a Genetically Modified Reassortant H5N1 Influenza A Virus Vaccine Candidate . . . " Virology 305:192-200.
Subbarao, et al., "Rescue of a Influenza A Virus Wild-Type PB2 Gene and a Mutant Derivative Bearing A Site-Specific . . . ," J. of Virology, 1993, pp. 7223-7228.
Scholtissek, et al., "The Nucleoprotein as a Possible Major Factor in Determining Host Specificity of Influenza H3N2 Viruses," Virology, 1985; 147:287-294.
Bergmann, et al., 1995, "The relative amount of an influenza A virus segment present in the viral particle is not affected . . . ", J. of Gen. Virology, 76:3211-3215.
Ghendon, "Cold-Adapted, Live Influenza Vaccines Developed in Russia," Textbook of Influenza, Chapter 29, pp. 391-399. 1998.
Keitel, et al., "Live Cold-Adapted, Reassortant Influenza Vaccines (USA)," Textbook of Influenza, Chapter 28, pp. 373-390. 1998.
Hoffman, Erich, Aufbau eines RNA-Polymerase I-Vektorsystems zur gezielten Mutagenase von Influenza A Viren, Gieben 1997 (Doctoral Dissertation).
Perez, Daniel R. et al., 1998 "The Matrix 1 Protein of Influenza A Virus Inhibits The Transcriptase Activity of a Model . . . ", Articel No. VY989318, Virology, 249:52-61.
Xu, Xiyan, et al., 1999 "Genetic Characterization of the Pathogenic Influenza A /Goose/Guangdong/ 1/96 (H5N1) Virus: . . . ", Article ID viro. 1999.9820. Virology 261:15-19.
Zhou, Yan, et al., "Membrane-Anchored Incorporation of a Foreign in Recombinant Influenza Virions", Article No. VY989169, Virology, 1998, vol. 246, pp. 83-94.
Erich Hoffmann et al., 2000 "Characterization of the Influenza A Virus Gene Pool in Avian Species in Southern China: Was H6N1 . . . ?" J. Virology, 74(14):6309-6315.
Flick, et al., "Promoter elements in the influenza vRNA terminal structure," RNA, 1996; 2(10):1046-1057.

* cited by examiner pAD3000 (SEQ ID NO:94)

| PB1 | PB2 | PA | HA | NP | NA | M | NS | bp
— 4000
— 2500
— 2000
— 1500
— 1000
— 750
— 500

PB1
G924

HA

NS
G416

2. Sequence in Genbank-format

```
LOCUS       pAD3000      2836 bp    DNA   circular          14-JAN-2002
DEFINITION  Derivative of pHW2000 with SV40 PolyA Signal replacing BGH

FEATURES             Location/Qualifiers
     promoter        2420..2799
                     /vntifkey="29"
                     /label=pCMV
                     /note="truncated CMV promoter (corresponding to 484-863
region of pcDNA3)"
     misc_marker     1422..2282
                     /vntifkey="22"
                     /label=bla
                     /note="beta lactamase"
     rep_origin      612..1172
                     /vntifkey="33"
                     /label=Col\E1ori
                     /note="Col E1 replication origin"
     terminator      11..45
                     /vntifkey="43"
                     /label=tI
                     /note="Pol I terminator"
     promoter        complement(65..276)
                     /vntifkey="29"
                     /label=PolI
                     /note="Human Pol I Promoter"
     exon            296..430
                     /vntifkey="61"
                     /label=pA
                     /note="pA(SV40)"
BASE COUNT      717 a      734 c      703 g      682 t
ORIGIN
        1 ctagcagtta accggagtac tggtcgacct ccgaagttgg gggggaggag acggtaccgt
       61 ctccaataac ccggcggccc aaaatgccga ctcggagcga aagatatacc tcccccgggg
      121 ccgggaggtc gcgtcaccga ccacgccgcc ggcccaggcg acgcgcgaca cggacacctg
      181 tccccaaaaa cgccaccatc gcagccacac acggagcgcc cggggccctc tggtcaaccc
      241 caggacacac gcgggagcag cgccgggccg gggacgccct cccggcggtc acctcagaca
      301 tgataagata cattgatgag tttggacaaa ccacaactag aatgcagtga aaaaaatgct
      361 ttatttgtga aatttgtgat gctattgctt tatttgtaac cattataagc tgcaataaac
      421 aaggatctgc attaatgaat cggccaacgc gcggggagag gcggtttgcg tattgggcgc
      481 tcttccgctt cctcgctcac tgactcgctg cgctcggtcg ttcggctgcg gcgagcggta
      541 tcagctcact caaaggcggt aatacggtta tccacagaat caggggataa cgcaggaaag
      601 aacatgtgag caaaaggcca gcaaaaggcc aggaaccgta aaaaggccgc gttgctggcg
      661 tttttccata ggctccgccc ccctgacgag catcacaaaa atcgacgctc aagtcagagg
      721 tggcgaaacc cgacaggact ataaagatac caggcgtttc cccctggaag ctccctcgtg
      781 cgctctcctg ttccgaccct gccgcttacc ggatacctgt ccgcctttct cccttcggga
      841 agcgtggcgc tttctcaatg ctcacgctgt aggtatctca gttcggtgta ggtcgttcgc
      901 tccaagctgg gctgtgtgca cgaacccccc gttcagcccg accgctgcgc cttatccggt
      961 aactatcgtc ttgagtccaa cccggtaaga cacgacttat cgccactggc agcagccact
     1021 ggtaacagga ttagcagagc gaggtatgta ggcggtgcta cagagttctt gaagtggtgg
     1081 cctaactacg gctacactag aaggacagta tttggtatct gcgctctgct gaagccagtt
     1141 accttcggaa aaagagttgg tagctcttga tccggcaaac aaaccaccgc tggtagcggt
     1201 ggtttttttg tttgcaagca gcagattacg cgcagaaaaa aaggatctca agaagatcct
     1261 ttgatctttt ctacggggtc tgacgctcag tggaacgaaa actcacgtta agggattttg
     1321 gtcatgagat tatcaaaaag gatcttcacc tagatccttt taaattaaaa atgaagtttt
```

Fig. 6

1381 aaatcaatct aaagtatata tgagtaaact tggtctgaca gttaccaatg cttaatcagt
1441 gaggcaccta tctcagcgat ctgtctattt cgttcatcca tagttgcctg actccccgtc
1501 gtgtagataa ctacgatacg ggagggctta ccatctggcc ccagtgctgc aatgataccg
1561 cgagacccac gctcaccggc tccagattta tcagcaataa accagccagc cggaagggcc
1621 gagcgcagaa gtggtcctgc aactttatcc gcctccatcc agtctattaa ttgttgccgg
1681 gaagctagag taagtagttc gccagttaat agtttgcgca acgttgttgc cattgctaca
1741 ggcatcgtgg tgtcacgctc gtcgtttggt atggcttcat tcagctccgg ttcccaacga
1801 tcaaggcgag ttacatgatc ccccatgttg tgcaaaaaag cggttagctc cttcggtcct
1861 ccgatcgttg tcagaagtaa gttggccgca gtgttatcac tcatggttat ggcagcactg
1921 cataattctc ttactgtcat gccatccgta agatgctttt ctgtgactgg tgagtactca
1981 accaagtcat tctgagaata gtgtatgcgg cgaccgagtt gctcttgccc ggcgtcaata
2041 cgggataata ccgcgccaca tagcagaact ttaaaagtgc tcatcattgg aaaacgttct
2101 tcggggcgaa aactctcaag gatcttaccg ctgttgagat ccagttcgat gtaacccact
2161 cgtgcaccca actgatcttc agcatctttt actttcacca gcgtttctgg gtgagcaaaa
2221 acaggaaggc aaaatgccgc aaaaaaggga ataagggcga cacggaaatg ttgaatactc
2281 atactcttcc tttttcaata ttattgaagc atttatcagg gttattgtct catgagcgga
2341 tacatatttg aatgtattta gaaaaataaa caaatagggg ttccgcgcac atttccccga
2401 aaagtgccac ctgacgtcga tatgccaagt acgcccccta ttgacgtcaa tgacggtaaa
2461 tggcccgcct ggcattatgc ccagtacatg accttatggg actttcctac ttggcagtac
2521 atctacgtat tagtcatcgc tattaccatg gtgatgcggt tttggcagta catcaatggg
2581 cgtggatagc ggtttgactc acggggattt ccaagtctcc accccattga cgtcaatggg
2641 agtttgtttt ggcaccaaaa tcaacgggac tttccaaaat gtcgtaacaa ctccgcccca
2701 ttgacgcaaa tgggcggtag gcgtgtacgg tgggaggtct atataagcag agctctctgg
2761 ctaactagag aacccactgc ttactggctt atcgaaatta atacgactca ctatagggag
2821 acccaagctg ttaacg

Fig. 6 Cont.

ALIGNMENT OF CONSENSUS SEQUENCE OF MDV-B WITH CDNA IN THE EIGHT PLASMIDS (PAB12[N-SEGMENT])
(SEQ ID NOS:95-102)

PB1

```
                      *        20         *        40         *
pAB121-PB1 : .................................................. :   50
MDV-B-PB1  : .................................................. :   50
             AGCAGAAGCGGAGCCTTTAAGATGAATATAAATCCTTATTTTCTCTTCAT

                     60         *        80         *       100
pAB121-PB1 : .................................................. :  100
MDV-B-PB1  : .................................................. :  100
             AGATGTACCCATACAGGCAGCAATTTCAACAACATTCCCATACACCGGTG

                      *       120         *       140         *
pAB121-PB1 : .................................................. :  150
MDV-B-PB1  : .................................................. :  150
             TTCCCCCTTATTCCCATGGAACGGGAACAGGCTACACAATAGACACCGTG

                    160         *       180         *       200
pAB121-PB1 : .................................................. :  200
MDV-B-PB1  : .................................................. :  200
             ATTAGAACACATGAGTACTCAAACAAGGGAAAACAATACATTTCTGATGT

                      *       220         *       240         *
pAB121-PB1 : .................................................. :  250
MDV-B-PB1  : .................................................. :  250
             TACAGGATGTGCAATGGTAGATCCAACAAATGGGCCATTACCCGAAGATA

                    260         *       280         *       300
pAB121-PB1 : .................................................. :  300
MDV-B-PB1  : .................................................. :  300
             ATGAGCCGAGTGCCTATGCACAATTGGATTGCGTTCTGGAGGCTTTGGAT

                      *       320         *       340         *
pAB121-PB1 : .................................................. :  350
MDV-B-PB1  : .................................................. :  350
             AGAATGGATGAAGAACATCCAGGTCTGTTTCAAGCAGCCTCACAGAATGC

                    360         *       380         *       400
pAB121-PB1 : .................................................. :  400
MDV-B-PB1  : .................................................. :  400
             CATGGAGGCACTAATGGTCACAACTGTAGACAAATTAACCCAGGGGAGAC

                      *       420         *       440         *
pAB121-PB1 : .................................................. :  450
MDV-B-PB1  : .................................................. :  450
             AGACTTTTGATTGGACAGTGTGCAGAAACCAACCTGCTGCAACGGCACTG

                    460         *       480         *       500
pAB121-PB1 : .................................................. :  500
MDV-B-PB1  : .................................................. :  500
             AACACAACAATAACCTCTTTTAGGTTGAATGATTTGAATGGAGCCGACAA
```

Fig. 7

```
                        *        520         *        540         *
pAB121-PB1 : .................................................. :  550
MDV-B-PB1  : .................................................. :  550
             GGGTGGATTAGTACCCTTTTGCCAAGATATCATTGATTCATTGGACAAAC

                      560         *        580         *        600
pAB121-PB1 : .................................................. :  600
MDV-B-PB1  : .................................................. :  600
             CTGAAATGACTTTCTTCTCGGTAAAGAATATAAAGAAAAAATTGCCTGCT

                        *        620         *        640         *
pAB121-PB1 : .................................................. :  650
MDV-B-PB1  : .................................................. :  650
             AAAAACAGAAAGGGTTTCCTCATAAAGAGAATACCAATGAAGGTAAAAGA

                      660         *        680         *        700
pAB121-PB1 : .................................................. :  700
MDV-B-PB1  : .................................................. :  700
             CAGAATAACCAGAGTGGAATACATCAAAAGAGCATTATCATTAAACACAA

                        *        720         *        740         *
pAB121-PB1 : .................................................. :  750
MDV-B-PB1  : .................................................. :  750
             TGACAAAAGATGCTGAAAGAGGCAAACTAAAAAGAAGAGCAATTGCCACC

                      760         *        780         *        800
pAB121-PB1 : .................................................. :  800
MDV-B-PB1  : .................................................. :  800
             GCTGGGATACAAATCAGAGGGTTTGTATTAGTAGTTGAAAACTTGGCTAA

                        *        820         *        840         *
pAB121-PB1 : .................................................. :  850
MDV-B-PB1  : .................................................. :  850
             AAATATCTGTGAAAATCTAGAACAAAGTGGTTTGCCAGTAGGTGGGAACG

                      860         *        880         *        900
pAB121-PB1 : .................................................. :  900
MDV-B-PB1  : .................................................. :  900
             AGAAGAAGGCCAAACTGTCAAATGCAGTGGCCAAAATGCTCAGTAACTGC

                        *        920         *        940         *
pAB121-PB1 : .......................G.......................... :  950
MDV-B-PB1  : .................................................. :  950
             CCACCAGGAGGGATCAGCATGACAGTGACAGGAGACAATACTAAATGGAA

                      960         *        980         *       1000
pAB121-PB1 : .................................................. : 1000
MDV-B-PB1  : .................................................. : 1000
             TGAATGCTTAAATCCAAGAATCTTTTTGGCTATGACTGAAAGAATAACCA

                        *       1020         *       1040         *
pAB121-PB1 : .................................................. : 1050
MDV-B-PB1  : .................................................. : 1050
             GAGACAGCCCAATTTGGTTCCGGGATTTTTGTAGTATAGCACCGGTCTTG

                     1060         *       1080         *       1100
```

```
pAB121-PB1 : .................................................. : 1100
MDV-B-PB1  : .................................................. : 1100
             TTCTCCAATAAAATAGCCAGATTGGGAAAAGGGTTCATGATAACAAGCAA

                     *       1120          *       1140          *
pAB121-PB1 : .................................................. : 1150
MDV-B-PB1  : .................................................. : 1150
             AACAAAAAGACTGAAGGCTCAAATACCTTGTCCCGATCTGTTTAATATAC

                  1160          *       1180          *       1200
pAB121-PB1 : .................................................. : 1200
MDV-B-PB1  : .................................................. : 1200
             CATTAGAAAGATATAATGAAGAAACAAGGGCAAAATTAAAAAAGCTGAAA

                     *       1220          *       1240          *
pAB121-PB1 : .................................................. : 1250
MDV-B-PB1  : .................................................. : 1250
             CCATTCTTCAATGAAGAAGGAACGGCATCTTTGTCGCCTGGGATGATGAT

                  1260          *       1280          *       1300
pAB121-PB1 : .................................................. : 1300
MDV-B-PB1  : .................................................. : 1300
             GGGAATGTTTAATATGCTATCTACCGTGTTGGGAGTAGCCGCACTAGGGA

                     *       1320          *       1340          *
pAB121-PB1 : .................................................. : 1350
MDV-B-PB1  : .................................................. : 1350
             TCAAAAACATTGGAAACAAAGAATACTTATGGGATGGACTGCAATCTTCT

                  1360          *       1380          *       1400
pAB121-PB1 : .................................................. : 1400
MDV-B-PB1  : .................................................. : 1400
             GATGATTTTGCTCTGTTTGTTAATGCAAAAGATGAAGAGACATGTATGGA

                     *       1420          *       1440          *
pAB121-PB1 : .................................................. : 1450
MDV-B-PB1  : .................................................. : 1450
             AGGAATAAACGATTTTTACCGAACATGTAAGCTATTGGGAATAAACATGA

                  1460          *       1480          *       1500
pAB121-PB1 : .................................................. : 1500
MDV-B-PB1  : .................................................. : 1500
             GCAAAAAGAAAAGTTACTGTAATGAAACTGGAATGTTTGAATTTACAAGC

                     *       1520          *       1540          *
pAB121-PB1 : .................................................. : 1550
MDV-B-PB1  : .................................................. : 1550
             ATGTTCTACAGAGATGGATTTGTATCTAATTTTGCAATGGAACTTCCTTC

                  1560          *       1580          *       1600
pAB121-PB1 : .................................................. : 1600
MDV-B-PB1  : .................................................. : 1600
             ATTTGGAGTTGCTGGAGTAAATGAATCAGCAGATATGGCAATAGGAATGA
```

Fig. 7 Cont.

```
                          *       1620          *       1640          *
pAB121-PB1 : .................................................. : 1650
MDV-B-PB1  : .................................................. : 1650
             CAATAATAAAGAACAATATGATCAACAATGGGATGGGTCCAGCAACAGCA

                      1660          *       1680          *       1700
pAB121-PB1 : .................................................. : 1700
MDV-B-PB1  : .................................................. : 1700
             CAAACAGCCATACAATTATTCATAGCTGATTATAGATACACCTACAAATG

                          *       1720          *       1740          *
pAB121-PB1 : T................................................. : 1750
MDV-B-PB1  : .................................................. : 1750
             CCACAGGGGAGATTCCAAAGTGGAAGGAAAGAGAATGAAAATTATAAAGG

                      1760          *       1780          *       1800
pAB121-PB1 : .................................................. : 1800
MDV-B-PB1  : .................................................. : 1800
             AGCTATGGGAAAACACTAAAGGAAGAGATGGTCTGTTAGTAGCAGATGGT

                          *       1820          *       1840          *
pAB121-PB1 : .................................................. : 1850
MDV-B-PB1  : .................................................. : 1850
             GGGCCTAACATTTACAATTTGAGAAACTTGCATATCCCAGAAATAGTATT

                      1860          *       1880          *       1900
pAB121-PB1 : .................................................. : 1900
MDV-B-PB1  : .................................................. : 1900
             AAAGTACAACCTAATGGACCCTGAATACAAAGGGCGGTTACTGCATCCTC

                          *       1920          *       1940          *
pAB121-PB1 : .................................................. : 1950
MDV-B-PB1  : .................................................. : 1950
             AAAATCCCTTTGTAGGACATTTGTCTATTGAGGGCATCAAAGAGGCAGAT

                      1960          *       1980          *       2000
pAB121-PB1 : .................................................. : 2000
MDV-B-PB1  : .................................................. : 2000
             ATAACCCCAGCACATGGTCCAGTAAAGAAAATGGACTATGATGCGGTATC

                          *       2020          *       2040          *
pAB121-PB1 : .................................................. : 2050
MDV-B-PB1  : .................................................. : 2050
             TGGAACTCATAGTTGGAGAACCAAAAGGAACAGATCTATACTAAACACTG

                      2060          *       2080          *       2100
pAB121-PB1 : .................................................. : 2100
MDV-B-PB1  : .................................................. : 2100
             ATCAGAGGAACATGATTCTTGAGGAACAATGCTACGCTAAGTGTTGCAAC

                          *       2120          *       2140          *
pAB121-PB1 : .................................................. : 2150
MDV-B-PB1  : .................................................. : 2150
             CTTTTTGAGGCCTGTTTTAACAGTGCATCATACAGGAAACCAGTAGGTCA

                      2160          *       2180          *       2200
```

```
pAB121-PB1 : .................................................. : 2200
MDV-B-PB1  : .................................................. : 2200
             GCACAGCATGCTTGAGGCTATGGCCCACAGATTAAGAATGGATGCACGAC


                     *       2220         *       2240         *
pAB121-PB1 : .................................................. : 2250
MDV-B-PB1  : .................................................. : 2250
             TAGATTATGAATCAGGAAGAATGTCAAAGGATGATTTTGAGAAAGCAATG

                 2260         *       2280         *       2300
pAB121-PB1 : .................................................. : 2300
MDV-B-PB1  : .................................................. : 2300
             GCTCACCTTGGTGAGATTGGGTACATATAAGCTTCGAAGATGTCTATGGG

                     *       2320         *       2340         *
pAB121-PB1 : .................................................. : 2350
MDV-B-PB1  : .................................................. : 2350
             GTTATTGGTCATCATTGAATACATGCGGTACACAAATGATTAAAATGAAA

                 2360
pAB121-PB1 : ................... : 2369
MDV-B-PB1  : ................... : 2369
             AAAGGCTCGTGTTTCTACT
```

```
                      *        20         *        40         *
pAB122-PB2 : .................................................. :  50
MDV-B-PB2  : .................................................. :  50
             AGCAGAAGCGGAGCGTTTTCAAGATGACATTGGCCAAAATTGAATTGTTA

                     60         *        80         *       100
pAB122-PB2 : .................................................. : 100
MDV-B-PB2  : .................................................. : 100
             AAACAACTGTTAAGGGACAATGAAGCCAAAACGGTATTGAAACAAACAAC

                      *       120         *       140         *
pAB122-PB2 : .................................................. : 150
MDV-B-PB2  : .................................................. : 150
             GGTAGACCAATATAACATAATAAGAAAATTCAATACATCAAGAATTGAAA

                    160         *       180         *       200
pAB122-PB2 : .................................................. : 200
MDV-B-PB2  : .................................................. : 200
             AGAACCCTTCATTAAGGATGAAGTGGGCCATGTGTTCTAATTTTCCCTTG

                      *       220         *       240         *
pAB122-PB2 : .................................................. : 250
MDV-B-PB2  : .................................................. : 250
             GCTCTGACCAAGGGTGATATGGCAAATAGAATCCCCTTGGAATACAAGGG

                    260         *       280         *       300
pAB122-PB2 : .................................................. : 300
MDV-B-PB2  : .................................................. : 300
             AATACAACTTAAAACAAATGCTGAAGACATAGGAACCAAAGGCCAAATGT

                      *       320         *       340         *
pAB122-PB2 : .................................................. : 350
MDV-B-PB2  : .................................................. : 350
             GCTCAATAGCAGCAGTTACCTGGTGGAATACATATGGACCAATAGGAGAT

                    360         *       380         *       400
pAB122-PB2 : .................................................. : 400
MDV-B-PB2  : .................................................. : 400
             ACTGAAGGTTTCGAAAAGGTCTACGAAAGCTTTTTCTCAGAAAGATGAG

                      *       420         *       440         *
pAB122-PB2 : .................................................. : 450
MDV-B-PB2  : .................................................. : 450
             ACTTGACAATGCCACTTGGGGCCGAATAACTTTTGGCCCAGTTGAAAGAG

                    460         *       480         *       500
pAB122-PB2 : .................................................. : 500
MDV-B-PB2  : .................................................. : 500
             TGAGAAAAAGGGTACTGCTAAACCCTCTCACCAAGGAAATGCCTCCAGAT

                      *       520         *       540         *
pAB122-PB2 : .................................................. : 550
MDV-B-PB2  : .................................................. : 550
             GAAGCGAGCAATGTGATAATGGAAATATTGTTCCCTAAAGAAGCAGGAAT

                    560         *       580         *       600
```

```
pAB122-PB2 : .................................................. :  600
MDV-B-PB2  : .................................................. :  600
             ACCAAGAGAATCTACTTGGATACATAGGGAACTGATAAAAGAAAAAAGAG

                     *       620         *       640         *
pAB122-PB2 : .................................................. :  650
MDV-B-PB2  : .................................................. :  650
             AAAAATTGAAAGGAACGATGATAACTCCCATTGTACTGGCATACATGCTT

                   660         *       680         *       700
pAB122-PB2 : .................................................. :  700
MDV-B-PB2  : .................................................. :  700
             GAGAGAGAACTGGTTGCCCGAAGAAGGTTCCTGCCAGTGGCAGGAGCAAC

                     *       720         *       740         *
pAB122-PB2 : .................................................. :  750
MDV-B-PB2  : .................................................. :  750
             ATCAGCCGAGTTCATAGAAATGCTACACTGCTTACAAGGTGAAAATTGGA

                   760         *       780         *       800
pAB122-PB2 : .................................................. :  800
MDV-B-PB2  : .................................................. :  800
             GACAAATATATCACCCAGGAGGGAATAAACTAACTGAATCTAGGTCTCAA

                     *       820         *       840         *
pAB122-PB2 : .................................................. :  850
MDV-B-PB2  : .................................................. :  850
             TCAATGATTGTAGCTTGTAGAAAAATAATCAGAAGATCAATAGTCGCATC

                   860         *       880         *       900
pAB122-PB2 : .................................................. :  900
MDV-B-PB2  : .................................................. :  900
             AAACCCACTAGAGCTAGCTGTAGAAATTGCAAACAAGACTGTGATAGATA

                     *       920         *       940         *
pAB122-PB2 : .................................................. :  950
MDV-B-PB2  : .................................................. :  950
             CTGAACCTTTAAAATCATGTCTGGCAGCCATAGACGGAGGTGATGTAGCC

                   960         *       980         *      1000
pAB122-PB2 : .................................................. : 1000
MDV-B-PB2  : .................................................. : 1000
             TGTGACATAATAAGAGCTGCATTAGGACTAAAGATCAGACAAAGACAAAG

                     *      1020         *      1040         *
pAB122-PB2 : .................................................. : 1050
MDV-B-PB2  : .................................................. : 1050
             ATTTGGACGGCTTGAACTAAAGAGAATATCAGGAAGAGGATTCAAAAATG

                  1060         *      1080         *      1100
pAB122-PB2 : .................................................. : 1100
MDV-B-PB2  : .................................................. : 1100
             ATGAAGAAATATTAATCGGGAACGGAACAATACAGAAAATTGGAATATGG
```

Fig. 7 Cont.

```
                        *        1120         *        1140         *
pAB122-PB2 : .................................................. : 1150
MDV-B-PB2  : .................................................. : 1150
             GACGGAGAAGAGGAGTTCCATGTAAGATGTGGTGAATGCAGGGGAATATT

                  1160         *        1180         *        1200
pAB122-PB2 : .................................................. : 1200
MDV-B-PB2  : .................................................. : 1200
             AAAAAAGAGCAAAATGAGAATGGAAAAACTACTAATAAATTCAGCCAAAA

                        *        1220         *        1240         *
pAB122-PB2 : .................................................. : 1250
MDV-B-PB2  : .................................................. : 1250
             AGGAGGACATGAAAGATTTAATAATCTTGTGCATGGTATTTTCTCAAGAC

                  1260         *        1280         *        1300
pAB122-PB2 : .................................................. : 1300
MDV-B-PB2  : .................................................. : 1300
             ACTAGGATGTTCCAAGGAGTGAGAGGAGAAATAAATTTTCTTAATCGAGC

                        *        1320         *        1340         *
pAB122-PB2 : .................................................. : 1350
MDV-B-PB2  : .................................................. : 1350
             AGGCCAACTTTTATCTCCAATGTACCAACTCCAGCGATATTTTTTGAATA

                  1360         *        1380         *        1400
pAB122-PB2 : .................................................. : 1400
MDV-B-PB2  : .................................................. : 1400
             GGAGCAACGACCTTTTTGATCAATGGGGGTATGAGGAATCACCCAAAGCA

                        *        1420         *        1440         *
pAB122-PB2 : .................................................. : 1450
MDV-B-PB2  : .................................................. : 1450
             AGTGAACTACATGGGATAAATGAATTAATGAATGCATCTGACTATACGTT

                  1460         *        1480         *        1500
pAB122-PB2 : .................................................. : 1500
MDV-B-PB2  : .................................................. : 1500
             GAAAGGGGTTGTAGTAACAAAAAATGTGATTGATGACTTTAGTTCTACTG

                        *        1520         *        1540         *
pAB122-PB2 : .................................................. : 1550
MDV-B-PB2  : .................................................. : 1550
             AAACAGAAAAAGTATCTATAACAAAAAATCTTAGTTTAATAAAAAGGACT

                  1560         *        1580         *        1600
pAB122-PB2 : .................................................. : 1600
MDV-B-PB2  : .................................................. : 1600
             GGGGAAGTCATAATGGGGGCTAATGACGTAAGTGAATTAGAATCACAAGC

                        *        1620         *        1640         *
pAB122-PB2 : .................................................. : 1650
MDV-B-PB2  : .................................................. : 1650
             ACAGCTAATGATAACATATGATACACCTAAGATGTGGGAGATGGGAACAA

                  1660         *        1680         *        1700
```

```
pAB122-PB2 : .................................................. : 1700
MDV-B-PB2  : .................................................. : 1700
             CCAAAGAACTGGTGCAAAACACCTACCAATGGGTGCTAAAAAATTTGGTA

                       *       1720          *       1740          *
pAB122-PB2 : .................................................. : 1750
MDV-B-PB2  : .................................................. : 1750
             ACACTGAAGGCTCAGTTTCTTCTGGGAAAAGAAGACATGTTCCAATGGGA

                   1760          *       1780          *       1800
pAB122-PB2 : .................................................. : 1800
MDV-B-PB2  : .................................................. : 1800
             TGCATTTGAAGCATTTGAAAGCATAATCCCCCAGAAGATGGCTGGCCAGT

                       *       1820          *       1840          *
pAB122-PB2 : .................................................. : 1850
MDV-B-PB2  : .................................................. : 1850
             ACAGTGGATTTGCAAGAGCAGTGCTCAAACAAATGAGAGACCAAGAGGTT

                   1860          *       1880          *       1900
pAB122-PB2 : .................................................. : 1900
MDV-B-PB2  : .................................................. : 1900
             ATGAAAACTGACCAGTTCATAAAGTTGTTGCCTTTCTGTTTCTCACCACC

                       *       1920          *       1940          *
pAB122-PB2 : .................................................. : 1950
MDV-B-PB2  : .................................................. : 1950
             AAAATTAAGGAGAAATGGGGAGCCTTATCAATTCTTGAGGCTTATGTTGA

                   1960          *       1980          *       2000
pAB122-PB2 : .................................................. : 2000
MDV-B-PB2  : .................................................. : 2000
             AGGGAGGAGGGGAAAATTTCATCGAAGTAAGGAAAGGGTCCCCTCTATTC

                       *       2020          *       2040          *
pAB122-PB2 : .................................................. : 2050
MDV-B-PB2  : .................................................. : 2050
             TCCTACAATCCACAAACAGAAGTCCTAACTATATGCGGCAGAATGATGTC

                   2060          *       2080          *       2100
pAB122-PB2 : .................................................. : 2100
MDV-B-PB2  : .................................................. : 2100
             ATTAAAAGGAAAAATTGAAGATGAAGAAAGGAATAGATCAATGGGGAATG

                       *       2120          *       2140          *
pAB122-PB2 : .................................................. : 2150
MDV-B-PB2  : .................................................. : 2150
             CAGTATTGGCAGGCTTTCTCGTTAGTGGCAAGTATGACCCAGATCTTGGA

                   2160          *       2180          *       2200
pAB122-PB2 : .................................................. : 2200
MDV-B-PB2  : .................................................. : 2200
             GATTTCAAAACTATTGAAGAACTTGAAAAGCTAAAACCGGGGGAAAAAGC
```

Fig. 7 Cont.

```
                      *      2220         *      2240          *
pAB122-PB2 : .................................................. : 2250
MDV-B-PB2  : .................................................. : 2250
             AAACATCTTACTTTATCAAGGAAAGCCCGTTAAAGTAGTTAAAAGGAAAA

                 2260         *      2280         *      2300
pAB122-PB2 : .................................................. : 2300
MDV-B-PB2  : .................................................. : 2300
             GATATAGTGCTTTATCCAATGACATTTCACAAGGAATTAAGAGACAAAGA

                      *      2320         *      2340          *
pAB122-PB2 : .................................................. : 2350
MDV-B-PB2  : .................................................. : 2350
             ATGACAGTTGAGTCCATGGGGTGGGCCTTGAGCTAATATAAATTTATCCA

                 2360         *      2380         *
pAB122-PB2 : .............................................. : 2396
MDV-B-PB2  : .............................................. : 2396
             TTAATTCAATAGACACAATTGAGTGAAAAATGCTCGTGTTTCTACT
```

```
                    *        20         *        40         *
pAB123-PA : .................................................. :  50
MDV-B-PA  : .................................................. :  50
            AGCAGAAGCGGTGCGTTTGATTTGCCATAATGGATACTTTTATTACAAGA

                  60         *        80         *       100
pAB123-PA : .................................................. : 100
MDV-B-PA  : .................................................. : 100
            AACTTCCAGACTACAATAATACAAAAGGCCAAAAACACAATGGCAGAATT

                    *       120         *       140         *
pAB123-PA : .................................................. : 150
MDV-B-PA  : .................................................. : 150
            TAGTGAAGATCCTGAATTACAACCAGCAATGCTATTCAACATCTGCGTCC

                 160         *       180         *       200
pAB123-PA : .................................................. : 200
MDV-B-PA  : .................................................. : 200
            ATCTGGAGGTCTGCTATGTAATAAGTGATATGAATTTTCTTGATGAAGAA

                    *       220         *       240         *
pAB123-PA : .................................................. : 250
MDV-B-PA  : .................................................. : 250
            GGAAAAACATATACAGCATTAGAAGGACAAGGAAAAGAACAAAACTTGAG

                 260         *       280         *       300
pAB123-PA : .................................................. : 300
MDV-B-PA  : .................................................. : 300
            ACCACAATATGAAGTGATTGAGGGAATGCCAAGAAACATAGCATGGATGG

                    *       320         *       340         *
pAB123-PA : .................................................. : 350
MDV-B-PA  : .................................................. : 350
            TTCAAAGATCCTTAGCCCAAGAGCATGGAATAGAGACTCCAAGGTATCTG

                 360         *       380         *       400
pAB123-PA : .................................................. : 400
MDV-B-PA  : .................................................. : 400
            GCTGATTTGTTCGATTATAAAACCAAGAGGTTTATAGAAGTTGGAATAAC

                    *       420         *       440         *
pAB123-PA : .................................................. : 450
MDV-B-PA  : .................................................. : 450
            AAAGGGATTGGCTGACGATTACTTTTGGAAAAAGAAAGAAAAGCTGGGGA

                 460         *       480         *       500
pAB123-PA : .................................................. : 500
MDV-B-PA  : .................................................. : 500
            ATAGCATGGAACTGATGATATTCAGCTACAATCAAGACTATTCGTTAAGT

                    *       520         *       540         *
pAB123-PA : .................................................. : 550
MDV-B-PA  : .................................................. : 550
            AATGAATCCTCATTGGATGAGGAAGGAAAAGGGAGAGTGCTAAGCAGACT

                 560         *       580         *       600
pAB123-PA : .................................................. : 600
```

Fig. 7 Cont.

```
MDV-B-PA  : .................................................. :  600
            CACAGAACTTCAGGCTGAGTTAAGTCTGAAAAATCTATGGCAAGTTCTCA

                     *       620         *       640         *
pAB123-PA : .................................................. :  650
MDV-B-PA  : .................................................. :  650
            TAGGAGAAGAAGATATTGAAAAAGGAATTGACTTCAAACTTGGACAAACA

                   660         *       680         *       700
pAB123-PA : .................................................. :  700
MDV-B-PA  : .................................................. :  700
            ATATCTAAACTAAGGGATATATCTGTTCCAGCTGGTTTCTCCAATTTTGA

                     *       720         *       740         *
pAB123-PA : .................................................. :  750
MDV-B-PA  : .................................................. :  750
            AGGAATGAGGAGCTACATAGACAATATAGATCCTAAAGGAGCAATAGAGA

                   760         *       780         *       800
pAB123-PA : .................................................. :  800
MDV-B-PA  : .................................................. :  800
            GAAATCTAGCAAGGATGTCTCCCTTAGTATCAGTTACACCTAAAAAGTTG

                     *       820         *       840         *
pAB123-PA : .................................................. :  850
MDV-B-PA  : .................................................. :  850
            AAATGGGAGGACCTAAGACCAATAGGGCCTCACATTTACAACCATGAGCT

                   860         *       880         *       900
pAB123-PA : .................................................. :  900
MDV-B-PA  : .................................................. :  900
            ACCAGAAGTTCCATATAATGCCTTTCTTCTAATGTCTGATGAGTTGGGGC

                     *       920         *       940         *
pAB123-PA : .................................................. :  950
MDV-B-PA  : .................................................. :  950
            TGGCTAATATGACTGAAGGGAAGTCCAAGAAACCGAAGACCTTAGCCAAA

                   960         *       980         *      1000
pAB123-PA : .................................................. : 1000
MDV-B-PA  : .................................................. : 1000
            GAATGTCTAGAAAAGTACTCAACACTACGGGATCAAACTGACCCAATATT

                     *      1020         *      1040         *
pAB123-PA : .................................................. : 1050
MDV-B-PA  : .................................................. : 1050
            AATAATGAAAAGCGAAAAAGCTAACGAAAACTTCTTATGGAAGCTGTGGA

                  1060         *      1080         *      1100
pAB123-PA : .................................................. : 1100
MDV-B-PA  : .................................................. : 1100
            GGGACTGTGTAAATACAATAAGTAATGAGGAAACAAGTAACGAATTACAG
```

Fig. 7 Cont.

```
                *        1120          *        1140          *
pAB123-PA : .................................................. : 1150
MDV-B-PA  : .................................................. : 1150
            AAAACCAATTATGCCAAGTGGGCCACAGGAGATGGATTAACATACCAGAA

              1160          *        1180          *        1200
pAB123-PA : .................................................. : 1200
MDV-B-PA  : .................................................. : 1200
            AATAATGAAAGAAGTAGCAATAGATGACGAAACAATGTACCAAGAAGAGC

                *        1220          *        1240          *
pAB123-PA : .................................................. : 1250
MDV-B-PA  : .................................................. : 1250
            CCAAAATACCTAACAAATGTAGAGTGGCTGCTTGGGTTCAAACAGAGATG

              1260          *        1280          *        1300
pAB123-PA : .................................................. : 1300
MDV-B-PA  : .................................................. : 1300
            AATCTATTGAGCACTCTGACAAGTAAAAGGGCCCTGGATCTACCAGAAAT

                *        1320          *        1340          *
pAB123-PA : .................................................. : 1350
MDV-B-PA  : .................................................. : 1350
            AGGGCCAGACGTAGCACCCATGGAGCATGTAGGGAGTGAAAGAAGGAAAT

              1360          *        1380          *        1400
pAB123-PA : .................................................. : 1400
MDV-B-PA  : .................................................. : 1400
            ACTTTGTTAATGAAATCAACTACTGTAAGGCCTCTACCGTTATGATGAAG

                *        1420          *        1440          *
pAB123-PA : .................................................. : 1450
MDV-B-PA  : .................................................. : 1450
            TATGTACTTTTTCACACTTCATTATTAAATGAAAGCAATGCCAGCATGGG

              1460          *        1480          *        1500
pAB123-PA : .................................................. : 1500
MDV-B-PA  : .................................................. : 1500
            AAAATATAAAGTAATACCAATAACCAACAGAGTAGTAAATGAAAAAGGAG

                *        1520          *        1540          *
pAB123-PA : .................................................. : 1550
MDV-B-PA  : .................................................. : 1550
            AAAGTTTTGACATGCTTCATGGTCTGGCGGTTAAAGGGCAATCTCATCTG

              1560          *        1580          *        1600
pAB123-PA : .................................................. : 1600
MDV-B-PA  : .................................................. : 1600
            AGGGGAGATACTGATGTTGTAACAGTTGTGACTTTCGAATTTAGTAGTAC

                *        1620          *        1640          *
pAB123-PA : .................................................. : 1650
MDV-B-PA  : .................................................. : 1650
            AGATCCCAGAGTGGACTCAGGAAAGTGGCCAAAATATACTGTATTTAGAA

              1660          *        1680          *        1700
```

```
pAB123-PA : .................................................. : 1700
MDV-B-PA  : .................................................. : 1700
            TTGGCTCCTTATTTGTGAGTGGAAGGGAAAAATCTGTGTACCTATATTGC

                      *        1720           *        1740           *
pAB123-PA : .................................................. : 1750
MDV-B-PA  : .................................................. : 1750
            CGAGTGAATGGTACAAATAAGATCCAAATGAAATGGGGAATGGAAGCTAG

                1760          *        1780           *        1800
pAB123-PA : .................................................. : 1800
MDV-B-PA  : .................................................. : 1800
            AAGATGTCTGCTTCAATCAATGCAACAAATGGAAGCAATTGTTGAACAAG

                      *        1820           *        1840           *
pAB123-PA : .................................................. : 1850
MDV-B-PA  : .................................................. : 1850
            AATCATCGATACAAGGATATGACATGACCAAAGCTTGTTTCAAGGGAGAC

                1860          *        1880           *        1900
pAB123-PA : .................................................. : 1900
MDV-B-PA  : .................................................. : 1900
            AGAGTGAATAGTCCCAAAACTTTCAGTATTGGGACTCAAGAAGGAAAACT

                      *        1920           *        1940           *
pAB123-PA : .................................................. : 1950
MDV-B-PA  : .................................................. : 1950
            AGTAAAAGGATCCTTTGGGAAAGCACTAAGAGTAATATTCACCAAATGTT

                1960          *        1980           *        2000
pAB123-PA : .................................................. : 2000
MDV-B-PA  : .................................................. : 2000
            TGATGCACTATGTATTTGGAAATGCCCAATTGGAGGGGTTTAGTGCCGAA

                      *        2020           *        2040           *
pAB123-PA : .................................................. : 2050
MDV-B-PA  : .................................................. : 2050
            TCTAGGAGACTTCTACTGTTAATTCAGGCATTAAAGGACAGAAAGGGCCC

                2060          *        2080           *        2100
pAB123-PA : .................................................. : 2100
MDV-B-PA  : .................................................. : 2100
            TTGGGTATTCGACTTAGAGGGAATGTATTCTGGAATAGAAGAATGTATTA

                      *        2120           *        2140           *
pAB123-PA : .................................................. : 2150
MDV-B-PA  : .................................................. : 2150
            GTAACAACCCTTGGGTAATACAGAGTGCATACTGGTTTAATGAATGGTTG

                2160          *        2180           *        2200
pAB123-PA : .................................................. : 2200
MDV-B-PA  : .................................................. : 2200
            GGCTTTGAAAAAGAGGGGAGTAAAGTATTAGAATCAATAGATGAAATAAT
```

Fig. 7 Cont.

```
                      *        2220          *        2240          *
pAB123-PA : .................................................. : 2250
MDV-B-PA  : .................................................. : 2250
            GGATGAATGAAAGAAGGGCATAGCGCTCAATTTGGTACTATTTTGTTCAT

                   2260          *        2280          *        2300
pAB123-PA : .................................................. : 2300
MDV-B-PA  : .................................................. : 2300
            TATGTATCTAAACATCCAATAAAAAGAATTGAGAATTAAAAATGCACGTG

pAB123-PA : ........ : 2308
MDV-B-PA  : ........ : 2308
            TTTCTACT
```

```
                          *        20         *        40         *
MDV-B-HA   : .................................................. :   50
pAB124-HA  : .................................................. :   50
             AGCAGAAGCAGAGCATTTTCTAATATCCACAAAATGAAGGCAATAATTGT

                         60         *        80         *       100
MDV-B-HA   : .................................................. :  100
pAB124-HA  : .................................................. :  100
             ACTACTCATGGTAGTAACATCCAATGCAGATCGAATCTGCACTGGGATAA

                          *       120         *       140         *
MDV-B-HA   : .................................................t :  150
pAB124-HA  : .................................................. :  150
             CATCGTCAAACTCACCCCATGTGGTCAAAACTGCTACTCAAGGGGAAGTC

                        160         *       180         *       200
MDV-B-HA   : ..t............................................... :  200
pAB124-HA  : .................................................. :  200
             AACGTGACTGGTGTGATACCACTGACAACAACACCTACCAAATCTCATTT

                          *       220         *       240         *
MDV-B-HA   : .................................................. :  250
pAB124-HA  : .................................................. :  250
             TGCAAATCTCAAAGGAACACAGACCAGAGGGAAACTATGCCCAAACTGTC

                        260         *       280         *       300
MDV-B-HA   : .................................................. :  300
pAB124-HA  : .................................................. :  300
             TCAACTGCACAGATCTGGACGTGGCCTTGGGCAGACCAAAGTGTATGGGG

                          *       320         *       340         *
MDV-B-HA   : .................................................. :  350
pAB124-HA  : .................................................. :  350
             ACCATACCTTCGGCAAAAGCTTCAATACTCCACGAAGTCAAACCTGTTAC

                        360         *       380         *       400
MDV-B-HA   : .................................................. :  400
pAB124-HA  : .................................................. :  400
             ATCTGGGTGCTTTCCTATAATGCACGACAGAACAAAAATCAGACAGCTAC

                          *       420         *       440         *
MDV-B-HA   : .................................................. :  450
pAB124-HA  : .................................................. :  450
             CCAATCTTCTCAGAGGATATGAAAATATCAGGTTATCAGCCCGTAACGTT

                        460         *       480         *       500
MDV-B-HA   : .................................................. :  500
pAB124-HA  : .................................................. :  500
             ATCAACGCAGAAACGGCACCAGGAGGACCCTACATAGTTGGAACCTCAGG

                          *       520         *       540         *
MDV-B-HA   : .................................................. :  550
pAB124-HA  : .................................................. :  550
             ATCTTGCCCTAACGTTACCAATGGGAAAGGATTCTTCGCAACAATGGCTT

                        560         *       580         *       600
MDV-B-HA   : .................................................. :  600
```

Fig. 7 Cont.

```
pAB124-HA : .................................................. :  600
            GGGCTGTCCCAAAAAACAACAAAACCAAAACAGCAACGAACCCATTAACA

                    *       620         *       640         *
MDV-B-HA  : .................................................. :  650
pAB124-HA : .................................................. :  650
            GTAGAAGTACCATACATTTGTACAAAAGGAGAAGACCAAATTACTGTTTG

                  660         *       680         *       700
MDV-B-HA  : .................................................. :  700
pAB124-HA : .................................................. :  700
            GGGGTTCCATTCTGATGACGAAACCCAAATGGTAACACTCTATGGAGACT

                    *       720         *       740         *
MDV-B-HA  : .................................................. :  750
pAB124-HA : .................................................. :  750
            CGAAGCCTCAAAAGTTCACCTCATCTGCCAACGGAGTAACCACACATTAT

                  760         *       780         *       800
MDV-B-HA  : .................................................. :  800
pAB124-HA : .................................................. :  800
            GTTTCTCAGATTGGTGGCTTCCCAAATCAAACAGAAGACGAAGGGCTACC

                    *       820         *       840         *
MDV-B-HA  : .................................................. :  850
pAB124-HA : .................................................. :  850
            ACAAAGCGGCAGAATTGTTGTTGATTACATGGTGCAAAAACCTGGAAAAA

                  860         *       880         *       900
MDV-B-HA  : .................................................. :  900
pAB124-HA : .................................................. :  900
            CAGGAACAATTGTCTATCAAAGAGGTGTTTTATTGCCTCAAAAAGTGTGG

                    *       920         *       940         *
MDV-B-HA  : .................................................. :  950
pAB124-HA : .................................................. :  950
            TGCGCAAGTGGCAGGAGCAAGGTAATAAAAGGGGCCTTGCCTTTAATTGG

                  960         *       980         *      1000
MDV-B-HA  : .................................................. : 1000
pAB124-HA : .................................................. : 1000
            TGAAGCAGATTGCCTCCACGAAAAATACGGTGGATTAAACAAAAGCAAGC

                    *      1020         *      1040         *
MDV-B-HA  : .................................................. : 1050
pAB124-HA : .................................................. : 1050
            CTTACTACACAGGAGAACATGCAAAAGCCATAGGAAATTGCCCAATATGG

                 1060         *      1080         *      1100
MDV-B-HA  : .................................................. : 1100
pAB124-HA : .................................................. : 1100
            GTGAAAACACCCTTGAAGCTGGCCAATGGAACCAAATATAGACCTCCTGC
```

Fig. 7 Cont.

```
                     *      1120        *      1140         *
MDV-B-HA   : .................................................. : 1150
pAB124-HA  : .................................................. : 1150
             AAAACTATTAAAGGAAAGGGGTTTCTTCGGAGCTATTGCTGGTTTCTTGG

                  1160        *      1180        *      1200
MDV-B-HA   : .................................................. : 1200
pAB124-HA  : .................................................. : 1200
             AAGGAGGATGGGAAGGAATGATTGCAGGTTGGCACGGATACACATCTCAT

                     *      1220        *      1240         *
MDV-B-HA   : .................................................. : 1250
pAB124-HA  : .................................................. : 1250
             GGAGCACATGGAGTGGCAGTGGCAGCAGACCTTAAGAGTACGCAAGAAGC

                  1260        *      1280        *      1300
MDV-B-HA   : .................................................. : 1300
pAB124-HA  : .................................................. : 1300
             TATAAACAAGATAACAAAAAATCTCAATTCTTTAAGTGAGCTAGAAGTAA

                     *      1320        *      1340         *
MDV-B-HA   : .................................................. : 1350
pAB124-HA  : .................................................. : 1350
             AGAATCTTCAAAGACTAAGCGGTGCAATGGATGAACTCCACAACGAAATA

                  1360        *      1380        *      1400
MDV-B-HA   : .................................................. : 1400
pAB124-HA  : .................................................. : 1400
             CTCGAGCTGGATGAGAAAGTGGATGATCTCAGAGCTGATACAATAAGCTC

                     *      1420        *      1440         *
MDV-B-HA   : .................................................. : 1450
pAB124-HA  : .................................................. : 1450
             GCAAATAGAGCTTGCAGTCTTGCTTTCCAACGAAGGAATAATAAACAGTG

                  1460        *      1480        *      1500
MDV-B-HA   : .................................................. : 1500
pAB124-HA  : .................................................. : 1500
             AAGATGAGCATCTCTTGGCACTTGAAAGAAAACTGAAGAAAATGCTGGGC

                     *      1520        *      1540         *
MDV-B-HA   : .................................................. : 1550
pAB124-HA  : .................................................. : 1550
             CCCTCTGCTGTAGACATAGGGAATGGATGCTTCGAAACCAAACACAAATG

                  1560        *      1580        *      1600
MDV-B-HA   : .................................................. : 1600
pAB124-HA  : .................................................. : 1600
             CAACCAGACTTGCCTAGACAGGATAGCTGCTGGCACCTTTAATGCAGGAG

                     *      1620        *      1640         *
MDV-B-HA   : .................................................. : 1650
pAB124-HA  : .................................................. : 1650
             AATTTTCTCTTCCCACTTTTGATTCACTAAATATTACTGCTGCATCTTTA

                  1660        *      1680        *      1700
```

```
MDV-B-HA  : .................................................. : 1700
pAB124-HA : .................................................. : 1700
            AATGATGATGGATTGGATAATCATACTATACTGCTCTACTACTCAACTGC

                     *      1720         *      1740         *
MDV-B-HA  : .................................................. : 1750
pAB124-HA : .................................................. : 1750
            TGCTTCTAGTTTGGCTGTAACATTGATGATAGCTATCTTTATTGTTTATA

                  1760         *      1780         *      1800
MDV-B-HA  : .................................................. : 1800
pAB124-HA : .................................................. : 1800
            TGGTCTCCAGAGACAATGTTTCTTGCTCCATCTGTCTATAAGGAAAATTA

                     *      1820         *      1840         *
MDV-B-HA  : .................................................. : 1850
pAB124-HA : .................................................. : 1850
            AGCCCTGTATTTTCCTTTATTGTAGTGCTTGTTTGCTTGTCACCATTACA

                  1860         *      1880
MDV-B-HA  : ..................................- : 1884
pAB124-HA : ..................................- : 1884
            AAAAACGTTATTGAAAAATGCTCTTGTTACTACT
```

Fig. 7 Cont.

```
NP
                   10        20        30        40        50
pAB125-NP : .................................................. :   50
MDV-B-NP  : .................................................. :   50
            AGCAGAAGCACAGCATTTTCTTGTGAACTTCAAGTACCAACAAAAACTGA

                   60        70        80        90       100
pAB125-NP : .................................................. :  100
MDV-B-NP  : .................................................. :  100
            AAATCAAAATGTCCAACATGGATATTGACGGCATCAACACTGGAACAATT

                  110       120       130       140       150
pAB125-NP : .................................................. :  150
MDV-B-NP  : .................................................. :  150
            GACAAAACACCAGAAGAAATAACTTCCGGAACCAGTGGGGCAACCAGACC

                  160       170       180       190       200
pAB125-NP : .................................................. :  200
MDV-B-NP  : .................................................. :  200
            AATCATCAAACCAGCAACCCTTGCCCCACCAAGCAACAAACGAACCCGAA

                  210       220       230       240       250
pAB125-NP : .................................................. :  250
MDV-B-NP  : .................................................. :  250
            ACCCATCCCCGGAAAGGGCAGCCACAAGCAGTGAAGCTGATGTCGGAAGG

                  260       270       280       290       300
pAB125-NP : .................................................. :  300
MDV-B-NP  : .................................................. :  300
            AGAACCCAAAAGAAACAAACCCCGACAGAGATAAAGAAGAGCGTCTACAA

                  310       320       330       340       350
pAB125-NP : .................................................. :  350
MDV-B-NP  : .................................................. :  350
            TATGGTAGTGAAACTGGGTGAATTCTACAACCAGATGATGGTCAAAGCTG

                  360       370       380       390       400
pAB125-NP : .................................................. :  400
MDV-B-NP  : .................................................. :  400
            GACTCAACGATGACATGGAGAGAAACCTAATCCAAAATGCACATGCTGCG

                  410       420       430       440       450
pAB125-NP : .................................................. :  450
MDV-B-NP  : .................................................. :  450
            GAAAGAATTCTATTGGCTGCTACTGATGACAAGAAAACTGAATTCCAAAA

                  460       470       480       490       500
pAB125-NP : .................................................. :  500
MDV-B-NP  : .................................................. :  500
            GAAAAAGAATGCCAGAGATGTCAAAGAAGGGAAAGAAGAAATAGACCACA

                  510       520       530       540       550
pAB125-NP : .................................................. :  550
MDV-B-NP  : .................................................. :  550
            ACAAAACAGGAGGCACCTTTTACAAGATGGTAAGAGATGATAAAACCATC

                  560       570       580       590       600
pAB125-NP : .................................................. :  600
```

Fig. 7 Cont.

```
MDV-B-NP  : .................................................. :  600
            TACTTCAGCCCTATAAGAATTACCTTTTTAAAAGAAGAGGTGAAAACAAT

                     610       620       630       640       650
pAB125-NP : .................................................. :  650
MDV-B-NP  : .................................................. :  650
            GTACAAAACCACCATGGGGAGTGATGGTTTCAGTGGACTAAATCACATCA

                     660       670       680       690       700
pAB125-NP : .................................................. :  700
MDV-B-NP  : .................................................. :  700
            TGATTGGGCATTCACAGATGAACGATGTCTGTTTCCAAAGATCAAAGGCA

                     710       720       730       740       750
pAB125-NP : .................................................. :  750
MDV-B-NP  : .................................................. :  750
            CTAAAAAGAGTTGGACTTGACCCTTCATTAATCAGTACTTTTGCAGGAAG

                     760       770       780       790       800
pAB125-NP : .................................................. :  800
MDV-B-NP  : .................................................. :  800
            CACACTCCCCAGAAGATCAGGTGCAACTGGTGTTGCGATCAAAGGAGGTG

                     810       820       830       840       850
pAB125-NP : .................................................. :  850
MDV-B-NP  : .................................................. :  850
            GAACTTTAGTGGCAGAAGCCATTCGATTTATAGGAAGAGCAATGGCAGAC

                     860       870       880       890       900
pAB125-NP : .................................................. :  900
MDV-B-NP  : .................................................. :  900
            AGAGGGCTATTGAGAGACATCAGAGCCAAGACGGCCTATGAAAAGATTCT

                     910       920       930       940       950
pAB125-NP : .................................................. :  950
MDV-B-NP  : .................................................. :  950
            TCTGAATCTGAAAAACAAGTGCTCTGCGCCCCAACAAAAGGCTCTAGTTG

                     960       970       980       990      1000
pAB125-NP : .................................................. : 1000
MDV-B-NP  : .................................................. : 1000
            ATCAAGTGATCGGAAGTAGAAATCCAGGGATTGCAGACATAGAAGACCTA

                    1010      1020      1030      1040      1050
pAB125-NP : .................................................. : 1050
MDV-B-NP  : .................................................. : 1050
            ACCCTGCTTGCCCGAAGCATGGTCGTTGTCAGGCCCTCTGTAGCGAGCAA

                    1060      1070      1080      1090      1100
pAB125-NP : .................................................. : 1100
MDV-B-NP  : .................................................. : 1100
            AGTGGTGCTTCCCATAAGCATTTATGCCAAAATACCTCAACTAGGGTTCA
```

Fig 7. Cont.

```
                  1110      1120      1130      1140      1150
pAB125-NP : .................................................. : 1150
MDV-B-NP  : .................................................. : 1150
            ATGTTGAAGAATACTCTATGGTTGGGTATGAAGCCATGGCTCTTTATAAT

                  1160      1170      1180      1190      1200
pAB125-NP : .................................................. : 1200
MDV-B-NP  : .................................................. : 1200
            ATGGCAACACCTGTTTCCATATTAAGAATGGGAGACGATGCAAAAGATAA

                  1210      1220      1230      1240      1250
pAB125-NP : .................................................. : 1250
MDV-B-NP  : .................................................. : 1250
            ATCACAATTATTCTTCATGTCTTGCTTCGGAGCTGCCTATGAAGACCTAA

                  1260      1270      1280      1290      1300
pAB125-NP : .................................................. : 1300
MDV-B-NP  : .................................................. : 1300
            GAGTTTTGTCTGCACTAACAGGCACAGAATTCAAGCATAGGTCAGCATTA

                  1310      1320      1330      1340      1350
pAB125-NP : .................................................. : 1350
MDV-B-NP  : .................................................. : 1350
            AAGTGCAAGGGTTTCCACGTTCCAGCAAAGGAGCAAGTGGAAGGAATGGG

                  1360      1370      1380      1390      1400
pAB125-NP : .................................................. : 1400
MDV-B-NP  : .................................................. : 1400
            GGCAGCTCTGATGTCCATCAAGCTCCAGTTTTGGGCTCCAATGACCAGAT

                  1410      1420      1430      1440      1450
pAB125-NP : .................................................. : 1450
MDV-B-NP  : .................................................. : 1450
            CTGGGGGGAATGAAGTAGGTGGAGACGGAGGGTCTGGTCAAATAAGTTGC

                  1460      1470      1480      1490      1500
pAB125-NP : .................................................. : 1500
MDV-B-NP  : .................................................. : 1500
            AGCCCCGTGTTTGCAGTAGAAAGACCTATTGCTCTAAGCAAGCAAGCTGT

                  1510      1520      1530      1540      1550
pAB125-NP : .................................................. : 1550
MDV-B-NP  : .................................................. : 1550
            AAGAAGAATGCTGTCAATGAATATTGAGGGACGTGATGCAGATGTCAAAG

                  1560      1570      1580      1590      1600
pAB125-NP : .................................................. : 1600
MDV-B-NP  : .................................................. : 1600
            GAAATCTACTCAAGATGATGAATGATTCAATGACTAAGAAAACCAATGGA

                  1610      1620      1630      1640      1650
pAB125-NP : .................................................. : 1650
MDV-B-NP  : .................................................. : 1650
            AATGCTTTCATTGGGAAGAAAATGTTTCAAATATCAGACAAAAACAAAAC

                  1660      1670      1680      1690      1700
pAB125-NP : .................................................. : 1700
```

Fig 7. Cont.

```
MDV-B-NP  : .................................................. : 1700
            CAATCCCATTGAGATTCCAATTAAGCAGACCATCCCCAATTTCTTCTTTG


                  1710      1720      1730      1740      1750
pAB125-NP : .................................................. : 1750
MDV-B-NP  : .................................................. : 1750
            GGAGGGACACAGCAGAGGATTATGATGACCTCGATTATTAAAGCAACAAA

                  1760      1770      1780      1790      1800
pAB125-NP : .................................................. : 1800
MDV-B-NP  : .................................................. : 1800
            ATAGACACTATGGCTGTGACTGTTTCAGTACGTTTGGAATGTGGGTGTTT

                  1810      1820      1830      1840      1850
pAB125-NP : ..........................................-------- : 1842
MDV-B-NP  : ..........................................-------- : 1842
            ACTTTTATTGAAATAAATGTAAAAAATGCTGTTGTTTCTACT


pAB125-NP : -------- :
MDV-B-NP  : -------- :
```

```
                       *        20         *        40         *
pAB126-NA : .................................................. :  50
MDV-B-NA  : .................................................. :  50
            AGCAGAAGCAGAGCATCTTCTCAAAACTGAAGCAAATAGGCCAAAAATGA

                 60         *        80         *       100
pAB126-NA : .................................................. : 100
MDV-B-NA  : .................................................. : 100
            ACAATGCTACCTTCAACTATACAAACGTTAACCCTATTTCTCACATCAGG

                       *       120         *       140         *
pAB126-NA : .................................................. : 150
MDV-B-NA  : .................................................. : 150
            GGGAGTGTTATTATCACTATATGTGTCAGCTTCACTGTCATACTTATTGT

                160         *       180         *       200
pAB126-NA : .................................................. : 200
MDV-B-NA  : .................................................. : 200
            ATTCGGATATATTGCTAAAATTTTCACCAACAAAAATAACTGCACCAACA

                       *       220         *       240         *
pAB126-NA : .................................................. : 250
MDV-B-NA  : .................................................. : 250
            ATGTCATTGGATTGCGCGAACGTATCAAATGTTCAGGCTGTGAACCGTTC

                260         *       280         *       300
pAB126-NA : .................................................. : 300
MDV-B-NA  : .................................................. : 300
            TGCAACAAAAGAGATGACATTTCTTCTCCCAGAGCCGGAGTGGACATACC

                       *       320         *       340         *
pAB126-NA : .................................................. : 350
MDV-B-NA  : .................................................. : 350
            CTCGTTTATCTTGCCAGGGCTCAACCTTTCAGAAAGCACTCCTAATTAGC

                360         *       380         *       400
pAB126-NA : .................................................. : 400
MDV-B-NA  : .................................................. : 400
            CCTCATAGGTTCGGAGAAACCAGAGGAAACTCAGCTCCCTTGATAATAAG

                       *       420         *       440         *
pAB126-NA : .................................................. : 450
MDV-B-NA  : .................................................. : 450
            GGAACCCTTTGTTGCTTGTGGACCAAAGGAATGCAGACACTTTGCTCTAA

                460         *       480         *       500
pAB126-NA : .................................................. : 500
MDV-B-NA  : .................................................. : 500
            CCCATTATGCAGCTCAACCAGGGGGATACTACAATGGAACAAGAAAGGAC

                       *       520         *       540         *
pAB126-NA : .................................................. : 550
MDV-B-NA  : .................................................. : 550
            AGAAACAAGCTGAGGCATCTGATTTCAGTCAAATTAGGCAAAATCCCAAC

                560         *       580         *       600
```

```
pAB126-NA : .................................................. :  600
MDV-B-NA  : .................................................. :  600
            TGTAGAAAACTCCATTTTCCACATGGCAGCTTGGAGTGGGTCCGCATGCC

                    *       620         *       640         *
pAB126-NA : .................................................. :  650
MDV-B-NA  : .................................................. :  650
            ATGATGGTAGAGAATGGACATATATCGGAGTTGATGGCCCTGACAGTAAT

                  660         *       680         *       700
pAB126-NA : .................................................. :  700
MDV-B-NA  : .................................................. :  700
            GCACTGATCAAAATAAAATATGGAGAAGCATATACTGACACATACCATTC

                    *       720         *       740         *
pAB126-NA : .................................................. :  750
MDV-B-NA  : .................................................. :  750
            CTATGCAAACAACATCCTAAGAACACAAGAAAGTGCCTGCAATTGCATCG

                  760         *       780         *       800
pAB126-NA : .................................................. :  800
MDV-B-NA  : .................................................. :  800
            GGGGAGATTGTTATCTTATGATAACTGATGGCTCAGCTTCAGGAATTAGT

                    *       820         *       840         *
pAB126-NA : .................................................. :  850
MDV-B-NA  : .................................................. :  850
            AAATGCAGATTTCTTAAAATTCGAGAGGGTCGAATAATAAAAGAAATATT

                  860         *       880         *       900
pAB126-NA : .................................................. :  900
MDV-B-NA  : .................................................. :  900
            TCCAACAGGAAGAGTAGAGCATACTGAAGAATGCACATGCGGGTTCGCCA

                    *       920         *       940         *
pAB126-NA : .................................................. :  950
MDV-B-NA  : .................................................. :  950
            GCAATAAAACCATAGAATGTGCCTGTAGAGATAACAGTTACACAGCAAAA

                  960         *       980         *      1000
pAB126-NA : .................................................. : 1000
MDV-B-NA  : .................................................. : 1000
            AGACCCTTTGTCAAATTAAATGTGGAGACTGATACAGCTGAAATAAGATT

                    *      1020         *      1040         *
pAB126-NA : .................................................. : 1050
MDV-B-NA  : .................................................. : 1050
            GATGTGCACAGAGACTTATTTGGACACCCCCAGACCAGATGATGGAAGCA

                 1060         *      1080         *      1100
pAB126-NA : .................................................. : 1100
MDV-B-NA  : .................................................. : 1100
            TAACAGGGCCTTGCGAATCTAATGGGGACAAAGGGCTTGGAGGCATCAAA
```

Fig. 7 Cont.

```
                     *       1120          *       1140          *
pAB126-NA : .................................................. : 1150
MDV-B-NA  : .................................................. : 1150
            GGAGGATTTGTCCATCAAAGAATGGCATCTAAGATTGGAAGATGGTACTC

                 1160          *       1180          *       1200
pAB126-NA : .................................................. : 1200
MDV-B-NA  : .................................................. : 1200
            CCGAACGATGTCTAAAACTGAAAGAATGGGGATGGAACTGTATGTCAAGT

                     *       1220          *       1240          *
pAB126-NA : .................................................. : 1250
MDV-B-NA  : .................................................. : 1250
            ATGATGGAGACCCATGGACTGACAGTGACGCCCTTGCTCCTAGTGGAGTA

                 1260          *       1280          *       1300
pAB126-NA : .................................................. : 1300
MDV-B-NA  : .................................................. : 1300
            ATGGTTTCAATGAAAGAACCTGGTTGGTATTCTTTTGGCTTCGAAATAAA

                     *       1320          *       1340          *
pAB126-NA : .................................................. : 1350
MDV-B-NA  : .................................................. : 1350
            AGATAAGAAATGTGATGTCCCCTGTATTGGGATAGAGATGGTACACGATG

                 1360          *       1380          *       1400
pAB126-NA : .................................................. : 1400
MDV-B-NA  : .................................................. : 1400
            GTGGAAAAGAGACTTGGCACTCAGCAGCAACAGCCATTTACTGTTTGATG

                     *       1420          *       1440          *
pAB126-NA : .................................................. : 1450
MDV-B-NA  : .................................................. : 1450
            GGCTCAGGACAATTGCTATGGGACACTGTCACAGGTGTTGATATGGCTCT

                 1460          *       1480          *       1500
pAB126-NA : .................................................. : 1500
MDV-B-NA  : .................................................. : 1500
            GTAATGGAGGAATGGTTGAATCTGTTCTAAACCCTTTGTTCCTATTTTGT

                     *       1520          *       1540          *
pAB126-NA : .................................................. : 1550
MDV-B-NA  : .................................................. : 1550
            TTGAACAATTGTCCTTACTGGACTTAATTGTTTCTGAAAAATGCTCTTGT

pAB126-NA : ....... : 1557
MDV-B-NA  : ....... : 1557
            TACTACT
```

```
                    *        20         *        40         *
pAB127-M : .................................................. :   50
MDV-B-M  : .................................................. :   50
           AGCAGAAGCACGCACTTTCTTAAAATGTCGCTGTTTGGAGACACAATTGC

                   60         *        80         *       100
pAB127-M : .................................................. :  100
MDV-B-M  : .................................................. :  100
           CTACCTGCTTTCACTAACAGAAGATGGAGAAGGCAAAGCAGAACTAGCAG

                    *       120         *       140         *
pAB127-M : .................................................. :  150
MDV-B-M  : .................................................. :  150
           AAAAATTACACTGTTGGTTCGGTGGGAAAGAATTTGACCTAGACTCTGCT

                  160         *       180         *       200
pAB127-M : .................................................. :  200
MDV-B-M  : .................................................. :  200
           TTGGAATGGATAAAAAACAAAAGATGCCTAACTGATATACAAAAAGCACT

                    *       220         *       240         *
pAB127-M : .................................................. :  250
MDV-B-M  : .................................................. :  250
           AATTGGTGCCTCTATCTGCTTTTTAAAACCCAAAGACCAAGAAAGAAAAA

                  260         *       280         *       300
pAB127-M : .................................................. :  300
MDV-B-M  : .................................................. :  300
           GAAGATTCATCACAGAGCCCCTGTCAGGAATGGGAACAACAGCAACAAAA

                    *       320         *       340         *
pAB127-M : .................................................. :  350
MDV-B-M  : .................................................. :  350
           AAGAAAGGCCTGATTCTAGCTGAGAGAAAAATGAGAAGATGTGTGAGTTT

                  360         *       380         *       400
pAB127-M : .................................................. :  400
MDV-B-M  : .................................................. :  400
           TCATGAAGCATTTGAAATAGCAGAAGGCCATGAAAGCTCAGCACTACTAT

                    *       420         *       440         *
pAB127-M : .................................................. :  450
MDV-B-M  : .................................................. :  450
           ATTGTCTCATGGTCATGTACCTGAACCCTGGAAATTATTCAATGCAAGTA

                  460         *       480         *       500
pAB127-M : .................................................. :  500
MDV-B-M  : .................................................. :  500
           AAACTAGGAACGCTCTGTGCTTTATGCGAGAAACAAGCATCACATTCACA

                    *       520         *       540         *
pAB127-M : .................................................. :  550
MDV-B-M  : .................................................. :  550
           AAGAGCTCATAGCAGAGCAGCAAGATCTTCAGTGCCTGGAGTGAGGCGAG

                  560         *       580         *       600
pAB127-M : .................................................. :  600
```

Fig. 7 Cont.

```
MDV-B-M  : .................................................. :  600
           AAATGCAGATGGTTTCAGCTGTGAACACAGCAAAAACAATGAATGGAATG

                    *       620         *       640         *
pAB127-M : .................................................. :  650
MDV-B-M  : .................................................. :  650
           GGGAAGGGAGAAGACGTCCAAAAACTGGCAGAAGAGCTGCAAAGCAACAT

                  660         *       680         *       700
pAB127-M : .................................................. :  700
MDV-B-M  : .................................................. :  700
           TGGAGTATTGAGATCTCTGGGGGCAAGTCAAAAGAATGGAGAAGGAATTG

                    *       720         *       740         *
pAB127-M : .................................................. :  750
MDV-B-M  : .................................................. :  750
           CAAAGGATGTAATGGAAGTGCTAAAGCAGAGCTCTATGGGAAATTCAGCT

                  760         *       780         *       800
pAB127-M : .................................................. :  800
MDV-B-M  : .................................................. :  800
           CTTGTGAAGAAATACCTATAATGCTCGAACCATTTCAGATTCTTTCAATT

                    *       820         *       840         *
pAB127-M : .................................................. :  850
MDV-B-M  : .................................................. :  850
           TGTTCTTTCATTTTATCAGCTCTCCATTTCATGGCTTGGACAATAGGGCA

                  860         *       880         *       900
pAB127-M : .................................................. :  900
MDV-B-M  : .................................................. :  900
           TTTGAATCAAATAAAAAGAGGAGTAAACCTGAAAATACGAATAAGAAATC

                    *       920         *       940         *
pAB127-M : .................................................. :  950
MDV-B-M  : .................................................. :  950
           CAAATAAAGAGACAATAAACAGAGAGGTATCAATTTTGAGACACAGTTAC

                  960         *       980         *      1000
pAB127-M : .................................................. : 1000
MDV-B-M  : .................................................. : 1000
           CAAAAAGAAATCCAAGCCAAAGAAACAATGAAGGAAGTACTCTCTGACAA

                    *      1020         *      1040         *
pAB127-M : .................................................. : 1050
MDV-B-M  : .................................................. : 1050
           CATGGAGATATTGAGTGACCACATAGTAATTGAGGGGCTTTCTGCTGAAG

                 1060         *      1080         *      1100
pAB127-M : .................................................. : 1100
MDV-B-M  : .................................................. : 1100
           AGATAATAAAAATGGGTGAAACAGTTTTGGAGGTAGAAGAATTGCAGTAA
```

Fig. 7 Cont.

```
                     *        1120          *        1140          *
pAB127-M : .................................................. : 1150
MDV-B-M  : .................................................. : 1150
           ACCCAATTTTCACCGTATTTCTTGCTATGCATTTAAGCAAATTGTAATCA

                 1160          *        1180          *
pAB127-M : ........................................ : 1190
MDV-B-M  : ........................................ : 1190
           ATGTCAGCAAATAAACTGGAAAAAGTGCGTTGTTTCTACT
```

```
                         10        20        30        40        50
pAB128-NS : .................................................. :  50
MDV-B-NS  : .................................................. :  50
            AGCAGAAGCAGAGGATTTGTTTAGTCACTGGCAAACGGAAAAAAATGGCG

                         60        70        80        90       100
pAB128-NS : .................................................. : 100
MDV-B-NS  : .................................................. : 100
            GACAACATGACCACAACACAAATTGAGGTAGGTCCGGGAGCAACCAATGC

                        110       120       130       140       150
pAB128-NS : .................................................. : 150
MDV-B-NS  : .................................................. : 150
            CACCATAAACTTTGAAGCAGGAATTCTGGAGTGCTATGAAAGGCTTTCAT

                        160       170       180       190       200
pAB128-NS : .................................................. : 200
MDV-B-NS  : .................................................. : 200
            GGCAAAGAGCCCTTGACTACCCTGGTCAAGACCGCCTAAACAGACTAAAG

                        210       220       230       240       250
pAB128-NS : .................................................. : 250
MDV-B-NS  : .................................................. : 250
            AGAAAATTAGAATCAAGAATAAAGACTCACAACAAAAGTGAGCCTGAAAG

                        260       270       280       290       300
pAB128-NS : .................................................. : 300
MDV-B-NS  : .................................................. : 300
            TAAAAGGATGTCTCTTGAAGAGAGAAAAGCAATTGGGGTAAAAATGATGA

                        310       320       330       340       350
pAB128-NS : .................................................. : 350
MDV-B-NS  : .................................................. : 350
            AAGTGCTCCTATTTATGAATCCATCTGCTGGAATTGAAGGGTTTGAGCCA

                        360       370       380       390       400
pAB128-NS : .................................................. : 400
MDV-B-NS  : .................................................. : 400
            TACTGTATGAAAAATTCCTCAAATAGCAACTGTCCAAACTGCAATTGGAC

                        410       420       430       440       450
pAB128-NS : ...............G.................................. : 450
MDV-B-NS  : .................................................. : 450
            CGATTACCCTCCAACACCAGGAAAGTGCCTTGATGACATAGAAGAAGAAC

                        460       470       480       490       500
pAB128-NS : .................................................. : 500
MDV-B-NS  : .................................................. : 500
            CGGAGAATGTTGATGACCCAACTGAAATAGTATTGAGGGACATGAACAAC

                        510       520       530       540       550
pAB128-NS : .................................................. : 550
MDV-B-NS  : .................................................. : 550
            AAAGATGCAAGGCAAAAGATAAAGGAGGAAGTAAACACTCAGAAAGAAGG

                        560       570       580       590       600
pAB128-NS : .................................................. : 600
```

Fig. 7 Cont.

```
MDV-B-NS  : .................................................. :  600
            GAAGTTCCGTTTGACAATAAAAAGGGATATACGTAATGTGTTGTCCTTGA

                       610       620       630       640       650
pAB128-NS : .................................................. :  650
MDV-B-NS  : .................................................. :  650
            GAGTGTTGGTAAACGGAACATTCCTCAAGCACCCTAATGGATACAAGTCC

                       660       670       680       690       700
pAB128-NS : .................................................. :  700
MDV-B-NS  : .................................................. :  700
            TTATCAACTCTGCATAGATTGAATGCATATGACCAGAGTGGGAGGCTTGT

                       710       720       730       740       750
pAB128-NS : .................................................. :  750
MDV-B-NS  : .................................................. :  750
            TGCTAAACTTGTTGCTACTGATGATCTTACAGTGGAGGATGAAGAAGATG

                       760       770       780       790       800
pAB128-NS : .................................................. :  800
MDV-B-NS  : .................................................. :  800
            GCCATCGGATCCTCAACTCACTCTTCGAGCGTTTTAATGAAGGACATTCA

                       810       820       830       840       850
pAB128-NS : .................................................. :  850
MDV-B-NS  : .................................................. :  850
            AAGCCAATTCGAGCAGCTGAAACTGCGGTGGGAGTCTTATCCCAATTTGG

                       860       870       880       890       900
pAB128-NS : .................................................. :  900
MDV-B-NS  : .................................................. :  900
            TCAAGAGCACCGATTATCACCAGAGGAGGGAGACAATTAGACTGGTTACG

                       910       920       930       940       950
pAB128-NS : .................................................. :  950
MDV-B-NS  : .................................................. :  950
            GAAGAACTTTATCTTTTAAGTAAAAGAATTGATGATAACATATTGTTCCA

                       960       970       980       990      1000
pAB128-NS : .................................................. : 1000
MDV-B-NS  : .................................................. : 1000
            CAAAACAGTAATAGCTAACAGCTCCATAATAGCTGACATGATTGTATCAT

                      1010      1020      1030      1040      1050
pAB128-NS : .................................................. : 1050
MDV-B-NS  : .................................................. : 1050
            TATCATTATTGGAAACATTGTATGAAATGAAGGATGTGGTTGAAGTGTAC

                      1060      1070      1080      1090
pAB128-NS : ................................................ : 1098
MDV-B-NS  : ................................................ : 1098
            AGCAGGCAGTGCTTGTGAATTTAAAATAAAAATCCTCTTGTTACTACT
```

Fig. 7 Cont.

| | Log10 PFU/mL | | |
|---|---|---|---|
| | 33°C | 33°C<br>38°C | 33°C<br>39°C |
| PB2 | 9.2□ | 0.6* | 1.8*□ |
| PB1 | 9.1 | 0.6* | 1.7*□ |
| NP | 9.2 | 0.3*□ | 1.4* |
| PB1+PB2 | 8.9□ | 1.4*□ | 3.1* |
| PB1+PB2+NP | 9.0 | 3.4 | >5.0 |

| PA 431 | PA 497 | NP 55 | NP 114 | NP 410 | NP 509 | M1 159 | M1 183 | | MDCK log pfu/ml 33°C | MDCK log pfu/ml 37°C | MDCK Δlog | PCK log $TCID_{50}$/ml 33°C | PCK log $TCID_{50}$/ml 37°C | PCK Δlog |
|---|---|---|---|---|---|---|---|---|---|---|---|---|---|---|
| M | H | A | A | H | T | Q | V | ts | 6.6 | <2 | >3 | 5.6 | 3.0 | 2.6 |
| V | Y | T | V | P | A | H | M | non-ts | 7.6 | 6.6 | 1.0 | 8.1 | 7.4 | 0.7 |
| V | Y | A | V | P | A | H | M | non-ts | 7.6 | 7.1 | 0.5 | 7.4 | 6.5 | 0.95 |
| V | Y | A | V | P | A | H | M | non-ts | 8.1 | 7.1 | 1.0 | 7.7 | 6.5 | 1.20 |
| M | H | A | A | H | T | Q | V | ts | 7.1 | 3.1 | 4.0 | 7.1 | 3.5 | 3.6 |
| V | Y | T | V | P | A | H | M | non-ts | 8.1 | 7.1 | 1.0 | 8.7 | 7.8 | 0.9 |
| V | Y | A | V | P | A | H | M | non-ts | 8.1 | 7.2 | 0.9 | 8.5 | 7.8 | 0.7 |

Fig. 13

| PA 431 497 | NP 55 114 410 509 | M1 159 183 | | MDCK log pfu/ml 33°C | 37°C | Δlog | PCK log TCID50/ml 33°C | 37°C | Δlog |
|---|---|---|---|---|---|---|---|---|---|
| M H | A A HT | H M | ts | 7.1 | 3.2 | 3.9 | 6.2 | 3.3 | 2.9 |
| M H | A V PA | Q V | ts | n.d. | | | 5.8 | 2.9 | 2.9 |
| V Y | A A HT | Q V | ts | 6.2 | 3.2 | 3.0 | 6.1 | 2.7 | 3.4 |
| V Y | A A HT | H M | ts | 7.4 | 4.4 | 3.0 | 7.5 | 3.4 | 4.1 |
| V Y | A A HT | H M | ts | 7.6 | 4.2 | 3.4 | 8.3 | 4.3 | 4.0 |
| M H | A V PA | H M | ts | 7.4 | 4.4 | 3.0 | 8.1 | 4.3 | 3.8 |
| M H | T V PA | H M | ts | 8.0 | 6.0 | 2.0 | 8.4 | 4.3 | 4.1 |
| V Y | T V PA | Q V | non-ts | 5.6 | 6.0 | -0.4 | 6.4 | 4.5 | 1.9 |
| V Y | T V PA | Q V | non-ts | 6.6 | 5.8 | 0.8 | 6.8 | 4.8 | 2.0 |

Fig. 14

| PA 431 | PA 497 | NP 55 | NP 114 | NP 410 | NP 509 | M1 159 | M1 183 | | MDCK log pfu/ml 33°C | MDCK log pfu/ml 37°C | MDCK Δlog | PCK log $TCID_{50}$/ml 33°C | PCK log $TCID_{50}$/ml 37°C | PCK Δlog |
|---|---|---|---|---|---|---|---|---|---|---|---|---|---|---|
| V | Y | A | V | P | T | Q | V | non-ts | 6.2 | 5.2 | 1.0 | 6.8 | 5.5 | 1.4 |
| V | Y | A | A | P | T | Q | V | non-ts | 6.8 | 6.4 | 0.4 | 7.2 | 6.1 | 1.1 |
| V | Y | A | A | P | T | Q | V | non-ts | 6.4 | 6.2 | 0.2 | 7.1 | 5.7 | 1.4 |
| V | Y | T | A | H | T | Q | V | ts | 6.6 | 4.4 | 2.2 | 6.6 | 3.4 | 3.2 |
| V | Y | A | A | P | T | H | M | non-ts | 7.4 | 6.8 | 0.6 | 8.3 | 7.0 | 1.3 |
| V | Y | T | A | P | T | H | M | non-ts | n.d. | | | 8.0 | 7.2 | 0.8 |

Fig. 15

| | NP1 | NP2 | NP3 | NP4 | NP5 | NP6 |
|---|---|---|---|---|---|---|
| 55 | A | T | A | A | A | A |
| 114 | A | A | V | A | A | V |
| 410 | H | H | H | P | H | P |
| 509 | T | T | T | T | A | T |

| | PA1 | PA2 |
|---|---|---|
| 431 | M | V |
| 497 | Y | H |

Antigenically Drifted H3N2 strains Caused Influenza Outbreak in 2003-2004 Season Data Source: CDC: *Flu Activity Reports & Surveillance In the United States*

Flu season started uncommonly early, from October 2003

Mortality: 10.3% P & I in USA

144 Flu associated deaths in 18 years and younger

Influenza A predominant (99.4%), mostly H3N2 strains

Flu Shot was not effective (MMWR January 16, 2004)

Generation of Cold-adapted Live Attenuated Influenza Vaccines by Plasmids

Molecular Basis of Antigenic Drift of Epidemic A/Fujian/02-like Viruses

| Ag site | | | C | E | E | | A | B | B | | B | D | | D | Egg growth |
|---|---|---|---|---|---|---|---|---|---|---|---|---|---|---|---|
| | 21 | 25 | 50 | 75 | 83 | 128 | 131 | 155,6 | | 183 | 186 | 202 | 219 | 222,5,6 | |
| A/Panama/99 | S | L | R | H | E | T | A | H | Q | L | S | V | S | WGV | Yes |
| A/Wyoming/03 | P | I | G | Q | K | A | T | T | H | H | V | I | Y | RDI | Yes |
| • Flu274 | | | G | Q | K | | | | | | | | | | Yes |
| • Flu275 | | | | | | | T | | | | | | | RDI | Yes |
| • Flu276 | | | | | | | T | T | H | | | | | RDI | Yes |
| • Flu277 | | | | | | | T | | | | | | | | Yes |
| • Flu278 | | | | | | | | | | | | | | RDI | Yes |
| • Flu279 | | | | | | | | | | H | V | | | | No Yes (HA-V182F) |
| • Flu280 | | | | | | | | T | H | | | | | | No Yes (HA-P185L) |

Fig. 26

Minimal Genetic Change for Antigenic Drift of Epidemic H3N2 Strains

A/Panama /2007/99 → Site A: A131T → Site B: H155T, Q156H, S186G/V → Site C: R50G → Site D: V202D, S219F/Y, W222R, G225D, V226I → Site E: H75Q, E83K → S21P, T128A, L25I, L183H → A/Fujian /411/02

H155T, Q156H

Required for virus growth in eggs

Features of A/Fujian/411/2002-like Strains

| | Virus strain | A/Sendai H/F4962/02 | A/Fujian /411/02 | A/Wyoming[1] /03/03 |
|---|---|---|---|---|
| | Isolated | 12/4/02 | 8/11/02 | 2/13/04 |
| | Passages | CXE8/E2 | C1/C1 | spfPCK2E2/E8 |
| | Egg Growth | Yes | No | Yes |
| | Ferret Nose | Poor | ND | Good |
| HA | 128 | T | T | A |
| | 186 | G | G | V |
| | 219 | S | S | Y/F |
| | 226 | V | V | I |
| NA | 119 | Q[2] | E | E |
| | 136 | K | Q | Q |
| | 347 | Y | H | H |

[1] Vaccine strain for 2004-2005
[2] Neuraminidase inhibitors resistant site.

Fig. 29

Fig. 30 NA Neuraminidase Activities and Virus Replication

| NA# | SD-NA | 119E | 136Q | 347H | 119E/347H | 136Q/347H | 119E/136Q | Wy-NA (FJ) |
|---|---|---|---|---|---|---|---|---|
| 119 | Q | E | Q | Q | E | Q | E | E |
| 136 | K | K | Q | K | K | Q | Q | Q |
| 347 | Y | Y | Y | H | H | H | Y | H |
| MDCK | 6.9 | 6.5 | 6.6 | 6.2 | 6.6 | 6.7 | 6.6 | 6.5 | Log$_{10}$pfu/ml |
| Egg | 8.8 | <1.5 | 4.5 | 5.8 | 4.8 | <1.5 | <1.5 | <1.5 | Log$_{10}$pfu/ml |

Virus containing A/Sendai/02 HA, the indicated NA and the six internal segments of ca A/AA/6/60

119E and 136Q are Critical for NA Activity

Effect of HA Residues on Virus Replication in Eggs

| HA \ NA | | | | Wy-NA 119E/136Q /347H | 119E/136Q |
|---|---|---|---|---|---|
| 128 | 186 | 219 | 226 | | |
| T | G | S | V | <1.5 | <1.5 |
| T | V | S | V | 4.95 | 4.39 |
| T | G | S | I | 5.20 | 3.85 |
| T | V | S | I | 7.38 | 7.30 |
| T | V | Y | I | 7.40 | 7.40 |
| A | V | Y | I | 7.75 | 7.18 |

Four residues: HA-186V, 226I and HA-119E, 136Q are sufficient to restore virus replication in eggs.

Fig. 32

HA Receptor-Binding Sites

Ha et al. Virology 309: 209-218, 2003

Egg adapted A/Fujian/411/02

HA-H183L

HA-V226A

Balance Betweeb HA and NA Activities is Critical for Influenza Virus Replication

MULTI PLASMID SYSTEM FOR THE PRODUCTION OF INFLUENZA VIRUS

CROSS REFERENCE TO RELATED APPLICATIONS

This application claims the benefit under 35 U.S.C. § 119 (e) of the following U.S. Provisional Application Nos.: 60/578,962, filed Jun. 12, 2004; 60/643,278, filed Jan. 13, 2005; and U.S. 60/657,372, filed Mar. 2, 2005; and is a continuation in part and claims the benefit under 35 U.S.C. § 120 of U.S. patent application Ser. No. 11/018,624, filed Dec 22, 2004. The priority applications are hereby incorporated by reference herein in their entirety for all purposes.

BACKGROUND OF THE INVENTION

Influenza viruses are made up of an internal ribonucleoprotein core containing a segmented single-stranded RNA genome and an outer lipoprotein envelope lined by a matrix protein. Influenza A and B viruses each contain eight segments of single stranded RNA with negative polarity. The influenza A genome encodes at least eleven polypeptides. Segments 1-3 encode the three polypeptides, making up the viral RNA-dependent RNA polymerase. Segment 1 encodes the polymerase complex protein PB2. The remaining polymerase proteins PB1 and PA are encoded by segment 2 and segment 3, respectively. In addition, segment 1 of some influenza A strains encodes a small protein, PB1-F2, produced from an alternative reading frame within the PB1 coding region. Segment 4 encodes the hemagglutinin (HA) surface glycoprotein involved in cell attachment and entry during infection. Segment 5 encodes the nucleocapsid nucleoprotein (NP) polypeptide, the major structural component associated with viral RNA. Segment 6 encodes a neuramimidase (NA) envelope glycoprotein. Segment 7 encodes two matrix proteins, designated M1 and M2, which are translated from differentially spliced mRNAs. Segment 8 encodes NS1 and NS2 (NEP), two nonstructural proteins, which are translated from alternatively spliced mRNA variants.

The eight genome segments of influenza B encode 11 proteins. The three largest genes code for components of the RNA polymerase, PB1, PB2 and PA. Segment 4 encodes the HA protein. Segment 5 encodes NP. Segment 6 encodes the NA protein and the NB protein. Both proteins, NB and NA, are translated from overlapping reading frames of a biscistronic mRNA. Segment 7 of influenza B also encodes two proteins: M1 and BM2. The smallest segment encodes two products: NS1 is translated from the full length RNA, while NS2 is translated from a spliced mRNA variant.

Vaccines capable of producing a protective immune response specific for influenza viruses have been produced for over 50 years. Vaccines can be characterized as whole virus vaccines, split virus vaccines, surface antigen vaccines and live attenuated virus vaccines. While appropriate formulations of any of these vaccine types is able to produce a systemic immune response, live attenuated virus vaccines are also able to stimulate local mucosal immunity in the respiratory tract.

FluMist™ is a live, attenuated vaccine that protects children and adults from influenza illness (Belshe et al. (1998) *The efficacy of live attenuated, cold-adapted, trivalent, intranasal influenza virus vaccine in children N Engl J Med* 338:1405-12; Nichol et al. (1999) *Effectiveness of live, attenuated intranasal influenza virus vaccine in healthy, working adults: a randomized controlled trial JAMA* 282:137-44). FluMist™ vaccine strains contain HA and NA gene segments derived from the currently circulating wild-type strains along with six gene segments, PB1, PB2, PA, NP, M and NS, from a common master donor virus (MDV). The MDV for influenza A strains of FluMist (MDV-A), was created by serial passage of the wt A/Ann Arbor/6/60 (A/AA/6/60) strain in primary chicken kidney tissue culture at successively lower temperatures (Maassab (1967) *Adaptation and growth characteristics of influenza virus at 25 degrees C. Nature* 213:612-4). MDV-A replicates efficiently at 25° C. (ca, cold adapted), but its growth is restricted at 38 and 39° C. (ts, temperature sensitive). Additionally, this virus does not replicate in the lungs of infected ferrets (att, attenuation). The ts phenotype is believed to contribute to the attenuation of the vaccine in humans by restricting its replication in all but the coolest regions of the respiratory tract. The stability of this property has been demonstrated in animal models and clinical studies. In contrast to the ts phenotype of influenza strains created by chemical mutagenesis, the ts property of MDV-A did not revert following passage through infected hamsters or in shed isolates from children (for a recent review, see Murphy & Coelingh (2002) *Principles underlying the development and use of live attenuated cold-adapted influenza A and B virus vaccines Viral Immunol* 15:295-323).

Clinical studies in over 20,000 adults and children involving 12 separate 6:2 reassortant strains have shown that these vaccines are attenuated, safe and efficacious (Belshe et al. (1998) *The efficacy of live attenuated, cold-adapted, trivalent, intranasal influenza virus vaccine in children N Engl J Med* 338:1405-12; Boyce et al. (2000) *Safety and immunogenicity of adjuvanted and unadjuvanted subunit influenza vaccines administered intranasally to healthy adults Vaccine* 19:217-26; Edwards et al. (1994) *A randomized controlled trial of cold adapted and inactivated vaccines for the prevention of influenza A disease J Infect Dis* 169:68-76; Nichol et al. (1999) *Effectiveness of live, attenuated intranasal influenza virus vaccine in healthy, working adults: a randomized controlled trial JAMA* 282:137-44). Reassortants carrying the six internal genes of MDV-A and the two HA and NA gene segments of the wt virus (6:2 reassortant) consistently maintain ca, ts and att phenotypes (Maassab et al. (1982) *Evaluation of a cold-recombinant influenza virus vaccine in ferrets J Infect Dis* 146:780-900).

To date, all commercially available influenza vaccines in the United States have been propagated in embryonated hen's eggs. Although influenza virus grows well in hen's eggs, production of vaccine is dependent on the availability of eggs. Supplies of eggs must be organized, and strains for vaccine production selected months in advance of the next flue season, limiting the flexibility of this approach, and often resulting in delays and shortages in production and distribution. Unfortunately, some influenza vaccine strains, such as the prototype A/Fujian/411/02 strain that circulated during the 2003-04 season, do not replicate well in embryonated chicken eggs, and have to be isolated by cell culture a costly and time consuming procedure. The present invention further provides a new technology to increase the ability of vaccine strains to replicate in embryonated chicken eggs. Furthermore, the present invention allows for more efficient and cost effective production of influenza vaccines.

Systems for producing influenza viruses in cell culture have also been developed in recent years (See, e.g., Furminger. *Vaccine Production*, in Nicholson et al. (eds) *Textbook of Influenza* pp. 324-332; Merten et al. (1996) *Production of influenza vines in cell cultures for vaccine preparation*, in Cohen & Shafferman (eds) *Novel Strategies in Design and Production of Vaccines* pp. 141-151). Typically, these methods involve the infection of suitable immortalized host cells with a selected strain of virus. While eliminating many of the difficulties related to vaccine production in hen's eggs, not all pathogenic strains of influenza grow well and can be produced according to established tissue culture methods. In addition, many strains with desirable characteristics, e.g., attenuation, temperature sensitivity and cold adaptation, suitable for production of live attenuated vaccines, have not been successfully grown in tissue culture using established methods.

Production of influenza viruses from recombinant DNA would significantly increase the flexibility and utility of tissue culture methods for influenza vaccine production. Recently, systems for producing influenza A viruses from recombinant plasmids incorporating cDNAs encoding the viral genome have been reported (See, e.g., Neumann et al. (1999) *Generation of influenza A virus entirely from cloned cDNAs. Proc Natl Acad Sci USA* 96:9345-9350; Fodor et al. (1999) *Rescue of influenza A virus from recombinant DNA. J. Virol* 73:9679-9682; Hoffmann et al. (2000) *A DNA transfection system for generation of influenza A vines from eight plasmids Proc Natl Acad Sci USA* 97:6108-6113; WO 01/83794). These systems offer the potential to produce recombinant viruses, and reassortant viruses expressing the immunogenic HA and NA proteins from any selected strain. However, unlike influenza A virus, no reports have been published describing plasmid-only systems for influenza B virus.

Additionally, none of the currently available plasmid only systems are suitable for generating attenuated, temperature sensitive, cold adapted strains suitable for live attenuated vaccine production. The present invention provides an eight plasmid system for the generation of influenza B virus entirely from cloned cDNA, and methods for the production of attenuated live influenza A and B virus suitable for vaccine formulations, such as live virus vaccine formulations useful for intranasal administration, as well as numerous other benefits that will become apparent upon review of the specification.

SUMMARY OF THE INVENTION

The present invention relates to a multi-vector system for the production of influenza viruses in cell culture, and to methods for producing recombinant and reassortant influenza viruses, including, e.g., attenuated (att), cold adapted (ca) and/or temperature sensitive (ts) influenza viruses, suitable as vaccines, including live attenuated influenza vaccines, such as those suitable for administration in an intranasal vaccine formulation.

In a first aspect the invention provides vectors and methods for producing recombinant influenza B virus in cell culture, e.g., in the absence of helper virus (i.e., a helper virus free cell culture system). The methods of the invention involve introducing a plurality of vectors, each of which incorporates a portion of an influenza B virus into a population of host cells capable of supporting viral replication. The host cells are cultured under conditions permissive for viral growth, and influenza viruses are recovered. In some embodiments, the influenza B viruses are attenuated viruses, cold adapted viruses and/or temperature sensitive viruses. For example, in an embodiment, the vector-derived recombinant influenza B viruses are attenuated, cold adapted, temperature sensitive viruses, such as are suitable for administration as a live attenuated vaccine, e.g., in a intranasal vaccine formulation. In an exemplary embodiment, the viruses are produced by introducing a plurality of vectors incorporating all or part of an influenza B/Ann Arbor/1/66 virus genome, e.g., a ca B/Ann Arbor/1/66 virus genome.

For example, in some embodiments, the influenza B viruses are artificially engineered influenza viruses incorporating one or more amino acid substitutions which influence the characteristic biological properties of influenza strain ca B/Ann Arbor/1/66. Such influenza viruses include mutations resulting in amino acid substitutions at one or more of positions $PB1^{391}$, $PB1^{581}$, $PB1^{661}$, $PB2^{265}$ and $NP^{34}$, such as: $PB1^{391}$ (K391E), $PB1^{581}$ (E581G), $PB1^{661}$ (A661T), $PB2^{265}$ (N265S) and $NP^{34}$ (D34G). Any mutation (at one or more of these positions) which individually or in combination results in increased temperature sensitivity, cold adaptation or attenuation relative to wild type viruses is a suitable mutation in the context of the present invention.

In some embodiments, a plurality of vectors incorporating at least the 6 internal genome segments of a one influenza B strain along with one or more genome segments encoding immunogenic influenza surface antigens of a different influenza strain are introduced into a population of host cells. For example, at least the 6 internal genome segments of a selected attenuated, cold adapted and/or temperature sensitive influenza B strain, e.g., a ca, att, ts strain of B/Ann Arbor/1/66 or an artificially engineered influenza B strain including an amino acid substitution at one or more of the positions specified above, are introduced into a population of host cells along with one or more segments encoding immunogenic antigens derived from another virus strain. Typically the immunogenic surface antigens include either or both of the hemagglutinin (HA) and/or neuramimidase (NA) antigens. In embodiments where a single segment encoding an immunogenic surface antigen is introduced, the 7 complementary segments of the selected virus are also introduced into the host cells.

In certain embodiments, a plurality of plasmid vectors incorporating influenza B virus genome segments are introduced into a population of host cells. For example, 8 plasmids, each of which incorporates a different genome segment are utilized to introduce a complete influenza B genome into the host cells. Alternatively, a greater number of plasmids, incorporating smaller genomic subsequences can be employed.

Typically, the plasmid vectors of the invention are bi-directional expression vectors. A bi-directional expression vector of the invention typically includes a first promoter and a second promoter, wherein the first and second promoters are operably linked to alternative strands of the same double stranded cDNA encoding the viral nucleic acid including a segment of the influenza virus genome. Optionally, the bi-directional expression vector includes a polyadenylation signal and/or a terminator sequence. For example, the polyadenylation signal and/or the terminator sequence can be located flanking a segment of the influenza virus genome internal to the two promoters. One favorable polyadenylation signal in the context of the invention is the SV40 polyadenylation signal. An exemplary plasmid vector of the invention is the plasmid pAD3000, illustrated in FIG. 1.

The vectors are introduced into host cells capable of supporting the replication of influenza virus from the vector promoters. Favorable examples of host cells include Vero cells, Per.C6 cells, BHK cells, PCK cells, MDCK cells, MDBK cells, 293 cells (e.g., 293T cells), and COS cells. In combination with the pAD3000 plasmid vectors described herein, Vero cells, 293 cells, and COS cells are particularly suitable. In some embodiments, co-cultures of a mixture of at least two of these cell lines, e.g., a combination of COS and MDCK cells or a combination of 293T and MDCK cells, constitute the population of host cells.

The host cells including the influenza B vectors are then grown in culture under conditions permissive for replication and assembly of viruses. Typically, host cells incorporating the influenza B plasmids of the invention are cultured at a temperature below 37° C., preferably at a temperature equal to, or less than, 35° C. Typically, the cells are cultured at a temperature between 32° C. and 35° C. In some embodiments, the cells are cultured at a temperature between about 32° C. and 34° C., e.g., at about 33° C. Following culture for a suitable period of time to permit replication of the virus to high titer, recombinant and/or reassortant viruses are recovered. Optionally, the recovered viruses can be inactivated.

The invention also provides broadly applicable methods of producing recombinant influenza viruses in cell culture by introducing a plurality of vectors incorporating an influenza virus genome into a population of host cells capable of supporting replication of influenza virus, culturing the cells at a temperature less than or equal to 35° C., and recovering influenza viruses.

In certain embodiments, a plurality of plasmid vectors incorporating influenza virus genome segments are introduced into a population of host cells. In certain embodiments, 8 plasmids, each of which incorporates a different genome segment are utilized to introduce a complete influenza genome into the host cells. Typically, the plasmid vectors of the invention are bi-directional expression vectors. An exemplary plasmid vector of the invention is the plasmid pAD3000, illustrated in FIG. 1.

In some embodiments, the influenza viruses correspond to an influenza B virus. In some embodiments, the influenza viruses correspond to an influenza A virus. In certain embodiments, the methods include recovering recombinant and/or reassortant influenza viruses capable of eliciting an immune response upon administration, e.g., intranasal administration, to a subject. In some embodiments, the viruses are inactivated prior to administration, in other embodiments, live-attenuated viruses are administered. Recombinant and reassortant influenza A and influenza B viruses produced according to the methods of the invention are also a feature of the invention.

In certain embodiments, the viruses include an attenuated influenza virus, a cold adapted influenza virus, a temperature sensitive influenza virus, or a virus with any combination of these desirable properties. In one embodiment, the influenza virus incorporates an influenza B/Ann Arbor/1/66 strain virus, e.g., a cold adapted, temperature sensitive, attenuated strain of B/Ann Arbor/1/66. In another embodiment, the influenza virus incorporates an influenza A/Ann Arbor/6/60 strain virus, e.g., a cold adapted, temperature sensitive, attenuated strain of A/Ann Arbor/6/60. In another embodiment of the invention, the viruses are artificially engineered influenza viruses incorporating one or more substituted amino acid which influences the characteristic biological properties of, e.g., ca A/Ann Arbor/6/60 or ca B/Ann Arbor/1/66. Such substituted amino acids favorably correspond to unique amino acids of ca A/Ann Arbor/6/60 or ca B/Ann Arbor/1/66, e.g., in an A strain virus: $PB1^{391}$ (K391E), $PB1^{581}$ (E581G), $PB1^{661}$ (A661T), $PB2^{265}$ (N265S) and $NP^{34}$ (D34G); and, in a B strain virus: $PB2^{630}$ (S630R); $PA^{431}$ (V431M); $PA^{497}$ (Y497H); $NP^{55}$ (T55A); $NP^{114}$ (V114A); $NP^{410}$ (P410H); $NP^{509}$ (A509T); $M1^{159}$ (H159Q) and $M1^{183}$ (M183V). Similarly, other amino acid substitutions at any of these positions resulting in temperature sensitivity, cold adaptation and/or attenuation are encompassed by the viruses and methods of the invention. It will be understood that some A or B viruses may already have the recited residues at the indicated positions. In this case, the substitutions would be done such that the resulting virus will have all of the preferred substitutions.

Optionally, reassortant viruses are produced by introducing vectors including the six internal genes of a viral strain selected for its favorable properties regarding vaccine production, in combination with the genome segments encoding the surface antigens (HA and NA) of a selected, e.g., pathogenic strain. For example, the HA segment is favorably selected from a pathogenically relevant H1, H3 or B strain, as is routinely performed for vaccine production. Similarly, the HA segment can be selected from an emerging pathogenic strain such as an H2 strain (e.g., H2N2), an H5 strain (e.g., H5N1) or an H7 strain (e.g., H7N7). Alternatively, the seven complementary gene segments of the first strain are introduced in combination with either the HA or NA encoding segment. In certain embodiments, the internal gene segments are derived from the influenza B/Ann Arbor/1/66 or the A/Ann Arbor/6/60 strain.

Additionally, the invention provides methods for producing novel influenza viruses with desirable properties relevant to vaccine production, e.g., temperature sensitive, attenuated, and/or cold adapted, influenza viruses, as well as influenza vaccines including such novel influenza viruses. In certain embodiments, novel influenza A strain virus is produced by introducing mutations that result amino acid substitutions at one or more specified positions demonstrated herein to be important for the temperature sensitive phenotype, e.g., $PB1^{391}$, $PB1^{581}$, $PB1^{661}$, $PB2^{265}$ and $NP^{34}$. For example, mutations are introduced at nucleotide positions $PB1^{1195}$, $PB1^{1766}$, $PB1^{2005}$, PB2 $^{821}$ and $NP^{146}$, or other nucleotide positions resulting in an amino acid substitution at the specified amino acid position. Any mutation (at one or more of these positions) which individually or in combination results in increased temperature sensitivity, cold adaptation or attenuation relative to wild type viruses is a suitable mutation in the context of the present invention. For example, mutations selected from among $PB1^{391}$ (K391E), $PB1^{581}$ (E581G), $PB1^{661}$ (A661T), $PB2^{265}$ (N265S) and $NP^{34}$ (D34G) are favorably introduced into the genome of a wild type influenza A strain, e.g., PR8, to produce a temperature sensitive variant suitable for administration as a live attenuated vaccine. To increase stability of the desired phenotype, a plurality of mutations are typically introduced. Following introduction of the selected mutation(s) into the influenza genome, the mutated influenza genome is replicated under conditions in which virus is produced. For example, the mutated influenza virus genome can be replicated in hens' eggs. Alternatively, the influenza virus genome can be replicated in cell culture. In the latter case, the virus is optionally further amplified in hens' eggs to increase the titer. Temperature sensitive, and optionally, attenuated and/or cold adapted viruses produced according to the methods of the invention are also a feature of the invention, as are vaccines including such viruses. Similarly, novel recombinant viral nucleic acids incorporating one or more mutations at positions $PB1^{391}$, $PB1^{581}$, $PB1^{661}$, $PB2^{265}$ and $NP^{34}$, e.g., mutations selected from among $PB1^{391}$ (K391E), $PB1^{581}$ (E581G), $PB1^{661}$ (A661T), $PB2^{265}$ (N265S) and $NP^{34}$ (D34G), and polypeptides with such amino acid substitutions are a feature of the invention.

Likewise, the methods presented herein are adapted to producing novel influenza B strains with temperature sensitive, and optionally attenuated and/or cold adapted phenotypes by introducing one or more specified mutations into an influenza B genome. For example, one or more mutations resulting in an amino acid substitution at a position selected from among $PB2^{630}$; $PA^{431}$; $PA^{497}$; $NP^{55}$; $NP^{114}$; $NP^{410}$; $NP^{509}$; $M1^{159}$ and $M1^{183}$ are introduced into an influenza B strain genome to produce a temperature sensitive influenza B virus. Exemplary amino acid substitutions include the following: $PB2^{630}$ (S630R); $PA^{431}$ (V431M); $PA^{497}$ (Y497H); $NP^{55}$ (T55A); $NP^{114}$ (V114A); $NP^{410}$ (P410H); $NP^{509}$ (A509T); $M1^{159}$ (H159Q) and $M1^{183}$ (M183V). As indicated above, vaccines incorporating such viruses as well as nucleic acids and polypeptides incorporating these mutations and amino acid substitutions are all features of the invention. In one preferred embodiment, the methods presented herein are adapted to producing novel influenza B strains with temperature sensitive and attenuated phenotypes comprising or alternatively consisting of introducing the following amino acid substitutions: $PA^{431}$ (V431M); $NP^{114}$ (V114A); $NP^{410}$ (P410H); $M1^{159}$ (H159Q) and $M1^{183}$ (M183V). It is specifically contemplated that conservative and non-conservative amino acid substitutions at these positions are also within the scope of the invention. In another preferred embodiment, the methods presented herein are adapted to producing novel influenza B strains with temperature sensitive and attenuated phenotypes comprising or alternatively consisting of introducing a mutation at the following amino acid positions: $PA^{431}$; $NP^{114}$; $NP^{410}$; $M1^{159}$ and $M1^{183}$. In another preferred embodiment, the methods presented herein are adapted to producing novel influenza B strains with temperature sensitive and attenuated phenotypes comprising or alternatively consisting of introducing a mutation at the following amino acid positions: $PA^{431}$; $NP^{14}$; $NP^{410}$; and $M1^{183}$. In another preferred embodiment, the methods presented herein are adapted to producing novel influenza B strains with temperature sensitive and attenuated phenotypes comprising or alternatively consisting of introducing a mutation at the following amino acid positions: $PA^{431}$; $NP^{114}$; $NP^{410}$; and $M1^{159}$. In one preferred embodiment, the methods presented herein are adapted to producing novel influenza B strains with temperature sensitive and attenuated phenotypes comprising or alternatively consisting of introducing the following amino acid substitutions: $PA^{431}$ (V431M); $NP^{114}$ (V114A); $NP^{410}$ (P410H); $M1^{159}$ (H159Q) $M1^{183}$ (M183V); and $PA^{497}$ (Y497H). In one preferred embodiment, the methods presented herein are adapted to producing novel influenza B strains with temperature sensitive and attenuated phenotypes comprising or alternatively consisting of introducing the following amino acid substitutions: $PA^{431}$ (V431M); $NP^{114}$ (V114A); $NP^{410}$ (P410H); ($M1^{159}$ (H159Q) and/or $M1^{183}$ (M183V)); and $PA^{497}$ (Y497H). It is specifically contemplated that conservative and non-conservative amino acid substitutions at these positions are also within the scope of the invention. It will be understood that some B viruses may already have the recited residues at the indicated positions. In this case, the substitutions would be done such that the resulting virus will have all of the preferred substitutions. In another preferred embodiment, the methods presented herein are adapted to producing novel influenza B strains with temperature sensitive and attenuated phenotypes comprising or alternatively consisting of introducing a mutation at the following amino acid positions: $PA^{431}$; $NP^{114}$; $NP^{410}$; $M1^{159}$; $M1^{183}$; and $PA^{497}$.

Accordingly, influenza viruses incorporating the mutations of the invention are a feature of the invention regardless of the method in which they are produced. That is, the invention encompasses influenza strains including the mutations of the invention, e.g., any influenza A virus with an amino acid substitution relative to wild type at one or more positions selected from among: $PB1^{391}$, $PB1^{581}$, $PB1^{661}$, $PB2^{265}$ and $NP^{34}$ or any influenza B virus with an amino acid substitution relative to wild type at one or more positions selected from among: $PB2^{630}$; $PA^{431}$; $PA^{497}$; $NP^{55}$; $NP^{114}$; $NP^{410}$; $NP^{509}$; $M1^{159}$ and $M1^{183}$, with the proviso that the strains ca A/Ann Arbor/6/60 and B/Ann Arbor/1/66 are not considered a feature of the present invention. In certain preferred embodiments, the influenza A viruses include a plurality of mutations selected from among $PB1^{391}$ (K391E), $PB1^{581}$ (E581G), $PB1^{661}$ (A661T), $PB2^{265}$ (N265S) and $NP^{34}$ (D34G); and the influenza B viruses include a plurality of mutations selected from among $PB2^{630}$ (S630R); $PA^{431}$ (V431M); $PA^{497}$ (Y497H); $NP^{55}$ (T55A); $NP^{114}$ (V114A); $NP^{410}$ (P410H); $NP^{509}$ (A509T); $M1^{159}$ (H159Q) and $M1^{183}$ (M183V), respectively. It will be understood that some A viruses may already have the recited residues at the indicated positions. In this case, the substitutions would be done such that the resulting virus will have all of the preferred substitutions. In one preferred embodiment, the novel influenza B strains with temperature sensitive and attenuated phenotypes comprise or alternatively consist of amino acid substitutions/mutations at the following positions: $PA^{431}$ (V431M); $NP^{114}$ (V114A); $NP^{410}$ (P410H); $M1^{159}$ (H159Q) and $M1^{183}$ (M183V). It will be understood that some B viruses may already have the recited residues at the indicated positions. In this case, the substitutions would be done such that the resulting virus will have all of the preferred substitutions. In another preferred embodiment, the novel influenza B strains with temperature sensitive and attenuated phenotypes comprise or alternatively consist of amino acid substitutions/mutations at the following positions: $PA^{431}$ (V431M); $NP^{114}$ (V114A); $NP^{410}$ (P410H); and $M1^{159}$ (H159Q). In another preferred embodiment, the novel influenza B strains with temperature sensitive and attenuated phenotypes comprise or alternatively consist of amino acid substitutions/mutations at the following positions: $PA^{431}$ (V431M); $NP^{114}$ (V114A); $NP^{410}$ (P410H); and $M1^{183}$ (M183V). It will be understood that some B viruses may already have the recited residues at the indicated positions. In this case, the substitutions would be done such that the resulting virus will have all of the preferred substitutions. It is specifically contemplated that conservative and non-conservative amino acid substitutions at these positions are also within the scope of the invention. In another preferred embodiment, the novel influenza B strains with temperature sensitive and attenuated phenotypes comprise or alternatively consist of amino acid substitutions/mutations at the following positions: $PA^{431}$; $NP^{114}$; $NP^{410}$; $M1^{159}$ and $M1^{183}$. In another preferred embodiment, the novel influenza B strains with temperature sensitive and attenuated phenotypes comprise or alternatively consist of amino acid substitutions/mutations at the following positions: $PA^{431}$; $NP^{114}$; $NP^{410}$; and $M1^{159}$. In another preferred embodiment, the novel influenza B strains with temperature sensitive and attenuated phenotypes comprise or alternatively consist of amino acid substitutions/mutations at the following positions: $PA^{431}$; $NP^{114}$; $NP^{410}$; and $M1^{183}$. In another preferred embodiment, the novel influenza B strains with temperature sensitive and attenuated phenotypes comprise or alternatively consist of amino acid substitutions/mutations at the following positions: $PA^{431}$ (V431M); $NP^{114}$ (V114A); $NP^{410}$ (P410H); $M1^{159}$ (H159Q) $M1^{183}$ (M183V); and $PA^{497}$ (Y497H). It will be understood that some B viruses may already have the recited residues at the indicated positions. In this case, the substitutions would be done such that the resulting virus will have all of the preferred substitutions. In another preferred embodiment, the novel influenza B strains with temperature sensitive and attenuated phenotypes comprise or alternatively consist of amino acid substitutions/mutations at the following positions: $PA^{431}$; $NP^{114}$; $NP^{410}$; $M1^{159}$; $M1^{183}$; and $PA^{497}$. It will be understood that some B viruses may already have the recited residues at the indicated positions. In this case, the substitutions would be done such that the resulting virus will have all of the preferred substitutions.

In one embodiment, a plurality of plasmid vectors incorporating the influenza virus genome are introduced into host cells. For example, segments of an influenza virus genome can be incorporated into at least 8 plasmid vectors. In one preferred embodiment, segments of an influenza virus genome are incorporated into 8 plasmids. For example, each of 8 plasmids can favorably incorporate a different segment of the influenza virus genome.

The vectors of the invention can be bi-directional expression vectors. A bi-directional expression vector of the invention typically includes a first promoter and a second promoter, wherein the first and second promoters are operably linked to alternative strands of the same double stranded viral nucleic acid including a segment of the influenza virus genome. Optionally, the bi-directional expression vector includes a polyadenylation signal and/or a terminator sequence. For example, the polyadenylation signal and/or the terminator sequence can be located flanking a segment of the influenza virus genome internal to the two promoters. One favorable polyadenylation signal in the context of the invention is the SV40 polyadenylation signal. An exemplary plasmid vector of the invention is the plasmid pAD3000, illustrated in FIG. 1.

Any host cell capable of supporting the replication of influenza virus from the vector promoters is suitable in the context of the present invention. Favorable examples of host cells include Vero cells, Per.C6 cells, BHK cells, PCK cells, MDCK cells, MDBK cells, 293 cells (e.g., 293T cells), and COS cells. In combination with the pAD3000 plasmid vectors described herein, Vero cells, 293 cells, COS cells are particularly suitable. In some embodiments, co-cultures of a mixture of at least two of these cell lines, e.g., a combination of COS and MDCK cells or a combination of 293T and MDCK cells, constitute the population of host cells.

A feature of the invention is the culture of host cells incorporating the plasmids of the invention at a temperature below 37° C., preferably at a temperature equal to, or less than, 35° C. Typically, the cells are cultured at a temperature between 32° C. and 35° C. In some embodiments, the cells are cultured at a temperature between about 32° C. and 34° C., e.g., at about 33° C.

Another aspect of the invention relates to novel methods for rescuing recombinant or reassortant influenza A or influenza B viruses (i.e., wild type and variant strains of influenza A and/or influenza viruses) from Vero cells in culture. A plurality of vectors incorporating an influenza virus genome is electroporated into a population of Vero cells. The cells are grown under conditions permissive for viral replication, e.g., in the case of cold adapted, attenuated, temperature sensitive virus strains, the Vero cells are grown at a temperature below 37° C., preferably at a temperature equal to, or less than, 35° C. Typically, the cells are cultured at a temperature between 32° C. and 35° C. In some embodiments, the cells are cultured at a temperature between about 32° C. and 34° C., e.g., at about 33° C. Optionally (e.g., for vaccine production), the Vero cells are grown in serum free medium without any animal-derived products.

In the methods of the invention described above, viruses are recovered following culture of the host cells incorporating the influenza genome plasmids. In some embodiments, the recovered viruses are recombinant viruses. In some embodiments, the viruses are reassortant influenza viruses having genetic contributions from more than one parental strain of virus. Optionally, the recovered recombinant or reassortant viruses are further amplified by passage in cultured cells or in hens' eggs.

Optionally, the recovered viruses are inactivated. In some embodiments, the recovered viruses comprise an influenza vaccine. For example, the recovered influenza vaccine can be a reassortant influenza viruses (e.g., 6:2 or 7:1 reassortant viruses) having an HA and/or NA antigen derived from a selected strain of influenza A or influenza B. In certain favorable embodiments, the reassortant influenza viruses have an attenuated phenotype. Optionally, the reassortant viruses are cold adapted and/or temperature sensitive, e.g., an attenuated, cold adapted or temperature sensitive influenza B virus having one or more amino acid substitutions selected from the substitutions of Table 17. Such influenza viruses are useful, for example, as live attenuated vaccines for the prophylactic production of an immune response specific for a selected, e.g., pathogenic influenza strain. Influenza viruses, e.g., attenuated reassortant viruses, produced according to the methods of the invention are a feature of the invention.

In another aspect, the invention relates to methods for producing a recombinant influenza virus vaccine involving introducing a plurality of vectors incorporating an influenza virus genome into a population of host cells capable of supporting replication of influenza virus, culturing the host cells at a temperature less than or equal to 35° C., and recovering an influenza virus capable of eliciting an immune response upon administration to a subject. The vaccines of the invention can be either influenza A or influenza B strain viruses. In some embodiments, the influenza vaccine viruses include an attenuated influenza virus, a cold adapted influenza virus, or a temperature sensitive influenza virus. In certain embodiments, the viruses possess a combination of these desirable properties. In an embodiment, the influenza virus contains an influenza A/Ann Arbor/6/60 strain virus. In another embodiment, the influenza virus incorporates an influenza B/Ann Arbor/1/66 strain virus. Alternatively, the vaccine includes artificially engineered influenza A or influenza B viruses incorporating at least one substituted amino acid which influences the characteristic biological properties of ca A/Ann Arbor/6/60 or ca/B/Ann Arbor/1/66, such as a unique amino acid of these strains. For example, vaccines encompassed by the invention include artificially engineered recombinant and reassortant influenza A viruses including at least one mutation resulting in an amino acid substitution at a position selected from among $PB1^{391}$, $PB1^{581}$, $PB1^{661}$, $PB2^{265}$ and $NP^{34}$ and artificially engineered recombinant and reassortant influenza B viruses including at least one mutation resulting in an amino acid substitution at a position selected from among $PB2^{630}$, $PA^{431}$, $PA^{497}$, $NP^{55}$, $NP^{114}$, $NP^{410}$, $NP^{509}$, $M1^{159}$ and $M1^{183}$.

In some embodiments, the virus includes a reassortant influenza virus (e.g., a 6:2 or 7:1 reassortant) having viral genome segments derived from more than one influenza virus strain. For example, a reassortant influenza virus vaccine favorably includes an HA and/or NA surface antigen derived from a selected strain of influenza A or B, in combination with the internal genome segments of a virus strain selected for its desirable properties with respect to vaccine production. Often, it is desirable to select the strain of influenza from which the HA and/or NA encoding segments are derived based on predictions of local or world-wide prevalence of pathogenic strains (e.g., as described above). In some cases, the virus strain contributing the internal genome segments is an attenuated, cold adapted and/or temperature sensitive influenza strain, e.g., of A/Ann Arbor/6/60, B/Ann Arbor/1/66, or an artificially engineered influenza strain having one or more amino acid substitutions resulting in the desired phenotype, e.g., influenza A viruses including at least one mutation resulting in an amino acid substitution at a position selected from among $PB1^{391}$, $PB1^{581}$, $PB1^{661}$, $PB2^{265}$ and $NP^{34}$ and influenza B viruses including at least one mutation resulting in an amino acid substitution at a position selected from among $PB2^{630}$, $PA^{43}$, $PA^{497}$, $NP^{55}$, $NP^{114}$, $NP^{410}$, $NP^{509}$, $M1^{159}$ and $M1^{183}$. For example, favorable reassortant viruses include artificially engineered influenza A viruses with one or more amino acid substitution selected from among $PB1^{391}$ (K391E), $PB1^{581}$ (E581G), $PB1^{661}$ (A661T), $PB2^{265}$ (N265S) and $NP^{34}$ (D34G); and influenza B viruses including one or more amino acid substitutions selected from among $PB2^{630}$ (S630R); $PA^{431}$ (V431M); $PA^{497}$ (Y497H); $NP^{55}$ (T55A); $NP^{114}$ (V114A); $NP^{410}$ (P410H); $NP^{509}$ (A509T); $M1^{159}$ (H159Q) and $M1^{183}$ (M183V).

If desired, the influenza vaccine viruses are inactivated upon recovery.

Influenza virus vaccines, including attenuated live vaccines, produced by the methods of the invention are also a feature of the invention. In certain favorable embodiments the influenza virus vaccines are reassortant virus vaccines.

Another aspect of the invention provides plasmids that are bi-directional expression vectors. The bi-directional expression vectors of the invention incorporate a first promoter inserted between a second promoter and a polyadenylation site, e.g., an SV40 polyadenylation site. In an embodiment, the first promoter and the second promoter can be situated in opposite orientations flanking at least one cloning site. An exemplary vector of the invention is the plasmid pAD3000, illustrated in FIG. 1.

In some embodiments, at least one segment of an influenza virus genome is inserted into the cloning site, e.g., as a double stranded nucleic acid. For example, a vector of the invention includes a plasmid having a first promoter inserted between a second promoter and an SV40 polyadenylation site, wherein the first promoter and the second promoter are situated in opposite orientations flanking at least one segment of an influenza virus.

Kits including one or more expression vectors of the invention are also a feature of the invention. Typically, the kits also include one or more of: a cell line capable of supporting influenza virus replication, a buffer, a culture medium, an instruction set, a packaging material, and a container. In some embodiments, the kit includes a plurality of expression vectors, each of which includes at least one segment of an influenza virus genome. For example, kits including a plurality of expression vectors each including one of the internal genome segments of a selected virus strain, e.g., selected for its desirable properties with respect to vaccine production or administration, are a feature of the invention. For example, the selected virus strain can be an attenuated, cold adapted and/or temperature sensitive strain, e.g., A/Ann Arbor/6/60 or B/Ann Arbor/1/66, or an alternative strain with the desired properties, such as an artificially engineered strain having one or more amino acid substitutions as described herein, e.g., in Table 17. In an embodiment, the kit includes a expression vectors incorporating members of a library of nucleic acids encoding variant HA and/or NA antigens.

Productively growing cell cultures including at least one cell incorporating a plurality of vectors including an influenza virus genome, at a temperature less than or equal to 35° C., is also a feature of the invention. The composition can also include a cell culture medium. In some embodiments, the plurality of vectors includes bi-directional expression vectors, e.g., comprising a first promoter inserted between a second promoter and an SV40 polyadenylation site. For example, the first promoter and the second promoter can be situated in opposite orientations flanking at least one segment of an influenza virus. The cell cultures of the invention are maintained at a temperature less than or equal to 35° C., such as between about 32° C. and 35° C., typically between about 32° C. and about 34° C., for example, at about 33° C.

The invention also includes a cell culture system including a productively growing cell culture of at least one cell incorporating a plurality of vectors comprising a an influenza virus genome, as described above, and a regulator for maintaining the culture at a temperature less than or equal to 35° C. For example, the regulator favorably maintains the cell culture at a temperature between about 32° C. and 35° C., typically between about 32° C. and about 34° C., e.g., at about 33° C.

Another feature of the invention are artificially engineered recombinant or reassortant influenza viruses including one or more amino acid substitutions which influence temperature sensitivity, cold adaptation and/or attenuation. For example, artificially engineered influenza A viruses having one or more amino acid substitution at a position selected from among: $PB1^{391}$, $PB1^{581}$, $PB1^{661}$, $PB2^{265}$ and $NP^{34}$ and artificially engineered influenza B viruses having one or more amino acid substitutions at a position selected from among $PB2^{630}$, $PA^{431}$, $PA^{497}$, $NP^{55}$, $NP^{114}$, $NP^{410}$, $NP^{509}$, $M1^{159}$ and $M1^{183}$ are favorable embodiments of the invention. Exemplary embodiments include influenza A viruses with any one or more of the following amino acid substitutions: $PB1^{391}$ (K391E), $PB1^{581}$ (E581G), $PB1^{661}$ (A661T), $PB2^{265}$ (N265S) and $NP^{34}$ (D34G); and influenza B viruses with any one or more of the following amino acid substitutions: $PB2^{630}$ (S630R); $PA^{431}$ (V431M); $PA^{497}$ (Y497H); $NP^{55}$ (T55A); $NP^{114}$ (V114A); $NP^{410}$ (P410H); $NP^{509}$ (A509T); $M1^{159}$ (H159Q) and $M1^{183}$ (M183V). In certain embodiments, the viruses include a plurality of mutations, such as one, two, three, four, five, six, seven, eight or nine amino acid substitutions at positions identified above. Accordingly, artificially engineered influenza A viruses having amino acid substitutions at all five positions indicated above, e.g., $PB1^{391}$ (K391E), $PB1^{581}$ (E581G), $PB1^{661}$ (A661T), $PB2^{265}$ (N265S) and $NP^{34}$ (D34G) and artificially engineered influenza B viruses having amino acid substitutions at eight or all nine of the positions indicated above, e.g., $PB2^{630}$ (S630R); $PA^{431}$ (V431M); $PA^{497}$ (Y497H); $NP^{55}$ (T55A); $NP^{114}$ (V114A); $NP^{410}$ (P410H); $NP^{509}$ (A509T); $M1^{159}$ (H159Q) and $M1^{183}$ (M183V), are encompassed by the invention. In addition, the viruses can include one or more additional amino acid substitutions not enumerated above. In addition, artificially engineered influenza A or B viruses having amino acid substitutions at the following five positions: $PA^{431}$; $NP^{114}$; $NP^{410}$; $M1^{159}$ and $M1^{183}$ are encompassed by the invention. In addition, the viruses can include one or more additional amino acid substitutions not enumerated above.

In certain embodiments, the artificially engineered influenza viruses are temperature sensitive influenza viruses, cold adapted influenza viruses and/or attenuated influenza viruses. For example, a temperature sensitive influenza virus according to the invention typically exhibits between about 2.0 and 5.0 $\log_{10}$ reduction in growth at 39° C. as compared to a wild type influenza virus. For example, a temperature sensitive virus favorably exhibits at least about 2.0 $\log_{10}$, at least about 3.0 $\log_{10}$, at least about 4.0 $\log_{10}$, or at least about 4.5 $\log_{10}$ reduction in growth at 39° C. relative to that of a wild type influenza virus. Typically, but not necessarily, a temperature sensitive influenza virus retains robust growth characteristics at 33° C. An attenuated influenza virus of the invention typically exhibits between about a 2.0 and a 5.0 log10 reduction in growth in a ferret attenuation assay as compared to a wild type influenza virus. For example, an attenuated influenza virus of the invention exhibits at least about a 2.0 $\log_{10}$, frequently about a 3.0 $\log_{10}$, and favorably at least about a 4.0 $\log_{10}$ reduction in growth in a ferret attenuation assay relative to wild type influenza virus.

In one embodiment, a method is provided for producing influenza viruses in cell culture, the method comprising: i) introducing a plurality of vectors comprising an influenza virus genome into a population of host cells, which population of host cells is capable of supporting replication of influenza virus; ii) culturing the population of host cells at a temperature less than or equal to 35° C.; and, iii) recovering a plurality of influenza viruses.

In a nonexclusive embodiment, the above methods of the invention comprise introducing a plurality of vectors comprising at least an influenza B/Ann Arbor/1/66 virus or an artificially engineered influenza B virus genome encoding at least one substituted amino acid, which substituted amino acid influences the characteristic biological properties of B/Ann Arbor/1/66.

In another nonexclusive embodiment, the above methods of the invention comprise introducing a plurality of vectors into a population of host cells comprising at least an influenza B/Ann Arbor/1/66 virus or an artificially engineered influenza B virus genome encoding at least one substituted amino acid at the following positions: $PB2^{630}$; $PA^{431}$; $NP^{114}$; $NP^{410}$; and $NP^{509}$. In a preferred embodiment, the influenza B strain virus genome further comprises a substituted amino acid at the one or more of the following positions: $M1^{159}$ and $M1^{183}$.

In another nonexclusive embodiment, the above methods of the invention comprise introducing a plurality of vectors into a population of host cells comprising at least an influenza B/Ann Arbor/1/66 virus or an artificially engineered influenza B virus genome, wherein the genome encodes one or more of the amino acid substitutions selected from the group consisting of: $PB2^{630}$ (S630R); $PA^{431}$ (V431M); $NP^{114}$ (V114A); $NP^{410}$ (P410H); and $NP^{509}$ (A509T). In a preferred embodiment, the influenza B strain virus genome comprises at least all five amino acid substitutions.

In a preferred embodiment, a method of producing a cold adapted (ca) influenza virus is provided, the method comprising: (a) introducing at least one mutation at the following amino acid positions: $PB2^{630}$, $PA^{431}$, $NP^{114}$, $NP^{410}$, and $NP^{509}$ influenza B virus genome; and (b) replicating the mutated influenza virus genome under conditions whereby virus is produced.

In another preferred embodiment, a method of producing a cold adapted (ca) influenza virus is provided, the method comprising: (a) introducing at least the following mutations: $PB2^{630}$ (S630R), $PA^{431}$ (V431M), $NP^{114}$ (V114A), $NP^{410}$ (P410H), and $NP^{509}$ (A509T) into an influenza B virus genome; and (b) replicating the mutated influenza virus genome under conditions whereby virus is produced.

In another preferred embodiment, a method of producing a cold adapted (ca) influenza virus that replicates efficiently at 25° C. is provided, the method comprising: (a) introducing at least one mutation at the following amino acid positions: $PB2^{630}$, $PA^{431}$, $NP^{114}$, $NP^{410}$, and $NP^{509}$ into an influenza B virus genome; and (b) replicating the mutated influenza virus genome under conditions whereby virus is produced.

In another preferred embodiment, a method of producing a cold adapted (ca) influenza virus that replicates efficiently at 25° C. is provided, the method comprising: (a) introducing at least the following mutations: $PB2^{630}$ (S630R), $PA^{431}$ (V431M), $NP^{114}$ (V114A), $NP^{410}$ (P410H), and $NP^{509}$ (A509T) into an influenza B virus genome; and (b) replicating the mutated influenza virus genome under conditions whereby virus is produced.

In another preferred embodiment, an influenza virus (and immunogenic compositions comprising the same) produced by the above methods is provided.

In another preferred embodiment, a cold adapted virus (and immunogenic compositions comprising the same) produced by the above methods is provided.

The present invention also relates to the identification and manipulation of amino acid residues in HA and NA which affect influenza virus replication in cells and embryonated chicken eggs. The present invention further relates to the use of reverse genetics technology to generate HA and NA influenza virus vaccine variants with improved replication in embryonated chicken eggs and/or cells. The invention further relates to methods for modulating HA receptor binding activity and/or NA neuramimidase activity. Additionally, the invention provides influenza viruses with enhanced ability to replicate in embryonated chicken eggs and/or cells.

In one embodiment the invention provides methods for manipulating the amino acid residues of HA and/or NA to increase the ability of an influenza virus to replicate in embryonated chicken eggs and/or cells. The method involves the introduction of amino acid residues substitutions in HA and/or NA and makes use of methods of producing influenza virus in cell culture by introducing a plurality of vectors incorporating an influenza virus genome into a population of host cells capable of supporting replication of influenza virus, culturing the cells and recovering influenza virus. Preferably, the recovered influenza virus has increase ability to replicate in embryonated chicken eggs and/or cells. In another embodiment, the present invention provides influenza virus variants with increase ability to replicate in embryonated chicken eggs (referred to herein as "replication enhanced influenza variant(s)") when compared to unmodified influenza viral strains.

BRIEF DESCRIPTION OF THE DRAWINGS

FIG. 6: Sequence of pAD3000 (SEQ ID NO: 94) in GeneBank format.

FIG. 7: Sequence alignment with MDV-B and eight plasmids (SEQ ID NOS: 95-102).

FIG. 13: Schematic illustration of triple-gene recombinants with wild type residues in PA, NP, and M1 proteins.

FIG. 14: Tabulation of growth of single-gene and double-gene recombinant viruses.

FIG. 15: Tabulation of amino acid residue of the nucleoprotein corresponding to non-ts phenotype.

FIGS. 24-28: Show molecular basis for antigenic drift from A/Panama/99 to A/Fujian/02-like.

FIGS. 29-35: Detail modifications in strains to produce increased virus growth in embryonated eggs.

DETAILED DESCRIPTION

Figure 1:
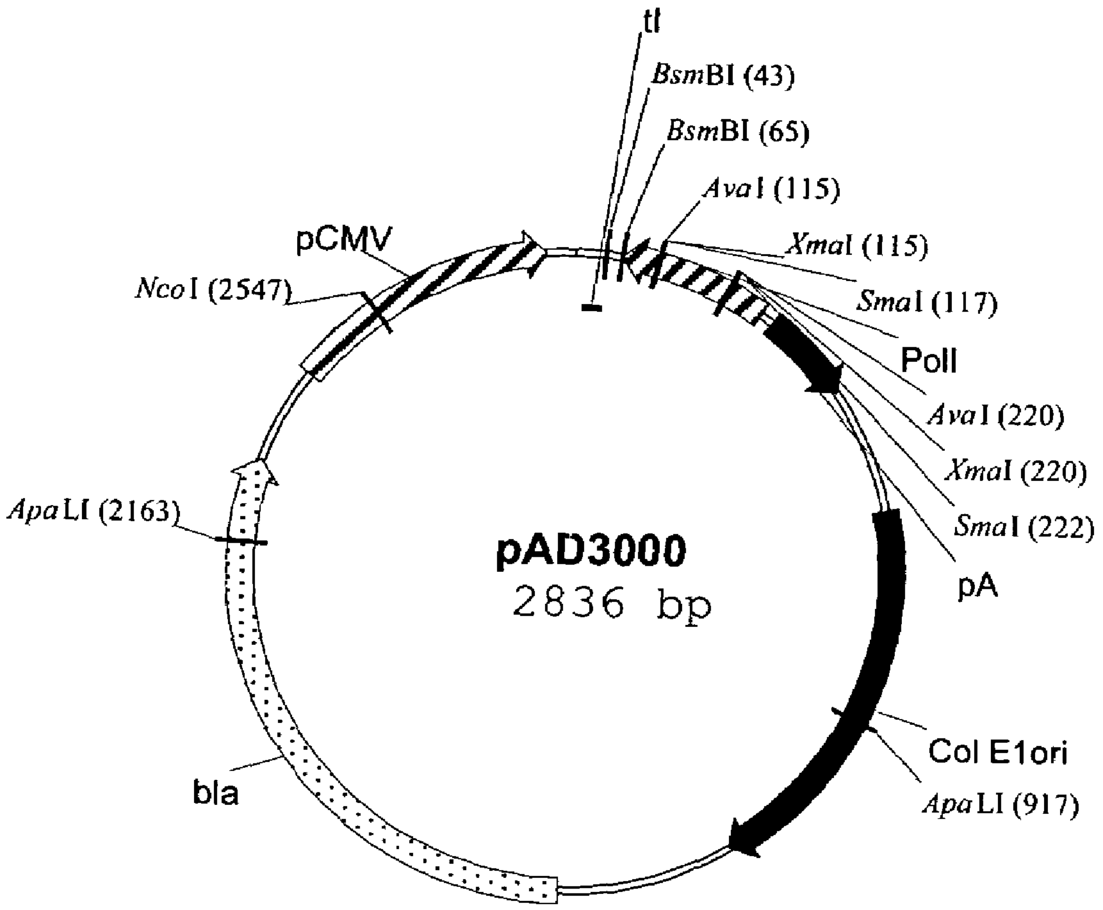
FIG. 1: Illustration of pAD3000 plasmid (SEQ ID NO: 94).

Many pathogenic influenza virus strains grow only poorly in tissue culture, and strains suitable for production of live attenuated virus vaccines (e.g., temperature sensitive, cold adapted and/or attenuated influenza viruses) have not been successfully grown in cultured cells for commercial production. The present invention provides a multi-plasmid transfection system which permits the growth and recovery of influenza virus strains which are not adapted for growth under standard cell culture conditions. An additional challenge in developing and producing influenza vaccines is that one or more of the circulating influenza strains may not replicate well in embryonic chicken eggs. The present invention identifies several amino acid residues which influence the activities of the HA and NA proteins and have identified specific amino acid substitutions which can modulate these activities. The present invention discloses that modulation of the HA receptor binding activity and/or the NA neuramimidase activity can enhance the replication of influenza in eggs and/or host cells (e.g., Vero or MDCK cells). Specifically the present invention discloses combinations of amino acid substitutions in HA and/or NA can enhance viral replication in eggs and/or cells and demonstrates that these amino acid substitutions have no significant impact on antigenicity of these recombinant influenza viruses. Thus, the present invention provides for the use of reverse genetic technology to improve the manufacture of influenza virus vaccines.

In a first aspect, the methods of the invention provide vectors and methods for producing recombinant influenza B virus in cell culture entirely from cloned viral DNA. In another aspect, the methods of the present invention are based in part on the development of tissue culture conditions which support the growth of virus strains (both A strain and B strain influenza viruses) with desirable properties relative to vaccine production (e.g., attenuated pathogenicity or phenotype, cold adaptation, temperature sensitivity, etc.) in vitro in cultured cells. Influenza viruses are produced by introducing a plurality of vectors incorporating cloned viral genome segments into host cells, and culturing the cells at a temperature not exceeding 35° C. When vectors including an influenza virus genome are transfected, recombinant viruses suitable as vaccines can be recovered by standard purification procedures. Using the vector system and methods of the invention, reassortant viruses incorporating the six internal gene segments of a strain selected for its desirable properties with respect to vaccine production, and the immunogenic HA and NA segments from a selected, e.g., pathogenic strain, can be rapidly and efficiently produced in tissue culture. Thus, the system and methods described herein are useful for the rapid production in cell culture of recombinant and reassortant influenza A and B viruses, including viruses suitable for use as vaccines, including live attenuated vaccines, such as vaccines suitable for intranasal administration.

Typically, a single Master Donor Virus (MDV) strain is selected for each of the A and B subtypes. In the case of a live attenuated vaccine, the Master Donor Virus strain is typically chosen for its favorable properties, e.g., temperature sensitivity, cold adaptation and/or attenuation, relative to vaccine production. For example, exemplary Master Donor Strains include such temperature sensitive, attenuated and cold adapted strains of A/Ann Arbor/6/60 and B/Ann Arbor/1/66, respectively. The present invention elucidates the underlying mutations resulting in the ca, ts and att phenotypes of these virus strains, and provides methods for producing novel strains of influenza suitable for use as donor strains in the context of recombinant and reassortant vaccine production.

For example, a selected master donor type A virus (MDV-A), or master donor type B virus (MDV-B), is produced from a plurality of cloned viral cDNAs constituting the viral genome. In an exemplary embodiment, recombinant viruses are produced from eight cloned viral cDNAs. Eight viral cDNAs representing either the selected MDV-A or MDV-B sequences of PB2, PB1, PA, NP, HA, NA, M and NS are cloned into a bi-directional expression vector, such as a plasmid (e.g., pAD3000), such that the viral genomic RNA can be transcribed from an RNA polymerase I (pol I) promoter from one strand and the viral mRNAs can be synthesized from an RNA polymerase II (pol II) promoter from the other strand. Optionally, any gene segment can be modified, including the HA segment (e.g., to remove the multi-basic cleavage site).

Infectious recombinant MDV-A or MDV-B virus is then recovered following transfection of plasmids bearing the eight viral cDNAs into appropriate host cells, e.g., Vero cells, co-cultured MDCK/293T or MDCK/COS7 cells. Using the plasmids and methods described herein, the invention is useful, e.g., for generating 6:2 reassortant influenza vaccines by co-transfection of the 6 internal genes (PB1, PB2, PA, NP, M and NS) of the selected virus (e.g., MDV-A, MDV-B) together with the HA and NA derived from different corresponding type (A or B) influenza viruses. For example, the HA segment is favorably selected from a pathogenically relevant H1, H3 or B strain, as is routinely performed for vaccine production. Similarly, the HA segment can be selected from a strain with emerging relevance as a pathogenic strain such as an H2 strain (e.g., H2N2), an H5 strain (e.g., H5N1) or an H7 strain (e.g., H7N7). Reassortants incorporating seven genome segments of the MDV and either the HA or NA gene of a selected strain (7:1 reassortants) can also be produced. In addition, this system is useful for determining the molecular basis of phenotypic characteristics, e.g., the attenuated (att), cold adapted (ca), and temperature sensitive (ts) phenotypes, relevant to vaccine production.

In another aspect the invention provides methods for manipulating the amino acid residues of HA and/or NA to increase the ability of an influenza virus to replicate in embryonated chicken eggs and/or cells. For example, the methods of the present invention can be use to modulate HA receptor binding activity and/or NA neuramimidase activity to increase the ability of an influenza virus to replicate in eggs and/or cells. Additionally, the invention provides influenza viruses with enhanced ability to replicate in embryonated chicken eggs and/or cells.

Definitions

Unless defined otherwise, all scientific and technical terms are understood to have the same meaning as commonly used in the art to which they pertain. For the purpose of the present invention the following terms are defined below.

The terms "nucleic acid," "polynucleotide," "polynucleotide sequence" and "nucleic acid sequence" refer to single-stranded or double-stranded deoxyribonucleotide or ribonucleotide polymers, or chimeras or analogues thereof. As used herein, the term optionally includes polymers of analogs of naturally occurring nucleotides having the essential nature of natural nucleotides in that they hybridize to single-stranded nucleic acids in a manner similar to naturally occurring nucleotides (e.g., peptide nucleic acids). Unless otherwise indicated, a particular nucleic acid sequence of this invention encompasses complementary sequences, in addition to the sequence explicitly indicated.

The term "gene" is used broadly to refer to any nucleic acid associated with a biological function. Thus, genes include coding sequences and/or the regulatory sequences required for their expression. The term "gene" applies to a specific genomic sequence, as well as to a cDNA or an mRNA encoded by that genomic sequence.

Genes also include non-expressed nucleic acid segments that, for example, form recognition sequences for other proteins. Non-expressed regulatory sequences include "promoters" and "enhancers," to which regulatory proteins such as transcription factors bind, resulting in transcription of adjacent or nearby sequences. A "Tissue specific" promoter or enhancer is one which regulates transcription in a specific tissue type or cell type, or types.

The term "vector" refers to the means by which a nucleic can be propagated and/or transferred between organisms, cells, or cellular components. Vectors include plasmids, viruses, bacteriophage, pro-viruses, phagemids, transposons, and artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that are not autonomously replicating. Most commonly, the vectors of the present invention are plasmids.

An "expression vector" is a vector, such as a plasmid, which is capable of promoting expression, as well as replication of a nucleic acid incorporated therein. Typically, the nucleic acid to be expressed is "operably linked" to a promoter and/or enhancer, and is subject to transcription regulatory control by the promoter and/or enhancer.

A "bi-directional expression vector" is typically characterized by two alternative promoters oriented in the opposite direction relative to a nucleic acid situated between the two promoters, such that expression can be initiated in both orientations resulting in, e.g., transcription of both plus (+) or sense strand, and negative (−) or antisense strand RNAs. Alternatively, the bi-directional expression vector can be an ambisense vector, in which the viral mRNA and viral genomic RNA (as a cRNA) are expressed from the same strand.

In the context of the invention, the term "isolated" refers to a biological material, such as a nucleic acid or a protein, which is substantially free from components that normally accompany or interact with it in its naturally occurring environment. The isolated material optionally comprises material not found with the material in its natural environment, e.g., a cell. For example, if the material is in its natural environment, such as a cell, the material has been placed at a location in the cell (e.g., genome or genetic element) not native to a material found in that environment. For example, a naturally occurring nucleic acid (e.g., a coding sequence, a promoter, an enhancer, etc.) becomes isolated if it is introduced by non-naturally occurring means to a locus of the genome (e.g., a vector, such as a plasmid or virus vector, or amplicon) not native to that nucleic acid. Such nucleic acids are also referred to as "heterologous" nucleic acids.

The term "recombinant" indicates that the material (e.g., a nucleic acid or protein) has been artificially or synthetically (non-naturally) altered by human intervention. The alteration can be performed on the material within, or removed from, its natural environment or state. Specifically, when referring to a virus, e.g., an influenza virus, the virus is recombinant when it is produced by the expression of a recombinant nucleic acid.

The term "reassortant," when referring to a virus, indicates that the virus includes genetic and/or polypeptide components derived from more than one parental viral strain or source. For example, a 7:1 reassortant includes 7 viral genomic segments (or gene segments) derived from a first parental virus, and a single complementary viral genomic segment, e.g., encoding hemagglutinin or neuramimidase, from a second parental virus. A 6:2 reassortant includes 6 genomic segments, most commonly the 6 internal genes from a first parental virus, and two complementary segments, e.g., hemagglutinin and neuramimidase, from a different parental virus.

The term "introduced" when referring to a heterologous or isolated nucleic acid refers to the incorporation of a nucleic acid into a eukaryotic or prokaryotic cell where the nucleic acid can be incorporated into the genome of the cell (e.g., chromosome, plasmid, plastid or mitochondrial DNA), converted into an autonomous replicon, or transiently expressed (e.g., transfected mRNA). The term includes such methods as "infection," "transfection," "transformation" and "transduction." In the context of the invention a variety of methods can be employed to introduce nucleic acids into prokaryotic cells, including electroporation, Calcium phosphate precipitation, lipid mediated transfection (lipofection), etc.

The term "host cell" means a cell which contains a heterologous nucleic acid, such as a vector, and supports the replication and/or expression of the nucleic acid, and optionally production of one or more encoded products including a polypeptide and/or a virus. Host cells can be prokaryotic cells such as *E. coli*, or eukaryotic cells such as yeast, insect, amphibian, avian or mammalian cells, including human cells. Exemplary host cells in the context of the invention include Vero (African green monkey kidney) cells, Per.C6 cells (human embryonic retinal cells), BHK (baby hamster kidney) cells, primary chick kidney (PCK) cells, Madin-Darby Canine Kidney (MDCK) cells, Madin-Darby Bovine Kidney (MDBK) cells, 293 cells (e.g., 293T cells), and COS cells (e.g., COS1, COS7 cells). The term host cell encompasses combinations or mixtures of cells including, e.g., mixed cultures of different cell types or cell lines (e.g., Vero and CEK cells). A co-cultivation of electroporated sf vero cells is described for example in PCT/US04/42669 filed Dec. 22, 2004, which is incorporated by reference in their entirety.

The terms "temperature sensitive," "cold adapted" and "attenuated" are well known in the art. For example, the term "temperature sensitive" ("ts") indicates that the virus exhibits a 100 fold or greater reduction in titer at 39° C. relative to 33° C. for influenza A strains, and that the virus exhibits a 100 fold or greater reduction in titer at 37° C. relative to 33° C. for influenza B strains. For example, the term "cold adapted" ("ca") indicates that the virus exhibits growth at 25° C. within 100 fold of its growth at 33° C. For example, the term "attenuated" ("att") indicates that the virus replicates in the upper airways of ferrets but is not detectable in lung tissues, and does not cause influenza-like illness in the animal. It will be understood that viruses with intermediate phenotypes, i.e., viruses exhibiting titer reductions less than 100 fold at 39° C. (for A strain viruses) or 37° C. (for B strain viruses), exhibiting growth at 25° C. that is more than 100 fold than its growth at 33° C. (e.g., within 200 fold, 500 fold, 1000 fold, 10,000 fold less), and/or exhibit reduced growth in the lungs relative to growth in the upper airways of ferrets (i.e., partially attenuated) and/or reduced influenza like illness in the animal, which possess one or more of the amino acid substitutions described herein are also useful viruses encompassed by the invention. Growth indicates viral quantity as indicated by titer, plaque size or morphology, particle density or other measures known to those of skill in the art.

The expression "artificially engineered" is used herein to indicate that the virus, viral nucleic acid or virally encoded product, e.g., a polypeptide, a vaccine, comprises at least one mutation introduced by recombinant methods, e.g., site directed mutagenesis, PCR mutagenesis, etc. The expression "artificially engineered" when referring to a virus (or viral component or product) comprising one or more nucleotide mutations and/or amino acid substitutions indicates that the viral genome or genome segment encoding the virus (or viral component or product) is not derived from naturally occurring sources, such as a naturally occurring or previously existing laboratory strain of virus produced by non-recombinant methods (such as progressive passage at 25° C.), e.g., a wild type or cold adapted A/Ann Arbor/6/60 or B/Ann Arbor/1/66 strain.

Influenza Virus

The genome of Influenza viruses is composed of eight segments of linear (−) strand ribonucleic acid (RNA), encoding the immunogenic hemagglutinin (HA) and neuramimidase (NA) proteins, and six internal core polypeptides: the nucleocapsid nucleoprotein (NP); matrix proteins (M); non-structural proteins (NS); and 3 RNA polymerase (PA, PB1, PB2) proteins. During replication, the genomic viral RNA is transcribed into (+) strand messenger RNA and (−) strand genomic cRNA in the nucleus of the host cell. Each of the eight genomic segments is packaged into ribonucleoprotein complexes that contain, in addition to the RNA, NP and a polymerase complex (PB1, PB2, and PA).

In the present invention, viral genomic RNA corresponding to each of the eight segments is inserted into a recombinant vector for manipulation and production of influenza viruses. A variety of vectors, including viral vectors, plasmids, cosmids, phage, and artificial chromosomes, can be employed in the context of the invention. Typically, for ease of manipulation, the viral genomic segments are inserted into a plasmid vector, providing one or more origins of replication functional in bacterial and eukaryotic cells, and, optionally, a marker convenient for screening or selecting cells incorporating the plasmid sequence. An exemplary vector, plasmid pAD3000 is illustrated in FIG. 1.

Most commonly, the plasmid vectors of the invention are bi-directional expression vectors capable of initiating transcription of the inserted viral genomic segment in either direction, that is, giving rise to both (+) strand and (−) strand viral RNA molecules. To effect bi-directional transcription, each of the viral genomic segments is inserted into a vector having at least two independent promoters, such that copies of viral genomic RNA are transcribed by a first RNA polymerase promoter (e.g., Pol I), from one strand, and viral mRNAs are synthesized from a second RNA polymerase promoter (e.g., Pol II). Accordingly, the two promoters are arranged in opposite orientations flanking at least one cloning site (i.e., a restriction enzyme recognition sequence) preferably a unique cloning site, suitable for insertion of viral genomic RNA segments. Alternatively, an "ambisense" vector can be employed in which the (+) strand mRNA and the (−) strand viral RNA (as a cRNA) are transcribed from the same strand of the vector.

Expression Vectors

The influenza virus genome segment to be expressed is operably linked to an appropriate transcription control sequence (promoter) to direct mRNA synthesis. A variety of promoters are suitable for use in expression vectors for regulating transcription of influenza virus genome segments. In certain embodiments, e.g., wherein the vector is the plasmid pAD3000, the cytomegalovirus (CMV) DNA dependent RNA Polymerase II (Pol II) promoter is utilized. If desired, e.g., for regulating conditional expression, other promoters can be substituted which induce RNA transcription under the specified conditions, or in the specified tissues or cells. Numerous viral and mammalian, e.g., human promoters are available, or can be isolated according to the specific application contemplated. For example, alternative promoters obtained from the genomes of animal and human viruses include such promoters as the adenovirus (such as Adenovirus 2), papilloma virus, hepatitis-B virus, polyoma virus, and Simian Virus 40 (SV40), and various retroviral promoters. Mammalian promoters include, among many others, the actin promoter, immunoglobulin promoters, heat-shock promoters, and the like. In addition, bacteriophage promoters can be employed in conjunction with the cognate RNA polymerase, e.g., the T7 promoter.

Transcription is optionally increased by including an enhancer sequence. Enhancers are typically short, e.g., 10-500 bp, cis-acting DNA elements that act in concert with a promoter to increase transcription. Many enhancer sequences have been isolated from mammalian genes (hemoglobin, elastase, albumin, alpha.-fetoprotein, and insulin), and eukaryotic cell viruses. The enhancer can be spliced into the vector at a position 5' or 3' to the heterologous coding sequence, but is typically inserted at a site 5' to the promoter. Typically, the promoter, and if desired, additional transcription enhancing sequences are chosen to optimize expression in the host cell type into which the heterologous DNA is to be introduced (Scharf et al. (1994) *Heat stress promoters and transcription factors Results Probl Cell Differ* 20:125-62; Kriegler et al. (1990) *Assembly of enhancers, promoters, and splice signals to control expression of transferred genes Methods in Enzymol* 185: 512-27). Optionally, the amplicon can also contain a ribosome binding site or an internal ribosome entry site (IRES) for translation initiation.

The vectors of the invention also favorably include sequences necessary for the termination of transcription and for stabilizing the mRNA, such as a polyadenylation site or a terminator sequence. Such sequences are commonly available from the 5' and, occasionally 3', untranslated regions of eukaryotic or viral DNAs or cDNAs. In one embodiment, e.g., involving the plasmid pAD3000, the SV40 polyadenylation sequences provide a polyadenylation signal.

In addition, as described above, the expression vectors optionally include one or more selectable marker genes to provide a phenotypic trait for selection of transformed host cells, in addition to genes previously listed, markers such as dihydrofolate reductase or neomycin resistance are suitable for selection in eukaryotic cell culture.

The vector containing the appropriate DNA sequence as described above, as well as an appropriate promoter or control sequence, can be employed to transform a host cell permitting expression of the protein. While the vectors of the invention can be replicated in bacterial cells, most frequently it will be desirable to introduce them into mammalian cells, e.g., Vero cells, BHK cells, MDCK cell, 293 cells, COS cells, for the purpose of expression.

Additional Expression Elements

Most commonly, the genome segment encoding the influenza virus protein includes any additional sequences necessary for its expression, including translation into a functional viral protein. In other situations, a minigene, or other artificial construct encoding the viral proteins, e.g., an HA or NA protein, can be employed. In this case, it is often desirable to include specific initiation signals which aid in the efficient translation of the heterologous coding sequence. These signals can include, e.g., the ATG initiation codon and adjacent sequences. To insure translation of the entire insert, the initiation codon is inserted in the correct reading frame relative to the viral protein. Exogenous transcriptional elements and initiation codons can be of various origins, both natural and synthetic. The efficiency of expression can be enhanced by the inclusion of enhancers appropriate to the cell system in use.

If desired, polynucleotide sequences encoding additional expressed elements, such as signal sequences, secretion or localization sequences, and the like can be incorporated into the vector, usually, in-frame with the polynucleotide sequence of interest, e.g., to target polypeptide expression to a desired cellular compartment, membrane, or organelle, or into the cell culture media. Such sequences are known to those of skill, and include secretion leader peptides, organelle targeting sequences (e.g., nuclear localization sequences, ER retention signals, mitochondrial transit sequences), membrane localization/anchor sequences (e.g., stop transfer sequences, GPI anchor sequences), and the like.

Influenza Virus Vaccine

Historically, influenza virus vaccines have been produced in embryonated hens' eggs using strains of virus selected based on empirical predictions of relevant strains. More recently, reassortant viruses have been produced that incorporate selected hemagglutinin and neuramimidase antigens in the context of an approved attenuated, temperature sensitive master strain. Following culture of the virus through multiple passages in hens' eggs, influenza viruses are recovered and, optionally, inactivated, e.g., using formaldehyde and/or β-propiolactone. However, production of influenza vaccine in this manner has several significant drawbacks. Contaminants remaining from the hens' eggs are highly antigenic, pyrogenic, and frequently result in significant side effects upon administration. More importantly, strains designated for production must be selected and distributed, typically months in advance of the next flu season to allow time for production and inactivation of influenza vaccine. Attempts at producing recombinant and reassortant vaccines in cell culture have been hampered by the inability of any of the strains approved for vaccine production to grow efficiently under standard cell culture conditions.

The present invention provides a vector system, and methods for producing recombinant and reassortant viruses in culture which make it possible to rapidly produce vaccines corresponding to one or many selected antigenic strains of virus. In particular, conditions and strains are provided that result in efficient production of viruses from a multi plasmid system in cell culture. Optionally, if desired, the viruses can be further amplified in Hens' eggs.

For example, it has not been possible to grow the influenza B master strain B/Ann Arbor/1/66 under standard cell culture conditions, e.g., at 37° C. In the methods of the present invention, multiple plasmids, each incorporating a segment of an influenza virus genome are introduced into suitable cells, and maintained in culture at a temperature less than or equal to 35° C. Typically, the cultures are maintained at between about 32° C. and 35° C., preferably between about 32° C. and about 34° C., e.g., at about 33° C.

Typically, the cultures are maintained in a system, such as a cell culture incubator, under controlled humidity and $CO_2$, at constant temperature using a temperature regulator, such as a thermostat to insure that the temperature does not exceed 35° C.

Reassortant influenza viruses can be readily obtained by introducing a subset of vectors corresponding to genomic segments of a master influenza virus, in combination with complementary segments derived from strains of interest (e.g., antigenic variants of interest). Typically, the master strains are selected on the basis of desirable properties relevant to vaccine administration. For example, for vaccine production, e.g., for production of a live attenuated vaccine, the master donor virus strain may be selected for an attenuated phenotype, cold adaptation and/or temperature sensitivity. In this context, Influenza A strain ca A/Ann Arbor/6/60; Influenza B strain ca B/Ann Arbor/1/66; or another strain selected for its desirable phenotypic properties, e.g., an attenuated, cold adapted, and/or temperature sensitive strain, such as an artificially engineered influenza A strain as described in Example 4; or an artificially engineered influenza B strain incorporating one or more of the amino acid substitutions specified in Table 17 are favorably selected as master donor strains.

In one embodiment, plasmids incorporating the six internal genes of the influenza master virus strain, (i.e., PB1, PB2, PA, NP, NB, M1, BM2, NS1 and NS2) are transfected into suitable host cells in combination with hemagglutinin and neuramimidase segments from an antigenically desirable strain, e.g., a strain predicted to cause significant local or global influenza infection. Following replication of the reassortant virus in cell culture at appropriate temperatures for efficient recovery, e.g., equal to or less than 35° C., such as between about 32° C. and 35° C., for example between about 32° C. and about 34° C., or at about 33° C., reassortant viruses is recovered. Optionally, the recovered virus can be inactivated using a denaturing agent such as formaldehyde or β-propiolactone.

Attenuated, Temperature Sensitive and Cold Adapted Influenza Virus Vaccines

In one aspect, the present invention is based on the determination of the mutations underlying the ts phenotype in preferred Master Donor Strains of virus. To determine the functional importance of single nucleotide changes in the MDV strain genome, reassortant viruses derived from highly related strains within the A/AA/6/60 lineage were evaluated for temperature sensitivity. The isogenic nature of the two parental strains enables the evaluation of single nucleotide changes on the ts phenotype. Accordingly, the genetic basis for the ts phenotype of MDV-A is mapped at the nucleotide level to specific amino acid residues within PB1, PB2, and NP.

Previous attempts to map the genetic basis of the ts phenotype of ca A/AA/6/60 utilized classical coinfection/reassortant techniques to create single and multiple gene reassortants between A/AA/6/60 and an unrelated wt strain. These studies suggested that both PB2, and PB1 contributed to the ts phenotype (Kendal et al. (1978) *Biochemical characteristics of recombinant viruses derived at sub-optimal temperatures: evidence that ts lesions are present in RNA segments* 1 *and* 3, *and that RNA* 1 *codes for the virion transcriptase enzyme, p.* 734-743. In B. W. J. Mahy, and R. D. Barry (ed.) *Negative Strand Viruses*, Academic Press; Kendal et al. (1977) *Comparative studies of wild-type and cold mutant (temperature sensitive) influenza viruses: genealogy of the matrix (M) and the non-structural (NS) proteins in recombinant cold-adapted H3N2 viruses J Gen Virol* 37:145-159; Kendal et al. (1979) *Comparative studies of wild-type and cold-mutant (temperature sensitive) influenza viruses: independent segregation of temperature-sensitivity of virus replication from temperature-sensitivity of virion transcriptase activity during recombination of mutant A/Ann Arbor/*6/60 *with wild-type H3N2 strains J Gen Virol* 44:4434-560; Snyder et al. (1988) *Four viral genes independently contribute to attenuation of live influenza A/Ann Arbor/*6/60 *(H2N2) cold-adapted reassortant vines vaccines J Virol* 62:488-95). Interpretation of these studies, however, was confounded by constellation effects, which were caused by mixing gene segments from two divergent influenza A strains. Weakened interactions could have occurred through changes between the A/AA/6/60 and wt gene segments other than those specifically involved in expression of the ts phenotype from the A/AA/6/60 background. Constellation effects were also shown to confound the interpretation of association of the M gene segment with the att phenotype (Subbarao et al. (1992) *The attenuation phenotype conferred by the M gene of the influenza A/Ann Arbor/*6/60 *cold-adapted virus (H2N2) on the A/Korea/*82 *(H3N2) reassortant vines results from a gene constellation effect Virus Res* 25:37-50).

In the present invention, mutations resulting in amino acid substitutions at positions $PB1^{391}$, $PB1^{581}$, $PB1^{661}$, $PB2^{265}$ and $NP^{34}$ are identified as functionally important in conferring the temperature sensitive phenotype on the MDV-A strain virus. As will be understood by those of skill in the art, mutations in nucleotides at positions $PB1^{1195}$, $PB1^{1766}$, $PB1^{2005}$, $PB2^{821}$ and $NP^{146}$ designate amino acid substitutions at $PB1^{391}$, $PB1^{581}$, $PB1^{661}$, $PB2^{265}$ and $NP^{34}$, respectively. Thus, any nucleotide substitutions resulting in substituted amino acids at these positions are a feature of the invention. Exemplary mutations $PB1^{391}$ (K391E), $PB1^{581}$ (E581G), $PB1^{661}$ (A661T), $PB2^{265}$ (N265S) and $NP^{34}$ (D34G), singly, and more preferably in combination, result in a temperature sensitive phenotype. Simultaneous reversion of these mutations to wild type abolishes the ts phenotype, while introduction of these mutations onto a wild-type background results in virus with a ts phenotype. Consistent with the stability of these phenotypes during passage of the virus, no single change can individually revert the temperature sensitivity profile of the resulting virus to that of wild-type. Rather, these changes appear to act in concert with one another to fully express the ts phenotype. This discovery permits the engineering of additional strains of temperature sensitive influenza A virus suitable for master donor viruses for the production of live attenuated influenza vaccines.

Similarly, substitutions of individual amino acids in a Master Donor Virus-B strain are correlated with the ts phenotype as illustrated in Table 17. Thus, the methods presented herein are adapted to producing novel influenza B strains with temperature sensitive, and optionally attenuated and/or cold adapted phenotypes by introducing one or more specified mutations into an influenza B genome. For example, one or more mutations resulting in an amino acid substitution at a position selected from among $PB2^{630}$; $PA^{431}$; $PA^{497}$; $NP^{55}$; $NP^{114}$; $NP^{410}$; NP509; $M1^{159}$ and $M1^{183}$ are introduced into an influenza B strain genome to produce a temperature sensitive influenza B virus. Exemplary amino acid substitutions include the following: $PB2^{630}$ (S630R); $PA^{431}$ (V431M); $PA^{497}$ (Y497H); $NP^{55}$ (T55A); $NP^{114}$ (V114A); $NP^{410}$ (P410H); $NP^{509}$ (A509T); $M1^{159}$ (H159Q) and $M1^{183}$ (M183V).

Influenza viruses incorporating the mutations of the invention are a feature of the invention regardless of the method in which they are produced. That is, the invention encompasses influenza strains including the mutations of the invention, e.g., any influenza A virus with an amino acid substitution relative to wild type at one or more positions selected from among: $PB1^{391}$, $PB1^{581}$, $PB1^{661}$, $PB2^{265}$ and $NP^{34}$ or any influenza B virus with an amino acid substitution relative to wild type at one or more positions selected from among: $PB2^{630}$; $PA^{431}$; $PA^{497}$; $NP^{55}$; $NP^{114}$; $NP^{410}$; NP509; $M1^{159}$ and $M1^{183}$, with the proviso that the strains ca A/Ann Arbor/6/60 and B/Ann Arbor/1/66 are not considered a feature of the present invention. In certain preferred embodiments, the influenza A viruses include a plurality of mutations (e.g., two, or three, or four, or five, or more mutations) selected from among $PB1^{391}$ (K391E), $PB1^{581}$ (E581G), $PB1^{661}$ (A661T), $PB2^{265}$ (N265S) and $NP^{34}$ (D34G); and the influenza B viruses include a plurality of mutations selected from among $PB2^{630}$ (S630R); $PA^{431}$ (V431M); $PA^{497}$ (Y497H); $NP^{55}$ (T55A); $NP^{114}$ (V114A); $NP^{410}$ (P410H); NP509 (A509T); $M1^{158}$ (H159Q) and $M1^{183}$ (M183V), respectively. For example, in addition to providing viruses with desired phenotypes relevant for vaccine production, viruses with a subset of mutations, e.g., 1, or 2, or 3, or 4, or 5 selected mutations, are useful in elucidating the contribution of additional mutations to the phenotype of the virus. In certain embodiments, the influenza viruses include at least one additional non-wild type nucleotide (e.g., possibly resulting in an additional amino acid substitution), which optionally refines the desired phenotype or confers a further desirable phenotypic attribute.

Enhanced Viral Replication

The present invention also provides a method of introducing of at least one amino acid residue substitution in HA and/or NA to increase the ability of an influenza virus to replicate in embryonated chicken eggs and/or host cells. The invention further provides influenza virus variants with increased ability to replicate in embryonated chicken eggs and/or host cells (referred to herein as "replication enhanced variants") when compared to HA and/or NA unsubstituted influenza virus. It is specifically contemplated that the method of the invention can be utilized to enhance the replication of an influenza virus in a host cell and that replication enhanced variants may have enhanced replication in chicken eggs and/or host cells. Suitable host cells for the replication of influenza virus include, e.g., Vero cells, Per.C6 cells, BHK cells, MDCK cells, 293 cells and COS cells, including 293T cells, COS7 cells.

In one embodiment, the method of the invention introduces at least one amino acid substitution into HA and/or NA which will enhance the ability of an influenza virus to replicate in eggs and/or host cells by at least 10%, or by at least 20%, or by at least 30%, or by at least 40%, or by at least 50%, or by at least 60%, or by at least 70%, or by at least 80%, or by at least 90%, or by at least 100%, or by at least 200%, or by at least 300%, or by at least 400%, or by at least 500% when compared to the unmodified influenza virus. It is specifically contemplated that amino acid substitutions may be made in both HA and NA. Preferably, the method of the invention does not significantly alter the antigenicity of the substituted influenza virus when compared to the unsubstituted virus. In a specific embodiment, the method of the invention reduces the antigenicity of the substituted influenza virus when compared to the unsubstituted virus by less then 10%, or by less then 20%, or by less then 30%, or by less then 40%, or by less then 50%, or by less then 60%, or by less then 70%, or by less then 80%, or by less then 90%, or by less then 100%. Methods to determine viral antigenicity are well known in the art (also see, "Example 11" supra).

In one embodiment, the method of the invention further incorporates an attenuated influenza virus, a cold adapted influenza virus, a temperature sensitive influenza virus, or a virus with any combination of these desirable properties. Preferably, the viruses incorporated by the method of the invention include but are not limited to, influenza B/Ann Arbor/1/66 strain virus, influenza A/Ann Arbor/6/60 strain virus. In another embodiment, the method of the invention introduces vectors including the six internal genes of a viral strain selected for its favorable properties regarding vaccine production, in combination with the genome segments encoding the desired manipulated HA and NA surface antigens to produce influenza viruses with enhanced ability to replicate in embryonated chicken eggs and/or host cells (see, supra and "Example 11"). In another embodiment, the method of the invention further incorporates a non-attenuated influenza virus.

In one embodiment, the method of the invention introduces at least one amino acid substitution which modulates the receptor binding activity of HA. Receptor binding activity of HA includes but is not limited to the binding of HA to sialic acid residues (e.g., 2,6-linked sialyl-galactosyl moieties [Siaα(2,6)Gal] and 2,3-linked sialyl-galactosyl moieties [Siaα(2,3)Gal]) present on the cell surface glycoproteins or glycolipids. One method to assay HA binding is presented in "Example 11" (infra), other methods are well known in the art. In another embodiment, the method of the invention introduces amino acid substitutions which modulate the receptor binding specificity of HA for [Siaα(2,6)Gal] and/or [Siaα(2,3)Gal] moieties. Preferably, the method will enhance the binding of HA to [Siaα(2,3)Gal] moieties.

In a one embodiment, the method of the invention introduces at least one amino acid substitution which enhances the receptor binding activity of HA. Preferably, the receptor binding activity is increased by at least 10%, or by at least 20%, or by at least 30%, or by at least 40%, or by at least 50%, or by at least 60%, or by at least 70%, or by at least 80%, or by at least 90%, or by at least 100%, or by at least 200%.

In a another embodiment, the method of the invention introduces at least one amino acid substitution which reduces the receptor binding activity of HA. Preferably, the receptor binding activity is reduced by at least 10%, or by at least 20%, or by at least 30%, or by at least 40%, or by at least 50%, or by at least 60%, or by at least 70%, or by at least 80%, or by at least 90%, or by at least 100%, or by at least 200%.

In a preferred embodiment, the method introduces at least one amino acid substitution in HA at positions 183, 186 and/or 226. Preferably, amino acid substitutions are made at positions 183 and 226 or at positions 186 and 226. Most preferably, amino acid substitutions are made such that position 183 is a leucine and position 226 is an alanine or such that position 186 is a valine and position 226 is an isoleucine.

In one embodiment, the method of the invention introduces at least one amino acid substitution which modulate the neuramimidase activity of NA. Neuramimidase activity of NA includes but is not limited to, the hydrolysis of substrates which contain alpha-ketosidically linked N-acetylneuraminic acid (Neu5Ac). Methods to determine the neuramimidase activity are well known in the art (see also, "Example 11" infra).

In a one embodiment, the method of the invention introduces at least one amino acid substitution which enhances the neuramimidase activity of NA. Preferably, the receptor binding activity is increased by at least 10%, or by at least 20%, or by at least 30%, or by at least 40%, or by at least 50%, or by at least 60%, or by at least 70%, or by at least 80%, or by at least 90%, or by at least 100%, or by at least 200%.

In a another embodiment, the method of the invention introduces at least one amino acid substitution which reduces the neuramimidase activity of NA. Preferably, the neuramimidase activity is reduced by at least 10%, or by at least 20%, or by at least 30%, or by at least 40%, or by at least 50%, or by at least 60%, or by at least 70%, or by at least 80%, or by at least 90%, or by at least 100%, or by at least 200%.

In a preferred embodiment, the method introduces at least one amino acid substitution in NA at positions 119 and/or 136. Preferably, amino acid substitutions are made such that position 119 is a is a glutamate and position 136 is a glutamine.

One skilled in the art would appreciate that in some cases the HA and/or NA protein will already have the preferred amino acid residues at one or more of the aforementioned positions. In this situation, substitution(s) will only be introduced at the remaining non-matching positions.

It is specifically contemplated that conservative amino acid substitutions may be made for said amino acid substitutions at positions 183, 186 and/or 226 of HA and positions 119 and/or 136 of NA, described supra.

It is well known in the art that "conservative amino acid substitution" refers to amino acid substitutions that substitute functionally-equivalent amino acids. Conservative amino acid changes result in silent changes in the amino acid sequence of the resulting peptide. For example, one or more amino acids of a similar polarity act as functional equivalents and result in a silent alteration within the amino acid sequence of the peptide. Substitutions that are charge neutral and which replace a residue with a smaller residue may also be considered "conservative substitutions" even if the residues are in different groups (e.g., replacement of phenylalanine with the smaller isoleucine). Families of amino acid residues having similar side chains have been defined in the art. Families of conservative amino acid substitutions include but are not limited to, non-polar (e.g., Trp, Phe, Met, Leu, Ile, Val, Ala, Pro), uncharged polar (e.g., Gly, Ser, Thr, Asn, Gln, Tyr, Cys), acidic/negatively charged (e.g., Asp, Glu), basic/positively charged (e.g., Arg, Lys, His), Beta-branched (e.g., Thr, Val, Ile), residues that influence chain orientation (e.g., Gly, Pro) and aromatic (e.g., Trp, Tyr, Phe, His). The term "conservative amino acid substitution" also refers to the use of amino acid analogs or variants. Guidance concerning how to make phenotypically silent amino acid substitutions is provided in Bowie et al., "Deciphering the Message in Protein Sequences: Tolerance to Amino Acid Substitutions," (1990, Science 247: 1306-10).

In one embodiment, the present invention provides modified influenza viruses, referred to herein as "replication enhanced influenza variant(s), which incorporate at least one amino acid substitution in HA and/or NA which enhances their replication in embryonated chicken eggs and/or host cells when compared to the unmodified influenza virus. Preferably, the ability of an replication enhanced influenza variant to replicate in eggs and/or host cells has been enhanced by at least 10%, or by at least 20%, or by at least 30%, or by at least 40%, or by at least 50%, or by at least 60%, or by at least 70%, or by at least 80%, or by at least 90%, or by at least 100%, or by at least 200%, or by at least 300%, or by at least 400%, or by at least 500% when compared to the unmodified influenza virus.

In certain embodiment, a replication enhanced influenza variant further incorporates an attenuated influenza virus, a cold adapted influenza virus, a temperature sensitive influenza virus, or a virus with any combination of these desirable properties. Preferably, the virus incorporated into a replication enhanced influenza variant includes but is not limited to, influenza B/Ann Arbor/1/66 strain virus, influenza A/Ann Arbor/6/60 strain virus. It is specifically contemplated that a replication enhanced influenza variant is produced by introducing vectors including the six internal genes of a viral strain selected for its favorable properties regarding vaccine production, in combination with the genome segments encoding the desired substituted HA and NA surface antigens (see, supra and "Example 11").

In one embodiment, a replication enhanced influenza variant incorporates at least one amino acid substitution in HA which modulates the receptor binding activity of HA (see supra). Preferably, the method will enhance the binding of HA to [Siaα(2,3)Gal] moieties.

In a specific embodiment, a replication enhanced influenza variant incorporates at least one amino acid substitution which enhances the receptor binding activity of HA. Preferably, the receptor binding activity is increased by at least 10%, or by at least 20%, or by at least 30%, or by at least 40%, or by at least 50%, or by at least 60%, or by at least 70%, or by at least 80%, or by at least 90%, or by at least 100%, or by at least 200%. It is specifically contemplated that an egg enhance influenza variant does not have significantly altered viral antigenicity when compared to the unsubstituted influenza virus. In a specific embodiment, a replication enhanced influenza variant has an antigenicity that is reduced by less then 10%, or by less then 20%, or by less then 30%, or by less then 40%, or by less then 50%, or by less then 60%, or by less then 70%, or by less then 80%, or by less then 90%, or by less then 100% when compared to the unsubstituted virus. Methods to determine viral antigenicity are well known in the art (also see, "Example 11" supra).

In another embodiment, a replication enhanced influenza variant incorporates incorporate at least one amino acid substitution which reduces the receptor binding activity of HA. Preferably, the receptor binding activity is reduced by at least 10%, or by at least 20%, or by at least 30%, or by at least 40%, or by at least 50%, or by at least 60%, or by at least 70%, or by at least 80%, or by at least 90%, or by at least 100%, or by at least 200%.

In a preferred embodiment, a replication enhanced influenza variant incorporates incorporate at least one amino acid substitution in HA at positions 183, 186 and/or 226. Preferably, amino acid substitutions are present at positions 183 and 226 or at positions 186 and 226. Most preferably, amino acid substitutions are present such that position 183 is a leucine and position 226 is an alanine or such that position 186 is a valine and position 226 is an isoleucine.

In one embodiment, a replication enhanced influenza variant incorporates at least one amino acid substitution which modulates the neuramimidase activity of NA (see supra).

In a one embodiment, a replication enhanced influenza variant incorporates at least one amino acid substitution which enhances the neuramimidase activity of NA. Preferably, the receptor binding activity is increased by at least 10%, or by at least 20%, or by at least 30%, or by at least 40%, or by at least 50%, or by at least 60%, or by at least 70%, or by at least 80%, or by at least 90%, or by at least 100%, or by at least 200%.

In a another embodiment, a replication enhanced influenza variant incorporates at least one amino acid substitution which reduces the neuramimidase activity of NA. Preferably, the neuramimidase activity is reduced by at least 10%, or by at least 20%, or by at least 30%, or by at least 40%, or by at least 50%, or by at least 60%, or by at least 70%, or by at least 80%, or by at least 90%, or by at least 100%, or by at least 200%.

In a preferred embodiment, a replication enhanced influenza variant incorporates at least one amino acid substitution in NA at positions 119 and/or 136. Preferably, amino acid substitutions are made such that position 119 is a is a glutamate and position 136 is a glutamine.

Cell Culture

Typically, propagation of the virus is accomplished in the media compositions in which the host cell is commonly cultured. Suitable host cells for the replication of influenza virus include, e.g., Vero cells, Per.C6 cells, BHK cells, MDCK cells, 293 cells and COS cells, including 293T cells, COS7 cells. Commonly, co-cultures including two of the above cell lines, e.g., MDCK cells and either 293T or COS cells are employed at a ratio, e.g., of 1:1, to improve replication efficiency. Typically, cells are cultured in a standard commercial culture medium, such as Dulbecco's modified Eagle's medium supplemented with serum (e.g., 10% fetal bovine serum), or in serum free medium, under controlled humidity and $CO_2$ concentration suitable for maintaining neutral buffered pH (e.g., at pH between 7.0 and 7.2). Optionally, the medium contains antibiotics to prevent bacterial growth, e.g., penicillin, streptomycin, etc., and/or additional nutrients, such as L-glutamine, sodium pyruvate, non-essential amino acids, additional supplements to promote favorable growth characteristics, e.g., trypsin, β-mercaptoethanol, and the like.

Procedures for maintaining mammalian cells in culture have been extensively reported, and are known to those of skill in the art. General protocols are provided, e.g., in Freshney (1983) *Culture of Animal Cells: Manual of Basic Technique*, Alan R. Liss, New York; Paul (1975) *Cell and Tissue Culture*, 5th ed., Livingston, Edinburgh; Adams (1980) *Laboratory Techniques in Biochemistry and Molecular Biology-Cell Culture for Biochemists*, Work and Burdon (eds.) Elsevier, Amsterdam. Additional details regarding tissue culture procedures of particular interest in the production of influenza virus in vitro include, e.g., Merten et al. (1996) *Production of influenza virus in cell cultures for vaccine preparation*. In Cohen and Shafferman (eds) *Novel Strategies in Design and Production of Vaccines*, which is incorporated herein in its entirety. Additionally, variations in such procedures adapted to the present invention are readily determined through routine experimentation.

Cells for production of influenza virus can be cultured in serum-containing or serum free medium. In some case, e.g., for the preparation of purified viruses, it is desirable to grow the host cells in serum free conditions. Cells can be cultured in small scale, e.g., less than 25 ml medium, culture tubes or flasks or in large flasks with agitation, in rotator bottles, or on microcarrier beads (e.g., DEAE-Dextran microcarrier beads, such as Dormacell, Pfeifer & Langen; Superbead, Flow Laboratories; styrene copolymer-tri-methylamine beads, such as Hillex, SoloHill, Ann Arbor) in flasks, bottles or reactor cultures. Microcarrier beads are small spheres (in the range of 100-200 microns in diameter) that provide a large surface area for adherent cell growth per volume of cell culture. For example a single liter of medium can include more than 20 million microcarrier beads providing greater than 8000 square centimeters of growth surface. For commercial production of viruses, e.g., for vaccine production, it is often desirable to culture the cells in a bioreactor or fermenter. Bioreactors are available in volumes from under 1 liter to in excess of 100 liters, e.g., Cyto3 Bioreactor (Osmonics, Minnetonka, Minn.); NBS bioreactors (New Brunswick Scientific, Edison, N.J.); laboratory and commercial scale bioreactors from B. Braun Biotech International (B. Braun Biotech, Melsungen, Germany).

Regardless of the culture volume, in the context of the present invention, it is important that the cultures be maintained at a temperature less than or equal to 35° C., to insure efficient recovery of recombinant and/or reassortant influenza virus using the multi plasmid system described herein. For example, the cells are cultured at a temperature between about 32° C. and 35° C., typically at a temperature between about 32° C. and about 34° C., usually at about 33° C.

Typically, a regulator, e.g., a thermostat, or other device for sensing and maintaining the temperature of the cell culture system is employed to insure that the temperature does not exceed 35° C. during the period of virus replication.

Introduction of Vectors into Host Cells

Vectors comprising influenza genome segments are introduced (e.g., transfected) into host cells according to methods well known in the art for introducing heterologous nucleic acids into eukaryotic cells, including, e.g., calcium phosphate co-precipitation, electroporation, microinjection, lipofection, and transfection employing polyamine transfection reagents. For example, vectors, e.g., plasmids, can be transfected into host cells, such as COS cells, 293T cells or combinations of COS or 293T cells and MDCK cells, using the polyamine transfection reagent TransIT-LT1 (Mirus) according to the manufacturer's instructions. Approximately 1 μg of each vector to be introduced into the population of host cells with approximately 2 μl of TransIT-LT1 diluted in 160 μl medium, preferably serum-free medium, in a total vol. of 200 μl. The DNA: transfection reagent mixtures are incubated at room temperature for 45 min followed by addition of 800 μl of medium. The transfection mixture is added to the host cells, and the cells are cultured as described above. Accordingly, for the production of recombinant or reassortant viruses in cell culture, vectors incorporating each of the 8 genome segments, (PB2, PB1, PA, NP, M, NS, HA and NA) are mixed with approximately 20 μl TransIT-LT1 and transfected into host cells. Optionally, serum-containing medium is replaced prior to transfection with serum-free medium, e.g., Opti-MEM I, and incubated for 4-6 hours.

Alternatively, electroporation can be employed to introduce vectors incorporating influenza genome segments into host cells. For example, plasmid vectors incorporating an influenza A or influenza B virus are favorably introduced into Vero cells using electroporation according to the following procedure. In brief, $5\times10^6$ Vero cells, e.g., grown in Modified Eagle's Medium (MEM) supplemented with 10% Fetal Bovine Serum (FBS) are resuspended in 0.4 ml OptiMEM and placed in an electroporation cuvette. Twenty micrograms of DNA in a volume of up to 25 μl is added to the cells in the cuvette, which is then mixed gently by tapping. Electroporation is performed according to the manufacturer's instructions (e.g., BioRad Gene Pulser II with Capacitance Extender Plus connected) at 300 volts, 950 microFarads with a time constant of between 28-33 msec. The cells are remixed by gently tapping and approximately 1-2 minutes following electroporation 0.7 ml MEM with 10% FBS is added directly to the cuvette. The cells are then transferred to two wells of a standard 6 well tissue culture dish containing 2 ml MEM, 10% FBS or OPTI-MEM without serum. The cuvette is washed to recover any remaining cells and the wash suspension is divided between the two wells. Final volume is approximately 3.5 mls. The cells are then incubated under conditions permissive for viral growth, e.g., at approximately 33° C. for cold adapted strains.

Recovery of Viruses

Viruses are typically recovered from the culture medium, in which infected (transfected) cells have been grown. Typically crude medium is clarified prior to concentration of influenza viruses. Common methods include filtration, ultrafiltration, adsorption on barium sulfate and elution, and centrifugation. For example, crude medium from infected cultures can first be clarified by centrifugation at, e.g., 1000-2000×g for a time sufficient to remove cell debris and other large particulate matter, e.g., between 10 and 30 minutes. Alternatively, the medium is filtered through a 0.8 μm cellulose acetate filter to remove intact cells and other large particulate matter. Optionally, the clarified medium supernatant is then centrifuged to pellet the influenza viruses, e.g., at 15,000×g, for approximately 3-5 hours. Following resuspension of the virus pellet in an appropriate buffer, such as STE (0.01 M Tris-HCl; 0.15 M NaCl; 0.0001 M EDTA) or phosphate buffered saline (PBS) at pH 7.4, the virus is concentrated by density gradient centrifugation on sucrose (60%-12%) or potassium tartrate (50%-10%). Either continuous or step gradients, e.g., a sucrose gradient between 12% and 60% in four 12% steps, are suitable. The gradients are centrifuged at a speed, and for a time, sufficient for the viruses to concentrate into a visible band for recovery. Alternatively, and for most large scale commercial applications, virus is elutriated from density gradients using a zonal-centrifuge rotor operating in continuous mode. Additional details sufficient to guide one of skill through the preparation of influenza viruses from tissue culture are provided, e.g., in Furminger. *Vaccine Production*, in Nicholson et al. (eds) *Textbook of Influenza* pp. 324-332; Merten et al. (1996) *Production of influenza virus in cell cultures for vaccine preparation*, in Cohen & Shafferman (eds) *Novel Strategies in Design and Production of Vaccines* pp. 141-151, and U.S. Pat. No. 5,690,937. If desired, the recovered viruses can be stored at −80° C. in the presence of sucrose-phosphate-glutamate (SPG) as a stabilizer Methods and Compositions for Prophylactic Administration of Vaccines Recombinant and reassortant viruses of the invention can be administered prophylactically in an appropriate carrier or excipient to stimulate an immune response specific for one or more strains of influenza virus. Typically, the carrier or excipient is a pharmaceutically acceptable carrier or excipient, such as sterile water, aqueous saline solution, aqueous buffered saline solutions, aqueous dextrose solutions, aqueous glycerol solutions, ethanol, allantoic fluid from uninfected Hens' eggs (i.e., normal allantoic fluid "NAF") or combinations thereof. The preparation of such solutions insuring sterility, pH, isotonicity, and stability is effected according to protocols established in the art. Generally, a carrier or excipient is selected to minimize allergic and other undesirable effects, and to suit the particular route of administration, e.g., subcutaneous, intramuscular, intranasal, etc.

Generally, the influenza viruses of the invention are administered in a quantity sufficient to stimulate an immune response specific for one or more strains of influenza virus. Preferably, administration of the influenza viruses elicits a protective immune response. Dosages and methods for eliciting a protective immune response against one or more influenza strains are known to those of skill in the art. For example, inactivated influenza viruses are provided in the range of about 1-1000 $HID_{50}$ (human infectious dose), i.e., about $10^5$-$10^8$ pfu (plaque forming units) per dose administered. Alternatively, about 10-50 μg, e.g., about 15 μg HA is administered without an adjuvant, with smaller doses being administered with an adjuvant. Typically, the dose will be adjusted within this range based on, e.g., age, physical condition, body weight, sex, diet, time of administration, and other clinical factors. The prophylactic vaccine formulation is systemically administered, e.g., by subcutaneous or intramuscular injection using a needle and syringe, or a needleless injection device. Alternatively, the vaccine formulation is administered intranasally, either by drops, large particle aerosol (greater than about 10 microns), or spray into the upper respiratory tract. While any of the above routes of delivery results in a protective systemic immune response, intranasal administration confers the added benefit of eliciting mucosal immunity at the site of entry of the influenza virus. For intranasal administration, attenuated live virus vaccines are often preferred, e.g., an attenuated, cold adapted and/or temperature sensitive recombinant or reassortant influenza virus. While stimulation of a protective immune response with a single dose is preferred, additional dosages can be administered, by the same or different route, to achieve the desired prophylactic effect.

Alternatively, an immune response can be stimulated by ex vivo or in vivo targeting of dendritic cells with influenza viruses. For example, proliferating dendritic cells are exposed to viruses in a sufficient amount and for a sufficient period of time to permit capture of the influenza antigens by the dendritic cells. The cells are then transferred into a subject to be vaccinated by standard intravenous transplantation methods.

Optionally, the formulation for prophylactic administration of the influenza viruses, or subunits thereof, also contains one or more adjuvants for enhancing the immune response to the influenza antigens. Suitable adjuvants include: saponin, mineral gels such as aluminum hydroxide, surface active substances such as lysolecithin, pluronic polyols, polyanions, peptides, oil or hydrocarbon emulsions, bacille Calmette-Guerin (BCG), *Corynebacterium parvum*, and the synthetic adjuvants QS-21 and MF59.

If desired, prophylactic vaccine administration of influenza viruses can be performed in conjunction with administration of one or more immunostimulatory molecules. Immunostimulatory molecules include various cytokines, lymphokines and chemokines with immunostimulatory, immunopotentiating, and pro-inflammatory activities, such as interleukins (e.g., IL-1, IL-2, IL-3, IL-4, IL-12, IL-13); growth factors (e.g., granulocyte-macrophage (GM)-colony stimulating factor (CSF)); and other immunostimulatory molecules, such as macrophage inflammatory factor, Flt3 ligand, B7.1; B7.2, etc. The immunostimulatory molecules can be administered in the same formulation as the influenza viruses, or can be administered separately. Either the protein or an expression vector encoding the protein can be administered to produce an immunostimulatory effect.

In another embodiment, the vectors of the invention including influenza genome segments can be employed to introduce heterologous nucleic acids into a host organism or host cell, such as a mammalian cell, e.g., cells derived from a human subject, in combination with a suitable pharmaceutical carrier or excipient as described above. Typically, the heterologous nucleic acid is inserted into a non-essential region of a gene or gene segment, e.g., the M gene of segment 7. The heterologous polynucleotide sequence can encode a polypeptide or peptide, or an RNA such as an antisense RNA or ribozyme. The heterologous nucleic acid is then introduced into a host or host cells by producing recombinant viruses incorporating the heterologous nucleic, and the viruses are administered as described above.

Alternatively, a vector of the invention including a heterologous nucleic acid can be introduced and expressed in a host cells by co-transfecting the vector into a cell infected with an influenza virus. Optionally, the cells are then returned or delivered to the subject, typically to the site from which they were obtained. In some applications, the cells are grafted onto a tissue, organ, or system site (as described above) of interest, using established cell transfer or grafting procedures. For example, stem cells of the hematopoietic lineage, such as bone marrow, cord blood, or peripheral blood derived hematopoietic stem cells can be delivered to a subject using standard delivery or transfusion techniques.

Alternatively, the viruses comprising a heterologous nucleic acid can be delivered to the cells of a subject in vivo. Typically, such methods involve the administration of vector particles to a target cell population (e.g., blood cells, skin cells, liver cells, neural (including brain) cells, kidney cells, uterine cells, muscle cells, intestinal cells, cervical cells, vaginal cells, prostate cells, etc., as well as tumor cells derived from a variety of cells, tissues and/or organs. Administration can be either systemic, e.g., by intravenous administration of viral particles, or by delivering the viral particles directly to a site or sites of interest by a variety of methods, including injection (e.g., using a needle or syringe), needleless vaccine delivery, topical administration, or pushing into a tissue, organ or skin site. For example, the viral vector particles can be delivered by inhalation, orally, intravenously, subcutaneously, subdermally, intradermally, intramuscularly, intraperitoneally, intrathecally, by vaginal or rectal administration, or by placing the viral particles within a cavity or other site of the body, e.g., during surgery.

The above described methods are useful for therapeutically and/or prophylactically treating a disease or disorder by introducing a vector of the invention comprising a heterologous polynucleotide encoding a therapeutically or prophylactically effective polypeptide (or peptide) or RNA (e.g., an antisense RNA or ribozyme) into a population of target cells in vitro, ex vivo or in vivo. Typically, the polynucleotide encoding the polypeptide (or peptide), or RNA, of interest is operably linked to appropriate regulatory sequences as described above in the sections entitled "Expression Vectors" and "Additional Expression Elements." Optionally, more than one heterologous coding sequence is incorporated into a single vector or virus. For example, in addition to a polynucleotide encoding a therapeutically or prophylactically active polypeptide or RNA, the vector can also include additional therapeutic or prophylactic polypeptides, e.g., antigens, co-stimulatory molecules, cytokines, antibodies, etc., and/or markers, and the like.

The methods and vectors of the present invention can be used to therapeutically or prophylactically treat a wide variety of disorders, including genetic and acquired disorders, e.g., as vaccines for infectious diseases, due to viruses, bacteria, and the like.

Kits

To facilitate use of the vectors and vector systems of the invention, any of the vectors, e.g., consensus influenza virus plasmids, variant influenza polypeptide plasmids, influenza polypeptide library plasmids, etc., and additional components, such as, buffer, cells, culture medium, useful for packaging and infection of influenza viruses for experimental or therapeutic purposes, can be packaged in the form of a kit. Typically, the kit contains, in addition to the above components, additional materials which can include, e.g., instructions for performing the methods of the invention, packaging material, and a container.

Manipulation of Viral Nucleic Acids and Proteins

In the context of the invention, influenza virus nucleic acids and/or proteins are manipulated according to well known molecular biology techniques. Detailed protocols for numerous such procedures, including amplification, cloning, mutagenesis, transformation, and the like, are described in, e.g., in Ausubel et al. *Current Protocols in Molecular Biology* (supplemented through 2000) John Wiley & Sons, New York ("Ausubel"); Sambrook et al. *Molecular Cloning—A Laboratory Manual* (2nd Ed.), Vol. 1-3, Cold Spring Harbor Laboratory, Cold Spring Harbor, N.Y., 1989 ("Sambrook"), and Berger and Kimmel *Guide to Molecular Cloning Techniques, Methods in Enzymology* volume 152 Academic Press, Inc., San Diego, Calif. ("Berger").

In addition to the above references, protocols for in vitro amplification techniques, such as the polymerase chain reaction (PCR), the ligase chain reaction (LCR), Qβ-replicase amplification, and other RNA polymerase mediated techniques (e.g., NASBA), useful e.g., for amplifying cDNA probes of the invention, are found in Mullis et al. (1987) U.S. Pat. No. 4,683,202; *PCR Protocols A Guide to Methods and Applications* (Innis et al. eds) Academic Press Inc. San Diego, Calif. (1990) ("Innis"); Arnheim and Levinson (1990) *C&EN* 36; *The Journal Of NIH Research* (1991) 3:81; Kwoh et al. (1989) *Proc Natl Acad Sci USA* 86, 1173; Guatelli et al. (1990) *Proc Natl Acad Sci USA* 87:1874; Lomell et al. (1989) *J Clin Chem* 35:1826; Landegren et al. (1988) *Science* 241: 1077; Van Brunt (1990) *Biotechnology* 8:291; Wu and Wallace (1989) *Gene* 4: 560; Barringer et al. (1990) *Gene* 89:117, and Sooknanan and Malek (1995) *Biotechnology* 13:563. Additional methods, useful for cloning nucleic acids in the context of the present invention, include Wallace et al. U.S. Pat. No. 5,426,039. Improved methods of amplifying large nucleic acids by PCR are summarized in Cheng et al. (1994) *Nature* 369:684 and the references therein.

Certain polynucleotides of the invention, e.g., oligonucleotides can be synthesized utilizing various solid-phase strategies including mononucleotide- and/or trinucleotide-based phosphoramidite coupling chemistry. For example, nucleic acid sequences can be synthesized by the sequential addition of activated monomers and/or trimers to an elongating polynucleotide chain. See e.g., Caruthers, M. H. et al. (1992) *Meth Enzymol* 211:3.

In lieu of synthesizing the desired sequences, essentially any nucleic acid can be custom ordered from any of a variety of commercial sources, such as The Midland Certified Reagent Company (mcrc@oligos.com), The Great American Gene Company (www.genco.com), ExpressGen, Inc. (www.expressgen.com), Operon Technologies, Inc. (www.operon.com), and many others.

In addition, substitutions of selected amino acid residues in viral polypeptides can be accomplished by, e.g., site directed mutagenesis. For example, viral polypeptides with amino acid substitutions functionally correlated with desirable phenotypic characteristic, e.g., an attenuated phenotype, cold adaptation, temperature sensitivity, can be produced by introducing specific mutations into a viral nucleic acid segment encoding the polypeptide. Methods for site directed mutagenesis are well known in the art, and described, e.g., in Ausubel, Sambrook, and Berger, supra. Numerous kits for performing site directed mutagenesis are commercially available, e.g., the Chameleon Site Directed Mutagenesis Kit (Stratagene, La Jolla), and can be used according to the manufacturers instructions to introduce, e.g., one or more amino acid substitutions described in Table 6 or Table 17, into a genome segment encoding a influenza A or B polypeptide, respectively.

EXAMPLES

Example 1

Construction of pAD3000

The plasmid pHW2000 (Hoffmann et al. (2000) *A DNA transfection system for generation of influenza A virus from eight plasmids Proc Natl Acad Sci USA* 97:6108-6113) was modified to replace the bovine growth hormone (BGH) polyadenylation signals with a polyadenylation signal sequences derived from Simian virus 40 (SV40).

Sequences derived from SV40 were amplified with Taq MasterMix (Qiagen) using the following oligonucleotides, designated in the 5' to 3' direction: polyA.1:

```
AACAATTGAGATCTCGGTCACCTCAGACATGATAAGA (SEQ ID NO:1)
TACATTGATGAGT

polyA.2: TATAACTGCAGACTAGTGATATCCTTGT (SEQ ID NO:2)
TTATTGCAGCTTATAATGGTTA
```

The plasmid pSV2His was used as a template. A fragment consistent with the predicted 175 bp product was obtained and cloned into pcDNA3.1, using a Topo TA cloning vector (Invitrogen) according to the manufacturer's directions. The desired 138 bp fragment containing the SV40 polyadenylation signals was excised from the resulting plasmid with EcoRV and BstEII, isolated from an agarose gel, and ligated between the unique PvuII and BstEII sites in pHW2000 using conventional techniques (see, e.g., Ausubel, Berger, Sambrook). The resulting plasmid, pAD3000 (FIG. 1), was sequenced and found to contain the SV40 polyadenylation site in the correct orientation. Nucleotides 295-423 in pAD3000 correspond to nucleotides 2466-2594, respectively, in SV40 strain 777 (AF332562).

Example 2

Eight Plasmid System for Production of MDV-A

A cold-adapted influenza virus type A strain A/AA/6/60 variant has commonly been used as a master donor virus for the production of nasally administered Influenza A vaccines. This strain is an exemplary Master Donor Virus (MDV) in the context of the present invention. For simplicity, this strain A/AA/6/60 variant is designated herein MDV-A. MDV-A viral RNA was extracted using the RNeasy mini kit (Qiagen) and the eight corresponding cDNA fragments were amplified by RT-PCR using the primers listed in Table 1.

TABLE 1

Sequence of the primers used for cloning MDV-A eight segments

| SEQ ID NO. | Primer | Sequence (5'-3') |
|---|---|---|
| | MDV-A FORWARD PRIMERS | |
| 3 | Aarl PB2 long | CAC TTA TAT TCA CCT GCC TCA GGG AGC GAA AGC AGG TC |
| 4 | BsmBI-PBI | TAT TCG TCT CAG GGA GCG AAA GCA GGC AAA |
| 5 | BsmBI-PA | TAT TCG TCT CAG GGA GCG AAA GCA GGT ACT |
| 6 | BsmBI-NP | TAT TCG TCT CAG GGA GCA AAA GCA GGG TAG A |
| 7 | AarI HA-long | CAC TTA TAT TCA CCT GCC TCA GGG AGC AAA AGC AGG GG |
| 8 | BsmBI-NA | TAT TCG TCT CAG GGA GCA AAA GCA GGA GTG A |
| 9 | BsmBI-M | TAT TCG TCT CAG GGA GCA AAA GCA GGT AGA T |
| 10 | BsmBI-NS | TAT TCG TCT CAG GGA GCA AAA GCA GGG TGA |
| | MDV-A REVERSE PRIMERS | |
| 11 | AarI PB2-long | CCT AAC ATA TCA CCT GCC TCG TAT TAG TAG AAA CAA GGT CGT TT |
| 12 | BsmBI-PBI | ATA TCG TCT CGT ATT AGT AGA AAC AAG GCA TTT |
| 13 | BsmBI-PA | ATA TCG TCT CGT ATT AGT AGA AAC AAG GTA CTT |
| 14 | BsmBI-NP | ATA TCG TCT CGT ATT AGT AGA AAC AAG GGT ATT |
| 15 | AarI HA-long | CCT AAC ATA TCA CCT GCC TCG TAT TAG TAG AAA CAA GGG TGT T |
| 16 | BsmBI-NA | ATA TCG TCT CGT ATT AGT AGA AAC AAG GAG TTT |
| 17 | BsmBI-M | ATA TCG TCT CGT ATT AGT AGA AAC AAG GTA GTT |
| 18 | BsmBI-NS | ATA TCG TCT CGT ATT AGT AGA AAC AAG GGT GTT |

With the exception of the influenza genome segments encoding HA and PB2, which were amplified using the primers containing Aar I restriction enzyme recognition site, the remaining 6 genes were amplified with primers containing the BsmB I restriction enzyme recognition site. Both AarI and BsmB I cDNA fragments were cloned between the two BsmB I sites of the pAD3000 vector.

Sequencing analysis revealed that all of the cloned cDNA fragments contained mutations with respect to the consensus MDV-A sequence, which were likely introduced during the cloning steps. The mutations found in each gene segment are summarized in Table 2.

TABLE 2

Mutations introduced into the MDV-A clones in pAD3000

| Gene segment | Mutation positions (nt) | Amino acid changes |
|---|---|---|
| PB2 | A954(G/C/T), G1066A, T1580C, T1821C | Silent, Gly to Ser, Val to Ala, Silent |
| PB1 | C1117T | Arg to Stop |
| PA | G742A, A1163G, A1615G, T1748C, C2229del | Gly to Ser, Asp to Gly, Arg to Gly, Met to Thr, non-coding |
| HA | A902C, C1493T | Asn to His, Cys to Arg |

TABLE 2-continued

| Mutations introduced into the MDV-A clones in pAD3000 | | |
|---|---|---|
| Gene segment | Mutation positions (nt) | Amino acid changes |
| NP | C113A, T1008C | Thr to Asn, silent |
| NA | C1422T | Pro to Leu |
| M | A191G | Thr to Ala |
| NS | C38T | Silent |

All the mutations were corrected back to the consensus MDV-A sequence using a QuikChange Site-directed Mutagenesis Kit (Stratagene) and synthetic oligonucleotide primers as shown in Table 3.

TABLE 3

| Primers used for correcting the mutations in the MDV-A clones | | | | |
|---|---|---|---|---|
| | HJ67 | PB2A954G | 5/P/gcaagctgtggaaatatgcaaggc | (SEQ ID NO:19) |
| | HJ68 | PB2A954G.as | gccttgcatatttccacagcttgc | (SEQ ID NO:20) |
| | HJG9 | PB2G1066A | 5/P/gaagtgcttacgggcaatcttcaaac | (SEQ ID NO:21) |
| PB2 | HJ70 | PB2G1066A.as | gtttgaagattgcccgtaagcacttc | (SEQ ID NO:22) |
| | HJ71 | PB2T1580A | 5/P/cctgaggaggtcagtgaaacac | (SEQ ID NO:23) |
| | HJ72 | PB2T1580A.as | gtgtttcactgacctcctcagg | (SEQ ID NO:24) |
| | HJ73 | PB21821C | 5/P/gtttgttaggactctattccaac | (SEQ ID NO:25) |
| | HJ74 | PB21821C.as | gttggaatagagtcctaacaaac | (SEQ ID NO:26) |
| PB1 | HJ75 | PB1C1117T | gacagtaagctccqaacacaaatac | (SEQ ID NO:27) |
| | HJ76 | PB1C1117T.as | gtatttgtgttcggagcttcatgc | (SEQ ID NO:28) |
| | HJ77 | PA-G742A | 5/P/cgaaccgaacggctacattgaggg | (SEQ ID NO:29) |
| | HJ78 | PA-G742A.as | ccctcaatgtagccgttcggttcg | (SEQ ID NO:30) |
| | HJ79 | PA-A1163G | 5/P/cagagaaggtagatttgacgactg | (SEQ ID NO:31) |
| | HJ80 | PA-A1163G.as | cagtcgtcaaagtctaccttctctg | (SEQ ID NO:32) |
| PA | HJ81 | PA-A1615G | 5/P/cactgacccaagacttgagccac | (SEQ ID ND:33) |
| | HJ82 | PA-A1615G.as | gtggctcaagtcttqggtcagtg | (SEQ ID NO:34) |
| | HJ83 | PA-T1748C | 5/P/caaagattaaaatgaaatggggaatg | (SEQ ID NO:35) |
| | HJ84 | PA-T1748C.as | cattccccatttcattttaatctttg | (SEQ ID NO:36) |
| | HJ85 | PA-C2229 | 5/P/gtaccttgtttctactaataacccgg | (SEQ ID NO:37) |
| | HJ86 | PA-C2230.as | ccgggttattagtagaaacaaggtac | (SEQ ID NO:38) |
| | HJ87 | HA-A902C | 5/P/ggaacacttgagaactgtgagacc | (SEQ ID NO:39) |
| HA | HJ88 | HA-A902C.as | ggtctcacagttctcaagtgttcc | (SEQ ID NO:40) |
| | HJ89 | HA-C1493T | 5/P/gaattttatcacaaatgtgatgatgaatg | (SEQ ID NO:41) |
| | HJ90 | HA-C1493T.as | cattcatcatcacatttgtgataaaattc | (SEQ ID ND:42) |
| | HJ91 | NP-C113A | 5/P/gccagaatgcaactgaaatcagagc | (SEQ ID NO:43) |

TABLE 3-continued

| Primers used for correcting the mutations in the MDV-A clones | | | |
|---|---|---|---|
| NP | HJ92 NP-C113A.as | gctctgatttcagtttcattctggc | (SEQ ID NO:44) |
| | HJ93 NP-T1008C | 5/P/ccgaatgagaatccagcacacaag | (SEQ ID NO:45) |
| | HJ94 NP-T1008C.as | cttgtgtgctggattctcattcgg | (SEQ ID NO:46) |
| | HJ95 NA-C1422T | catcaatttcatgcctatataagctttc | (SEQ ID NO:47) |
| NS | HJ96 NA-C1422T.as | gaaagcttatataggcatgaaattgatg | (SEQ ID NO:48) |
| | HJ97 NS-C38T | cataatggatcctaacactgtgtcaagc | (SEQ ID NO:49) |
| | HJ98 NS-C38T.as | gcttgacacagtgttaggatccattatg | (SEQ ID NO:50) |
| PA | HJ99 PA6C375T | ggagaatagattcatcgagattggag | (SEQ ID NO:51) |
| | HJ100PA6C375T.as | ctccaatctcgatgaatctattctcc | (SEQ ID NO:52) |

Example 3

Generation of Infectious Recombinant MDV-A and Reassorted Influenza Virus

Madin-Darby canine kidney (MDCK) cells and human COS7 cells were maintained in modified Eagle Medium (MEM) containing 10% fetal bovine serum (FBS). Human embryonic kidney cells (293T) were maintained in Opti-MEM I (Life Technologies) containing 5% FBS. MDCK and either COS7 or 293T cells were co-cultured in 6-well plates at a ratio of 1:1 and the cells were used for transfection at a confluency of approximately 80%. 293T and COS7 cells have a high transfection efficiency, but are not permissive for influenza virus replication. Co-culture with MDCK cells ensures efficient replication of the recombinant viruses. Prior to transfection, serum-containing media were replaced with serum free medium (Opti-MEM I) and incubated for 4-6 hours. Plasmid DNA transfection was performed using TransIT-LT1 (Mirus) by mixing 1 μg of each of the 8 plasmid DNAs (PB2, PB1, PA, NP, M, NS, HA and NA) with 20 μl of TransIT-LT1 diluted in 160 μl Opti-MEM I in a total volume of 200 μl. The DNA:transfection reagent mixtures were incubated at room temperature for 45 min followed by addition of 800 μl of Opti-MEM I. The transfection mixture was then added to the co-cultured MDCK/293T or MDCK/COS7 cells. The transfected cells were incubated at 35° C. or 33° C. for between 6 hours and 24 hours, e.g., overnight, and the transfection mixture was replaced with 1 ml of Opti-MEM I in each well. After incubation at 35° C. or 33° C. for 24 hours, 1 ml of Opti-MEM I containing 1 g/ml TPCK-trypsin was added to each well and incubated for an additional 12 hours. The recovered virus was then amplified in confluent MDCK cells or directly amplified in embryonated chick eggs. MDCK cells in 12-well plate were infected with 0.2 ml of the transfection mixture for 1 hour at room temperature, the mixture was then removed and replaced with 2 ml of Opti-MEM I containing 1 μg/ml TPCK-trypsin. The cells were incubated at 35° C. or 33° C. for 3-4 days. The amplified viruses were stored at −80° C. in the presence of SPG stabilizer or plaque-purified and amplified in MDCK cells or chicken embryonic eggs.

Functional Expression of MDV-A Polymerase Proteins

Functional activity of the four MDV-A polymerase proteins, PB2, PB1, PA and NP, were analyzed by their ability to replicate an influenza virus minigenome encoding an EGFP reporter gene. A set of 8 expression plasmids (see, e.g., Table 4) (Hoffmann et al. (2001) *Eight plasmid rescue system for influenza A virus; Options for the control of influenza International Congress Series* 1219:1007-1013) that contained the cDNAs of A/PR/8/34 strain (H1N1) and an influenza virus minigenome containing a reporter gene encoding the enhanced green fluorescent protein (EGFP, pHW72-EGFP).

The MDV-A PB1, PB2, PA and NP or PB1, PA, NP (-PB2 as a negative control) were transfected into the co-cultured MDCK/293T cells together with a plasmid representing an influenza A virus EGFP minigenome (pHW72-EGFP) (Hoffmann et al. (2000) *"Ambisense" approach for the generation of influenza A virus: vRNA and mRNA synthesis from one template Virology* 15:267(2):310-7). The transfected cells were observed under phase contrast microscope or fluorescence microscope at 48 hours post-transfection. Alternatively, flow cytometry can be employed to detect EGFP expression.

Figure 2:
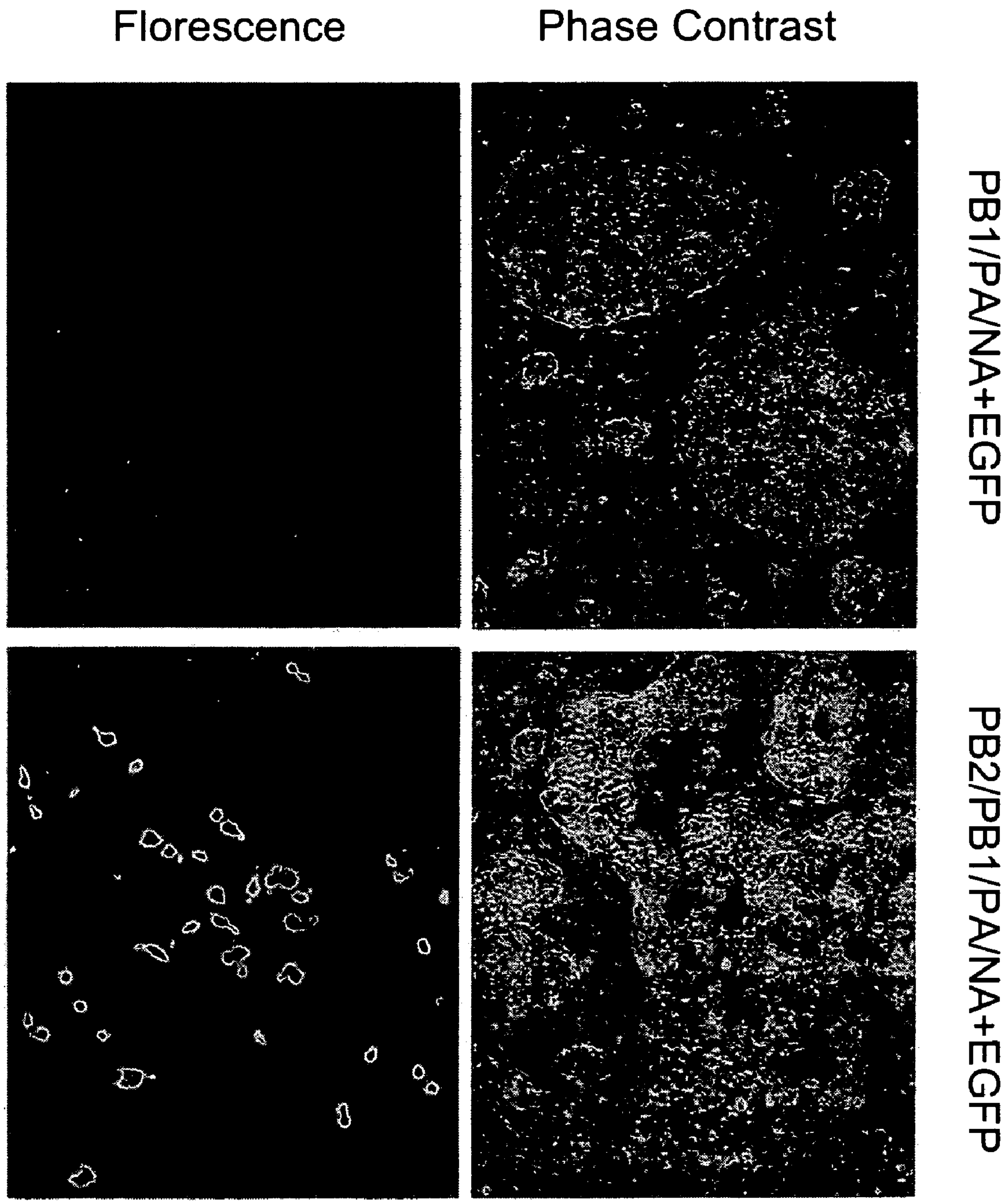
FIG. 2: Micrographs of infected cells.

As shown in FIG. 2, green fluorescence, indicating expression of the EGFP minigenome was observed in the cells transfected with PB2, PB1, PA and NP of MDV-A, but not in the cells transfected with only three polymerase proteins. This indicated that the MDV-A polymerase proteins in pAD3000 were functional.

In other assays a minigenome including the chloramphenicol acetyl transferase (CAT) gene, designated pFlu-CAT is utilized to measure polymerase activity. In such an assay, CAT expression is measured at the protein (e.g., by ELISA) or RNA level, as an indicator of minigenome replication.

Analysis of the MDV-A Plasmids by Single Gene Reassortant Experiment

Each of the 8 MDV-A genome segments cloned in pAD3000 was shown to be functionally expressed in a reassortant experiment by co-transfecting a single gene segment from MDA-A together with the complementary seven segments from control A/PR/8/34 strain. All eight single genome segment plasmids in combination with complementary control segments generated infectious reassortant virus, which caused cytopathic effects in infected MDCK cells, indicating that all eight plasmids encode functional MDV-A proteins. Table 4.

TABLE 4

Recovery of 7 + 1 reassortants by plasmids

| Virus gene seg-ment | PB2 | PB1 | PA | NP |
|---|---|---|---|---|
| 1 | PMDV-A-PB2 | pHW191-PB2 | pHW191-PB2 | pHW191-PB2 |
| 2 | PHW192-PB1 | pMDV-A-PB1 | pHW192-PB1 | pHW192-PB1 |
| 3 | PHW193-PA | pHW193-PA | pMDV-A-PA | pHW193-PA |
| 4 | PHW195-NP | pHW195-NP | pHW195-NP | pMDV-A-NP |
| 5 | PHW197-M | pHW197-M | pHW197-M | pHW197-M |
| 6 | PHW198-NS | pHW198-NS | pHW198-NS | pHW198-NS |
| 7 | PHW194-HA | pHW194-HA | pHW194-HA | pHW194-HA |
| 8 | PHW-196-NA | pHW-196-NA | pHW-196-NA | pHW-196-NA |
| CPE | (+) | (+) | (+) | (+) |

TABLE 4-continued

Recovery of 7 + 1 reassortants by plasmids

| Virus gene seg-ment | M | NS | HA | NA |
|---|---|---|---|---|
| 1 | PHW191-PB2 | pHW191-PB2 | pHW191-PB2 | pHW191-PB2 |
| 2 | PHW192-PB1 | pHW192-PB1 | pHW192-PB1 | pHW192-PB1 |
| 3 | PHW193-PA | pHW193-PA | pHW193-PA | pHW193-PA |
| 4 | PHW195-NP | pHW195-NP | pHW195-NP | pHW195-NP |
| 5 | PMDV-A-M | pHW197-M | pHW197-M | pHW197-M |
| 6 | PHW198-NS | pMDV-A-NS | pHW198-NS | pHW198-NS |
| 7 | PHW194-HA | pHW194-HA | pMDV-A-HA | pHW194-HA |
| 8 | PHW-196-NA | pHW-196-NA | pHW-196-NA | pMDV-A-NA |
| CPE | (+) | (+) | (+) | (+) |

To further determine the packaging constraints of influenza A virus, the NS segment was separated into two separate gene segments: one encoding the NS1 genomic segment and the other encoding the NS2 genomic segment. The nine plasmids incorporating the genomic segments of influenza A were transfected into MDCK/COS cells as described above, and the recovered viruses were amplified in embryonated chicken eggs prior to titration on MDCK cells. Reduced plaque size was observed for the nine-plasmid system as compared to the eight-plasmid system described above. RT-PCR analysis demonstrated that only the NS2 segment was present in the virions, and that the NS1 gene segment was not packaged.

Recovery of MDV-A and 6:2 Reassortant Viruses

Following the procedures described above, three days post transfection with either the 8 MDV-A plasmids (recombinant), or with plasmids incorporating the 6 MDV-A internal genes, and HA and NA derived from A/PR/8/34 (6:2 reassortant), transfected culture supernatants were used to infect fresh MDCK cells, and the infected cells were incubated at 33° C. for three days in the presence of 1 μg/ml TPCK-trypsin. The cytoplasmic effect of the recombinant virus on infected MDCK cells was observed using a microscope. Expression of viral hemagglutinin was monitored using a standard hemagglutination assay (HA). HA assays were performed by mixing 50 μl of serially 2-fold diluted culture supernatants with 50 μl of 1% chick red blood cells in 96-well plates. A HA titer of approximately 1:254-1:1024 was detected for the amplified viruses derived from either the transfected 8 MDV-A plasmids, or the 6:2 reassortant virus. The transfection reaction using the 8 A/PR/8/34 plasmid obtained from Dr. E. Hoffman was used as a positive control. Infectious influenza viruses were produced from these three transfection reactions as indicated in Table 5.

TABLE 5

Plasmids used for recovery of A/PR/8/34, MDV-A and 6:2 reassortant

| Virus gene segment | A/PR/8/34 (H1N1) | rMDV-A(H2N2) | 6:2 reassortant |
|---|---|---|---|
| 1 | pHW191-PB2 (AD731) | pMDV-A-PB2#2 (AD760) | pMDV-A-PB2#2 (AD760) |
| 2 | pHW192-PB1(AD732) | pMDV-A-PB1 (AD754) | pMDV-A-PB1 (AD754) |
| 3 | pHW193-PA (AD733) | pMDV-A-PA (AD755) | pMDV-A-PA (AD755) |
| 4 | pHW195-NP (AD735) | pMDV-A-NP#1 (AD757) | pMDV-A-NP#1 (AD757) |
| 5 | pHW197-M (AD737) | pMDV-A-M (AD752) | pMDV-A-M (AD752) |
| 6 | pHW198-NS (AD738) | pMDV-A-NS (AD750) | pMDV-A-NS (AD750) |
| 7 | pHW194-HA (AD734) | pMDV-A-HA (AD756) | pHW 194-HA (AD734) |
| 8 | pHW-196-NA(AD735) | pMDV-A-NA#4 (AD759) | pHW196-NA (AD736) |
| CPE | + | + | + |

Figure 3:
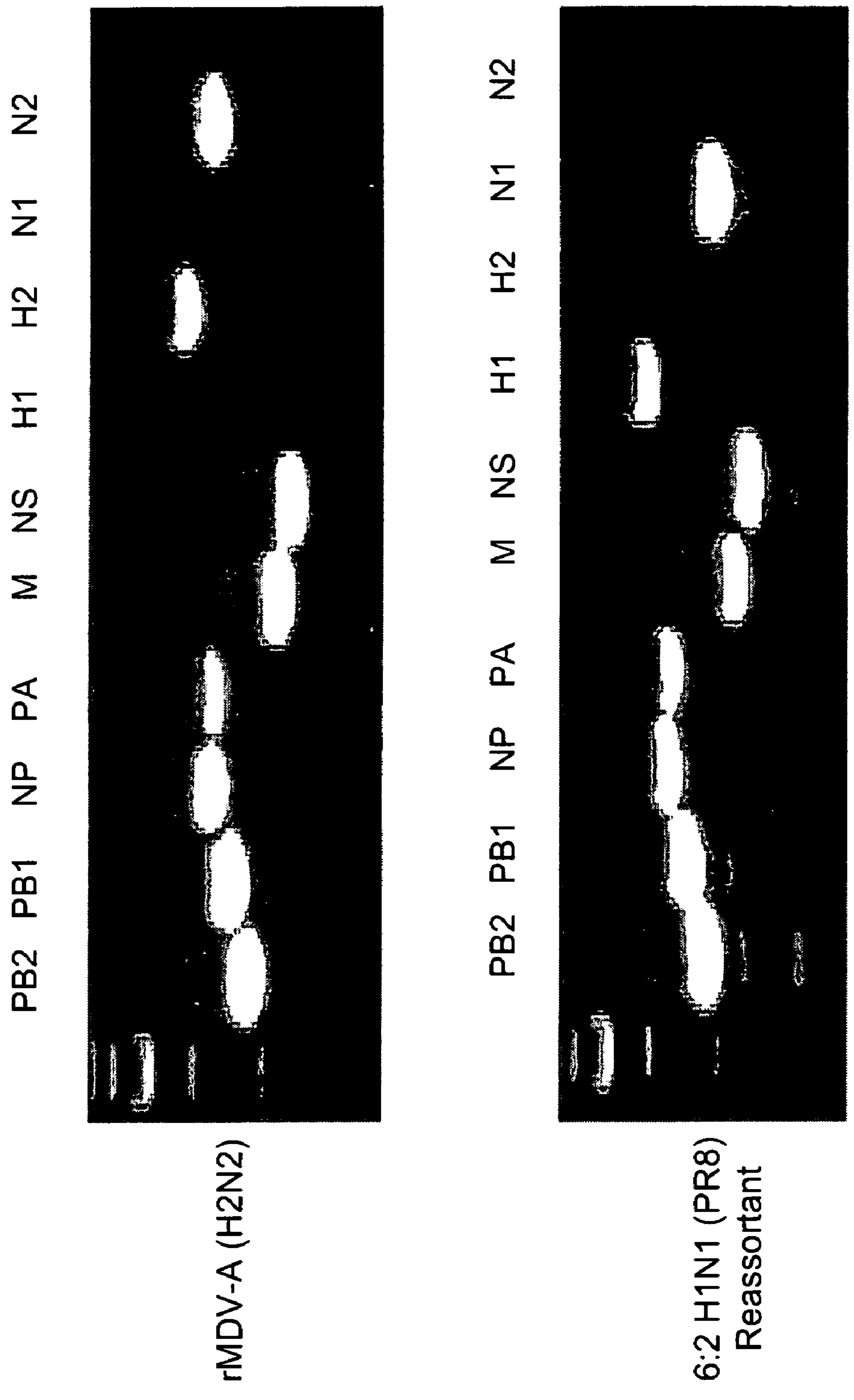
FIG. 3: Genotyping analysis of rMDV-A and 6:2 H1N1 reassortant virus from plasmid transfection.

RT-PCR was performed to map the genotypes of the recovered viruses. Viral RNA was isolated from the infected cell culture supernatant using the RNeasy mini Kit (Qiagen) and the eight influenza virus segments were amplified by RT-PCR using primers specific to each MDV-A gene segment and H1- and N1-specific primers. As shown in FIG. 3, rMDV-A contained PB2, PB1, NP, PA, M and NS that were specific to MDV-A and HA and NA specific to the H2 and N2 subtype. The 6:2 reassortant contained the 6 internal genes derived from MDV-A, and the HA and NA derived from A/PR/8/34 (H1N1). This confirmed that viruses generated from the transfected plasmids had the correct genotypes.

The rescued viruses were titrated by plaque assay on MDCK cells and the plaques were confirmed to be influenza virus by immunostaining using chicken serum raised against MDV-A. MDCK cells at 100% confluency on 12-well plates were infected with 100 μl of 10-fold serially diluted virus at RT for 1 hour with gentle rocking. The inoculum was removed and the cells were overlaid with 1×L15 containing 0.8% agarose and 1 μg/ml TPCK-trypsin. The plates were incubate at 35° C. or 33° C. for three days, fixed with 100% methanol, blocked by 5% milk in PBS, and incubated with 1:2000 diluted chicken anti-MDV-A antiserum for 1 hour followed by incubation with HRP-conjugated rabbit anti-chicken IgG for 1 hr. The plaques were visualized by addition of the HRP substrate solution (DAKO). All the recovered viruses exhibited positive immunostaining.

Example 4

Mapping the Genetic Basis of ca, ts, att Phenotypes of MDV-A

The MDV-A influenza virus vaccine strain has several phenotypes relevant to the production of vaccines, e.g., live attenuated vaccines: cold adaptation (ca), temperature sensitivity (ts) and attenuation (att). Sequence comparison of the MDV-A strain with the non-ts virulent wt A/AA/6/60 strain revealed that a minimal of 17 nt differences between these two strains (Table 6). Several of the changes in the MDV-A sequence are unique to this strain as compared to all the available influenza type A viruses in the GeneBank database, suggesting that one or more of these amino acid substitutions is functionally related to the att, ca and ts phenotype(s). The single amino acid change at PB2821 was the only nucleotide position that had been previously reported as a determinant in the ts phenotype of MDV-A (Subbarao et al. (1995) *Addition of Temperature-Sensitive Missense Mutations into the PB2 Gene of Influenza A Transfectant Viruses Can Effect an Increase in Temperature Sensitivity and Attenuation and Permits the Rational Design of a Genetically Engineered Live Influenza A Virus Vaccine J. Virol.* 69:5969-5977).

In order to pinpoint the minimal substitutions involved in the MDV-A phenotypes, the nucleotides in the MDV-A clone that differ from wt A/AA/6/60 were individually changed to those of wt A/AA/6/60 (i.e., "reverted"). Each reverted gene segment was then introduced into host cells in combination with complementary segments of MDV-A to recover the single gene reassortants. In addition, the reverted gene segment and the corresponding MDV-A segment can also be transfected in combination with segments derived from other wild type strains, e.g., strain A/PR/8/34, to assess the contribution of each gene segment to the virus phenotypes. Using the recombinant MDV-A plasmid system described above, site-directed mutagenesis was performed to further modify the six internal genes to produce a non-ts reassortant. A total of 15 nucleotides substitution mutations were introduced into the six MDV-A plasmids to represent the recombinant wild type A/AA/6/60 genome (rWt, Flu064) as listed in Table 6. Madin-Darby canine kidney (MDCK) cells and COS-7 cells were maintained and transfected as described above. The recovered virus was then passaged in MDCK cells once, followed by amplification in the allantoic cavities of embryonic chicken eggs. Transfection and virus growth in MDCK and eggs were performed at 33° C., a temperature permissive for both ca and wt viruses to minimize any temperature selection pressures. Virus genotype was confirmed by sequence analysis of cDNA fragments amplified from viral RNA.

TABLE 6

Sequence Comparisons of "wt" A/AA/6/60 and MDV-A

| RNA Segment | Base (ammo acid) Position | E10SE2 | MDV-A | rWT (Flu044) |
|---|---|---|---|---|
| PB2 | **141** | A | G | A |
| | **821 (265)** | A (Asn) | G(Ser) | A |
| | 1182 | A | T | T |
| | 1212 | C | T | T |
| | **1933** | T | C | T |
| PB1 | 123 | A | G | G |
| | **1195 (391)** | A (Lys) | G (Glu) | A |
| | **1395 (457)** | G (Glu) | T (Asp) | C |
| | **1766 (581)** | A(Glu) | G (Gly) | A |
| | **2005 (661)** | C (Ala) | A (Thr) | A |
| | **2019** | C | T | C |
| PA | **20** | T | C | T |
| | **1861 (613)** | A (Lys) | C (Glu) | C |
| | **2167/8 (715)** | TT (Leu) | CC (Pro) | TT |
| NP | **146 (34)** | A (Asp) | C (Gly) | G |
| | 1550 | '5A' | '6A' | '6A' |
| M | **969 (M2-86)** | G (Ala) | T (Ser) | C |
| NS | **483 (NS1-153)** | G (Ala) | A (Thr) | G |

Numbers in bold represent the differences between rMDV-A and rWt.
Words in bold (15) are the changes between rmdv-a and rwt.

Phenotypic characteristics were determined by procedures known in the art, e.g., as previously described in U.S. Pat. No. 6,322,967 to Parkin entitled "Recombinant tryptophan mutants of influenza," which is incorporated herein in its entirety. Briefly, temperature sensitivity of the recombinant viruses was determined by plaque assay on MDCK cells at 33, 38 and 39° C. MDCK cells in 6-well plates were infected with 400 µl of 10-fold serially diluted virus and adsorbed at room temperature for 60 min. The innoculants were removed and replaced with 1×L15/MEM containing 1% agarose and 1 µg/ml TPCK-trypsin. The infected cells were incubated at 33° C. in a $CO_2$ incubator or in water-tight containers containing 5% $CO_2$ submerged in circulating water baths maintained at 38±0.1° C. or 39±0.1° C. (Parkin et al. (1996) *Temperature sensitive mutants of influenza A virus generated by reverse genetics and clustered charged to alanine mutagenesis. Vir. Res.* 46:31-44). After three days' incubation, the monolayers were immunostained using chicken anti-MDV polyclonal antibodies and the plaques were enumerated. Plaque counts obtained at each of the temperatures were compared to assess the ts phenotype of each virus and each assay was performed a minimum of three times. The shut-off temperature was defined as the lowest temperature that had a titer reduction of 100-fold or greater compared to 33° C.

Infectious virus obtained from the cocultured COS-7/MDCK cells transfected with the eight plasmids (pMDV-PB2, pMDV-PB 1, pMDV-PA, pMDV-NP, pMDV-HA, pMDV-NA, pMDV-M, and pMDV-NS) was amplified in chicken embryonated eggs, and was shown to exhibit the characteristic ts phenotype of nonrecombinant, biological derived MDV-A (Table 7). Neither MDV-A nor rMDV-A formed distinct plaques at 39° C., although both formed easily visualized plaques at 33° C.

TABLE 7

Replication of MDV/Wt reassortants at various temperatures

| Virus with Wt genes | 33° C. | 38° C. | 33° C./38° C. | 39° C. | 33° C./ 39° C. |
|---|---|---|---|---|---|
| MDV | 8.91 | 6.10 | 2.82 | <4.0† | >4.91 |
| rMDV-A | 8.72 | 6.19 | 2.53 | <4.0 | >4.72 |

TABLE 7-continued

Replication of MDV/Wt reassortants at various temperatures

| Virus with Wt genes | 33° C. | 38° C. | 33° C./38° C. | 39° C. | 33° C./ 39° C. |
|---|---|---|---|---|---|
| Wt (E10SE2) | 8.86 | 8.87 | −0.01 | 8.87 | −0.01 |
| rWT (Flu064) | 9.02 | 9.07 | −0.05 | 8.96 | 0.06 |
| Wt-PB2 | 8.46 | 7.87 | 0.59 | 5.80* | 2.66 |
| Wt-PB1 | 8.92 | 8.74 | 0.18 | 7.86* | 1.06 |
| Wt-NP | 8.40 | 7.24 | 1.15 | <4.0 | >4.40 |
| Wt-PA | 8.57 | 6.10 | 2.48 | <4.0 | >4.57 |
| Wt-M | 8.80 | 6.68 | 2.12 | <4.0 | >4.80 |
| Wt-NS | 8.72 | 6.10 | 2.62 | <4.0 | >4.72 |
| Wt-PB1/PB2 | 8.94 | 8.89 | 0.05 | 8.10* | 0.85 |
| Wt-PB1/PB2/NP | 8.52 | 8.38 | 0.14 | 8.41 | 0.1 |

*Indicates reduction in plaque size compared to rWt.
†The underlined indicates that no plaques were detected at $10^{-4}$-fold dilution In order to perform a systematic, detailed analysis of the genetic basis of the ts phenotype of MDV-A, the sequences of several closely related non-ts, non-att wt A/AA/6/60 strains with 17-48 nt differences from the ca A/AA/6/60, including the highly related isolate, wt A/AA/6/60 E10SE2, were utilized for comparison. A total of 19 nt differences exist between E10SE2 and MDV-A (Table 6). E10SE2 was shown to be non-ts (Table 7) and non-att in ferrets. In order to generate a recombinant non-ts virus, the MDV-A plasmids were altered by site directed mutagenesis to incorporate 15 of the 19 differences representing 10 amino acids changes. Four of the nucleotide positions, PB2-1182, 1212, PB1-123, and NP-1550, that differed between MDV-A and E10SE2 were not altered from the MDV-A sequence, since these nucleotides were observed in other non-ts isolates of A/AA/6/60 and, therefore, not expected to have a role in expression of the ts phenotype (Herlocher et al. (1996) *Sequence comparisons of A/AA/6/60 influenza viruses: mutations which may contribute to attenuation. Virus Research* 42:11-25). Recombinant virus (rWt, Flu064), encoding the 15 nucleotide changes, was obtained from the cocultured COS-7/MDCK cells transfected with a set of 8 plasmids, pWt-PB2, pWt-PB1, pWt-PA, pWt-NP, pWt-M, pWt-NS, pMDV-HA, and pMDV-NA. Sequencing analysis indicated that rWt contained the designed genetic changes and was non-ts at 39° C., identical to the biologically derived wt A/AA/6/60. These observations demonstrated that the ts phenotype mapped to a subset of these 15 nt changes.

Contribution of the Six Internal Gene Segments to Virus ts Phenotype

The effect of each wt gene segment on the MDV-A ts phenotype was assessed by creating recombinant, single-gene reassortants (Table 7). Introduction of wt PB2 into rMDV-A resulted in a virus that was only non-ts at 38° C.; however, it remained ts at 39° C. The reduction in virus titer at 38° C. and 39° C. (relative to 33° C.) was 0.6 $\log_{10}$ and 2.7 $\log_{10}$, respectively, as measured by plaque assay in MDCK cells. The reassortant containing the wt PB1 gene segment was non-ts, with respect to its ability to form plaques at both 38 and 39° C. The plaque size of this recombinant, however, was influenced by increased temperature and was significantly reduced at 39° C. as compared to rWt. Introduction of the wt NP gene segment into rMDV-A resulted in a virus that was also non-ts at 38° C., but in contrast to the wt PB2 recombinant, the virus containing the wt NP gene segment did not form plaques at 39° C. Introduction of wt PA, M or NS gene segments independently into rMDV-A did not alter the ts phenotype, indicating that these three gene segments had minimal role in maintenance of this phenotype.

Because neither wt PB1, wt PB2 or wt NP expressed individually on the MDV-A background could create a plaque efficiency and plaques size profile identical to non-ts rWT, these gene segments were introduced into MDV-A in various combinations. The combination of wt PB1 and wt PB2 resulted in a virus that was non-ts at both 38 and 39° C. (Table 7). Although the plaque size was larger than that of either single gene reassortant, it was significantly smaller than rWt. The triple combination of wt PB1/PB2/NP in rMDV-A resulted in a virus that was similar or identical to rWt in its plaquing efficiency and plaque size at 39° C. Therefore, whereas the wt PB2, PB1 and NP gene segments only partially reverted the ts phenotype when introduced individually, the combination of all three wt gene segments was able to fully revert the ts phenotype to a non-ts behavior identical to rWt.

Figure 10:
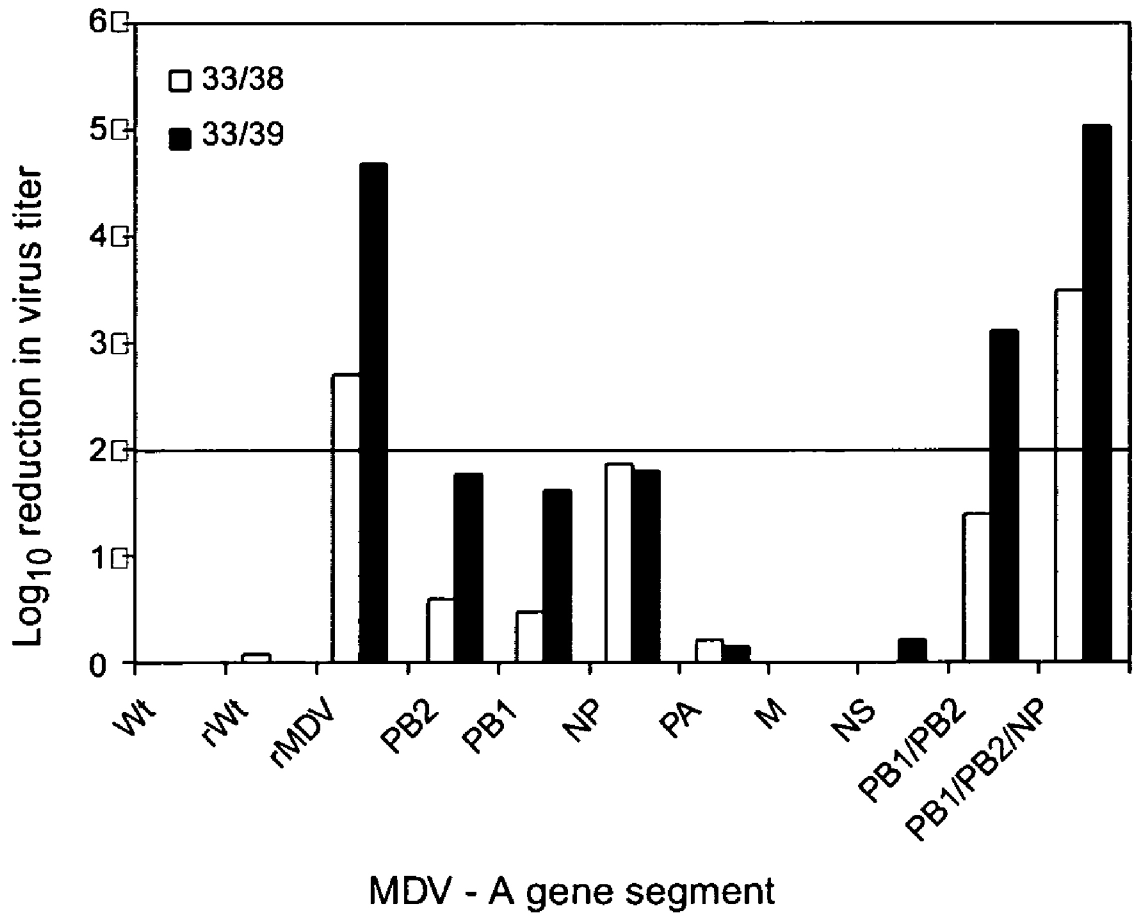
FIG. 10: Bar graph illustrating relative titers of reassortant virus under permissive and restrictive temperatures (temperature sensitivity).

In order to determine whether these 3 gene segments were capable of imparting the characteristic MDV-A ts phenotype to rWt, the six internal gene segments derived from MDV-A were introduced into rWt individually or in combination. Introduction of single PB1, PB2, or NP gene segment into rWt resulted in a reduction of virus titer at 38° C. and a greater reduction at 39° C., however, none of these single gene reassortants was as restricted at high temperature as rMDV-A (FIG. 10). The PA, M and NS gene segments derived from MDV-A did not influence the non-ts phenotype of rWt. Consistent with the previous reassortments, it was demonstrated that introduction of both MDV-A PB1 and PB2 genes into rWt backbone greatly increased virus ts phenotype at 38° C.; however, complete reversion of virus ts phenotype required addition of the NP gene. Thus, the PB1, PB2 and NP gene segments derived from MDV-A were important in conferring the complete ts phenotype.

Mapping the Genetic Loci that Determined MDV-A ts Phenotype.

The specific differences between the PB1, PB2 and NP gene segments of rWt and rMDV-A were addressed systematically to identify those changes that played a significant role in the ts phenotype. The NP gene of rMDV-A differed from rWt NP only at nt 146 (G34D, Table 6). The PB2 gene of rMDV-A differed from rWt at three sites, but only nt 821 resulted in an amino acid change (N265S, Table 6) and presumably represented the ts locus located in the PB2 gene segment. The PB1 gene of MDV-A differed from wt PB1 at 6 nt positions, of which 4 were coding changes (Table 6). Each of the wt amino acid residue substitutions was substituted individually into the PB1 gene segment of rMDV-A to assess their role in the ts phenotype. 1395G (Glu-457) and 2005G (Ala) did not affect the MDV-A ts phenotype. 1195A (Lys-391) and 1766A (Glu-581) each resulted in a slight reduction in the ts phenotype at 38° C., but had no effect at 39° C. (Table 8). These data indicated that 1195A and 1766A were the likely ts loci in the PB1 gene segment. However, combination of both 1195A and 1766A did not produce a ts phenotype similar to wt PB1 (Table 6). Addition of 2005G but not 1395A to PB1-1195A/1766A further decreased the virus ts phenotype at 39° C., demonstrating that 2005A also had a role in the expression of the ts phenotype specified by the PB1 segment of MDV-A.

TABLE 8

Mapping the residues in PB1 that determine ts phenotype

| Virus with Wt sequence | 33° C. | 38° C. | 33° C./ 38° C. $\log_{10}$ PFU/ mL | 39° C. | 33° C./ 39° C. |
|---|---|---|---|---|---|
| rMDV-A | 8.67 | 6.00 | 2.67 | <4.0† | >4.67 |
| rWt | 9.04 | 9.01 | 0.03 | 9.03 | 0.01 |
| PB1-1195A | 8.06 | 6.68 | 1.38 | <4.0 | >4.06 |
| PB1-1395G | 8.72 | 5.88 | 2.85 | <4.0 | >4.72 |

TABLE 8-continued

Mapping the residues in PB1 that determine ts phenotype

| Virus with Wt sequence | 33° C. | 38° C. | 33° C./ 38° C. log$_{10}$ PFU/ mL | 39° C. | 33° C./ 39° C. |
|---|---|---|---|---|---|
| PB1-1766A | 8.07 | 6.70 | 1.37 | <u>≤4.0</u> | >4.07 |
| PB1-2005G | 8.76 | 6.31 | 2.45 | <u>≤4.0</u> | >4.76 |
| PB1-1195A1766A | 8.65 | 7.60 | 1.05 | 5.98* | 2.68 |
| PB1-1195A1395G1766A | 8.84 | 8.13 | 0.71 | 6.38* | 2.46 |
| PB1-1195A1766A2005G | 8.79 | 8.12 | 0.66 | 7.14* | 1.64 |
| PB1/PB2/NP | 8.26 | 8.63 | 0.12 | 8.59 | 0.16 |
| PB2/NP | 8.81 | 8.21 | 0.59 | 7.56* | 1.25 |
| PB1-1195A/PB2/NP | 8.86 | 8.81 | 0.05 | 7.60* | 1.26 |
| PB1-1766A/PB2/NP | 9.33 | 8.84 | 0.50 | 8.71* | 0.62 |
| PB1-1766A2005G/ PB2/NP | 8.30 | 8.22 | 0.08 | 8.11* | 0.18 |
| PB1-1766A1395G/ PB2/NP | 8.88 | 8.85 | 0.03 | 8.39* | 0.49 |
| PB1-1195A1766A/ PB2/NP | 8.45 | 8.48 | 0.06 | 8.10 | 0.35 |

*Indicates reduction in plaque size compared to rWt.
†The underlined indicates that no plaques were detected at 10$^{-4}$-fold dilution.

PB1 single site mutations were then introduced together with wt PB2 and wt NP into rMDV-A. Wt PB2/NP and rMDV-A reassortant was non-ts at 38° C. and had a titer reduction of 1.25 log$_{10}$ at 39° C. but its plaque size was much reduced compared to rWt. Addition of either PB1-1195A or 1766A did not significantly change the phenotype of wt PB2/NP reassortant. Only the combination of PB1-1195A and 1766A, together with a wt PB2 and wt NP, resulted in a virus that had the same non-ts phenotype as wt PB1/PB2/NP and rMDV-A reassortant (Table 8). Addition of PB1-1395G or 2005G to wt PB1-1766/PB2/NP did not convert the virus to a characteristic rWt non-ts phenotype. These data, therefore, demonstrated that the four amino acids distributed in the three PB1, PB2 and NP genes could completely revert the MDV-A ts phenotype.

Host Cell Restriction of MDV-A and Reassortant Viruses

Figure 20A:
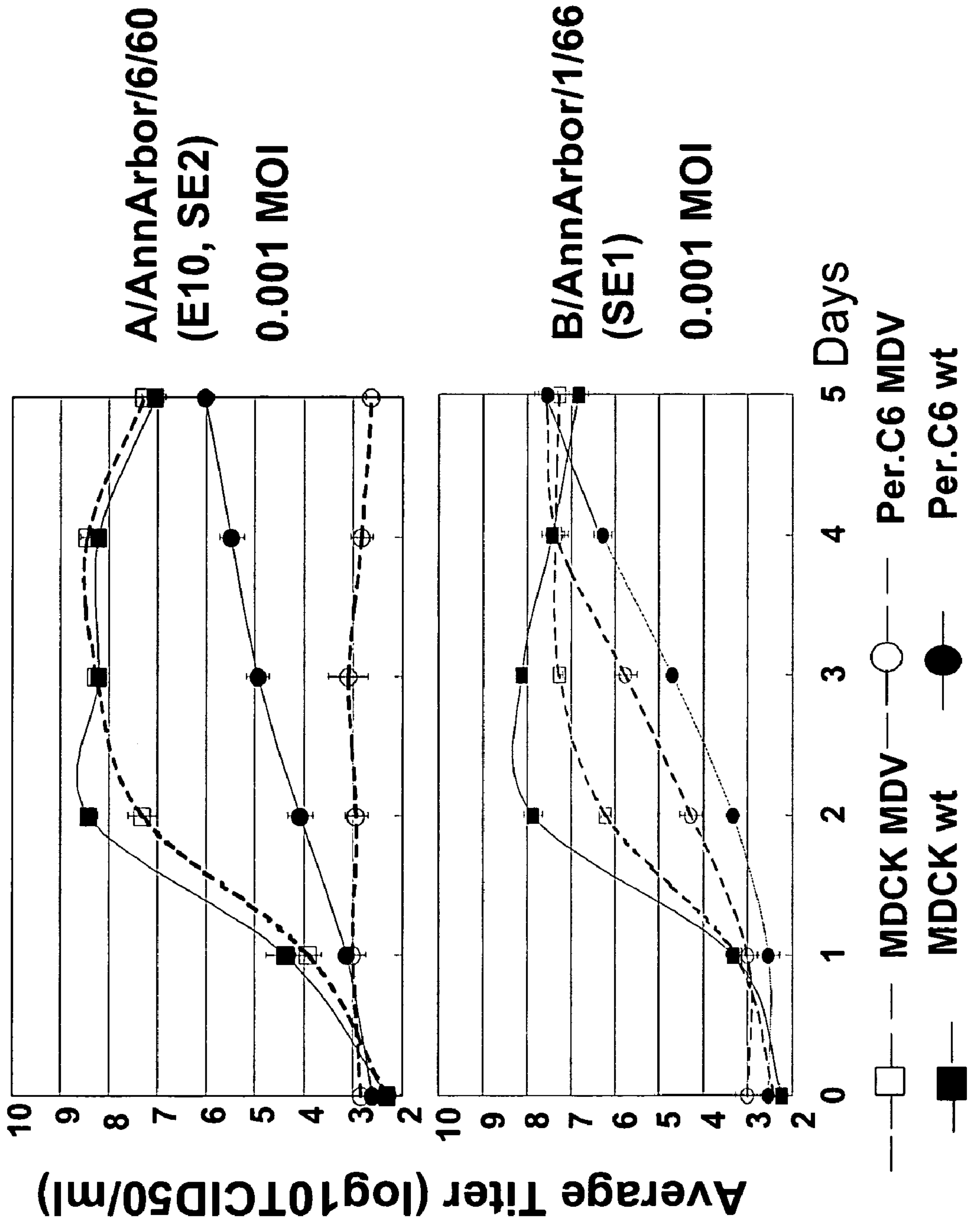
FIG. 20: A. Line graphs illustrating differential replication of MDV-A and MDV-B in Per.C6 cells relative to replication in MDCK cells; B. Line graph illustrating differential replication of MDV-A single gene reassortants in Per.C6 cells.
Figure 20B:
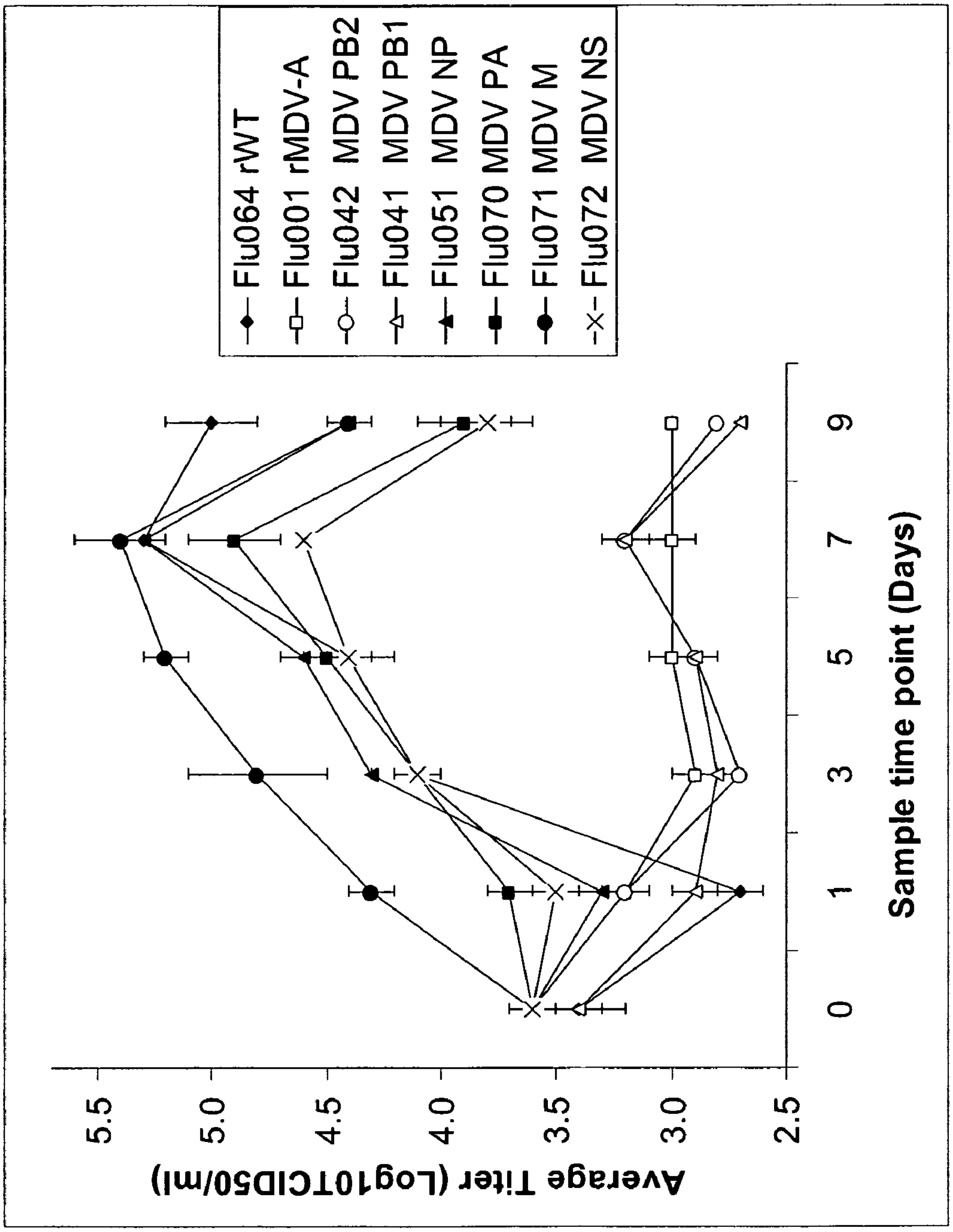

In addition to the temperature sensitivity and attenuation phenotypes exhibited by the MDV-A virus and reassortant viruses with one or more MDV-A derived segment as described above, the MDV-A virus exhibited host cell restriction as indicated by reduced growth in Per.C6 cells relative to growth in MDCK cells. MDV-A and reassortant viruses with MDV-A derived PB1 and PB2 segments exhibited significantly reduced growth in Per.C6 cells relative to their growth in MDCK cells, as shown in FIG. 20 A and B.

Engineering of a Temperature Sensitive, Attenuated Virus Strain

Figure 11:
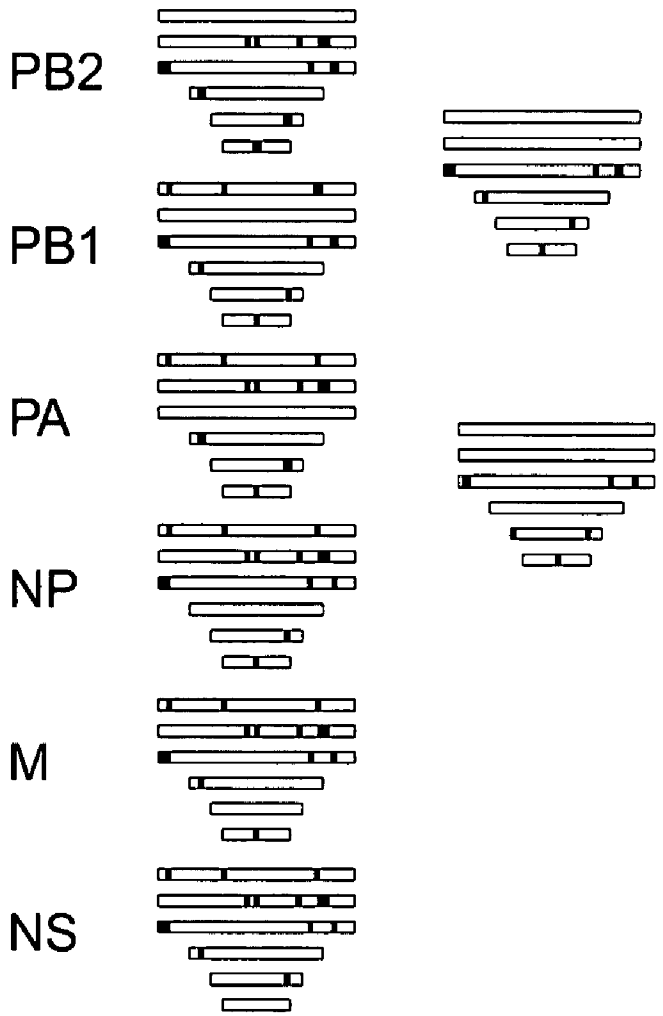
FIG. 11: Graphic representation of reassortant viruses incorporating specific mutations (knock-in) correlating with temperature sensitivity (left panel) and relative titers at permissive and restrictive temperatures (temperature sensitivity) (right panel).

To determine whether the five amino acids identified in the PB1, PB2 and NP gene segments of MDV-A would reproduce the ts and att phenotypes of MDV-A, PB1-391 E, 581G, 661T, PB2-265S, NP-34G were introduced into a divergent wild type virus strain (A/PR/8/34; "PR8"), and the resulting virus exhibited 1.9 log$_{10}$ reduction in virus titer at 38° C. and 4.6 log$_{10}$ reduction at 39° C., which was very similar to that of rMDV-A (FIG. 11).

Figure 16:
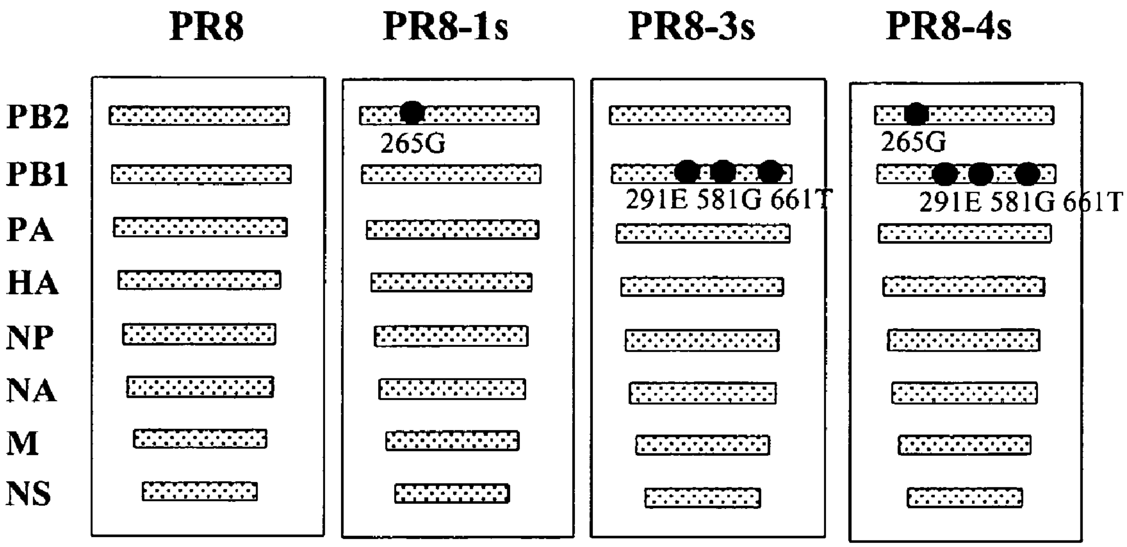
FIG. 16: Schematic diagram of recombinant PR8 mutants. The mutations introduced in PB1 and/or PB2 genes are indicated by the filled dots.

Sequence comparison between the PB 1, PB2 and NP genes of ca A/AA/6/60 (MDV-A) and A/PR/8/34 revealed that the four substituted amino acids identified in the PB1 and PB2 genes of MDV-A are unique. NP$^{34}$ is conserved between MDV-A and PR8, Therefore, the three ts sites, PB1$^{391}$ (K391E), PB1$^{158}$ (E581G) and PB1$^{661}$ (A661T), identified in the PB1 gene of MDV-A were introduced into PB1 of A/PR/8/34 and the PB2$^{265}$ (N265S) was introduced into PB2 of A/PR/8/34 by site-directed mutagenesis. The mutations introduced into the PB1 and PB2 genes were verified by sequencing analysis. The primer pairs used for mutagenesis reaction are listed as in Table 9. These viruses are shown schematically in FIG. 16.

TABLE 9

Primers used for introducing ts mutations into PR8 PB1 and PB2 genes

| HJ240 | PR8-PB1A1195G    | 5' GAAAGAAGATTGAAGAAATCCGACCGCTC    | (SEQ ID NO:79) |
| HJ241 | PR8-PB1A1195G.as | 5' GAGCGGTCGGATTTCTTCAATCTTCTTTC    | (SEQ ID NO:80) |
| HJ242 | PR8-PB1A1766G    | 5' GAAATAAAGAAACTGTGGGGGCAAACCCGTTCC | (SEQ ID NO:81) |
| HJ243 | PR8-PB1A1766G.as | 5' GGAACGGGTTTGCCCCCACAGTTTCTTTATTTC | (SEQ ID NO:82) |
| HJ244 | PR8-PB1G2005A    | 5' GTATGATGCTGTTACAACAACACACTC C    | (SEQ ID NO:83) |
| HJ245 | PR8-PB1G2005A.as | 5' GGAGTGTGTTGTTGTAACAGCATCATAC     | (SEQ ID NO:84) |
| HJ246 | PR8-PB2A821G     | 5' ATTGCTGCTAGGAGCATAGTGAGAAGAGC    | (SEQ ID NO:85) |
| HJ247 | PR8-PB2A821G.as  | 5' GCTCTTCTCACTATGCTCCTAGCAGCAAT    | (SEQ ID NO:86) |

To examine if the ts mutations introduced into PB1 and PB2 genes of PR8 confer the ts phenotype in vitro, a minigenome assay was performed. The influenza minigenome reporter, designated pFlu-CAT, contained the negative sense CAT gene cloned under the control of the pol I promoter. Expression of the CAT protein depended on the expression of influenza PB1, PB2, PA, and NP proteins.

Briefly, HEp-2 cells were transfected with 1 µg of each of PB1, PB2, PA, NP and pFlu-CAT minigenome by lipofectamine 2000 (Invitrogen). After overnight (approximately 18 hour) incubation at 33° C. or 39° C., the cell extracts were analyzed for CAT protein expression by CAT ELISA kit (Roche Bioscience). The level of CAT mRNA was measured by primer extension assay. At 48 hr post-transfection, total cellular RNA was extracted by TRIzol reagent (Invitrogen) and ⅓ of RNA was mixed with an excess of DNA primer (5'-ATGTTCTTTACGATGCGATTGGG (SEQ ID NO:89) labeled at its 5' end with [r-$^{32}$P]-ATP and T4 polynucleotide kinase in 6 µl of water. Following denaturing at 95° C. for 3 min, primer extension was performed after addition of 50 U of superscript reverse transcriptase (Invitrogen) in the reaction buffer provided with the enzyme containing 0.5 mM dNTP for 1 hr at 42° C. Transcription products were analyzed on 6% polyacrylamide gels containing 8M urea in TBE buffer and were detected by autoradiograph.

Figure 12A:
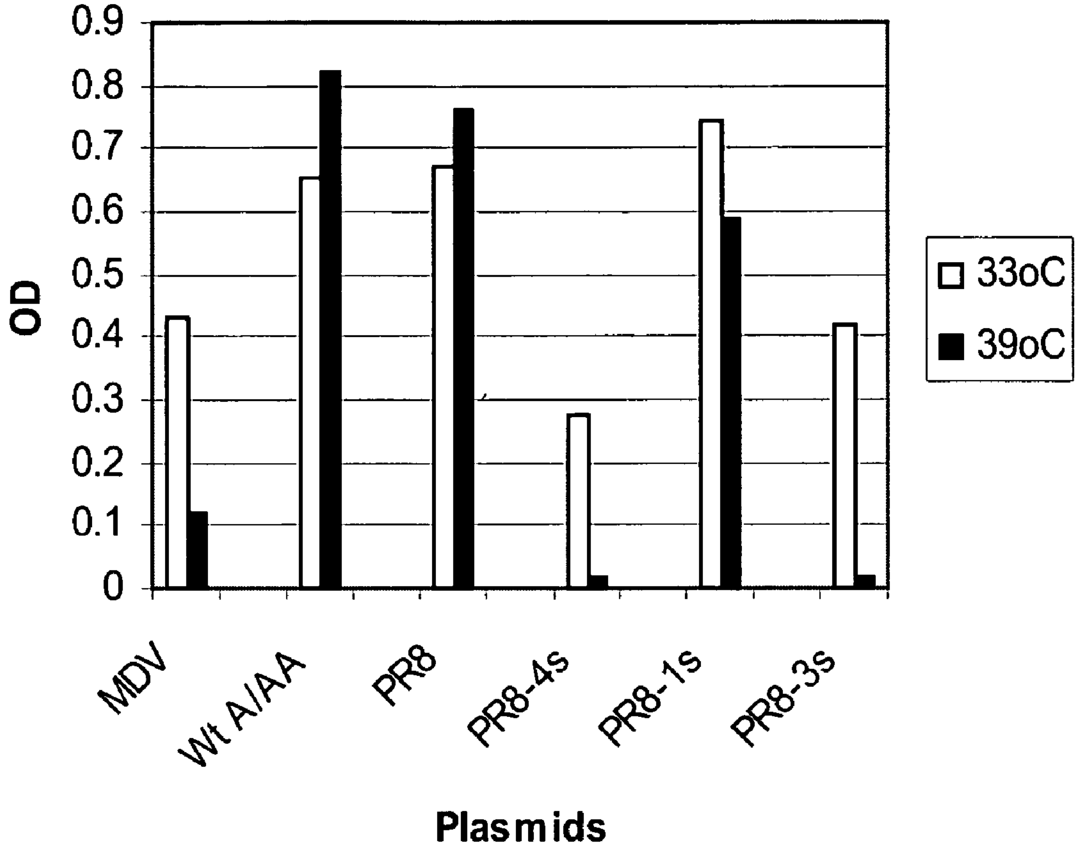
FIG. 12: Determination of ts mutations in a minigenome assay. A. HEp-2 cells were transfected with PB1, PB2, PA, NP and pFlu-CAT, incubated at 33 or 39° C. for 18 hr and cell extracts were analyzed for CAT reporter gene expression. B. CAT mRNA expression by primer extension assay.
Figure 12B:
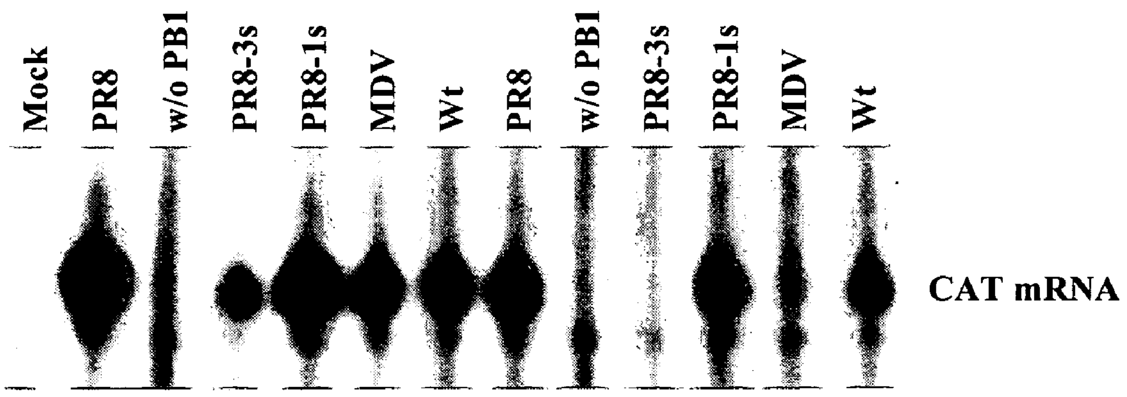

As shown in FIGS. 12A and B, the PB1 gene carrying three amino acid substitutions (PR8-3s), $PB1^{391}$ (K391E), $PB1^{581}$ (E581G) and $PB1^{661}$ (A661T), had reduced activity at 33° C. compared to PR8 control. A greater reduction in CAT protein expression (FIG. 12A) was observed for this mutant at 39° C., indicating PB1 gene with the three introduced MDV-A ts sites exhibited temperature sensitive replication in this in vitro assay. Introduction of $PB2^{265}$ (N265S) into PR8 had very little effect on its activity at both permissive (33° C.) and nonpermissive temperatures (39° C.). Combination of both PB1-3s and PB2-1s resulted in greater reduction in protein activity (PR8-4s), which appeared to be even more ts than MDV-A. As expected, a low level activity (15%) was detected in cells transfected with PB1, PB2, PA, NP genes derived from MDV-A at 39° C. compared to wt A/AA/6/60 (wt A/AA).

PR8 mutant viruses were generated and recovered as described above. In brief, co-cultured cos7 and MDCK cells were transfected with eight plasmids encoding PR8 HA, NA, PB1, PB2, PA, NP, M and NS genes derived from PR8. To make a virus carrying four ts loci (PR8-4s), PB1-3s containing three changes in PB1 at positions nt 1195 (K391E), nt 1766 (E581G) and nt 2005 (A661T) and PB1-1s containing one change in PB2 at position 821 (N265S) were used. In addition, PR8 virus carrying either three mutations in PB1 (PR8-3s) or one mutation in PB2 (PR8-1s) was also recovered separately. These viruses are shown schematically in FIG. 16. All four of the recombinant mutant PR8 viruses grew to very high titer in embryonic eggs, reaching a titer of 9.0 log10pfu/ml or greater as shown in Table 10.

To examine viral protein synthesis in infected cells, MDCK cells were infected with virus at an m.o.i of 5 and cells were labeled with $^{35}$S-Trans at 7 hr post-infection for 1 hr. The labeled cell lysate was electrophoresed on 1.5% polyacrylamide gel containing SDS and autoradiographed. Protein synthesis was also studied by Western blotting. Virus infected cells were harvested at 8 hr postinfection and electrophoresed on 4-15% gradient gel. The blot was probed with anti-M1 antibody or chicken anti-MDV-A polyclonal antibody, followed by incubation with HRP-conjugated secondary antibody. The antibody-conjugated protein bands were detected by the Chemiluminescent Detection System (Invitrogen) followed by exposure to X-ray film.

Figure 19:
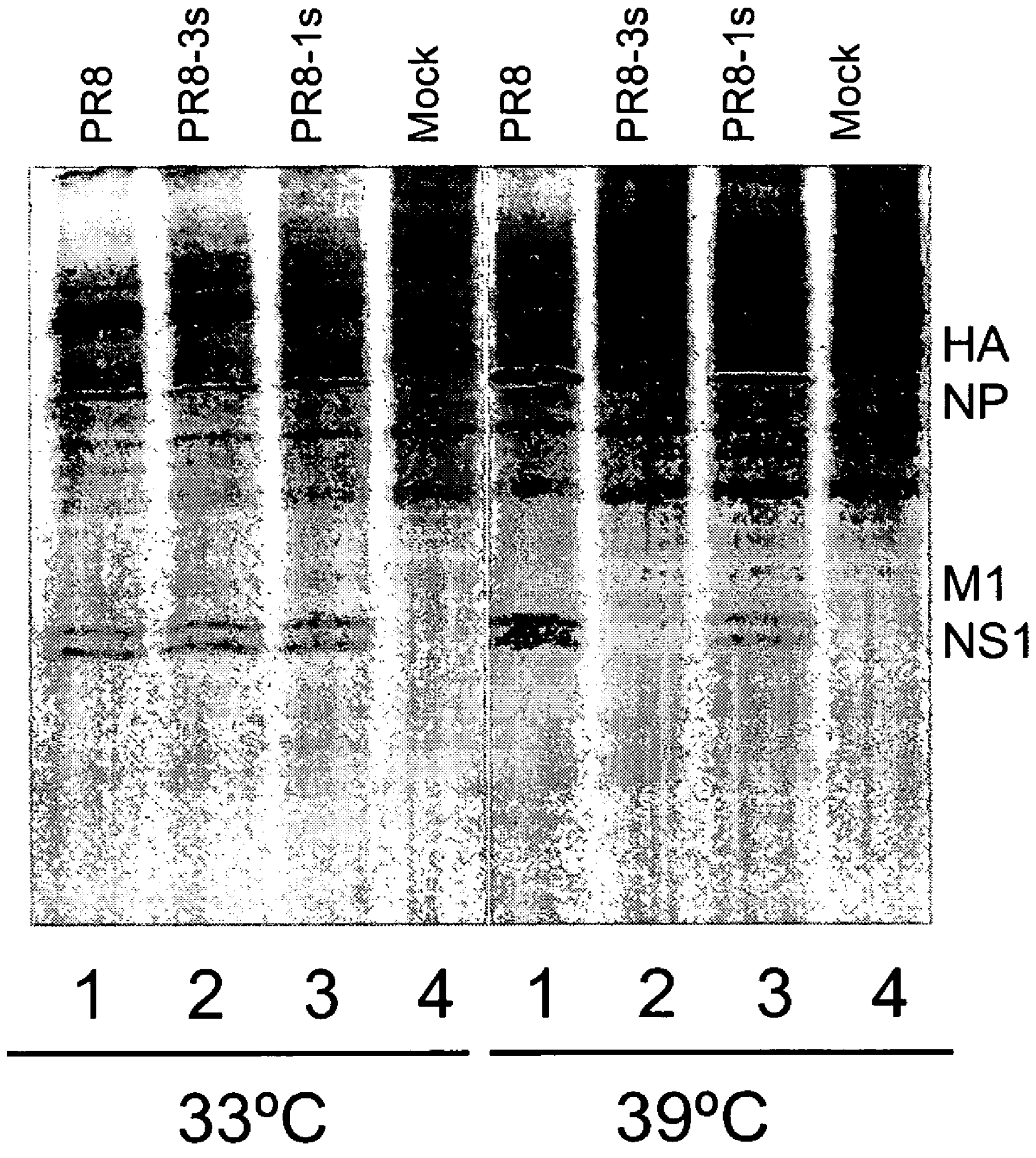
FIG. 19: Protein synthesis at permissive and nonpermissive temperatures. MDCK cells were infected with viruses as indicated and incubated at 33 or 39° C. overnight. Radiolabeled labeled polypeptides were electrophoresed on an SDS-PAGE and autoradiographed. Viral proteins, HA, NP, M1 and NS are indicated.

As shown in FIG. 19, all had a similar level of protein synthesis at 33° C., however, at 39° C. the level of protein synthesis was reduced slightly for PR8-1s but greatly reduced in PR8-3s and PR8-4s infected cells. Western blotting analysis also showed that reduced protein synthesis in the order of PR8-4s>PR8-3s>PR8-1s. Thus, the reduced replication of the ts mutants was likely the result of their reduced replication at the nonpermissive temperatures.

Temperature sensitivity of the PR8 mutant viruses was determined by plaque assay on MDCK cells at 33° C., 37° C., 38° C. and 39° C. The recovered viruses were amplified in embryonic eggs and introduced into cells as described above. After incubation of virus-infected cells for three days at the designated temperatures, cell monolayers were immunostained using chicken anti-MDV polyclonal antibodies and the plaques were enumerated. Plaque counts obtained at each of the temperatures were compared to assess the ts phenotype of each virus. The shut-off temperature was defined as the lowest temperature that had a titer reduction of 100-fold or greater compared to 33° C.

Figure 17:
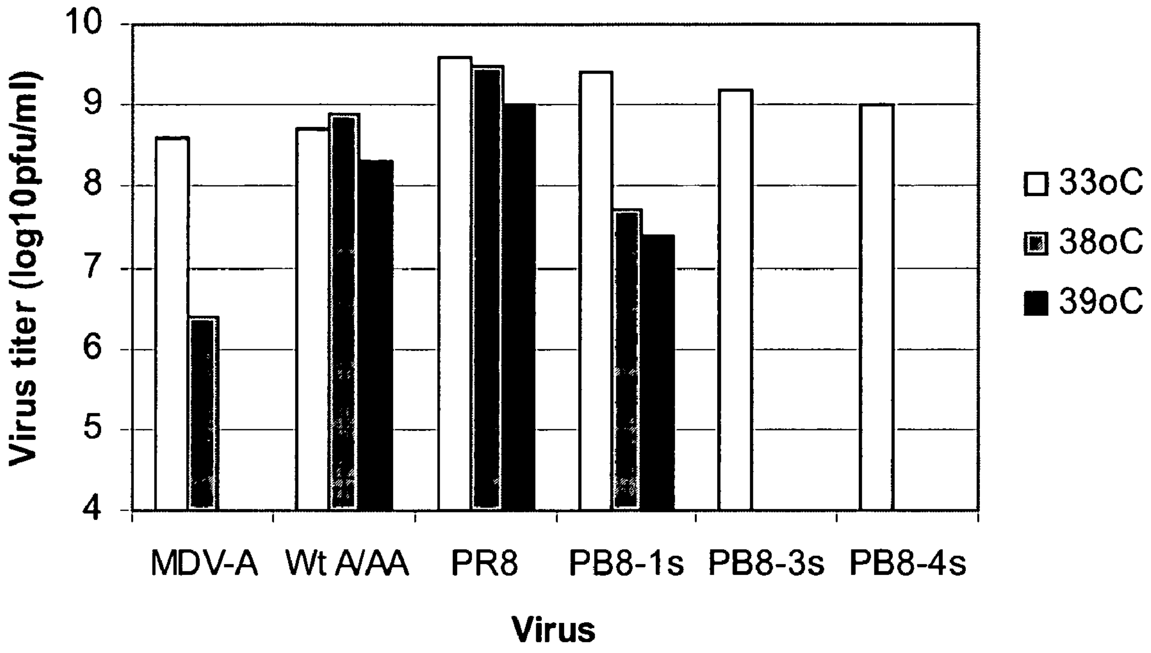
FIG. 17: Bar graph illustrating relative titers at 33° C. and 39° C.
Figure 18:
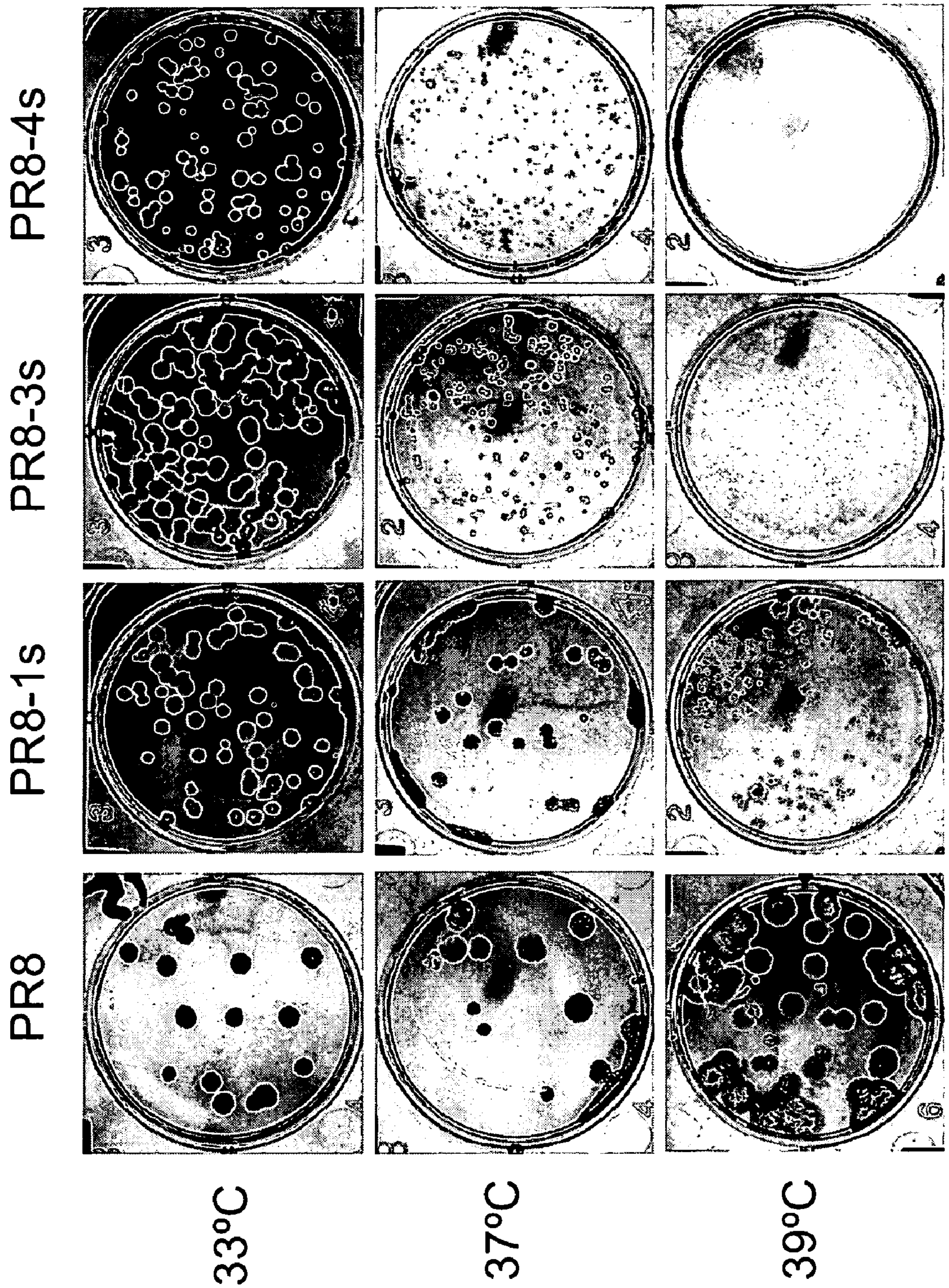
FIG. 18: Photomicrographs illustrating plaque morphology of PR8 mutants at various temperatures. MDCK cells were infected with virus as indicated and incubated at 33, 37 and 39° C. for three days. Virus plaques were visualized by immunostaining and photographed.

As shown in Table 10 and FIG. 17, all mutants replicated well at 33° C. although a slight reduction in virus titer was observed. At 38° C., a significant reduction in virus titer was observed for all the mutants. At 39° C., a reduction in virus titer greater than 4.0 $log_{10}$ was observed for viruses carrying the three ts loci in the PB1 gene (PR8-3s and PR8-4s). PR8-1s was also ts at 39° C. The ts phenotype of PR8-4s was very similar to that of MDV-A that had a reduction of 4.6 $log_{10}$ at 39° C. compared to 33° C. Although all the three PR8 mutants did not have greater than 2.0 $log_{10}$ reduction in virus titer at 37° C., their plaque morphology was different from those at 33° C. As shown in FIG. 18, the plaque size for each mutant was only slightly reduced at 33° C. compared to PR8. A significant reduction in plaque size at 37° C. was observed for PR8-3s and greater for PR8-4s. PR8-1s did not have significant reduction in plaque size at 37° C. At 39° C., only a few pin-point sized plaques were observed for both PR8-3s and PR8-4s. The plaque size of approximately 30% of that wt PR8 was observed for PR8-1 s.

TABLE 10

Temperature sensitivity of PR8 with the introduced ts loci

| Virus | Virus titer ($log_{10}$pfu/ml) 33° C. | 37° C. | 38° C. | 39° C. |
|---|---|---|---|---|
| MDV-A | 8.6 | 7.0 | 6.4 | 4* |
| Wt A/AA | 8.7 | 8.7 | 8.9 | 8.3 |
| PR8 | 9.6 | 9.5 | 9.5 | 9 |
| PB8-1s | 9.4 | 8.9 | 7.7 | 7.4 |
| PB8-3s | 9.2 | 8.8 | 7.8 | 5.2 |
| PB8-4s | 9.5 | 7.8 | 7.1 | 4.4 |

A titer of 4.0 was assigned when no virus was detected at 10,000 dilutions.

Attenuation of the mutant PR8 viruses was examined in ferrets. In brief, male ferrets 9-10 weeks old were used to assess virus replication in the respiratory tracts of an animal host. Ferrets were housed individually and inoculated intranasally with 8.5 $log_{10}$pfu of virus. Three days after infection, ferrets were sedated with ketamine-HCL, lungs and nasal turbinates (NT) were harvested. The lung tissue homogenates were serially diluted and titrated in 10-day-old embryonated chicken eggs. Virus titer ($log_{10}EID_{50}$/ml) in lungs was calculated by the Karber methods. Virus replication in NT was determined by plaque assay and expressed as $log_{10}$pfu/ml.

The levels of virus replication in lungs and nasal turbinates were measured by $EID_{50}$ or plaque assays (Table 11). Three days after infection, PR8 replicated to a level of 5.9 $log_{10}EID_{50}$/gram lung tissues. However, PR8-1s exhibited a 3.0 $log_{10}$ reduction in replication of ferret lungs and very little replication was detected for PR8-3s. No replication was detected for PR8-4s that was studied in two virus groups infected with virus obtained independently. Virus detection limit in ferret lungs by $EID_{50}$ assay is 1.5 log10 and thus a titer of 1.5 $log_{10}EID_{50}$ was assigned for PR8-4s. As a control, MDV-A did not replicate in ferret lungs and wt A/AA/6/60 replicated to a titer of 4.4 $log_{10}$. Virus replication in nasal turbinates (NT) was examined by plaque assay on MDCK cells. PR8 replicated to a titer of 6.6 $log_{10}$pfu/g in the nose. Only slight reductions in virus titer were observed for PR8-1s and PR8-3s. A reduction of 2.2 $log_{10}$ was observed for PR8-4s (A), whereas a 4.3 $log_{10}$ reduction was observed for PR8-4s (B), which carried a change in the PB1 gene (E390G). The greatly reduced replication of PR8-4s (B) correlates well with its ts phenotype at 37° C. An infectious dose of 8.5 log10pfu was used here instead of 7.0 log10pfu that was usually used for evaluating the attenuation phenotype of MDV-A derived influenza vaccines. This result indicated that PR8 carrying the four ts loci derived from MDV-A was attenuated in replication in the lower respiratory tracts of ferrets.

TABLE 11

Replication of PR8 mutants in ferrets

| Virus | Ferrets | Dose ($log_{10}$pfu) | Virus titer in lungs ($log_{10}$EID50/g ± SE) | Virus titer in nasal turbinates ($log_{10}$/g ± SE) |
|---|---|---|---|---|
| PR8 | 4 | 8.5 | 5.9 ± 0.3 | 6.6 ± 0.1 |
| PR8-1s | 4 | 8.5 | 3.8 ± 0.4 | 5.9 ± 0.2 |
| PR8-3s | 4 | 8.5 | 1.7 ± 0.1 | 5.8 ± 0.3 |
| PR8-4s (A) | 4 | 8.5 | 1.5 ± 0.0[a] | 4.6 ± 0.2 |
| PR8-4s (B)[b] | 4 | 8.5 | 1.5 ± 0.0 | 2.3 ± 0.3 |
| MDV-A | 4 | 8.5 | 1.5 ± 0.0 | 4.6 ± 0.1 |
| Wt A/AA | 4 | 8.5 | 4.4 ± 0.1 | 5.4 ± 0.1 |

no virus was detected and a titer of 1.5 $log_{10}$EID50/g was assigned

The virus contains an additional change in PB1-1193 (E390G)

In both the ts and att assays, the PR8 mutant virus exhibited both ts and att phenotypes that were very similar to that of MDV-A. These data indicate that introduction of the unique amino acid substitutions of the MDV-A into a divergent influenza virus strain results in a virus exhibiting the temperature sensitive and attenuated phenotypes desirable for producing, e.g., live attenuated, vaccines. Additionally, the ts, att, PR-8 virus grew to a high titer that suitable for use as a master donor virus for the production of live attenuated or inactivated influenza vaccines. These results indicate that the five MDV-A mutations: PB1-391E, PB1-581G, PB1-661T, PB2-265S, and NP-34G can impart the ts and att phenotypes to any influenza A strains. Similarly, novel ts, att B strains suitable for vaccine production can be produced by introducing the mutations of the MDV-B strain into influenza B strain viruses. In addition to producing live attenuated virus vaccines, introduction of these mutations into donor strains will lead to the production of safer inactivated vaccines.

Example 5

Eight Plasmid System for Production of MDV-B

Viral RNA from a cold adapted variant of influenza B/Ann Arbor/1/66 (ca/Master Ann Arbor/1/66 P1 Aviron Oct. 2, 1997), an exemplary influenza B master donor strain (MDV-B) was extracted from 100 µl of allantoic fluid from infected embryonated eggs using the RNeasy Kit (Qiagen, Valencia, Calif.), and the RNA was eluted into 40 µl $H_2O$. RT-PCR of genomic segments was performed using the One Step RT-PCR kit (Qiagen, Valencia, Calif.) according to the protocol provided, using 1 µl of extracted RNA for each reaction. The RT-reaction was performed 50 min at 50° C., followed by 15 min at 94° C. The PCR was performed for 25 cycles at 94° C. for 1 min, 54° C. for 1 min, and 72° C. for 3 min. The P-genes were amplified using segment specific primers with BsmBI-sites that resulted in the generation of two fragments (Table 12).

TABLE 12

RT-PCR primers for amplification of the eight vRNAs of influenza ca B/Ann Arbor/1/66.

| | Forward primer | Reverse primer |
|---|---|---|
| PB1 [1A] | **Bm-PB1b-1:** (SEQ ID NO:53) TATTCGTCTCAGGG**AGCAGAAGCGGAGC-CTTTAAGATG** | **Bm-PB1b-1200R:** (SEQ ID NO:54) TATTCGTCTC**GATGCCGTTCCTTCT-TCATTGAAGAATGG** |
| PB1 [1B] | **Bm-PB1b-1220:** (SEQ ID NO:55) TATTCGTCTCG**GCATCTTTGTCGCCTGG-GATGATGATG** | **Bm-PB1b-2369R:** (SEQ ID NO:56) ATATCGTCTCGTATT**AGTAGAAACACGAGCCTT** |
| PB2 [2A] | **Bm-PB2b-1:** (SEQ ID NO:57) TATTCGTCTCAGGG**AGCAGAAGCG-GAGCGTTTTCAAGATG** | **Bm-PB2b-1145R:** (SEQ ID NO:58) TATTCGTCTC**TCTCATTTTGCTCTTTTT-TAATATTCCCC** |
| PB2 [2B] | **Bm-PB2b-1142:** (SEQ ID NO:59) TATTCGTCTCATG**AGAATGGAAAAAC-TACTAATAAATTCAGC** | **Bm-PB2b-2396R:** (SEQ ID NO:60) ATATCGTCTCGTATT**AGTAGAAACACGAGCATT** |
| PA [3A] | **Bm-Pab-1:** (SEQ ID NO:61) TATTCGTCTCAGGG**AGCAGAAGCGGT-GCGTTTGA** | **Bm-PAb-1261R:** (SEQ ID NO:62) TATTCGTCTCC**CAGGGCCCTTTTACT-TGTCAGAGTGC** |
| PA [3B] | **Bm-Pab-1283:** (SEQ ID NO:63) TATTCGTCTC**TCCTGGATCTACCA-GAAATAGGGCCAGAC** | **Bm-PAb-2308R:** (SEQ ID NO:64) ATATCGTCTCGTATT**AGTAGAAACACGTGCATT** |
| HA | **MDV-B 5'BsmBI-HA:** (SEQ ID NO:65) TATTCGTCTCAGGG**AGCAGAAGCAGAG-CATTTTCTAATATC** | **MDV-B 3'BsmBI-HA:** (SEQ ID NO:66) ATATCGTCTCGTATT**AGTAGTAACAA-GAGCATTTTTC** |
| NP | **Ba-NPb-1:** (SEQ ID NO:67) TATTGGTCTCAGGG**AGCAGAAGCACAG-CATTTTCTTGT** | **Ba-NPb-1842R:** (SEQ ID NO:68) ATATGGTCTCGTATT**AGTAGAAACAA-CAGCATTTTT** |
| NA | **MDV-B 5'BsmBI-NA:** (SEQ ID NO:69) TATTCGTCTCAGGG**AGCAGAAGCAGAG-CATCTTCTCAAAAC** | **MDV-B 3'BsmBI-NA:** (SEQ ID NO:70) ATATCGTCTCGTATT**AGTAGTAACAA-GAGCATTTTTCAG** |
| M | **MDV-B 5'BsmBI-M:** (SEQ ID NO:71) TATTCGTCTCAGGG**AGCAGAAGCACG-CACTTTCTTAAAATG** | **MDV-B 3'BsmBI-M:** (SEQ ID NO:72) ATATCGTCTCGTATT**AGTAGAAACAACG-CACTTTTTCCAG** |
| NS | **MDV-B 5'BsmBI-NS:** (SEQ ID NO:73) TATTCGTCTCAGGG**AGCAGAAGCAGAG-GATTTGTTTAGTC** | **MDV-B 3'BsmBI-NS:** (SEQ ID NO:74) ATATCGTCTCGTATT**AGTAGTAACAA-GAGGATTTTTAT** |

The sequences complementary to the influenza sequences are shown in bold. The 5'-ends have recognition sequences for the restriction endonucleases BsmBI (Bm) or BsaI (Ba).

Cloning of Plasmids

Figure 4:
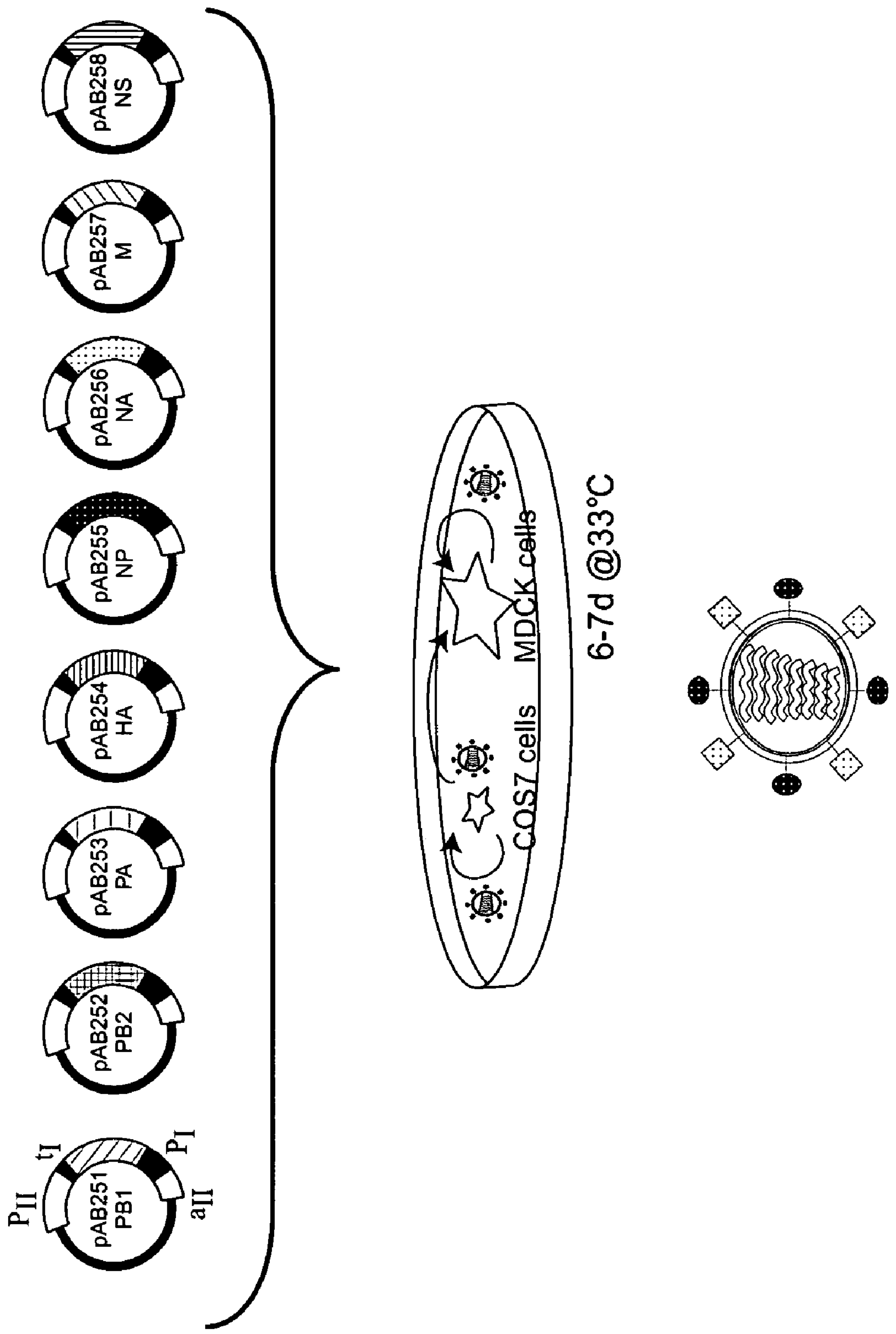
FIG. 4: Illustration of eight plasmid system for the production of influenza B virus.

PCR fragments were isolated, digested with BsmBI (or BsaI for NP) and inserted into pAD3000 (a derivative of pHW2000 which allows the transcription of negative sense vRNA and positive mRNA) at the BsmBI site as described above. Two to four each of the resultant plasmids were sequenced and compared to the consensus sequence of MDV-B based on sequencing the RT-PCR fragments directly. Plasmids which had nucleotide substitutions resulting in amino acid changes different from the consensus sequence were "repaired" either by cloning of plasmids or by utilizing the Quikchange kit (Stratagene, La Jolla, Calif.). The resultant B/Ann Arbor/1/66 plasmids were designated pAB121-PB1, pAB122-PB2, pAB123-PA, pAB124-HA, pAB125-NP, pAB126-NA, pAB127-M, and pAB128-NS. Using this bi-directional transcription system all viral RNAs and proteins are produced intracellularly, resulting in the generation of infectious influenza B viruses (FIG. 4).

It is noteworthy that pAB121-PB1 and pAB124-HA had 2 and pAB128-NS had 1 silent nucleotide substitution compared to the consensus sequence (Table 13). These nucleotide changes do not result in amino acid alterations, and are not anticipated to affect viral growth and rescue. These silent substitutions have been retained to facilitate genotyping of the recombinant viruses.

TABLE 13

Plasmid set representing the eight segments of B/Ann Arbor/1/66 (MDV-B)

| Seg. | plasmids | nucleotides | protein |
|---|---|---|---|
| PB1 | PAB121-PB1 | A924 > G924; C1701 > T1701 | silent |
| PB2 | PAB122-PB2 | consensus | — |
| PA | PAB123-PA | consensus | — |
| HA | PAB124-HA | T150 > C150; T153 > C153 | silent |
| NP | PAB125-NP | consensus | — |
| NA | PAB126-NA | consensus | — |
| M | PAB127-M | consensus | — |
| NS | PAB128-NS | A416 > G416 | NS1: silent |

For construction of the plasmids with nucleotide substitution in PA, NP, and M1 genes the plasmids pAB123-PA, pAB125-NP, pAB127-M were used as templates. Nucleotides were changed by Quikchange kit (Stratagene, La Jolla, Calif.). Alternatively, two fragments were amplified by PCR using primers which contained the desired mutations, digested with BsmBI and inserted into pAD3000-BsmBI in a three fragment ligation reaction. The generated plasmids were sequenced to ensure that the cDNA did not contain unwanted mutations.

The sequence of template DNA was determined by using Rhodamine or dRhodamine dye-terminator cycle sequencing ready reaction kits with AmpliTaq® DNA polymerase FS (Perkin-Elmer Applied Biosystems, Inc, Foster City, Calif.). Samples were separated by electrophoresis and analyzed on PE/ABI model 373, model 373 Stretch, or model 377 DNA sequencers.

In a separate experiment, viral RNA from influenza B/Yamanshi/166/98 was amplified and cloned into pAD3000 as described above with respect to the MDV-B strain, with the exception that amplification was performed for 25 cycles at 94° C. for 30 seconds, 54° C. for 30 seconds and 72° C. for 3 minutes. Identical primers were used for amplification of the B/Yamanashi/166/98 strain segments, with the substitution of the following primers for amplification of the NP and NA segments: MDV-B 5'BsmBI-NP: TATTCGTCTCAGGGAGCAGAAGCACAGCATTTTCTTGTG (SEQ ID NO:75) and MDV-B 3'BsmBI-NP: ATATCGTCTCGTATTAGTAGAAACAACAGCATTTTTTAC (SEQ ID NO:76) and Bm-NAb1: TATTCGTCTCAGGGAGCAGAAGCAGAGCA (SEQ ID NO:77) and Bm-NAb-1557R: ATATCGTCTCGTATTAGTAGTAACAAGAGCATTTT (SEQ ID NO:78), respectively. The B/Yamanashi/166/98 plasmids were designated pAB251-PB1, pAB252-PB2, pAB253-PA, pAB254-HA, pAB255-NP, pAB256-NA, pAB257-M, and pAB258-NS. Three silent nucleotide differences were identified in PA facilitating genotyping of recombinant and reassortant B/Yamanashi/166/98 virus.

Example 6

Generation of Infectious Recombinant Influenza B and Reassorted Influenza Virus

To overcome the obstacles encountered in attempting to grow influenza B in a helper virus free cell culture system, the present invention provides novel vectors and protocols for the production of recombinant and reassortant B strain influenza viruses. The vector system used for the rescue of influenza B virus is based on that developed for the generation of influenza A virus (Hoffmann et al. (2000) *A DNA transfection system for generation of influenza A virus from eight plasmids Proc Natl Acad Sci USA* 97:6108-6113; Hoffmann & Webster (2000) *Unidirectional RNA polymerase I-polymerase II transcription system for the generation of influenza A virus from eight plasmids J Gen Virol* 81:2843-7). 293T or COS-7 cells (primate cells with high transfection efficiency and polI activity) were co-cultured with MDCK cells (permissive for influenza virus), 293T cells were maintained in OptiMEM I-AB medium containing 5% FBS cells, COS-7 cells were maintained in DMEM I-AB medium containing 10% FBS. MDCK cells were maintained in 1×MEM, 10% FBS with the addition of antibiotic and antimycotic agents. Prior to transfection with the viral genome vectors, the cells were washed once with 5 ml PBS or medium without FBS. Ten ml trypsin-EDTA was added to confluent cells in a 75 $cm^2$ flask (MDCK cells were incubated for 20-45 min, 293T cells were incubated for 1 min). The cells were centrifuged, and resuspended in 10 ml OptiMEM I-AB. One ml of each suspended cell line was then diluted into 18 ml OptiMEM I-AB, and mixed. The cells were then aliquoted into a 6 well plate at 3 ml/well. After 6-24 hours, 1 μg of each plasmid was mixed in an 1.5 ml Eppendorf tube with OptiMEM I-AB to the plasmids (x μl plasmids+x μl OptiMEM I-AB+x μl TransIT-LT1=200 μl); 2 μl TransIT-LT1 per μg of plasmid DNA. The mixture was incubated at room temperature for 45 min. Then 800 μl of OptiMEM I-AB was added. The medium was removed from the cells, and the transfection mixture was added to the cells (t=0) at 33° C. for 6-15 hours. The transfection mixture was slowly removed from the cells, and 1 ml of OptiMEM I-AB was added, and the cells were incubated at 33° C. for 24 hours. Forty-eight hours following transfection, 1 ml of OptiMEM I-AB containing 1 μg/ml TPCK-trypsin was added to the cells. At 96 hours post-transfection, 1 ml of OptiMEM I-AB containing 1 μg/ml TPCK-trypsin was added to the cells.

Between 4 days and 7 days following transfection 1 ml of the cell culture supernatant was withdrawn and monitored by HA or plaque assay. Briefly, 1 ml of supernatant was aliquoted into an Eppendorf tube and centrifuge at 5000 rpm for 5 min. Nine hundred μl of supernatant was transferred to a new tube, and serial dilutions were performed at 500 μl/well to MDCK cells (e.g., in 12 well plates). The supernatant was incubated with the cells for 1 hour then removed, and replaced with infection medium (1×MEM) containing 1 μg/ml of TPCK-trypsin. HA assay or plaque assays were then performed. For example, for the plaque assays supernatants were titrated on MDCK cells which were incubated with an 0.8% agarose overlay for three days at 33° C. For infection of eggs the supernatant of transfected cells were harvested six or seven days after transfection, 100 μl of the virus dilutions in Opti-MEM I were injected into 11 days old embryonated chicken eggs at 33° C. The titer was determined three days after inoculation by $TCID_{50}$ assay in MDCK cells.

To generate MDV-B, either co-cultured 293T-MDCK or COS-7-MDCK cells were transfected with 1 μg of each plasmid. When examined at 5 to 7 days post-transfection the co-cultured MDCK cells showed cytopathic effects (CPE), indicating the generation of infectious MDV-B virus from cloned cDNA. No CPE was observed in cells transfected with seven plasmids (Table 14). To determine the efficiency of the DNA transfection system for virus generation, supernatants of cells were titrated seven days after transfection on MDCK cells and the virus titer was determined by plaque assay. The virus titer of the supernatant of co-cultured 293T-MDCK was $5.0\times10^6$ pfu/ml and $7.6\times10^6$ pfu/ml in COS7-MDCK cells.

TABLE 14

Generation of infectious Influenza-B virus from eight plasmids

| segment | 1 | 2 | 3 | 4 |
|---|---|---|---|---|
| PB1 | pAB121-PB1 | — | PAB121-PB1 | — |
| PB2 | pAB122-PB2 | pAB122-PB2 | PAB122-PB2 | pAB122-PB2 |
| PA | pAB123-PA | pAB123-PA | pAB123-PA | pAB123-PA |
| HA | pAB124-HA | pAB124-HA | pAB124-HA | pAB124-HA |
| NP | pAB125-NP | pAB125-NP | pAB125-NP | pAB125-NP |
| NA | pAB126-NA | pAB126-NA | pAB126-NA | pAB126-NA |
| M | pAB127-M | pAB127-M | pAB127-M | pAB127-M |
| NS | pAB128-NS | pAB128-NS | pAB128-NS | pAB128-NS |
| | co-cultured 293T-MDCK cells | | co-cultured COS-7-MDCK cells | |
| CPE | + | − | + | − |
| pfu/ml | $5.0 \times 10^6$ | 0 | $7.6 \times 10^6$ | 0 |

Transiently co-cultured 293T-MDCK (1, 2) or co-cultured COS7-MDCK cells (3, 4) were transfected with seven or eight plasmids. Cytopathic effect (CPE) was monitored seven days after transfection in the co-cultured MDCK cells. Seven days after transfection the supernatants of transfected cells were titrated on MDCK cells. The data of pfu/ml represent the average of multiple, (e.g., three or four) transfection experiments.

Comparable results were obtained in transfection experiments utilizing the B/Yamanashi/166/98 plasmid vectors. These results show that the transfection system allows the reproducible de novo generation of influenza B virus from eight plasmids.

Genotyping of Recombinant Influenza B

Figure 5A:
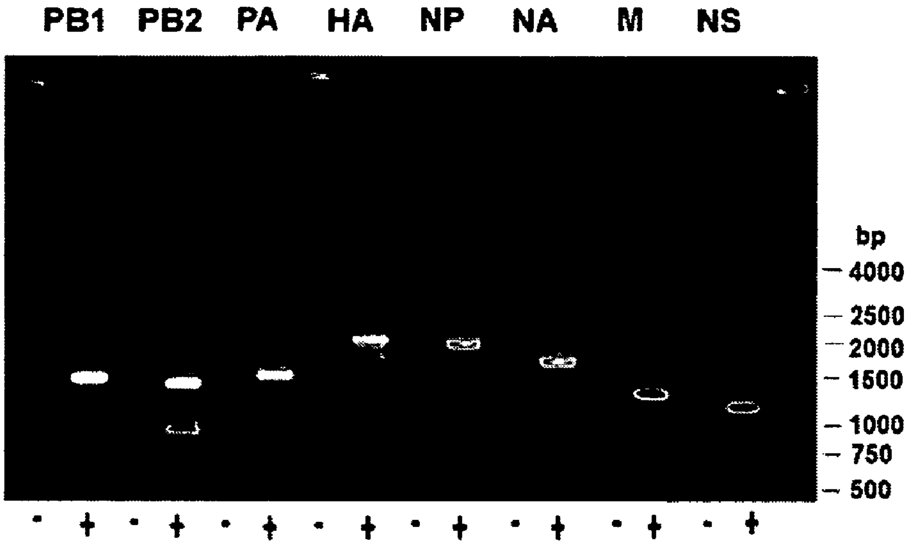
FIG. 5: A and B. Characterization of recombinant MDV-B virus by RT-PCR; Nucleotide sequences shown in 5B are from PB 1 (SEQ ID NO:103), HA (nucleotides 143-159 of SEQ ID NO:98), and NS (SEQ ID NO:104). C and D. Characterization of recombinant B/Yamanashi/166/98 by RT PCR; Nucleotide sequences shown in 5D are from wt-B/Yamanashill166/98 (SEQ ID NO:105) and rec-B/Yamanashi/166/98 (nucleotides 1675-1695 of SEQ ID NO:97).
Figure 5B:
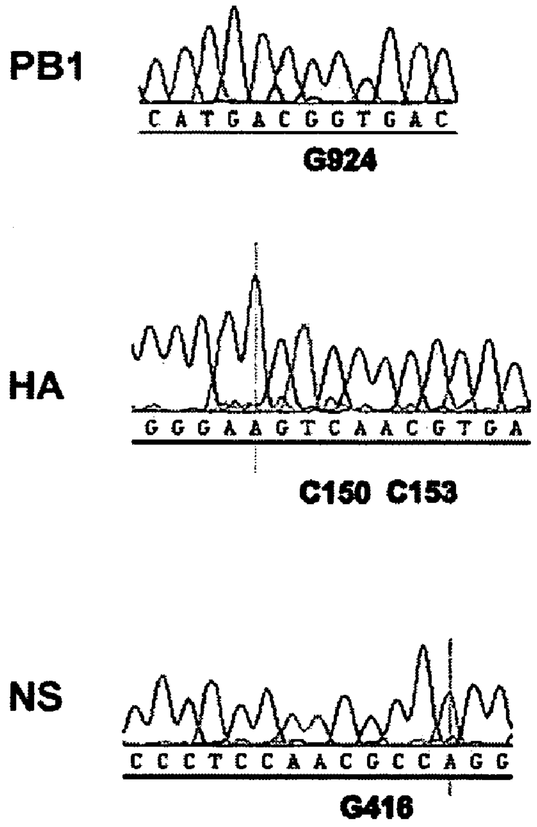

After a subsequent passage on MDCK cells, RT-PCR of the supernatant of infected cells was used to confirm the authenticity of the generated virus. RT-PCR was performed with segment specific primers for all eight segments (Table 12). As shown in FIG. 5A, PCR products were generated for all segments. Direct sequencing of the PCR products of the PB1, HA, and NS segments revealed that the four nucleotides analyzed were the same as found in the plasmid pAB121-PB1, pAB124-HA, and pAB128-NS. These results confirmed that the generated virus was generated from the designed plasmids and exclude (in addition to the negative controls) any possible laboratory contamination with the parent virus (FIG. 5B).

Figure 5C:
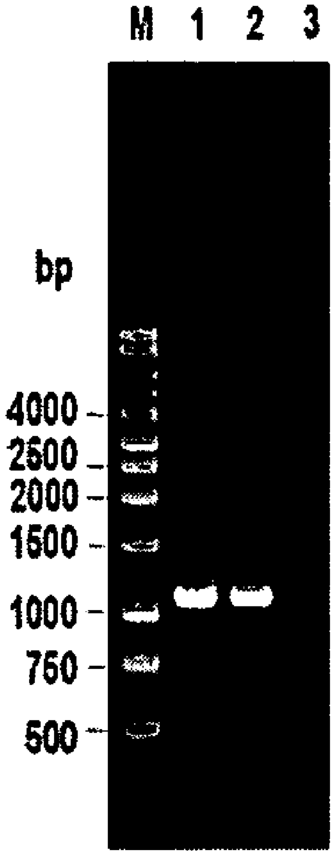
Figure 5D:
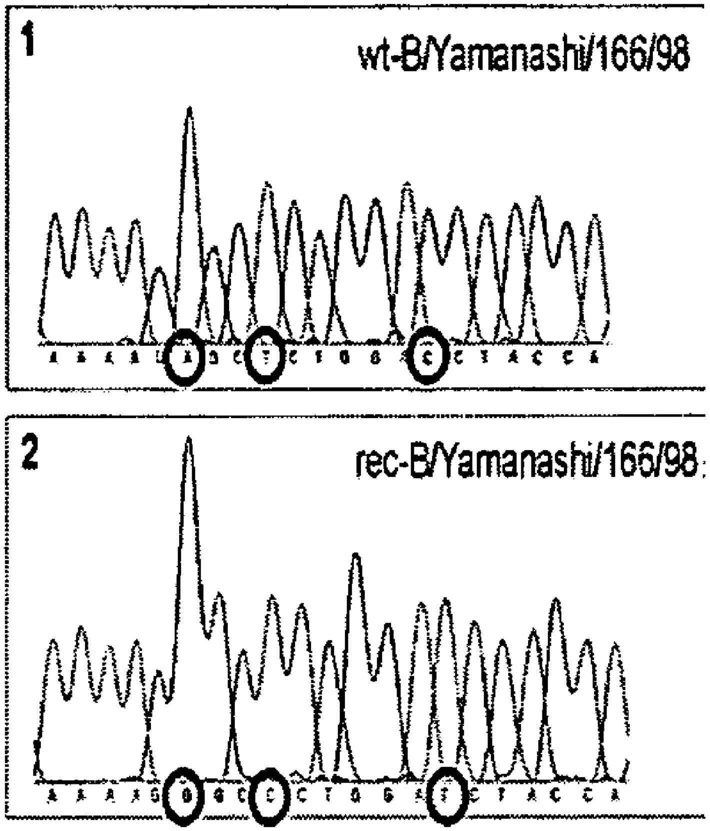

Similarly, following transfection with the B/Yamanashi/166/98 plasmid vectors, virus was recovered and the region encompassing nucleotides 1280-1290 of the PA segment were amplified. Sequencing confirmed that the recovered virus corresponded to the plasmid-derived recombinant B/Yamanashi/166/98 (FIGS. 5C and D).

Phenotyping of rMDV-B

The MDV-B virus shows two characteristic phenotypes: temperature sensitivity (ts) and cold adaptation (ca). By definition a 2 log (or higher) difference in virus titer at 37° C. compared to 33° C. defines ts, ca is defined by less than 2 log difference in virus growth at 25° C. compared to 33° C. Primary chicken kidney (PCK) cells were infected with the parent virus MDV-B and with the transfected virus derived from plasmids to determine the viral growth at three temperatures.

For plaque assay confluent MDCK cells (ECACC) in six well plates were used. Virus dilutions were incubated for 30-60 min. at 33° C. The cells were overlayed with an 0.8% agarose overlay. Infected cells were incubated at 33° C. or 37° C. Three days after infection the cells were stained with 0.1% crystal violet solution and the number of plaques determined.

The ca-ts phenotype assay was performed by $TCID_{50}$ titration of the virus samples at 25, 33, and 37° C. This assay format measures the $TCID_{50}$ titer by examining the cytopathic effect (CPE) of influenza virus on primary chick kidney cell monolayers in 96-well cell culture plates at different temperatures (25° C., 33° C., 37° C.). This assay is not dependent on the plaque morphology, which varies with temperature and virus strains; instead it is dependent solely on the ability of influenza virus to replicate and cause CPE. Primary chicken kidney (PCK) cell suspension, prepared by trypsinization of the primary tissue, were suspended in MEM (Earl's) medium containing 5% FCS. PCK cells were seeded in 96 well cell culture plates for 48 hours in order to prepare monolayer with >90% confluency. After 48 hrs, the PCK cell monolayer were washed for one hour with serum free MEM medium containing 5 mM L-Glutamine, antibiotics, non-essential amino acid, referred as Phenotype Assay Medium (PAM). Serial ten-fold dilution of the virus samples were prepared in 96 well blocks containing PAM. The diluted virus samples were then plated onto the washed PCK monolayer in the 96 well plates. At each dilution of the virus sample, replicates of six wells were used for infection with the diluted virus. Un-infected cells as cell control were included as replicate of 6 wells for each sample. Each virus sample was titered in 2-4 replicates. Phenotype control virus with predetermined titers at 25° C., 33° C., and 37° C. is included in each assay. In order to determine the ts phenotype of the virus samples, the plates were incubated for 6 days at 33° C. and 37° C. in 5% $CO_2$ cell culture incubators. For ca-phenotype characterization the plates were incubated at 25° C. for 10 days. The virus titer was calculated by the Karber Method and reported as $Log_{10}$ Mean (n=4) $TCID_{50}$ Titer/ml±Standard Deviation. The standard deviations of the virus titers presented in FIG. 1-3 ranged from 0.1 to 0.3. The difference in virus titer at 33° C. and 37° C. were used to determine the ts phenotype and difference in titer at 25° C. and 33° C. of the virus were used to determine the ca phenotype.

The plasmid derived recombinant MDV-B (recMDV-B) virus expressed the two characteristic phenotypes in cell culture, ca and ts, as expected. The ca phenotype, efficient replication at 25° C., is functionally measured as a differential in titer between 25° C. and 33° C. of less than or equal to 2 log10 when assayed on PCK cells. Both the parental MDV-B and recMDV-B expressed ca; the difference between 25° C. and 33° C. was 0.3 and 0.4 log10, respectively (Table 15). The ts phenotype is also measured by observing the titers at two different temperatures on PCK cells; for this phenotype, however, the titer at 37° C. should be less than the titer at 33° C. by 2 log10 or more. The difference between 33° C. and 37° C. for the parental MDV-B and recMDV-B was 3.4 and 3.7 log10, respectively (Table 15). Thus, the recombinant plasmid-derived MDV-B virus expressed both the ca and ts phenotypes.

The recombinant virus had a titer of 7.0 $log_{10}$ $TCID_{50}$/ml at 33° C. and 3.3 $TCID_{50}$/ml at 37° C. and 8.8 $log_{10}$ $TCID_{50}$/ml at 25° C. (Table 15). Thus, the recombinant virus derived from transfection with the eight influenza MDV-B genome segment plasmids has both the ca and ts phenotype.

TABLE 15

Phenotype assay for MDV-B and rMDV-B generated from plasmids

| | Temperature (0 C.) | | | |
|---|---|---|---|---|
| Virus | 25 Log10 | 33 TCID50/ml | 37 (Mean + SD) | Phenotype |
| ca B/Ann Arbor/ 01/66 (MDV-B) | 8.8 + 0.3 | 8.5 + 0.05 | 5.1 + 0.1 | ca, ts |
| RecMDV-B | 7.4 + 0.3 | 7.0 + 0.13 | 3.3 + 0.12 | ca, ts |
| Rec53-MDV-B | 5.9 + 0.1 | 5.7 + 0.0 | 5.3 + 0.1 | ca, non-ts |

Primary chicken kidney cells were infected with the parent virus MDV-B and the plasmid-derived recombinant virus (recMDV-B). The virus titer was determined at three different temperatures.

Example 7

Production of Reassortant B/Yamanashi/166/98 Virus

Figure 8:
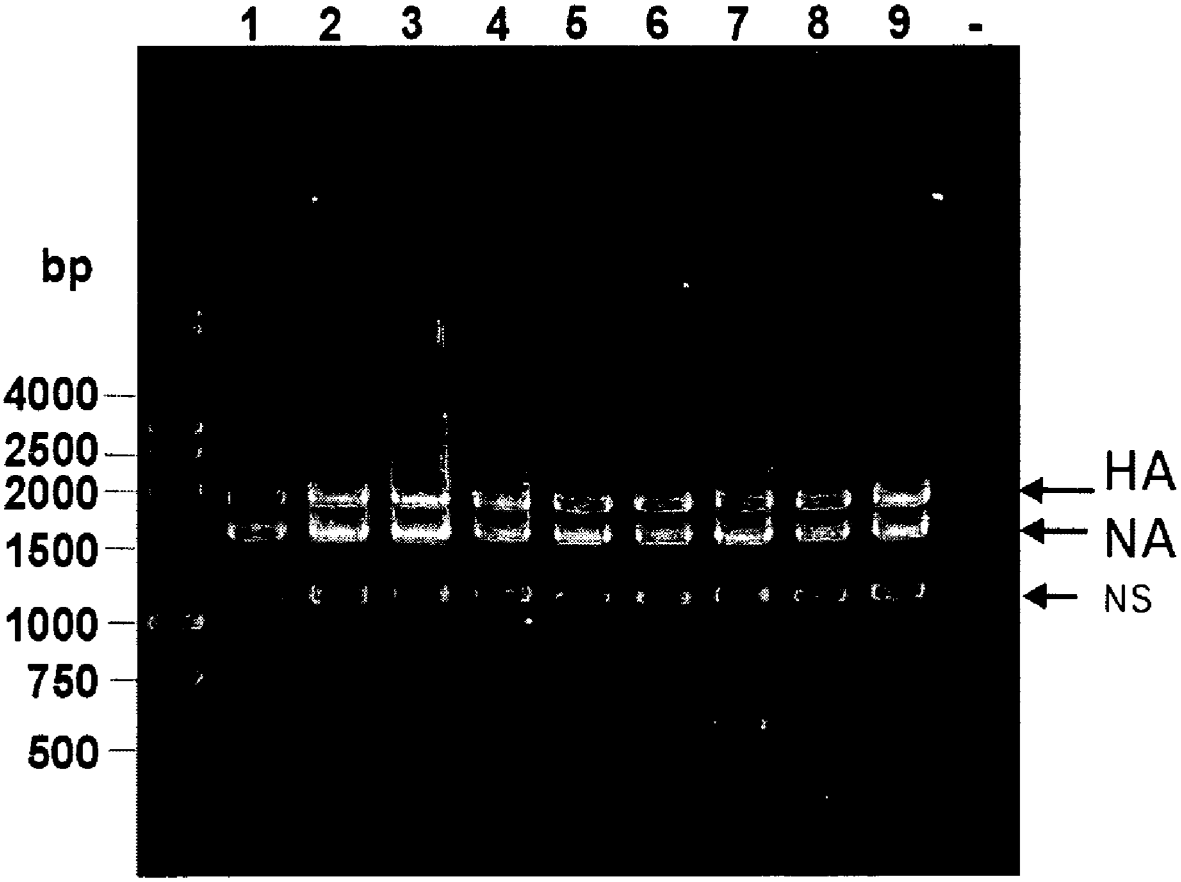
FIG. 8: RT-PCR products derived from simultaneous amplification of HA and NA segments of influenza B strains.

The HA and NA segments of several different strains representing the major lineages of influenza B were amplified and cloned into pAD3000, essentially as described above. The primers were optimized for simultaneous RT-PCR amplification of the HA and NA segments. Comparison of the terminal regions of the vRNA representing the non coding region of segment 4 (HA) and segment 6 (NB/NA) revealed that the 20 terminal nucleotides at the 5' end and 15 nucleotides at the 3'end were identical between the HA and NA genes of influenza B viruses. A primer pair for RT-PCR (underlined sequences are influenza B virus specific) Bm-NAb-1: TAT TCG TCT CAG GGAGCAGAAGCAGAGCA (SEQ ID NO:87); Bm-NAb-1557R: ATA TCG TCT CGT ATT AGTAGTAACAAGAGCATTTT (SEQ ID NO:88) was synthesized and used to simultaneously amplify the HA and NA genes from various influenza B strains (FIG. 8). The HA and NA PCR-fragments of B/Victoria/504/2000, B/Hawaii/10/2001, and B/Hong Kong/330/2001 were isolated, digested with BsmBI and inserted into pAD3000. These results demonstrated the applicability of these primers for the efficient generation of plasmids containing the influenza B HA and NA genes from several different wild type viruses representing the major lineages of influenza B. The RT-PCR products can be used for sequencing and/or cloning into the expression plasmids.

In order to demonstrate the utility of B/Yamanashi/166/98 (a B/Yamagata/16/88-like virus) to efficiently express antigens from various influenza B lineages, reassortants containing PB1, PB2, PA, NP, M, NS from B/Yamanashi/166/98 and the HA and NA from strains representing both the Victoria and Yamagata lineages (6+2 reassortants) were generated. Transiently cocultured COS7-MDCK cells were cotransfected with six plasmids representing B/Yamanashi/166/98 and two plasmids containing the cDNA of the HA and NA segments of two strains from the B/Victoria/2/87 lineage, B/Hong Kong/330/2001 and B/Hawaii/10/2001, and one strain from the B/Yamagata/16/88 lineage, B/Victoria/504/2000, according to the methods described above. Six to seven days after transfection the supernatants were titrated on fresh MDCK cells. All three 6+2 reassortant viruses had titers between 4-9×$10^6$ pfu/ml (Table 16). These data demonstrated that the six internal genes of B/Yamanashi/166/98 could efficiently form infectious virus with HA and NA gene segments from both influenza B lineages.

Supernatants of cocultured COS7-MDCK cells were titrated six or seven days after transfection and the viral titer determined by plaque assays on MDCK cells.

TABLE 16

Plasmid set used for the generation of B/Yamanashi/166/98 and 6 + 2 reassortants.

| segment | | | | | | |
|---|---|---|---|---|---|---|
| 1 | — | pAB251-PB1 | pAB251-PB1 | pAB251-PB1 | pAB251-PB1 |
| 2 | pAB252-PB2 | pAB252-PB2 | pAB252-PB2 | pAB252-PB2 | pAB252-PB2 |
| 3 | pAB253-PA | pAB253-PA | pAB253-PA | pAB253-PA | pAB253-PA |
| 4 | pAB254-HA | pAB254-HA | pAB281-HA | pAB285-HA | pAB287-HA |
| 5 | pAB255-NP | pAB255-NP | pAB255-NP | pAB255-NP | pAB255-NP |
| 6 | pAB256-NA | pAB256-NA | pAB291-NA | pAB295-NA | pAB297-NA |
| 7 | pAB257-M | pAB257-M | pAB257-M | pAB257-M | pAB257-M |
| 8 | pAB258-NA | pAB258-NA | pAB258-NA | pAB258-NA | pAB258-NA |
| Recombinant virus | | 8 B/Yamanashi/ 166/98 | 6 + 2 B/Victoria/504/ 2000 | 6 + 2 B/Hawaii/10/2001 | 6 + 2 B/Hong Kong/330/2001 |
| pfu/ml[a] | 0 | 4 × $10^6$ | 9 × $10^6$ | 6 × $10^6$ | 7 × $10^6$ |

Figure 9:
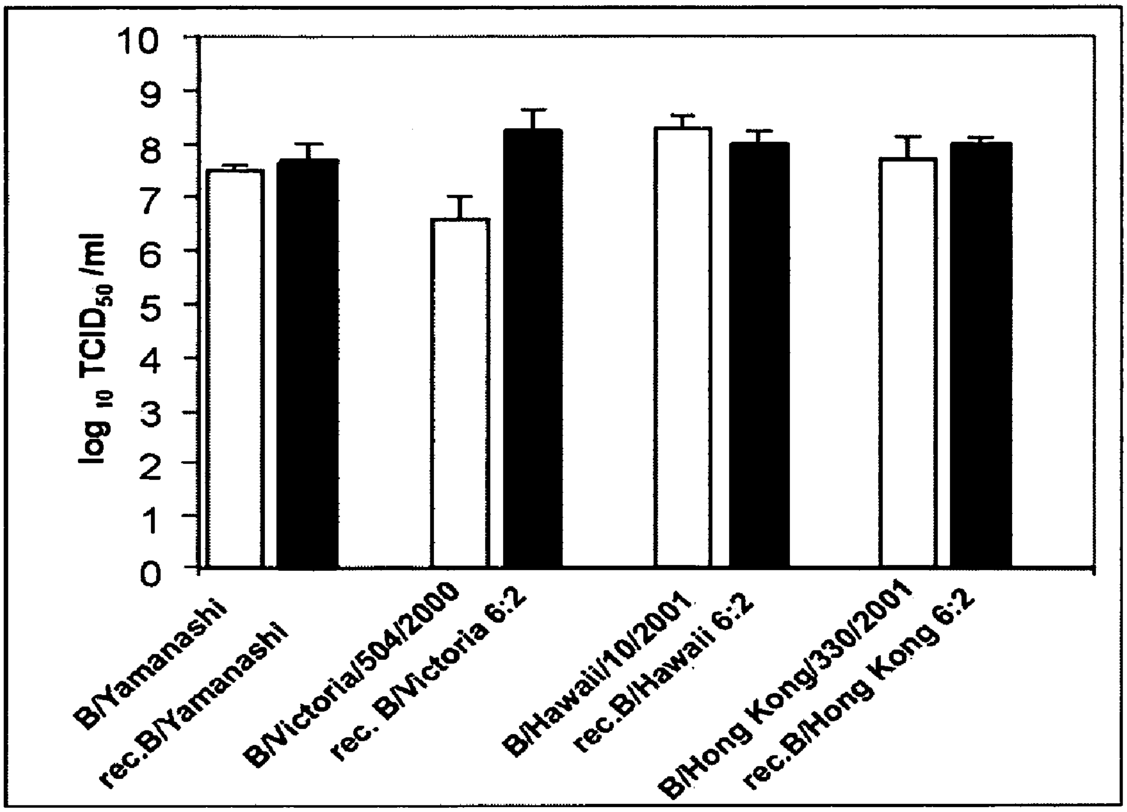
FIG. 9: Bar graph illustrating relative titers of recombinant and reassortant virus.

Relatively high titers are obtained by replication of wild type B/Yamanashi/166/98 in eggs. Experiments were performed to determine whether this property was an inherent phenotype of the six "internal" genes of this virus. To evaluate this property, the yield of wild type B/Victoria/504/2000, which replicated only moderately in eggs, was compared to the yield of the 6+2 reassortant expressing the B/Victoria/504/2000 HA and NA. These viruses in addition to wild type and recombinant B/Yamanashi/166/98 were each inoculated into 3 or 4 embryonated chicken eggs, at either 100 or 1000 pfu. Three day following infection, the allantoic fluids were harvested from the eggs and the $TCID_{50}$ titers determined on MDCK cells. The 6+2 reassortants produced similar quantities of virus in the allantoic fluid to the wt and recombinant B/Yamanashi/166/98 strain (FIG. 9). The difference in titer between B/Victoria/504/2000 and the 6+2 recombinant was approximately 1.6 $log_{10}$ $TCID_{50}$ (0.7-2.5 $log_{10}$ $TCID_{50}$/mL, 95% CI). The difference between B/Victoria/504/2000 and the 6+2 recombinant were confirmed on three separate experiments (P<0.001). These results demonstrated that the egg growth properties of B/Yamanashi/166/98 could be conferred to HA and NA antigens that are normally expressed from strains that replicated poorly in eggs.

Example 8

Molecular Basis for Attenuation of ca B/Ann Arbor/1/66

The MDV-B virus (ca B/Ann Arbor/1/66) is attenuated in humans, shows an attenuated phenotype in ferrets and shows a cold adapted and temperature sensitive phenotype in cell culture. The deduced amino acid sequences of the internal genes of MDV-B were compared with sequences in the Los Alamos influenza database (on the world wide web at: flu-.lanl.gov) using the BLAST search algorithm. Eight amino acids unique to MDV-B, and not present in any other strain were identified (Table 17). Genome segments encoding PB1, BM2, NS1, and NS2 show no unique substituted residues. The PA and M1 proteins each have two, and the NP protein has four unique substituted amino acids (Table 17). One substituted amino acid is found in PB2 at position 630 (an additional strain B/Harbin/7/94 (AF170572) also has an arginine residue at position 630).

The results suggested that the gene segments PB2, PA, NP and M1 may be involved in the attenuated phenotype of MDV-B. In a manner analogous to that described above for MDV-A, the eight plasmid system can be utilized to generate recombinant and reassortant (single and/or double, i.e., 7:1; 6:2 reassortants) in a helper independent manner simply by co-transfection of the relevant plasmids into cultured cells as described above with respect to MDV-A. For example, the 6 internal genes from B/Lee/40 can be used in conjunction with HA and NA segments derived from MDV-B to generate 6+2 reassortants.

In order to determine whether the 8 unique amino acid differences had any impact on the characteristic MDV-B phenotypes, a recombinant virus was constructed in which all eight nucleotide positions encoded the amino acid reflecting the wt influenza genetic complement. A set of plasmids was constructed in which the eight residues of the PA, NP, and M1 genes were changed by site directed mutagenesis to reflect the wild type amino acids (as indicated in Table 17). A recombinant with all eight changes, designated rec53-MDV-B, was generated by cotransfection of the constructed plasmids onto cocultured COS7-MDCK cells. The coculturing of MDCK cells and growth at 33° C. ensured that the supernatant contained high virus titers six to seven days after transfection. The supernatants of the transfected cells were titrated and the titer determined on MDCK cells by plaque assay and PCK cells at 33° C. and 37° C.

As shown in FIG. 13, in two different independent experiments, recMDV-B expressed the ts-phenotype in both MDCK cells and PCK cells. The triple reassortant virus rec53-MDV-B designed harboring all eight amino acid changes expressed the non-ts-phenotype, the difference in titer between 33° C. and 37° C. was only 0.7 $\log_{10}$ in PCK cells. This titer was less than the required 2 $\log_{10}$ difference characteristic of the ts definition and significantly lower than the ~3 $\log_{10}$ difference observed with recMDV-B. These results show that the alteration of the eight amino acids within PA, NP, and M1 proteins was sufficient to generate a non-ts, wild type-like virus with both homologous and heterologous glycoproteins.

The contribution of each gene segment to the ts phenotype was then determined. Plasmid derived recombinants harboring either the PA, NP, or M gene segment with the wild-type amino acid complement were generated by the DNA cotransfection technique. All single gene recombinants exhibited growth restriction at 37° C. in MDCK cells and in PCK cells (FIG. 14), indicating that changes in no one gene segment were capable of reverting the ts phenotype. In addition, recombinant viruses that carried both the NP and M or PA and M gene segments together also retained the ts-phenotype. In

TABLE 17

Unique substituted amino acids of B/Ann Arbor/1/66

| | Nr. | pos | ca B/Ann Arbor/1/66 amino acid | ca B/Ann Arbor/1/66 codon | Aligned sequences (wild type viruses) amino acid | Aligned sequences (wild type viruses) codon | Number of aligned sequences |
|---|---|---|---|---|---|---|---|
| PB1 | 0 | | — | — | | | 23 |
| PB2 | 1 | 630 | Arg630 | AGA | Ser630 | AGC | 23 |
| PA | 2 | 431 | Met431 | ATG | Val431 | GTG | 23 |
| | | 497 | His497 | CAT | Tyr497 | TAT | |
| NP | 4 | 55 | Ala55 | GCC | Thr55 | ACC | 26 |
| | | 114 | Ala114 | GCG | Val114 | GTG | |
| | | 410 | His410 | CAT | Pro410 | CCT, CCC | |
| | | 509 | Thr509 | GAC | Ala509 | GGC | |
| M1 | 2 | 159 | Gln159 | CAA | His159 | CAT | 24 |
| | | 183 | Val183 | GTG | M183 | ATG | |
| BM2 | 0 | | — | — | | | 24 |
| NS1 | 0 | | — | — | | | 80 |
| NS2 | 0 | | — | — | | | 80 |

The deduced amino acid sequence of eight proteins of ca B/Ann Arbor was used in a BLAST search. Amino acid position which were different between MDV-B and the aligned sequences are shown. The nucleotides in the codons that are underlined represent the substituted positions.

contrast, recombinant viruses that harbored both the PA and NP gene segments had a difference in titer between 37° C. and 33° C. of 2.0 $\log^{10}$ or less, similar to the rec53-MDV-B. These results show that the NP and PA genes have a major contribution to the ts-phenotype.

Figure 21:
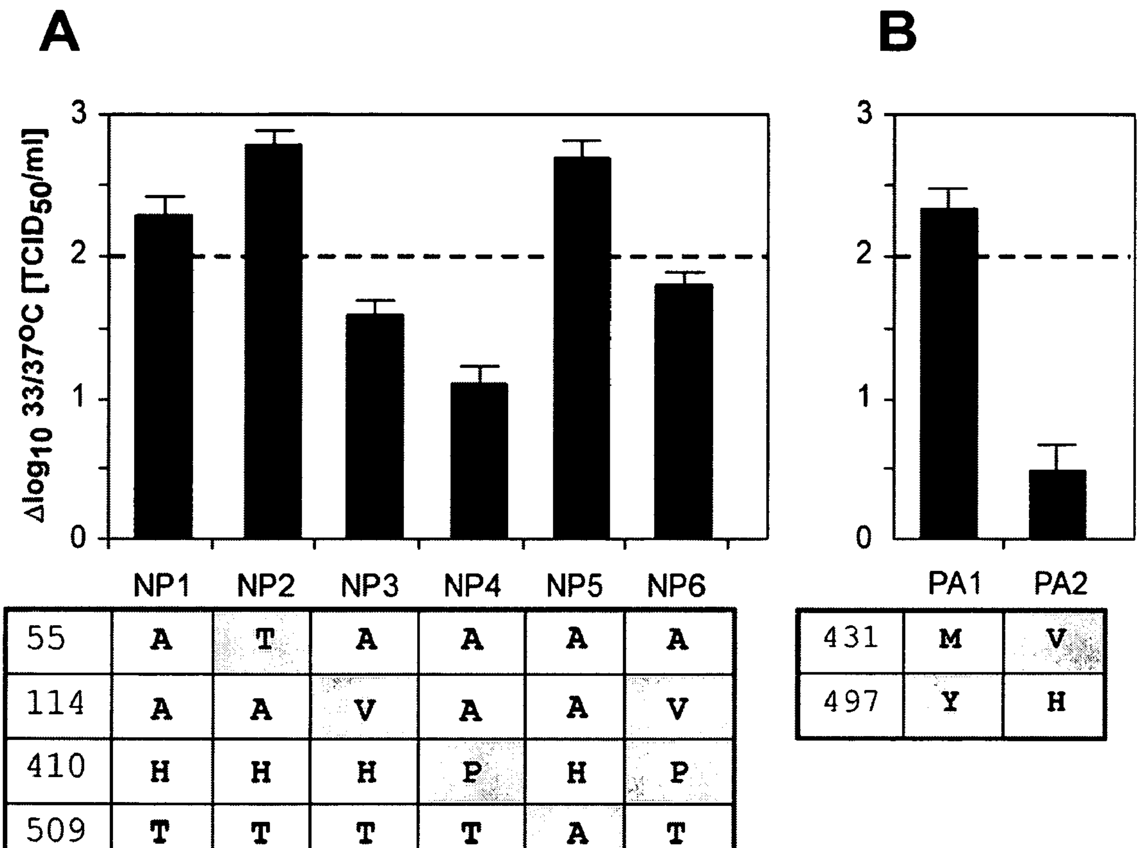
FIG. 21: Bar graphs illustrating differential replication of reassortant viruses. Gray boxes represent wild type amino acid residues. The dotted line represents the shut-off temperature (ts) of 2.0 $\log_{10}$.

To determine whether all of the four amino acids in the NP protein and two in the PA protein contribute to non-ts, triple gene and double-gene recombinants with altered NP and PA genes were generated (FIG. 15). The substitution of two amino acids in the NP protein, A114→V114 and H410→P410 resulted in non-ts phenotype. Viruses with single substitution H410→P410 in the nucleoprotein showed non-ts phenotype in MDCK and PCK. On the other hand, the single substitution A55→T55 showed a ts-phenotype, as did the single substitution at position 509. These results indicate that amino acid residues V114 and P410 in NP are involved in efficient growth at 37° C. (FIG. 21A). A similar strategy was employed to dissect the contribution of the two amino acids in the PA gene. A set of recombinants was constructed, each harboring an NP gene segment with four wild-type consensus amino acids and a PA gene with only one of the two consensus wild type amino acids. Substitution of H497→Y497 remained ts (FIG. 21B), demonstrating that this locus had little impact on expression of the phenotype. In contrast, substitution of M431 with V431 resulted in reversion of the ts phenotype. These results show that amino acids A114 and H410 in NP and M431 in PA are the major determinants for temperature sensitivity of MDV-B.

Based on prior evidence, a ts-phenotype and an attenuated phenotype are highly correlated. It is well established that ca B/Ann Arbor/1/66 virus is not detectable in lung tissue of infected ferrets, whereas non attenuated influenza B viruses viruses are detectable in lungs after intranasal infection. To determine whether identical mutation underlie the ts and att phenotypes, the following studies were performed.

Recombinant viruses obtained after transfection were passaged in embryonated chicken eggs to produce a virus stock. Nine week old ferrets were inoculated intranasaly with 0.5 ml per nostril of viruses with titers of 5.5, 6.0 or 7.0 $\log_{10}$ pfu/ml. Three days after infection ferrets were sacrificed and their lungs and turbinates were examined as described previously.

Ferrets (four animals in each group) were infected intranasaly with recMDV-B or rec53-MDV-B. Three days after infection virus nasal turbinates and lung tissue were harvested and the existence of virus was tested. No virus was detected in lung tissues of ferrets infected with 7.0 $\log_{10}$ pfu recMDV-B. From the four animals infected with rec53-MDV-B virus with 7.0 $\log_{10}$ pfu in three animals virus was detected in lung tissue (one animal in this group for unknown reasons). In two out of four lung tissues of ferrets infected with rec53-MDV-B at a lower dose (5.5 log pfu/ml) virus could be isolated from lung tissue. Thus, the change of the eight unique amino acids in PA, NP, and M1 protein into wild type residues were sufficient to convert a att phenotype into a non-att phenotype.

Since the data in cell culture showed that PA and NP are main contributors to the ts-phenotype, in a second experiment, ferrets were infected with rec53-MDV-B (PA,NP,M), rec62-MDV-B (PA), NP rec71-MDV-B (NP) with 6 log pfu. Two out of four animals infected with rec53-MDV-B had virus in the lung. None of the lung tissues of ferrets infected with single and double reassortant viruses had detectable levels of virus. Thus, in addition to the amino acids in the PA and NP proteins, the M1 protein is important for the att phenotype. Virus with wt PA and NP did not replicate in ferret lung, indicating that a subset of the mutations involved in attenuation are involved in the ts phenotype.

Thus, the ts and att phenotypes of B/Ann Arbor/1/66 are determined by at most three genes. The conversion of eight amino acids in the PA, NP, and M1 protein into wild type residues resulted in a recombinant virus that replicated efficiently at 37° C. Similarly, a 6+2 recombinant virus representing the six internal genes of MDV-B with the HA and NA segments from B/HongKong/330/01 showed a ts-phenotype and the triple recombinant was non-ts.

Our results using the MDV-B backbone indicated that six amino acids were sufficient to convert a ts/att phenotype into a non-ts/non-att phenotype. Therefore, we were interested in determining whether the introduction of those six 'attenuation' residues would transfer these biological properties to a heterologous wildtype, non attenuated influenza B virus, such as B/Yamanashi/166/98.

Recombinant wildtype B/Yamanashi/166/98 (recYam) (7) and a recombinant virus (rec6-Yam): with six amino acid changes PA (V431→M431, H497→Y497), NP (V114→A114, P410→H410), and M1 (H159→Q159, M183→V183) were produced. RecYam showed a 0.17 log10 titer reduction in titer at 37° C. compared to 33° C., whereas rec6Yam was clearly ts, the difference in viral titer between 37° C. and 33° C. was 4.6 log10. Virus was efficiently recovered from ferrets infected with recYam, as expected for a typical wildtype influenza B virus. When rec6Yam was inoculated into ferrets, no virus was detected in the lung tissues (Table 18). Thus, the transfer of the ts/att loci from MDV-B are sufficient to transfer the ts- and att-phenotypes to a divergent virus.

TABLE 18

Attenuation studies in ferrets

| Recombinant virus | wt components[a] | Ts-phenotype | ferrets | Dose [log10pfu] | Nasal turbinates[b] [log10pfu/g] | Lung tissue [log10EID50/g][c] |
|---|---|---|---|---|---|---|
| rMDV-B | none | ts | 4 | 6.0 | 4.01 | <1.5 |
| rec53-B | NP, PA, M | Non-ts | 4 | 6.0 | 4.65 | 3.81 |
| rec62-B | NP, PA | Non-ts | 4 | 6.0 | 4.69 | <1.5 |
| rec71NP-B | NP | ts | 4 | 6.0 | 4.13 | <1.5 |
| rec71M-B | M | ts | 4 | 6.0 | 4.17 | <1.5 |

TABLE 18-continued

Attenuation studies in ferrets

| Recombinant virus | wt components[a] | Ts-phenotype | ferrets | Dose [log10pfu] | Nasal turbinates[b] [log10pfu/g] | Lung tissue [log10EID50/g][c] |
|---|---|---|---|---|---|---|
| RecYam | | Non-ts | 4 | 6.0 | 4.92 | 3.31 |
| rec6Yam | | ts | 4 | 6.0 | 4.02 | <1.5 |

[a]Recombinant viruses with MDV-B backbone that differed in wildtype amino acids (for details see table 2) were used to infected ferrets intranassally. RecYam is recombinant B/Yamanashi/166/98 and Rec6Yam represents a virus that has six 'MDV-B-attenuation' amino acid changes in NP, PA, and M1 with a B/Yamanashi backbone.
[b]Three days after infection the virus titer of the nasal turbinates and lung tissue was determined, the average titer of four infected ferrets is shown.
[c]<1.5 indicates that no virus was detected.

As described above with respect to influenza A strains, substitution of the residues indicated above, e.g., $PB2^{630}$ (S630R); $PA^{431}$ (V431M); $PA^{497}$ (Y497H); $NP^{55}$ (T55A); $NP^{114}$ (V114A); $NP^{410}$ (P410H); NP509 (A509T); $M1^{159}$ (H159Q) and $M1^{183}$ (M183V), confers the ts and att phenotypes. Accordingly, artificially engineered variants of influenza B strain virus having one or more of these amino acid substitutions exhibit the ts and att phenotypes and are suitable for use, e.g., as master donor strain viruses, in the production of attenuated live influenza virus vaccines.

Example 9

Rescue of Influenza from Eight Plasmids by Electroporation of Vero Cells

Previously it has been suggested that recombinant influenza A can be rescued from Vero cells (Fodor et al. (1999) *Rescue of influenza A virus from recombinant DNA J. Virol.* 73:9679-82; Hoffmann et al. (2002) *Eight-plasmid system for rapid generation of influenza virus vaccine Vaccine* 20:3165-3170). The reported method requires the use of lipid reagents and has only been documented for a single strain of a highly replication competent laboratory strains of influenza A (A/WSN/33 and A/PR/8/34), making it of limited application in the production of live attenuated virus suitable for vaccine production. The present invention provides a novel method for recovering recombinant influenza virus from Vero cells using electroporation. These methods are suitable for the production of both influenza A and influenza B strain viruses, and permit the recovery of, e.g., cold adapted, temperature sensitive, attenuated virus from Vero cells grown under serum free conditions facilitating the preparation of live attenuated vaccine suitable for administration in, e.g., intranasal vaccine formulations. In addition to its broad applicability across virus strains, electroporation requires no additional reagents other than growth medium for the cell substrate and thus has less potential for undesired contaminants. In particular, this method is effective for generating recombinant and reassortant virus using Vero cells adapted to growth under serum free condition, such as Vero cell isolates qualified as pathogen free and suitable for vaccine production. This characteristic supports the choice of electroporation as an appropriate method for commercial introduction of DNA into cell substrates.

Electroporation was compared to a variety of methods for introduction of DNA into Vero cells, including transfection using numerous lipid based reagents, calcium phosphate precipitation and cell microinjection. Although some success was obtained using lipid based reagents for the rescue of influenza A, only electroporation was demonstrated to rescue influenza B as well as influenza A from Vero cells.

One day prior to electroporation, 90-100% confluent Vero cells were split, and seeded at a density of $9\times10^6$ cells per T225 flask in MEM supplemented with pen/strep, L-glutamine, nonessential amino acids and 10% FBS (MEM, 10% FBS). The following day, the cells were trypsinized and resuspend in 50 ml phosphate buffered saline (PBS) per T225 flask. The cells are then pelleted and resuspend in 0.5 ml OptiMEM I per T225 flask. Optionally, customized OptiMEM medium containing no human or animal-derived components can be employed. Following determination of cell density, e.g., by counting a 1:40 dilution in a hemocytometer, $5\times10^6$ cells were added to a 0.4 cm electroporation cuvette in a final volume of 400 µl OptiMEM I. Twenty µg DNA consisting of an equimolar mixture of eight plasmids incorporating either the MDV-A or MDV-B genome in a volume of no more than 25 µl was then added to the cells in the cuvette. The cells were mixed gently by tapping and electroporated at 300 volts, 950 microFarads in a BioRad Gene Pulser II with Capacitance Extender Plus connected (BioRad, Hercules, Calif.). The time constant should be in the range of 28-33 msec.

The contents of the cuvette were mixed gently by tapping and 1-2 min after electroporation, 0.7 ml MEM, 10% FBS was added with a 1 ml pipet. The cells were again mixed gently by pipetting up and down a few times and then split between two wells of a 6 well dish containing 2 ml per well MEM, 10% FBS. The cuvette was then washed with 1 ml MEM, 10% FBS and split between the two wells for a final volume of about 3.5 ml per well.

In alternative experiments, Vero cells adapted to serum free growth conditions, e.g., in OptiPro (SFM) (Invitrogen, Carlsbad, Calif.) were electroporated as described above except that following electroporation in OptiMEM I, the cells were diluted in OptiPro (SFM) in which they were subsequently cultured for rescue of virus.

The electroporated cells were then grown under conditions appropriate for replication and recovery of the introduced virus, i.e., at 33° C. for the cold adapted Master Donor Strains. The following day (e.g., approximately 19 hours after electroporation), the medium was removed, and the cells were washed with 3 ml per well OptiMEM I or OptiPro (SFM). One ml per well OptiMEM I or OptiPro (SFM) containing pen/strep was added to each well, and the supernatants were collected daily by replacing the media. Supernatants were stored at −80° C. in SPG. Peak virus production was typically observed between 2 and 3 days following electroporation.

TABLE 19

Results of 8 Plasmid Rescue of MDV strains on Different Cell Types and by Different Transfection Methods

| Substrate | Method | No of Test | Result (Infectious Virus Recovered) |
|---|---|---|---|
| | MDV-B | | |
| COS-7/MDCK | Lipo | 3 | positive |
| COS-7/MDCK | CaPO4 | 2 | positive |
| MRC-5 | Lipo | 5 | negative |
| MRC-5 | CaPO4 | 3 | negative |
| MRC-5 | Electroporation | 2 | negative |
| WI-38 | Lipo | 2 | negative |
| WI-38 | Electroporation | 4 | negative |
| WI-38 | Microinjection | 1 | negative |
| LF1043 | Lipo | 1 | negative |
| LF1043 | CaPO4 | 2 | negative |
| Vero | Lipo | 7 | negative |
| Vero | CaPO4 | 2 | negative |
| Vero/MDCK | Lipo | 1 | negative |
| Vero (serum) | Electroporation | 5 | positive (5/5) |
| Vero (serum free) | Electroporation | 4 | positive (4/4) |
| | MDV-A | | |
| Vero (serum) | Electroporation | 3 | positive (3/3) |
| Vero (serum Free) | Electroporation | 3 | positive (3/3) |

Example 10

Influenza Virus Vector System for Gene Delivery

The vectors of the present invention can also be used as gene delivery systems and for gene therapy. For such applications, it is desirable to generate recombinant influenza virus, e.g., recombinant influenza A or B virus expressing a foreign protein. For example, because segment 7 of the influenza B virus is not spliced, it provides a convenient genetic element for the insertion of heterologous nucleic acid sequences. The mRNA contains two cistrons with two open reading frames encoding the M1 and BM2 proteins. The open reading frame of BM2 or M1 is substituted by the heterologous sequence of interest, e.g., a gene encoding the enhanced green fluorescent protein (EGFP). Using the plasmid based vector system of the present invention, the cDNA encoding the open reading frame of M1-EGFP and BM2 are cloned on two different plasmids. The open reading frame is flanked by the non coding region of segment 7, which contains the signals required for replication and transcription. Alternatively, two plasmids are constructed: one containing M1 ORF and the other containing EGFP-BM2. Co-transfection of the resultant nine plasmids results in the generation of a recombinant influenza B virus containing the heterologous gene sequence. Similarly, EGFP can be expressed from the NS1 segment of influenza A.

The exemplary "green" influenza B virus can be used for standardization in virus assays, such as micro neutralization assays. The combination of the plasmid based technology and the simple detection of protein expression (fluorescence derived from EGFP can be monitored by microscopy, as illustrated in FIG. 2), permits the optimization of protein expression.

Example 11

Genetic Studies of Recent H3N2 Influenza Vaccine Strains

The live attenuated cold-adapted influenza A/AA/6/60 strain, in typical preferred embodiments, is the master donor virus (MDV-A) for influenza A FluMist™ vaccines. The 6 internal genes of MDV-A confer the cold-adapted (ca) temperature sensitive (ts) and attenuated (att) phenotypes to each of the vaccine strains. Using reverse genetics, it is demonstrated that multiple amino acids segregated among three gene segments: PB1-K391 E, E581G, A661T, PB2-N265S, and NP-D34G which control expression of the ts and att phenotypes of MDV-A. Plasmid rescue of 6:2 vaccine strains allows more efficient generation of influenza vaccines than classical reassortment techniques.

Figure 22:
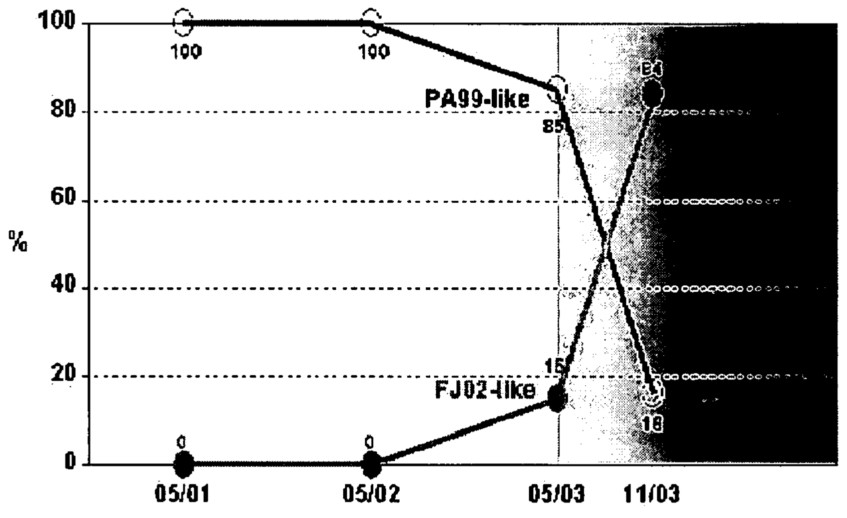
FIGS. 22-23: Antigenically compare A/Panama/99 (H3N2) and A/Fujian/411/02-like (H3N2).
Figure 23:
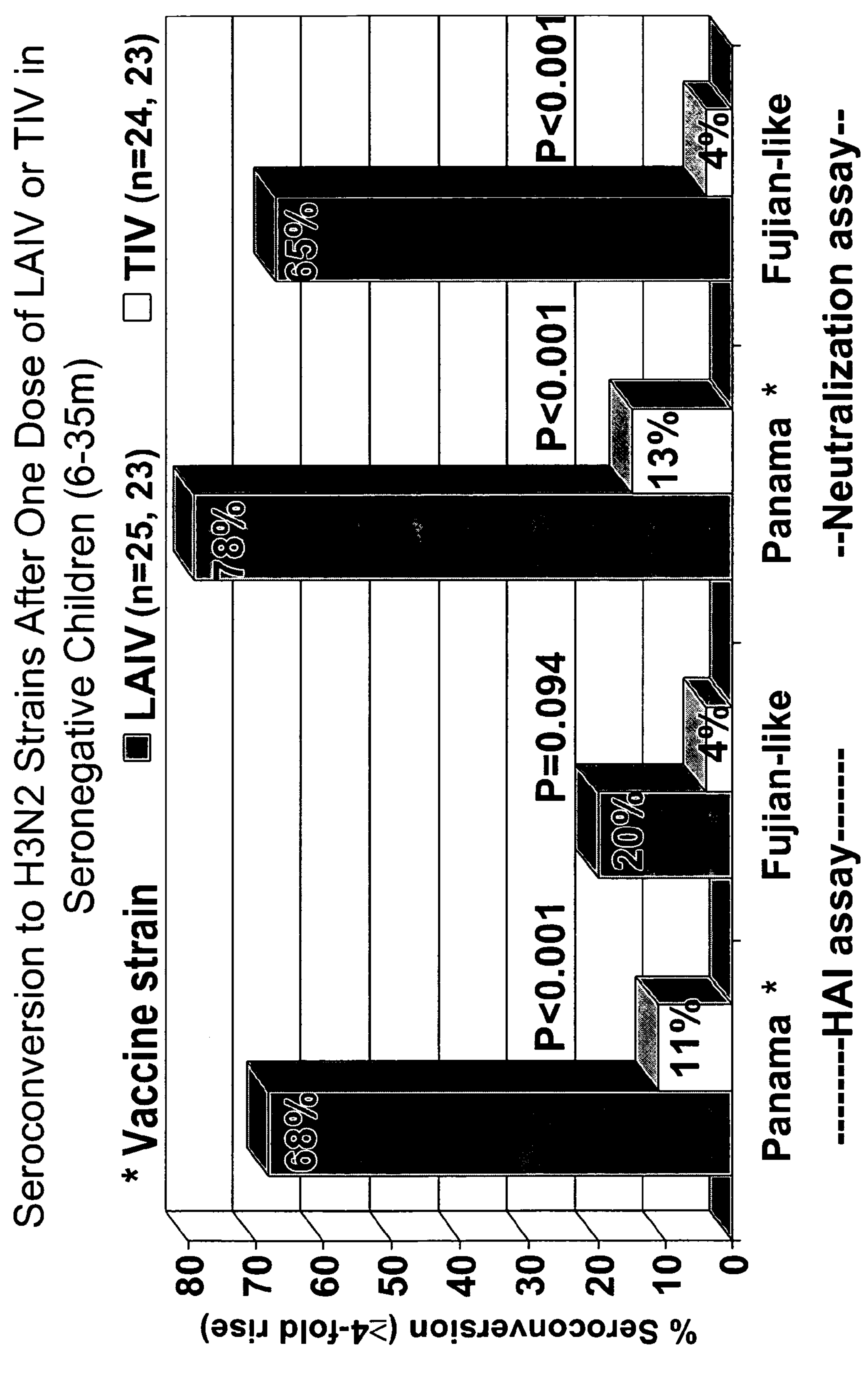

The inactivated influenza vaccines for the 2003-04 season contained the A/Panama/99 (H3N2) antigen and were unable to elicit robust antibody responses in seronegative children to the drifted A/Fujian/411/02-like H3N2 strains that circulated during this season. See FIGS. 22 and 23. Unfortunately, A/Fujian/411/02 did not replicate well in embryonated chicken eggs and, thus, prohibited its use for vaccine manufacture. Using the reverse genetics technology, we showed that the loss in the balance of the HA and NA activities was responsible for poor replication of the prototype A/Fujian/411/02 strain in eggs. See FIGS. 29 through 34. A/Fujian virus could gain its efficient replication in eggs by either increasing its HA activity or by reducing its NA activity. Specifically, we demonstrate that a while a several different single amino acid substitution were able to slightly enhance the replication of A/Fujian/411/02 strain in eggs several combination gave a much more robust enhancement. See FIGS. 35 through 38. This work has demonstrated the feasibility of improving influenza virus growth in embryonated chicken eggs and/or host cells by introducing specific changes in the HA or NA genes without affecting virus antigenicity.

To produce a strain viable in eggs, a set of related H3N2 6:2 reassortants of the A/Fujian/411/02 lineage were evaluated for their replication in MDCK cells, embryonated eggs and ferrets. While A/Fujian/411/02 did not grow in eggs, an egg-adaptation of this virus resulted in two amino acid substitutions in HA, H183L and V226A which allowed for virus growth in embryonated eggs. Additionally, an egg-adapted A/Wyoming/03/2003 strain that grew well in eggs and ferrets and the A/Sendai/H-F4962/02 vaccine that grew well in eggs, but replicated poorly in ferrets, were compared in terms of sequence. It was determined that G186V and V2261 in HA, and/or Q119E and K136Q in NA were required for efficient virus replication in vitro and in vivo. Nevertheless, these amino acid changes had no effect on virus antigenicity. Adoption of such techniques to produce strains capable of growth in eggs (for strains that are difficult/problematic to grow in eggs) or to produce strains more capable of growth in eggs (for strains that can already grow in eggs) for other influenza viruses is contemplated and expected.

Figure 24:
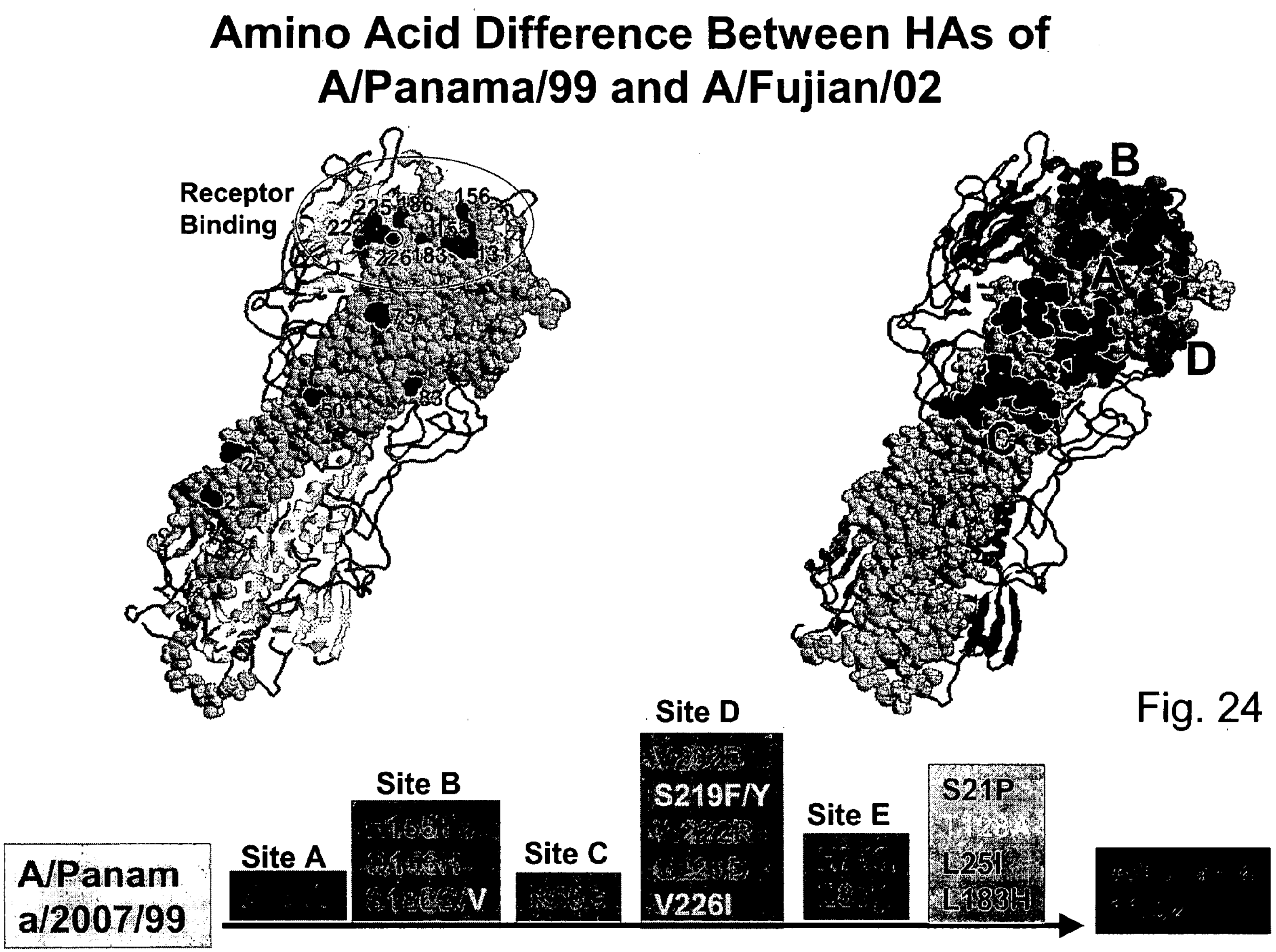
Figure 25:
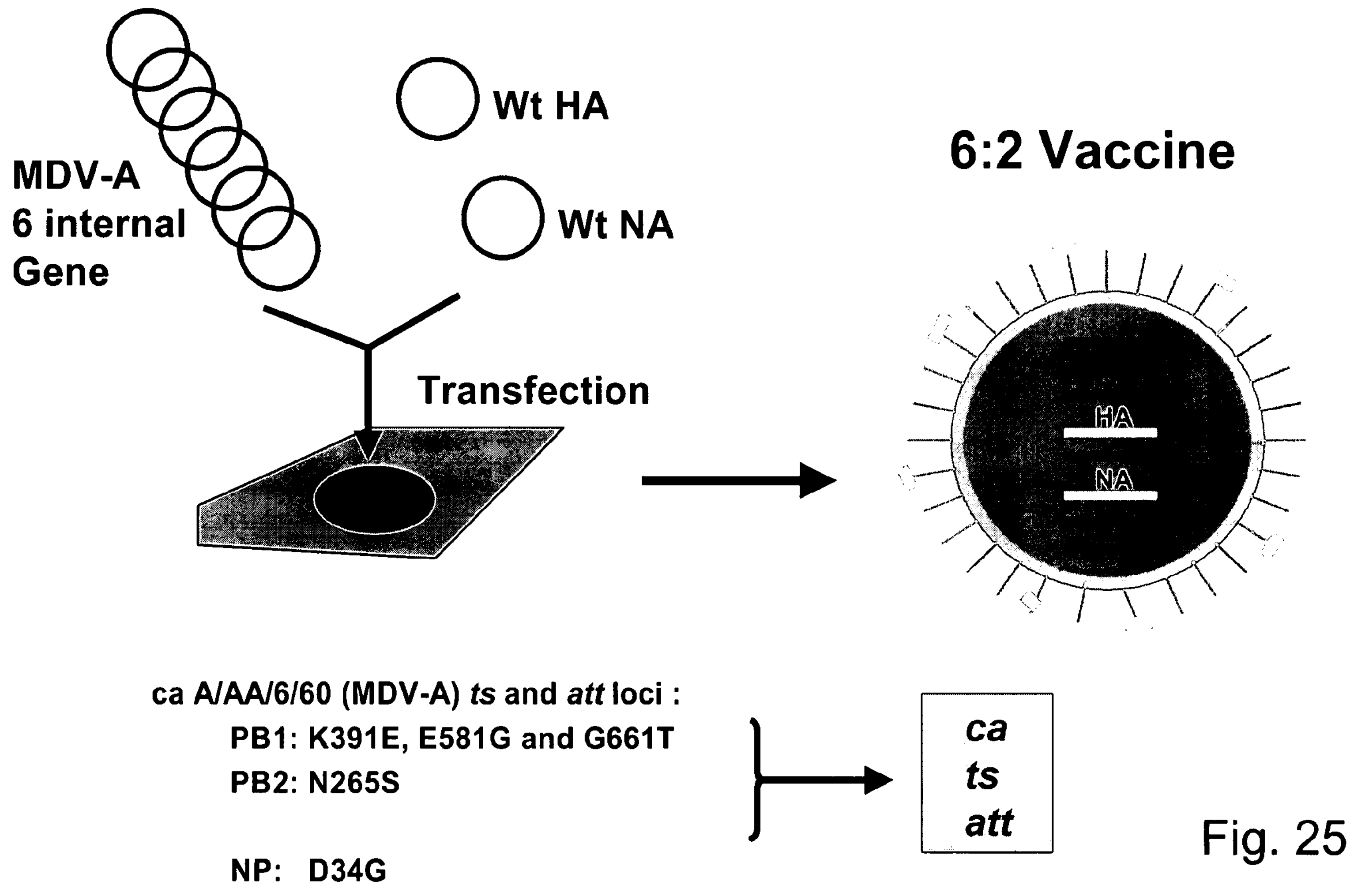
Figure 27:
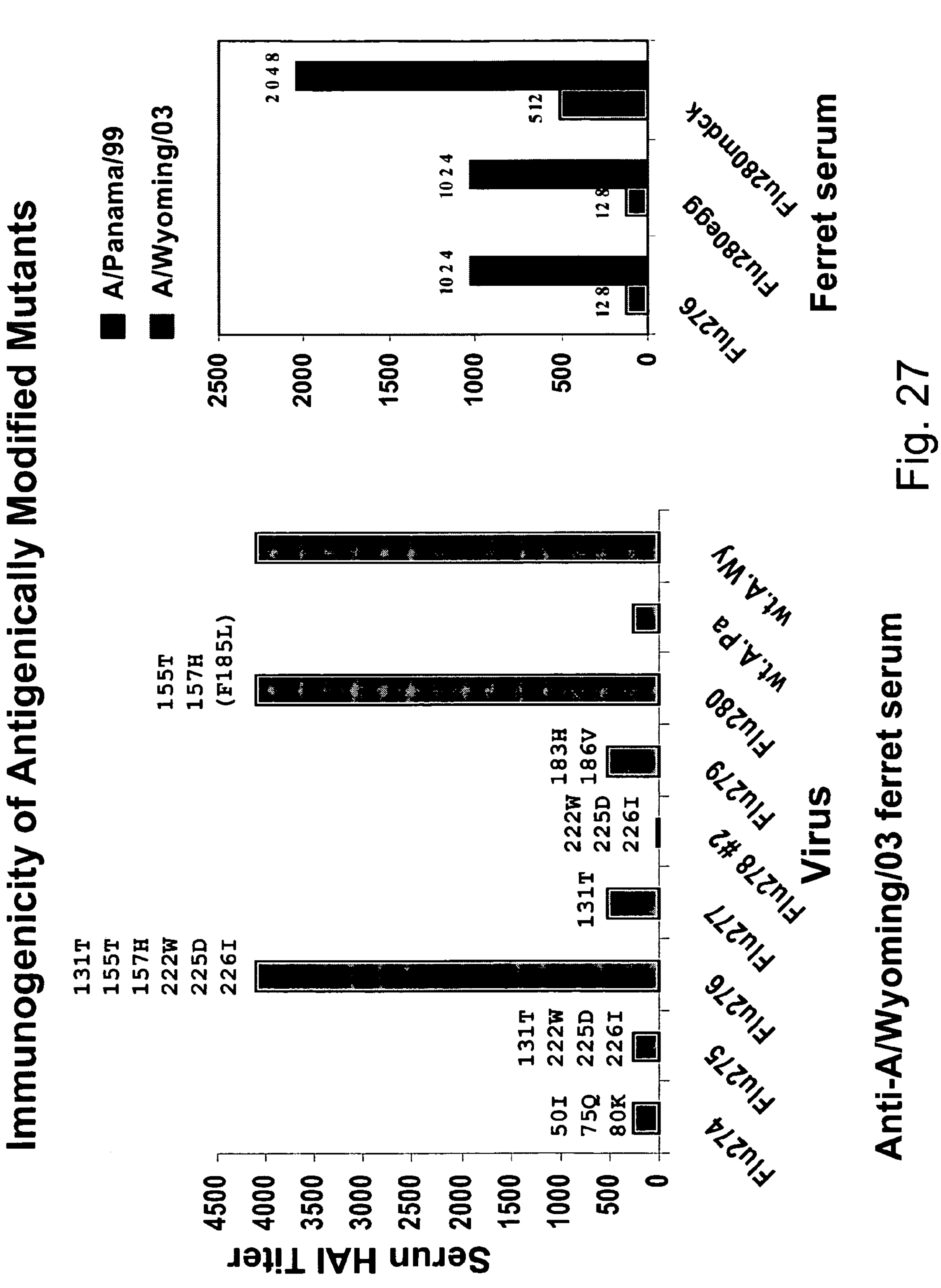
Figure 28:
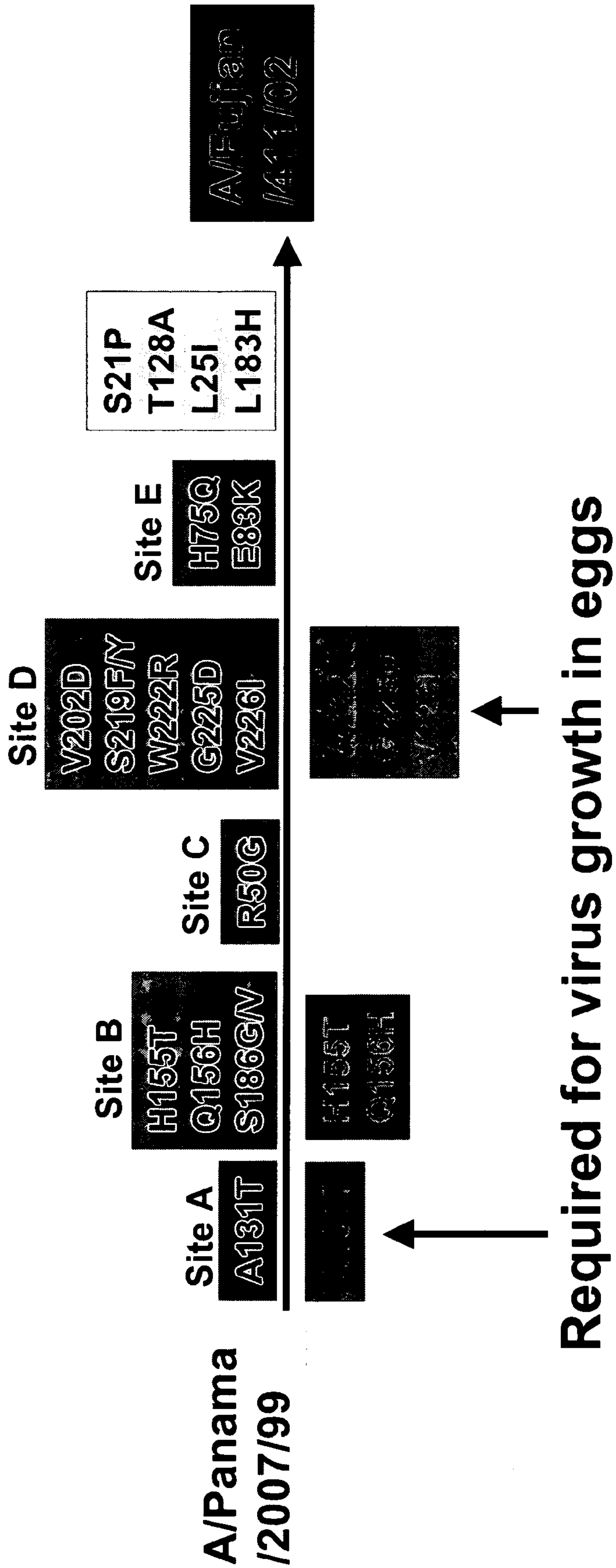
Figure 30:
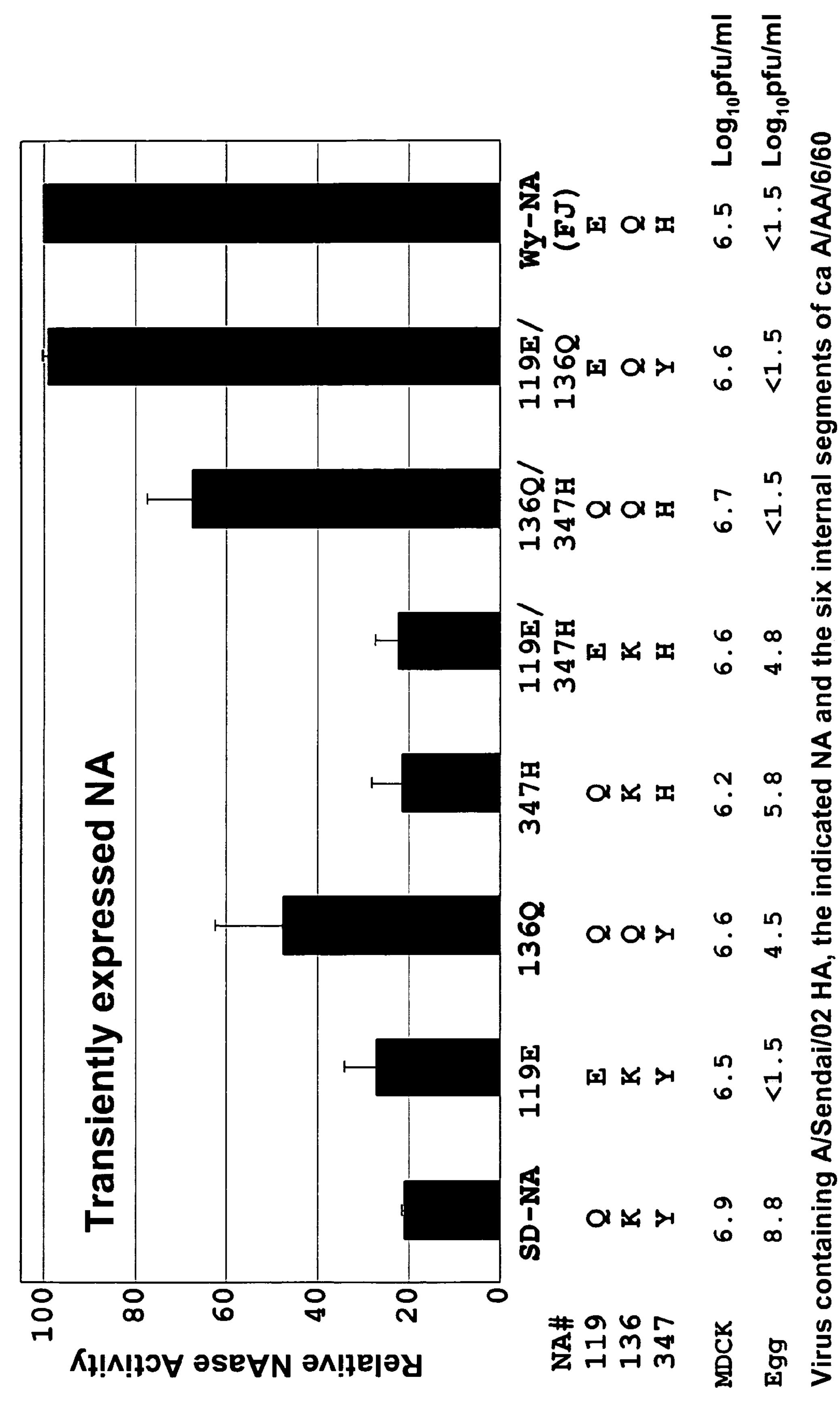
Figure 31:
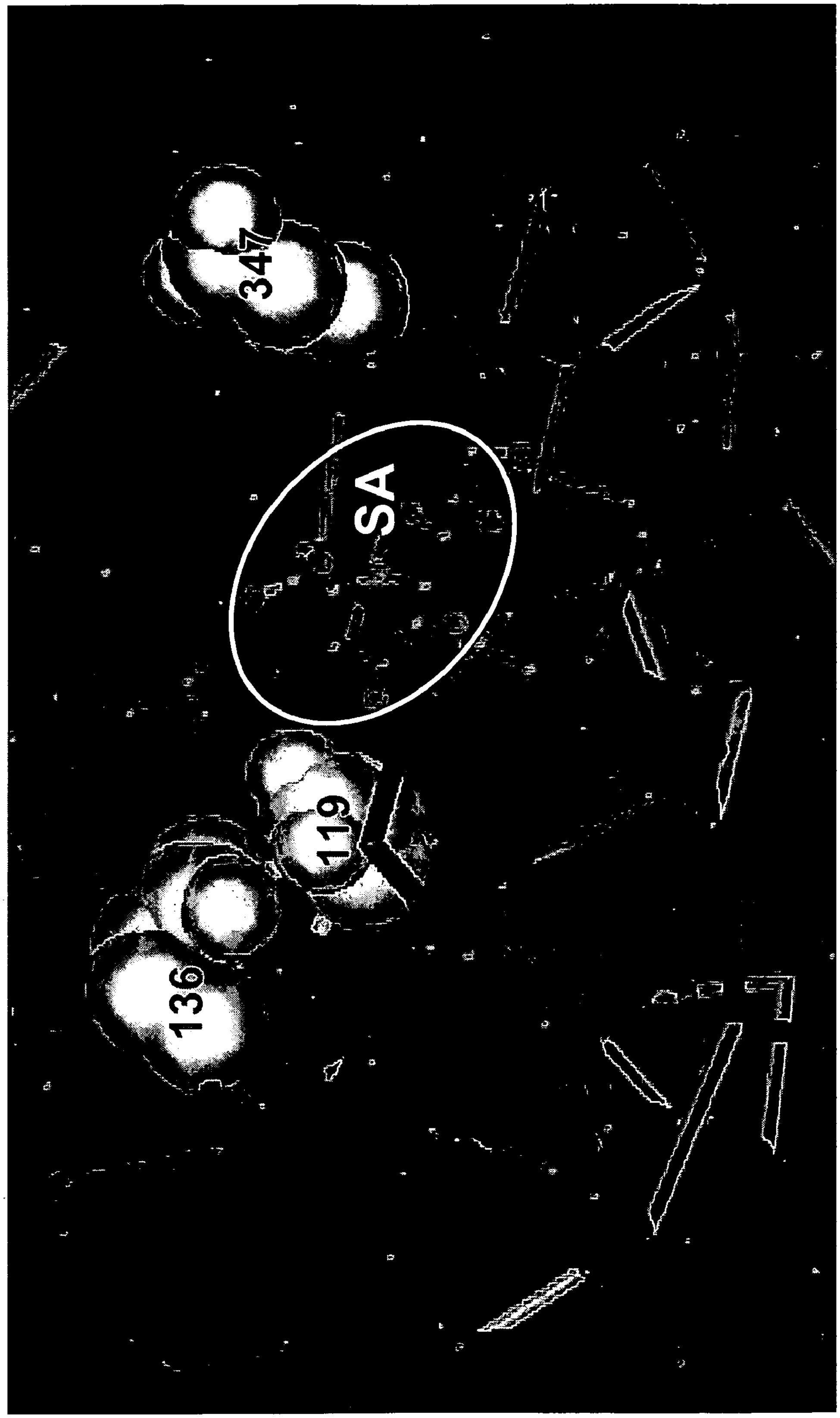
Figure 33:
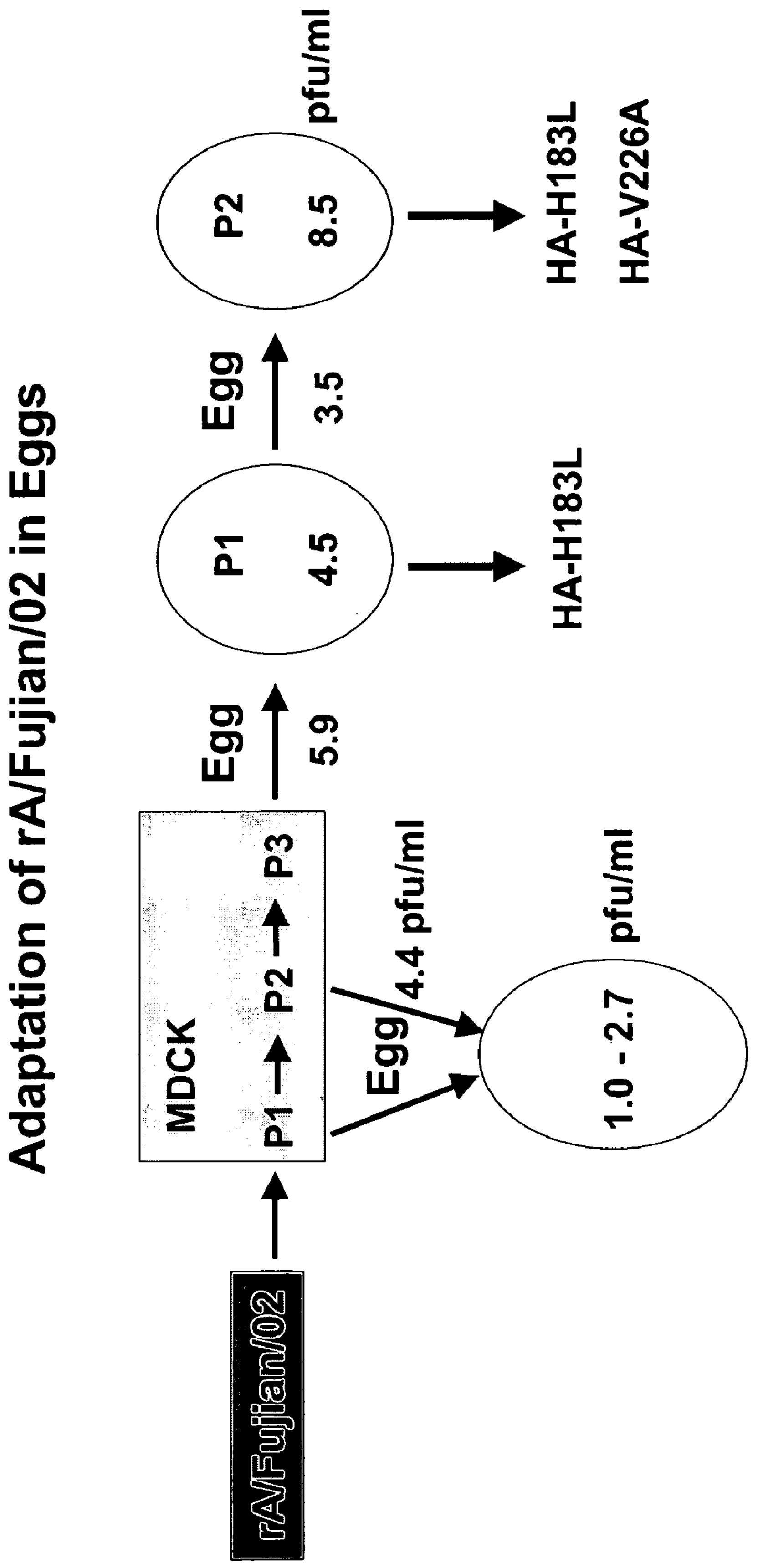
Figure 34:
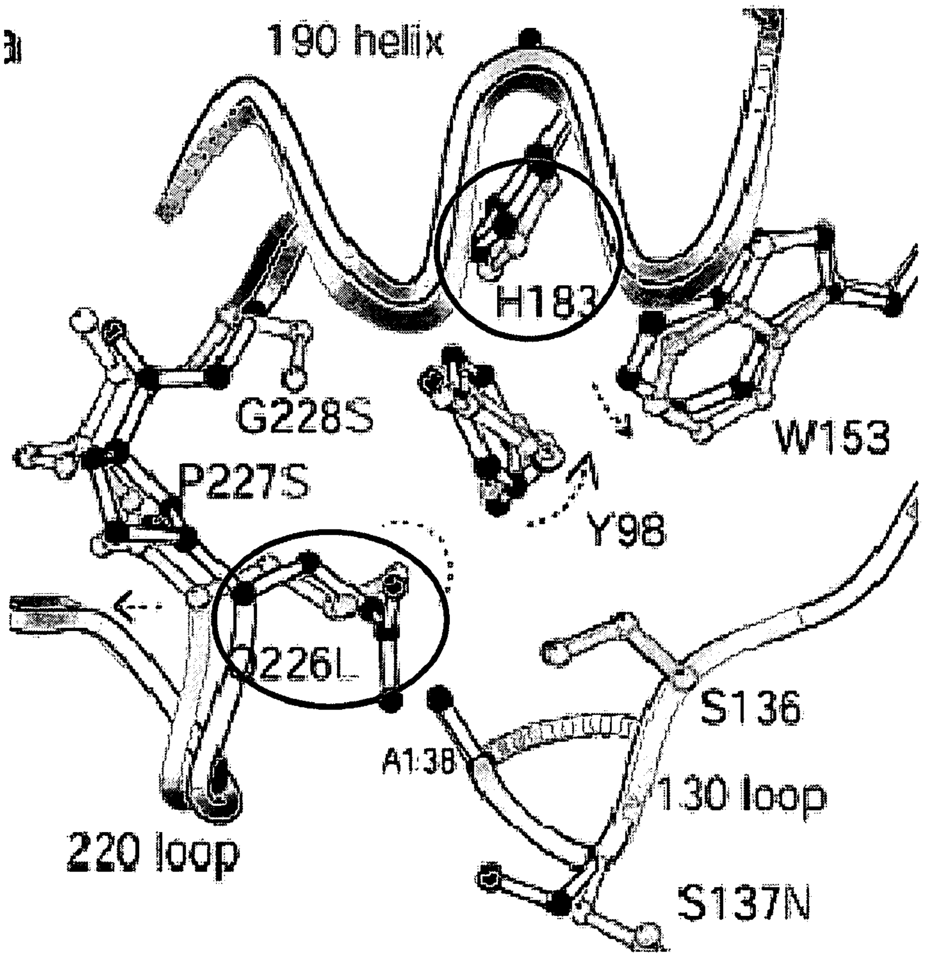
Figure 35:
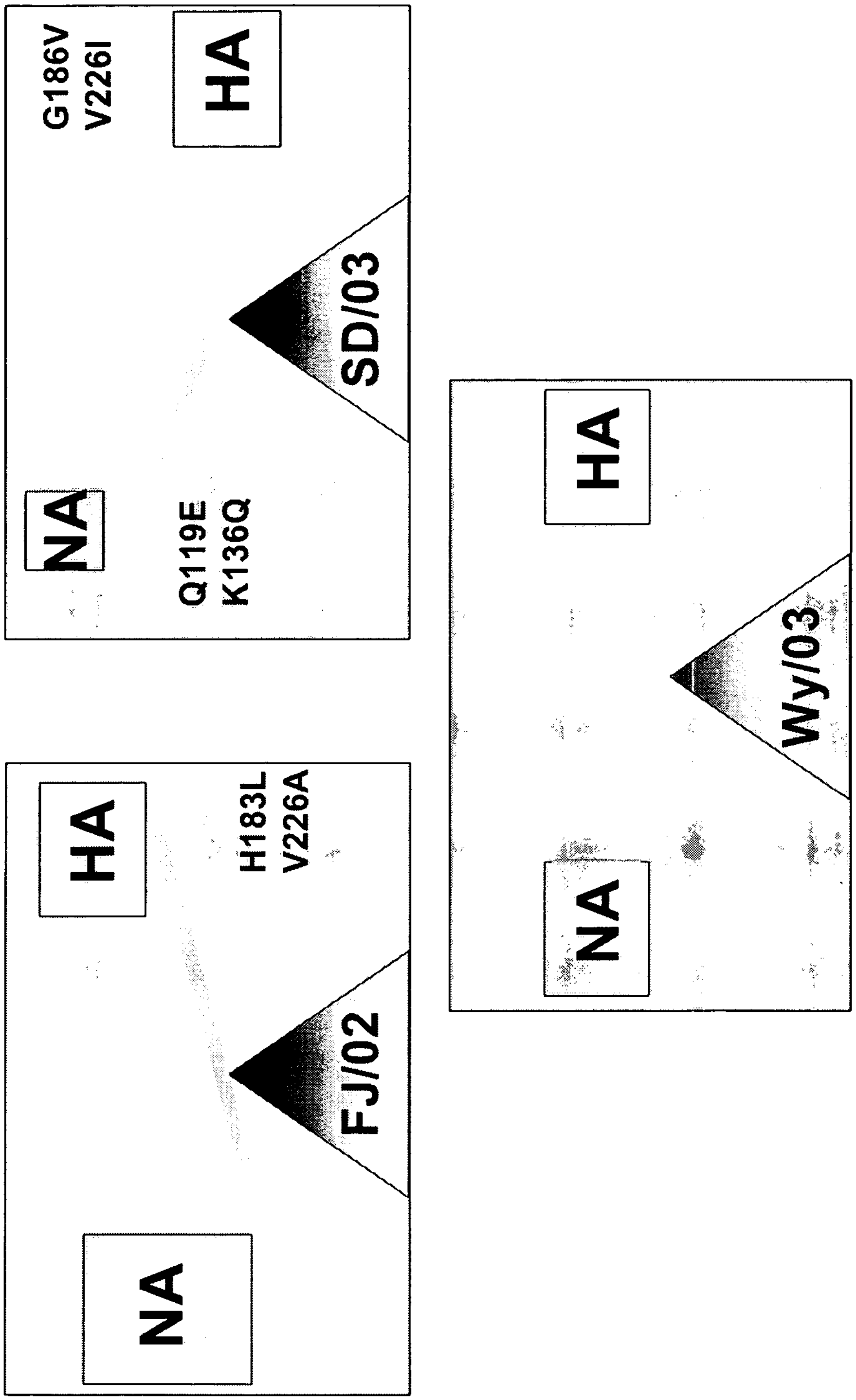

The molecular basis for the antigenic drift from A/Panama/99 to A/Fujian/02-like strains was studied by changing clusters of HA residues from A/Panama/99 to those of A/Wyoming/03. See FIG. 24. Antigenicity of the modified 6:2 reassortants were examined by HAI and microneutralization assays using ferret sera from animals immunized with either A/Panama/99 or A/Wyoming/03. See FIGS. 25 through 28. It was determined that only a few changes were responsible for antigenic drift while others had a more dramatic impact on virus replication. Thus, as indicated by the data, reverse genetics are optionally used to modify vaccine strains to increase vaccine yields without affecting virus antigenicity.

Materials and Methods

Virus strains, cells and antibodies: Wild-type (wt) influenza A virus strains, A/Fujina/411/02 (A/Fujian), A/Sendai-H/F4962/02 (A/Sendai) and A/Wyoming/03/03 (A/Wyoming), were obtained from the Center for Disease Control (Atlanta, Ga.) and amplified once in MDCK cells or in embryonated chicken eggs (eggs). The modified vaccinia virus Ankara strain expressing the bacteriophage T7 RNA polymerase (MVA-T7) was grown in CEK cells. HEp-2, COS-7 and MDCK cells (obtained from American Type Culture Collections, ATCC) were maintained in minimal essential medium (MEM) containing 5% fetal bovine serum (FBS). Polyclonal antisera against A/Ann Arbor/6/60, A/Sendai-H/F4962/02 and A/Wyoming/03/03 were produced in chicken. Monoclonal antibodies against the NP protein of influenza A were obtained from BioDesign (Saco, Mich.).

Generation of recombinant 6:2 reassortants: Recombinant 6:2 reassortants that contained the HA and NA RNA segments of the H3N2 strains reassorted into MDV-A, were generated according to the previously described procedures. Briefly, a set of six plasmids containing the internal genes of MDV-A together with the HA and NA expression plasmids were trasfected into the co-cultured COS-7/MDCK cells using TransIT LT1 reagents (Mirus, Madison, Wis.). The transfected cell culture supernatant was collected at 3 days post transfection and used to infect fresh MDCK cells and 10-day-old embryonated chicken eggs. The infected MDCK cells were incubated at 33° C. until 80-90% cells exhibited cytopathic effect. The infected embryonated chicken eggs were incubated at 33° C. for three days and the allantonic fluids were collected and stored at −80° C. in the presence of the SPG stabilizer (0.2 M sucrose, 3.8 mM $KH_2PO_4$, 7.2 mM $K_2HPO_4$, 5.4 mM monosodium glutamate). Virus titer was determined by plaque assay on MDCK cells incubated under an overlay that consisted of 1×L15/MEM, 1% agarose and 1 μg/ml TPCK-trypsin at 33° C. for 3 days. The plaques were enumerated by immunostaining using chicken anti-MDV-A polyclonal antibodies.

Cloning of HA and NA expression plasmids: To make recombinant 6:2 reassortant viruses containing the HA and NA segments of H3N2 subtype and the six internal MDV-A RNA segments, the HA and NA cDNAs of wt A/Sendai-H/F4962/02 and A/Wyoming/03/03 were amplified by RT-PCR using SuperscriptIII reverse transcriptase (Invitrogen, Carlsbad, Calif.) and pfu DNA polymerase (Stratagene, La Jolla, Calif.), the extracted vRNA as template and the H3 and N2 specific primers. HA-AarI5 (5'cacttatattcacctgcctcagggagcaaaagcagggg3' SEQ ID NO:90) and HA-AarI3 (5'cctaacatatcacctgcctcgtattagtagaaacaagggtgtt3' SEQ ID NO:91) primers were used to amplify the HA segment. N2-AarI5 (5'cacttatattcacctgcctcagggagcaaaagcaggagt3' SEQ ID NO:92) and N2-AarI3 (5'cctaacatatcacctgcctcgtattagtagaaacaaggagttt3' SEQ ID NO:93) primers were used to amplify the NA segment. Both the HA and NA primer pairs contained the Aar I restriction sites that was designed to be comparable to the BsmB I sites present in the pAD3000 pol I/pol II expression plasmid. The HA and NA cDNA clones were sequenced and compared to the consensus HA and NA sequences that were obtained by direct sequencing of the HA and NA RT-PCR amplified cDNA products. Any mutations introduced into the cDNA clones during the cloning process were corrected by QuickChange site-directed mutagenesis kit (Stratagene, La Jolla, Calif.).

HAI assay (Hemagglutionation Inhibition Assay for Influenza Virus): Reagents: 0.5% cRBC (washed three times with PBS-, can be used within 2-3 days); 96-well U botton microplate; PBS- (without Ca and Mg); Tips; Influenza virus; Serum samples and positive control serum of high and low titer Preparations: Determine HA titer of virus by HA assay (Use virus titer at 1:8 for HAI. If HA titer of a given virus is 1:256, divide it by 8. Thus, need to dilute virus 1:32. Prepare 2.5 ml of virus for each 96 well plate); Treat serum with RDE (receptor destroy enzyme) optional for ferrets samples; Prepare RDE as instructed by manufacturer; Combine RDE and serum sample at 1:4 dilution. For example, add 100 μl of serum to 300 μl of RDE. Vortex the mix and incubate overnight (18-20 hr) in 37° C. incubator. Heat mixture at 56° C. for 45-50 min. Screen serum for non-specific agglutinins; Mix 25 μl of RDE-treated serum with 25 μl of PBS- by pippetting up and down 3×; Add 50 μl of 0.5% cRBC to the mix and to the control well with only PBS-; Incubate at RT for 30-45 min (+: indicates partial or complete non-specific hemagglutination-: indicates no hemagglutination); Non-specific cRBC agglutinis can be removed by pre-incubation of serum with packed RBC at 20:1 ratio at 4° C. for 1 hr, followed by centrifugation at 200 rpm for 10 min at 4° C. 4) Controls can typically include the following: cRBC cell control; Virus back titration: 2-fold dilution of 8 units/50 μl virus diluted from 1:2 to 1:32 to make sure that virus used is at the correct concentrations; Positive serum control: dilute known titer serum 2-fold serially together with the test serum samples. A typical HAI protocol can comprise: Dilute serum samples two-fold serially; Add 25 μl of PBS- to each well; Add 25 μl of virus to well 1A (e.g., 1:2), mix by pippetting up and down 3×; Transfer 25 μl from well A to well B (e.g., 1:4) and mix as above 3×, repeat dilution until well H (e.g., 1:256); Add virus 25 μl (8 unit/50 μl) to diluted serum samples, mix up and down 3× and incubate at RT for 3040 min; Add 50 μl of 0.5% cRBC, mix well by pippeting up and down 3×; Incubate at RT for 30-45 min.; Record hemagglutination. The HAI titer is defined as the highest dilution of the serum that completely inhibits hemagglutination. If no inhibition is observed, the titer is <1:4. If all wells display inhibition, the titer is >1:256.

Measurement of the neuramimidase activity of the transiently expressed NA protein: To measure the neuramimidase activity of the NA proteins, wt NA and its modified derivatives were expressed from the plasmid transfected cells. To obtain a high level of expression of the NA proteins, the NA RNA was transcribed from the T7 and CMV promoters as the gene was inserted downstream of these dual promoters. HEp-2 cells in 10 cm dishes were infected with MVA-T7 at moi of 5.0 for 1 hr followed by transfection of 5 μg of the NA plasmid using Lipofectmine 2000 reagent (Invitrogen, Carlsbad, Calif.). The transfected cells were incubated at 35° C. for 48 hr. After washing with phosphate-buffered saline (PBS), the cells were scraped from the dishes and lysed in 100 μl of 0.125M NaOAc, pH 5.0. The neuramimidase activity in the transfected cells was determined by a fluorimetric assay. After one time of freezing-thawing, 50 μl of cell lysates were 2-fold serially diluted and incubated with 150 μl of 1.2 mM 2'-(4-methylumbelliferyl)-α-D-N-Acetylneuraminic Acid (MU-NANA) substrate (Sigma, St. Louis, Mo.) at 37° C. for 1 hr and stopped by 75 μl of 1.0 M Glycine (pH 5.5). The fluorescence level of the released chromophore 4-methylumbelliferone was determined at 362 nm on a SpectroMAX plate reader. The level of each NA protein expressed in the transfected cells was monitored by Western blotting using chicken anti-A/Wyoming antisera. The neuramimidase activities of wt A/Sendai and A/Wyoming viruses containing 6.0 log10 PFU in 100 μl were also measured by the fluorimetric assay.

Receptor binding and replication of 6:2 recombinants in MDCK cells: HA receptor-binding and growth kinetics of recombinant 6:2 reassortants were determined in MDCK cells. MDCK cells in six-well plates were infected with 6:2 A/Fujian, A/Sendai, A/Wyoming and two modified recombinant viruses at a moi of 1.0. After 30 min of adsorption at either 33° C. or 4° C., the infected cells were either washed three times with PBS, or directly overlaid with 3 ml of Opti-MEM I containing 1 μg/ml TPCK-trypsin and incubated at 33° C. One set of the infected plates was fixed with 1% paraformaldehyde at 6 hr post infection for 15 min at room temperature, and permeablized with 0.2% Triton X-100 in PBS for 15 min followed by immunofluorescence analysis using anti-NP monoclonal antibodies. The cell images captured by ORCA-100 digital camera were analyzed by Compix image capture and dynamic intensity analysis software, Version 5.3 (Cranberry Township, Pa.) to calculate the percentage of the infected cells. Another set of plates was incubated at 33° C. At various times of intervals, 250 μl of culture supernatant was collected and stored at −80° C. in the presence of SPG prior to virus titration. After each aliquot was removed, an equal amount of fresh medium was added to the cells. The virus titer in these aliquots was determined by plaque assay on MDCK cells at 33° C.

To determine whether the binding difference between these viruses affected virus growth kinetics in MDCK cells, the infected MDCK cells were incubated at 33° C. and the culture supernatants were collected at various times for virus titration. When adsorbed at 33° C., 6:2 A/Fujian had slower growth kinetics and lower titer (FIG. 2), 6:2 A/Sendai, A/Fujian with HA-V1861226 or HA-L183A226 behaved similarly to 6:2 A/Wyoming. When adsorption was done at 4° C., 6:2 A/Fujian as well as 6:2 A/Sendai had slower growth kinetics. 6:2 A/Wyoming and the two A/Fujian variants grew similarly. These results were consistent with the virus-binding assay whereas the washing step reduced efficient infection of A/Fujian at both temperatures.

Antigenicity of 6:2 recombinant viruses: Antigenicity of each virus was analyzed by hemaglutinin inhibition (HAI) assay using ferret anti-A/Sendai and anti-A/Wyoming sera. Aliquots of 25 μl of 2-fold serially diluted ferret antisera were incubated with 25 μl virus containing 4 HA units of 6:2 reassostant viruses at 37° C. for 1 hr followed by incubation with 50 μl of 0.5% turkey red blood cells (RBC) at 25° C. for 45 min. The HAI titer was defined as the reciprocal of the highest serum dilution that inhibited hemaglutinnation.

Generation of 6:2 A/Fujian, A/Sendai, and A/Wyoming Vaccine Strains

Wild-type (wt) influenza A virus strains, A/Fujian/411/02, A/Sendai-H/F4962/02 and A/Wyoming/03/03 were obtained from the Center for Disease Control (Atlanta, Ga.) and amplified once in MDCK cells or in embryonated chicken eggs. As indicated in Table 20, A/Fujian was only passaged for three times in cell culture, whereas A/Sendai and A/Wyoming went through 11 passages in eggs. The HA and NA sequences of these three strains were determined by sequencing of the RT-PCR products using vRNA extracted from these viruses. The difference in the HA and NA sequence of these three H3N2 strains is listed in Table 1. A/Sendai was identical to A/Fujian in its HA1 amino acid sequence but differed in the NA sequence at three amino acids at positions 119, 146 and 347. A/Wyoming had the NA sequence identical to that of A/Fujian, but differed from A/Fujian and A/Sendai in HA1 by four amino acids. In addition, both A/Sendai and A/Wyoming had Glu-150 instead of Gly-150 in the HA2. After one time of amplification in MDCK cells, the 183 residue in HA1 of wt A/Fujian mutated from His-183 to Leu-183 and it was difficult to isolate the wt A/Fujian virus with His-183, indicating that the virus with His-183 had growth advantage in vitro.

These three wt viruses grew differently in MDCK cells, reaching titers of 6.1, 8.1 and 6.7 $\log_{10}$PFU/ml for wt A/Fujian, wt A/Sendai and wt A/Wyoming, respectively. wt A/Fujian replicated poorly in eggs, reaching a titer of 4.1 $\log_{10}$PFU/ml (Table 20). The virus isolated from eggs had the H183L change in the HA. In contrast, wt A/Sendai and wt A/Wyoming grew well in eggs having titers of 9.0 and 8.9 $\log_{10}$PFU/ml, respectively.

To confirm that the HA and NA segments of these H3N2 strains controlled virus replication in eggs and cells, the HA and NA gene segments were reassorted with the internal gene segments of the cold adapted A/Ann Arbor/6/60 strain, the master donor virus for live attenuated influenza FluMist vaccines (MDV-A) to generate three 6:2 reassortant viruses. Replication of these three viruses was evaluated in MDCK cells and embryonated chicken eggs. 6:2 A/Fujian (6.2 $\log_{10}$PFU/ml) showed a lower titer than 6:2 A/Sendai (7.1 $\log_{10}$PFU/ml) and A/Wyoming (7.0 $\log_{10}$PFU/ml) in MDCK cells. Similar to wt A/Fujian, 6:2 A/Fujian replicated poorly in embryonated chicken eggs with a titer of 4.1 $\log_{10}$PFU/ml. Both 6:2 A/Sendai and A/Wyoming replicated to higher titers of 8.7 and 8.1 $\log_{10}$PFU/ml, respectively. Thus, the transfer of the wt HA and NA gene segments into MDV-A did not change the capability of each virus to replicate in eggs.

TABLE 20

Comparison of wt and recombinant 6:2 A/Fujian/411/02-like strains in HA and NA sequence and their replication in MDCK cells and eggs.

| | Amino acid positions | | | | | | | |
|---|---|---|---|---|---|---|---|---|
| | HA1 | | | | HA2 | NA | | |
| Virus strains | 128 | 186 | 219 | 226 | 150 | 119 | 136 | 347 |
| A/Fujian/411/02[1] (C1/C2) | T | G | S | V | G | E | Q | H |
| A/Sendai-H/F4962/02 (CxE8/E3) | — | — | — | — | E | Q | K | Y |
| A/Wyoming/03/03 (ck2E2/E9) | A | V | Y/F | I | E | — | — | — |

| Virus strains | Virus titer ($\log_{10}$PFU/ml ± SE)[3] | | | |
|---|---|---|---|---|
| | MDCK | | Eggs | |
| (Passage history) | wt | 6:2 | wt | 6:2 |
| A/Fujian/411/02[1] (C1/C2) | 6.1 ± 0.3 | 6.2 ± 0.3[2] | 4.1 ± 0.6 | 4.2 ± 0.5 |
| A/Sendai-H/F4962/02 (CxE8/E3) | 8.1 ± 0.2 | 7.1 ± 0.1 | 9.0 ± 0.3 | 8.7 ± 0.2 |
| A/Wyoming/03/03 (ck2E2/E9) | 6.7 ± 0.5 | 7.0 ± 0.4 | 8.9 ± 0.3 | 8.1 ± 0.1 |

[1]wt A/Fujian had the H183L change after one time passage in MDCK cells and eggs.
[2]Recombinant 6:2 A/Fujian contained E150 in HA2.
[2]Virus titers were expressed as mean $\log_{10}$PFU/ml ± SE from two or more samples.

Effect of Amino Acid Changes in the NA on Neuramimidase Activities and Virus Replication A/Fujian differed from A/Sendai by three amino acids in NA, E119Q, Q136K and H347Y (Table 20), it is hypothesized that one or more of these changes enabled A/Sendai to replicate in embryonated chicken eggs to a higher titer than A/Fujian. Substitutions of E119 by G, D, A or V residues have been reported for several anti-neuramimidase drug resistant strains that resulted in the reduced neuramimidase activity. To determine whether the E119Q or either of the other two changes in the NA had an effect on the NA activity of A/Fujian and on its ability to replicate in embryonated chicken eggs, single and double substitution mutations were introduced into A/Fujian NA expression plasmids and the NA activity in the transfected HEp-2 cells was measured. In addition, recombinant 6:2 recombinant viruses bearing mutations in the A/Fujian NA were also recovered and their growth in MDCK cells and eggs were compared (Table 21). A/Fujian (E119Q136H147) had approximately 80% higher NA activity compared to that of A/Sendai (Q119K136Y147). Single Q119 mutation had 66% of NA activity, Y347 change had minimal effect on NA activity but K136 only had 25% activity. Double mutations, K136Y347, Q119Y347, and Q119K136 had reduced NA activity at levels of 29%, 52% and 25% of that A/Fujian, respectively. These data indicated that these three NA residues affected the NA activity in the order of K136>Q19>Y347.

The correlation of the NA activity of the NA mutants with virus replication in embryonated chicken eggs was examined (Table 21). The six modified viruses were shown to replicate well in MDCK cells reaching titers ranging from 6.2 to 6.9 $\log_{10}$PFU/ml, but replicated significantly different in eggs. FJ-Q119 and FJ-347 that had 66% and 99% NA activity of A/Fujian were unable to grow in eggs. FJ-K136 with 25% NA activity was able to grow to a titer of 4.8 $\log_{10}$PFU/ml in eggs, but 4.0 $\log_{10}$ lower than that of A/Sendai (8.8 $\log_{10}$PFU/ml). Unexpectedly, although K136Y347 significantly decreased the NA activity in vitro, the recombinant virus carrying these two mutations (FJ-K136Y347) was not able to replicate in embryonated chicken eggs. Q119Y347 that had 52% of NA activity replicated in eggs to a titer of 4.5 $\log_{10}$fpu/ml. Q19K136 that had the NA activity slightly higher than that of A/Sendai replicated to a titer of 6.2 $\log_{10}$fpu/ml but was still 2.6 $\log_{10}$ lower than A/Sendai. These results indicated that each of the three NA residues differed between A/Fujian and A/Sendai impacted virus replication differently. Although several NA mutations could reduced the NA activity to the level close to that A/Sendai, only Q136K and E119Q changes could result in significant improvement in virus replication in embryonated chicken eggs. Since the Q119K136 double mutations did not replicate as efficiently as A/Sendai virus in eggs, the Y347 residue might also affect virus replication in eggs.

TABLE 21

Effects of NA residues on virus replication in MDCK cells and embryonated eggs.

| | NA residues | | | NA activity[1] | Virus[2] titer ($\log_{10}$PFU/ml) | |
|---|---|---|---|---|---|---|
| NA | 119 | 136 | 347 | (Mean ± SE) | MDCK | Eggs |
| A/Fujian | E | Q | H | 100 | 6.5 | <1.5 |
| FJ-Q119 | Q | — | — | 66 ± 3 | 6.7 | <1.5 |
| FJ-Y347 | — | — | Y | 99 ± 1 | 6.6 | <1.5 |
| FJ-K136 | — | K | — | 25 ± 1 | 6.6 | 4.8 |
| FJ-K136Y347 | — | K | Y | 29 ± 3 | 6.5 | <1.5 |
| FJ-Q119Y347 | Q | — | Y | 52 ± 4 | 6.6 | 4.5 |
| FJ-Q119K136 | Q | K | — | 25 ± 1 | 6.2 | 6.2 |
| A/SENDAI | Q | K | Y | 21 ± 1 | 6.9 | 8.8 |

[1]The NA activities in NA cDNA-transfected HEp-2 cells are expressed as the percentage of that of A/Fujian (mean ± standard error) from four independent experiments.
[2]Recombinant 6:2 viruses were generated using A/Fujian HA and NA or A/Fujian NA with mutations indicated.

Effects of HA Residues on Virus Replication

The changes of the four HA1 residues in A/Wyoming/03/03 that differed from A/Fujian were investigated for their roles in virus replication. The single and multiple substitution mutations were introduced into A/Fujian HA cDNA and the modified HA plasmids were introduced into MDV-A together with either A/Fujian NA. All of the 6:2 reassortant virus mutants replicated well in MDCK cells but grew differently in embryonated chicken eggs (Table 22). The 6:2 reassortants with A/Fujian HA (T128G186S219V226) were unable to replicate in eggs. A single T128A change did not improve virus growth in eggs. However, single G186V or V226I change resulted in increased virus replication in eggs. Double G186V and V226I changes in HA replicated efficiently in eggs. Additional substitutions at residues 128 and/or 219 did not significantly increase virus replication. Thus, a minimal of two G186V and V226I changes enabled 6:2 A/Fujian to grow efficiently in embryonated chicken eggs.

TABLE 22

EFFECTS OF HA RESIDUES ON VIRUS REPLICATION IN EMBRYONATED EGGS.

| | HA residues | | | | Virus titer in eggs |
|---|---|---|---|---|---|
| Virus[1] | 128 | 186 | 219 | 226 | ($\log_{10}$PFU/ml) |
| A/Fujian | T | G | S | V | <1.5 |
| HA-A128 | A | — | — | — | <1.5 |
| HA-V186 | — | V | — | — | 4.9 |
| HA-I226 | — | — | — | I | 5.2 |
| HA-V186I226 | — | V | — | I | 7.6 |
| HA-V186Y219I226 | — | V | Y | I | 7.5 |
| A/Wyoming | A | V | Y | I | 7.3 |

[1]Virus recovered from the transfected cells contained A/Fujian NA and HA with the indicated amino acid changes.

Adaptation of 6:2 A/Fujian/411/02

To determine whether 6:2 A/Fujian strain could be adapted to grow in embryonated chicken eggs, the virus was amplified in MDCK cells followed by passage in eggs (Table 23). When 3.0 $\log_{10}$PFU of virus was inoculated into an egg, less than 2.0 $\log_{10}$PFU/ml of virus was detected in the harvested allantonic fluid. Infectious virus could not be recovered following passages of this material. During the second passage experiment, the amount of virus inoculated into embryonated chicken eggs was increased to 5.9 $\log_{10}$PFU. A titer of 3.9 $\log_{10}$PFU/ml was detected in the harvested allantonic fluid (FJ-EP1) and an additional passage in eggs increased virus titer to 6.2 $\log_{10}$PFU/ml (FJ-EP2). A further passage in eggs (FJ-EP3) increased virus titer to 8.2 $\log_{10}$PFU/ml. Sequence analysis of the FJ-EP2 virus revealed an A to U mutation at nt 625 in the HA RNA segment which resulted in H183L change in the HA protein. Further analysis showed this change also occurred during virus amplification in MDCK cells. The H183L mutation was also found in the wt A/Fujain HA during its replication in MDCK and eggs as described previously. An additional U to C mutation at nt 754 of HA resulting in V226A substitution was found in the FJ-EP3 amplified virus (Table 23). No changes were detected in the NA segment.

To confirm that H183L and V226A mutations in HA were indeed responsible for the increased replication of 6:2 A/Fujian in eggs, H183L and V226A were introduced into A/Fujian HA singly or in combination. Three recombinant viruses were obtained and they grew to a titer of 7.4 $\log_{10}$PFU/ml for FJ-H183L, 7.9 $\log_{10}$PFU/ml for FJ-V226A and 8.4 $\log_{10}$PFU/ml for FJ-H183L/V226A (Table 23). Therefore, H183L and V226A independently contributed to the improved replication of A/Fujian virus in embryonated chicken eggs.

TABLE 23

Mutations in the HA of egg-adapted 6:2 A/Fujian revertants and their replication in embryonated eggs.

| Virus | Mutations at nucleotide (amino acid) | Virus titers ($Log_{10}$PFU/ml) |
|---|---|---|
| Egg-passaged | | |
| FJ-EP1 | ND[1] | 3.9 |
| FJ-EP2 | A625U (H183L) | 6.2 |
| FJ-EP3 | A625U (H183L), U745C (V226A) | 8.2 |
| Recombinants | | |
| FJ-183L | A625T (H183L) | 7.4 |
| FJ-226A | T745C (V226A) | 7.9 |
| FJ-183L/226A | A625U (H183L), U745C (V226A) | 8.4 |

[1]Not determined.

Receptor-Binding Properties and Replication of Recombinant Viruses

Figure 36:
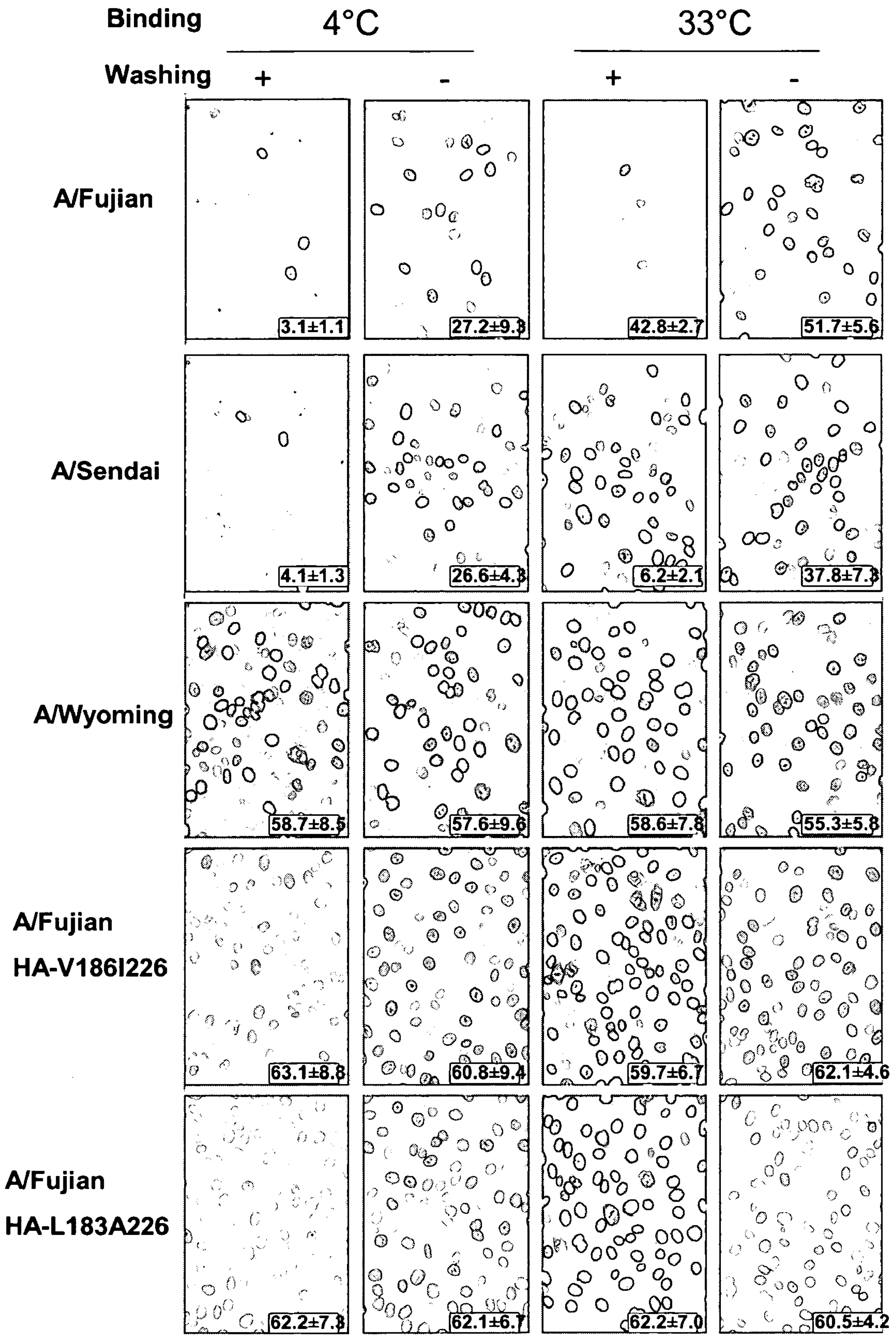
FIG. 36: HA receptor binding affinity of recombinant viruses. 6:2 A/Fujian, A/Sendai, A/Wyoming, and A/Fujian variants with V186 and I226 or L183 and A226 changes were adsorbed to MDCK cells at an moi of 1.0 at 4° C. or 33° C. for 30 min, and the infected cells were washed three times (+) or left untreated (−). After 6 hr of incubation at 33° C., the cells were processed for immunofluorescence staining. The percentage of infected cells (mean±SD) indicated in each image was an average of six images.
Figure 37:
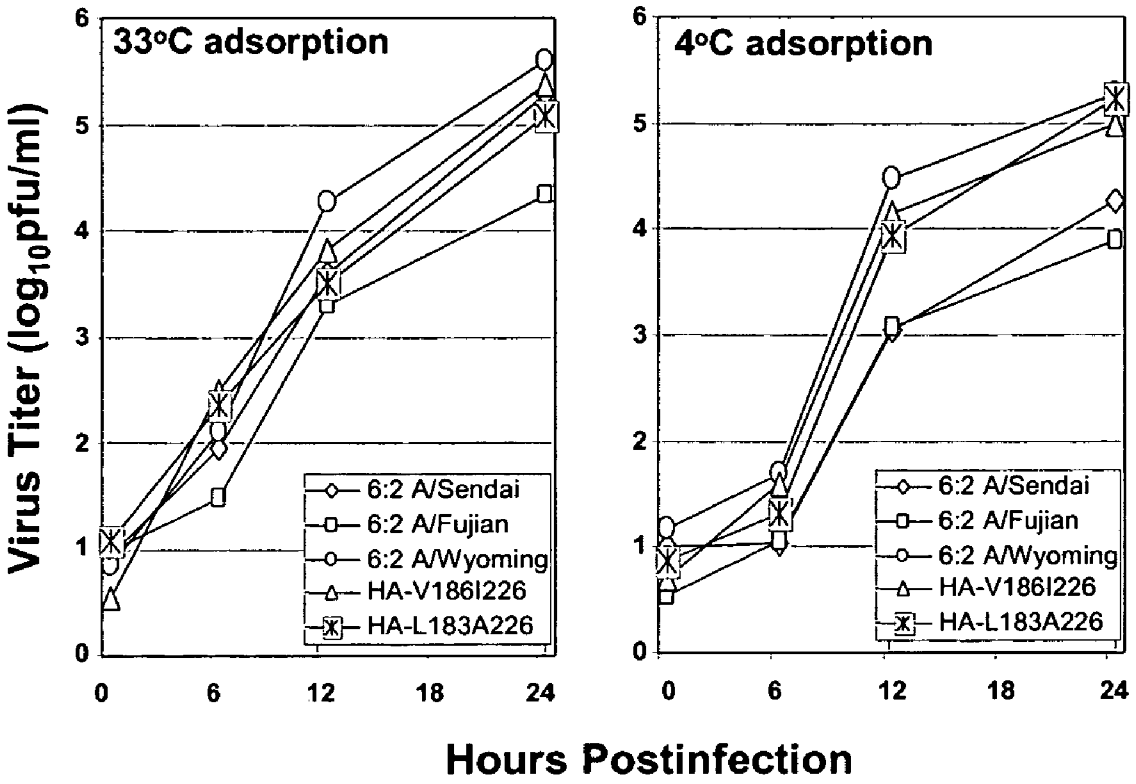
FIG. 37: Growth kinetics of recombinant viruses in MDCK cells. MDCK cells were infected at an moi of 1.0 at either 33° C. or 4° C. for 30 min, washed 3× with PBS. The infected cells were incubated at 33° C. and at the indicated time intervals the culture supernatants were collected and the virus amount was determined by plaque assay.
Figure 38:
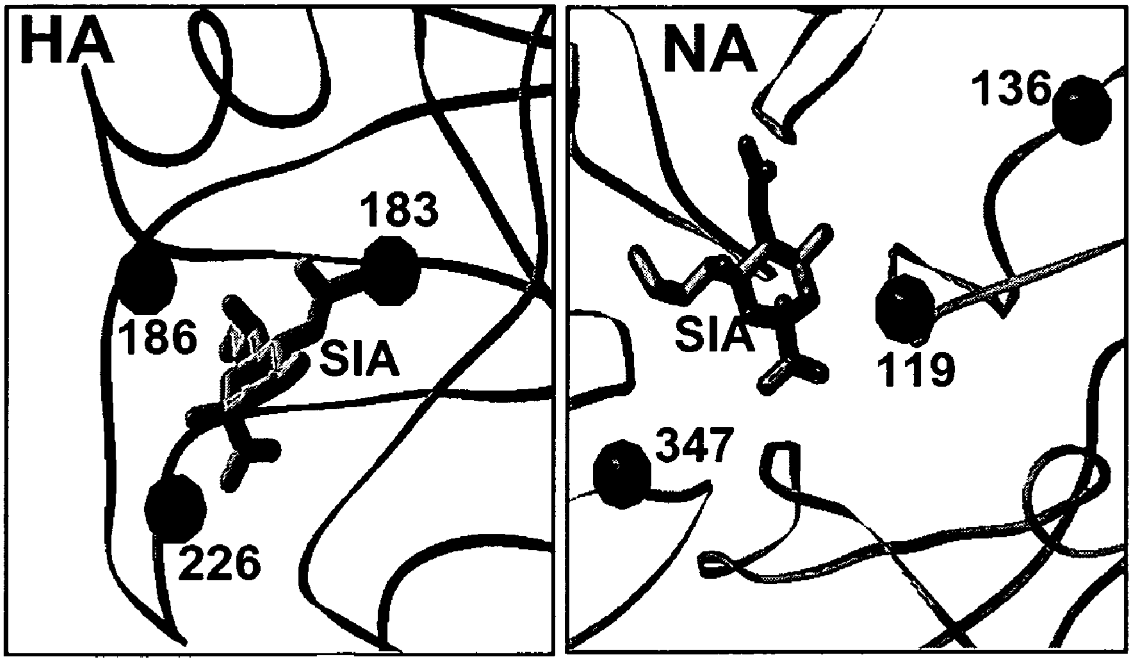
FIG. 38: receptor-binding sites in HA and NA of H3N2 subtypes. The residues that were shown to increase the HA receptor-binding affinity and to decrease the NA enzymatic activity in relation to sialic acid (SIA) binding sites are indicated. The HA monomer was modeled using 5HMG and the NA monomer was modeled based on 2BAT using WebLab ViewerLite 3.10 (Accelrys, San Diego, Calif.).

From the above studies, the NA changes that reduced the NA activity of A/Fujian were shown to be sufficient for this virus to grow in eggs. On the other hand, the HA changes (G186V and V2261 or H183L and V226A) might have increased receptor-binding affinity to compensate for the higher NA activity of A/Fujian. To determine whether the changes in the HA protein of A/Fujian increased its receptor-binding ability, adsorption of 6:2 A/Fujian carrying HA-V1861226 change and egg-adapted 6:2 A/Fujian that contained HA-L183A226 changes were compared to 6:2 A/Fujian, A/Sendai, and A/Wyoming. Each virus was adsorbed onto MDCK cells at moi of 1.0 for 30 min at 4° C. or 33° C., the inoculum was removed and the infected cells were washed three times or without the washing step. After 6 hr of incubation at 33° C., the percentage of the infected cells was determined by immunofluorescence analysis using anti-NP antibody. As shown in FIG. 36, 6:2 A/Fujian and A/Sendai infected 26-27% of cells when adsorption was performed at 4° C., but the majority of viruses were readily removed by the washing step. At 33° C., washing greatly reduced infection of 6:2 A/Fujian virus (6.2% compared to 37.8%) but did not have significant effect on the infection of 6:2 A/Sendai (42.8% compared to 51.7%). In contrast, 6:2 A/Wyoming, A/Fujian with HA-V1861226 or HA-L183A226 had similar infection rate no matter whether the cells were adsorbed at 4° C. or 33° C. and with or without a washing step. These data indicated that A/Fujian and A/Sendai HA had such a low binding affinity that the bound viruses at 4° C. could be readily washed off from the cells. The binding and virus entry kinetics were faster at 33° C., thus, the washing step had a minimal impact on 6:2 A/Sendai virus infection. However, the majority of the bound 6:2 A/Fujian was washed off at the similar condition because its higher NA activity prevented efficient virus binding at 33° C. (data not shown).

Antigenicity of Recombinant Viruses

To examine whether viruses with the modified HA and NA residues affected virus antigenicity, haemagglutination inhibition assay (HAI) was performed using ferret anti-A/Wyoming and anti-A/Sendai sera (Table 24). Anti-A/Wyoming or anti-A/Sendai ferret sera had a similar HAI titer when measured with either 6:2 A/Fujian or A/Sendai virus. A slightly higher HAI titer was detected with 6:2 A/Wyoming virus, probably due to the tighter binding of A/Wyoming HA to the cell receptor on the red blood cells. The two modified viruses (A/FujianHA-V1861226 and A/Fujian HA-L183A226) had HAI titer similar to A/Wyoming when measured by either serum. There results indicated that the amino acid difference between A/Sendai and A/Wyoming and the modified HA viruses generated in this study did not alter virus antigenicity.

TABLE 24

Antigenicity of modified 6:2 A/Fujian viruses

| | HA | | | | | NA | | | Antigenicity ($log_2$HAI)[(2)] | |
|---|---|---|---|---|---|---|---|---|---|---|
| Virus[(1)] | 128 | 183 | 186 | 219 | 226 | 119 | 136 | 347 | anti-A/WY | anti-A/SD |
| A/Fujian | T | H | G | S | V | E | Q | H | 9 | 9 |
| A/Wyoming | A | — | V | Y | I | — | — | — | 11 | 10 |
| HA-V1861226 | — | — | V | — | I | — | — | Y | 11 | 11 |
| HA-L183A226 | — | L | — | — | A | — | — | — | 11 | 11 |

[(1)]A/Fujian was grown in MDCK cells and the rest of viruses were grown in eggs.
[(2)]Antigenicity was measured by HAI assay using A/Wyoming (anti-A/WY) or A/Sendai (anti-A/SD) immunized ferret serum with the indicated virus antigens Example 12

Determination of the Loci Controlling the Cold-Adapted Phenotype of B/Ann Arbor/1/66 Influenza Virus The cold adapted (ca) B/Ann Arbor/1/66 is the master donor virus (MDV-B) for the live attenuated influenza B Flumist® vaccines. The 6:2 influenza B vaccines carrying the six internal genes derived from ca B/Ann Arbor/1/66 and the HA and NA surface glycoproteins from the circulating wild-type strains are characterized by the cold-adapted (ca), temperature-sensitive (ts) and attenuated (att) phenotypes. Sequence analysis revealed that MDV-B contains nine amino acids in the PB2, PA, NP and M1 proteins that are not found in wild-type influenza B strains. We have determined that three amino acids in the PA(M431V) and NP(A114V, H410P) determined the ts phenotype and, in addition to these three ts loci, two amino acids in the M1 (Q159H, V183M) conferred the att phenotype.

To understand the molecular basis of the ca phenotype, the plasmid-based reverse genetics system was used to evaluate the contribution of these nine MDV-B specific amino acids to the ca phenotype. Recombinant MDV-B replicated efficiently at 25° C. and 33° C. in the chicken embryonic kidney (CEK) cells. In contrast, recombinant wild type B/Ann Arbor/1/66, containing the nine wild type amino acids, replicated inefficiently at 25° C. It was determined that a total of five wild type amino acids, one in PB2 (R630S), one in PA(M431V) and three in NP(A114V, H410P, T509A), were required for to completely revert the MDV-B ca phenotype. In addition, replacing two amino acids in the M1 protein (Q159H, V183M) of MDV-B or 6:2 vaccine strains with the wild-type amino acids significantly increased virus replication at 33° C. but not at 25° C. in CEK cells; the V183M change had a larger impact on the change.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes.

The invention claimed is:

1. A reassortant influenza virus comprising:

i) an HA protein comprising a leucine at position 183 and an alanine at position 226; or ii) an HA protein comprising a valine at position 186 and an isoleucine at position 226; or iii) an HA protein comprising a valine at position 186 and an isoleucine at position 226 and an NA protein comprising a glutamate at position 119 and a glutamine at position 136;

wherein the HA protein is of the H3 type.

2. An immunogenic composition comprising the reassortant influenza virus of claim 1.

3. A method of making the reassortant influenza virus of claim 1, comprising:

(a) introducing at least one mutation in an influenza HA and/or NA gene, wherein the at least one mutation results in:

(i) an HA polypeptide comprising a leucine at position 183 and an alanine at position 226; or (ii) an HA polypeptide comprising a valine at position 186 and an isoleucine at position 226; or (iii) an HA polypeptide comprising a valine at position 186 and an isoleucine at position 226 and an NA comprising a glutamate at position 119 and a glutamine at position 136; wherein the HA protein is of the H3 type;

(b) introducing a plurality of vectors into a population of host cells, wherein the plurality of vectors corresponds to an influenza virus genome, wherein at least one of the plurality of vectors comprises an influenza HA and/or NA gene comprising the at least one mutation recited in (a), and wherein the population of host cells is capable of supporting replication of influenza virus;

(c) culturing the population of host cells; and (d) recovering the reassortant influenza virus.

4. A method of making the reassortant influenza virus of claim 1, comprising:

(a) introducing a plurality of vectors into a population of host cells, wherein the plurality of vectors corresponds to an influenza virus genome, wherein at least one of the plurality of vectors encodes:

(i) an HA polypeptide comprising a leucine at position 183 and an alanine at position 226; or (ii) an HA polypeptide comprising a valine at position 186 and an isoleucine at position 226; or (iii) an HA polypeptide comprising a valine at position 186 and an isoleucine at position 226 and an NA comprising a glutamate at position 119 and a glutamine at position 136; wherein the HA protein is of the H3 type;

and wherein the population of host cells is capable of supporting replication of influenza virus;

(b) culturing the population of host cells; and (c) recovering the reassortant influenza virus.

5. A method of stimulating an immune response, comprising:

administering the immunogenic composition of claim 2.

6. The method of claim 5, wherein the immunogenic composition is administered intranasally.

7. The method of claim 5, wherein the immunogenic composition is administered by subcutaneous injection.

8. The method of claim 5 wherein the immunogenic composition is administered by intramuscular injection.

9. The reassortant influenza virus of claim 1, wherein the virus is a 6:2 reassortant.

10. The reassortant influenza virus of claim 1, wherein the virus is a 7:1 reassortant.

* * * * *

SEQUENCE LISTING

```
<160> NUMBER OF SEQ ID NOS: 102

<210> SEQ ID NO 1
<211> LENGTH: 50
<212> TYPE: DNA
<213> ORGANISM: Artificial
<220> FEATURE:
<223> OTHER INFORMATION: oligonucleotide primer polyA.1

<400> SEQUENCE: 1

aacaattgag atctcggtca cctcagacat gataagatac attgatgagt              50


<210> SEQ ID NO 2
<211> LENGTH: 50
<212> TYPE: DNA
<213> ORGANISM: Artificial
<220> FEATURE:
<223> OTHER INFORMATION: oligonucleotide primer polyA.2

<400> SEQUENCE: 2

tataactgca gactagtgat atccttgttt attgcagctt ataatggtta              50


<210> SEQ ID NO 3
<211> LENGTH: 38
<212> TYPE: DNA
<213> ORGANISM: Artificial
<220> FEATURE:
<223> OTHER INFORMATION: oligonucleotide primer for MDV-A RT-PCR

<400> SEQUENCE: 3

cacttatatt cacctgcctc agggagcgaa agcaggtc                          38


<210> SEQ ID NO 4
<211> LENGTH: 30
<212> TYPE: DNA
<213> ORGANISM: Artificial
<220> FEATURE:
<223> OTHER INFORMATION: oligonucleotide primer for MDV-A RT-PCR

<400> SEQUENCE: 4

tattcgtctc agggagcgaa agcaggcaaa                                    30


<210> SEQ ID NO 5
<211> LENGTH: 30
<212> TYPE: DNA
<213> ORGANISM: Artificial
<220> FEATURE:
<223> OTHER INFORMATION: oligonucleotide primer for MDV-A RT-PCR

<400> SEQUENCE: 5

tattcgtctc agggagcgaa agcaggtact                                    30


<210> SEQ ID NO 6
<211> LENGTH: 31
```

-continued

<212> TYPE: DNA
<213> ORGANISM: Artificial
<220> FEATURE:
<223> OTHER INFORMATION: oligonucleotide primer for MDV-A RT-PCR

<400> SEQUENCE: 6
tattcgtctc agggagcaaa agcagggtag a 31

<210> SEQ ID NO 7
<211> LENGTH: 38
<212> TYPE: DNA
<213> ORGANISM: Artificial
<220> FEATURE:
<223> OTHER INFORMATION: oligonucleotide primer for MDV-A RT-PCR

<400> SEQUENCE: 7
cacttatatt cacctgcctc agggagcaaa agcagggg 38

<210> SEQ ID NO 8
<211> LENGTH: 31
<212> TYPE: DNA
<213> ORGANISM: Artificial
<220> FEATURE:
<223> OTHER INFORMATION: oligonucleotide primer for MDV-A RT-PCR

<400> SEQUENCE: 8
tattcgtctc agggagcaaa agcaggagtg a 31

<210> SEQ ID NO 9
<211> LENGTH: 31
<212> TYPE: DNA
<213> ORGANISM: Artificial
<220> FEATURE:
<223> OTHER INFORMATION: oligonucleotide primer for MDV-A RT-PCR

<400> SEQUENCE: 9
tattcgtctc agggagcaaa agcaggtaga t 31

<210> SEQ ID NO 10
<211> LENGTH: 30
<212> TYPE: DNA
<213> ORGANISM: Artificial
<220> FEATURE:
<223> OTHER INFORMATION: oligonucleotide primer for MDV-A RT-PCR

<400> SEQUENCE: 10
tattcgtctc agggagcaaa agcagggtga 30

<210> SEQ ID NO 11
<211> LENGTH: 44
<212> TYPE: DNA
<213> ORGANISM: Artificial
<220> FEATURE:
<223> OTHER INFORMATION: oligonucleotide primer for MDV-A RT-PCR

<400> SEQUENCE: 11
cctaacatat cacctgcctc gtattagtag aaacaaggtc gttt 44

<210> SEQ ID NO 12
<211> LENGTH: 33
<212> TYPE: DNA
<213> ORGANISM: Artificial
<220> FEATURE:
<223> OTHER INFORMATION: oligonucleotide primer for MDV-A RT-PCR

<400> SEQUENCE: 12

-continued atatcgtctc gtattagtag aaacaaggca ttt 33

<210> SEQ ID NO 13
<211> LENGTH: 33
<212> TYPE: DNA
<213> ORGANISM: Artificial
<220> FEATURE:
<223> OTHER INFORMATION: oligonucleotide primer for MDV-A RT-PCR

<400> SEQUENCE: 13
atatcgtctc gtattagtag aaacaaggta ctt 33

<210> SEQ ID NO 14
<211> LENGTH: 33
<212> TYPE: DNA
<213> ORGANISM: Artificial
<220> FEATURE:
<223> OTHER INFORMATION: oligonucleotide primer for MDV-A RT-PCR

<400> SEQUENCE: 14
atatcgtctc gtattagtag aaacaagggt att 33

<210> SEQ ID NO 15
<211> LENGTH: 43
<212> TYPE: DNA
<213> ORGANISM: Artificial
<220> FEATURE:
<223> OTHER INFORMATION: oligonucleotide primer for MDV-A RT-PCR

<400> SEQUENCE: 15
cctaacatat cacctgcctc gtattagtag aaacaagggt gtt 43

<210> SEQ ID NO 16
<211> LENGTH: 33
<212> TYPE: DNA
<213> ORGANISM: Artificial
<220> FEATURE:
<223> OTHER INFORMATION: oligonucleotide primer for MDV-A RT-PCR

<400> SEQUENCE: 16
atatcgtctc gtattagtag aaacaaggag ttt 33

<210> SEQ ID NO 17
<211> LENGTH: 33
<212> TYPE: DNA
<213> ORGANISM: Artificial
<220> FEATURE:
<223> OTHER INFORMATION: oligonucleotide primer for MDV-A RT-PCR

<400> SEQUENCE: 17
atatcgtctc gtattagtag aaacaaggta gtt 33

<210> SEQ ID NO 18
<211> LENGTH: 33
<212> TYPE: DNA
<213> ORGANISM: Artificial
<220> FEATURE:
<223> OTHER INFORMATION: oligonucleotide primer for MDV-A RT-PCR

<400> SEQUENCE: 18
atatcgtctc gtattagtag aaacaagggt gtt 33

<210> SEQ ID NO 19
<211> LENGTH: 24
<212> TYPE: DNA
<213> ORGANISM: Artificial

-continued

<220> FEATURE:
<223> OTHER INFORMATION: oligonucleotide primer for MDV-A mutation
correction

<400> SEQUENCE: 19
gcaagctgtg gaaatatgca aggc 24

<210> SEQ ID NO 20
<211> LENGTH: 24
<212> TYPE: DNA
<213> ORGANISM: Artificial
<220> FEATURE:
<223> OTHER INFORMATION: oligonucleotide primer for MDV-A mutation
correction

<400> SEQUENCE: 20
gccttgcata tttccacagc ttgc 24

<210> SEQ ID NO 21
<211> LENGTH: 26
<212> TYPE: DNA
<213> ORGANISM: Artificial
<220> FEATURE:
<223> OTHER INFORMATION: oligonucleotide primer for MDV-A mutation
correction

<400> SEQUENCE: 21
gaagtgctta cgggcaatct tcaaac 26

<210> SEQ ID NO 22
<211> LENGTH: 26
<212> TYPE: DNA
<213> ORGANISM: Artificial
<220> FEATURE:
<223> OTHER INFORMATION: oligonucleotide primer for MDV-A mutation
correction

<400> SEQUENCE: 22
gtttgaagat tgcccgtaag cacttc 26

<210> SEQ ID NO 23
<211> LENGTH: 22
<212> TYPE: DNA
<213> ORGANISM: Artificial
<220> FEATURE:
<223> OTHER INFORMATION: oligonucleotide primer for MDV-A mutation
correction

<400> SEQUENCE: 23
cctgaggagg tcagtgaaac ac 22

<210> SEQ ID NO 24
<211> LENGTH: 22
<212> TYPE: DNA
<213> ORGANISM: Artificial
<220> FEATURE:
<223> OTHER INFORMATION: oligonucleotide primer for MDV-A mutation
correction

<400> SEQUENCE: 24
gtgtttcact gacctcctca gg 22

<210> SEQ ID NO 25
<211> LENGTH: 23
<212> TYPE: DNA
<213> ORGANISM: Artificial
<220> FEATURE:

-continued

<223> OTHER INFORMATION: oligonucleotide primer for MDV-A mutation correction

<400> SEQUENCE: 25
gtttgttagg actctattcc aac 23

<210> SEQ ID NO 26
<211> LENGTH: 23
<212> TYPE: DNA
<213> ORGANISM: Artificial
<220> FEATURE:
<223> OTHER INFORMATION: oligonucleotide primer for MDV-A mutation correction

<400> SEQUENCE: 26
gttggaatag agtcctaaca aac 23

<210> SEQ ID NO 27
<211> LENGTH: 25
<212> TYPE: DNA
<213> ORGANISM: Artificial
<220> FEATURE:
<223> OTHER INFORMATION: oligonucleotide primer for MDV-A mutation correction

<400> SEQUENCE: 27
gacagtaagc tccgaacaca aatac 25

<210> SEQ ID NO 28
<211> LENGTH: 24
<212> TYPE: DNA
<213> ORGANISM: Artificial
<220> FEATURE:
<223> OTHER INFORMATION: oligonucleotide primer for MDV-A mutation correction

<400> SEQUENCE: 28
gtatttgtgt tcggagcttc atgc 24

<210> SEQ ID NO 29
<211> LENGTH: 24
<212> TYPE: DNA
<213> ORGANISM: Artificial
<220> FEATURE:
<223> OTHER INFORMATION: oligonucleotide primer for MDV-A mutation correction

<400> SEQUENCE: 29
cgaaccgaac ggctacattg aggg 24

<210> SEQ ID NO 30
<211> LENGTH: 24
<212> TYPE: DNA
<213> ORGANISM: Artificial
<220> FEATURE:
<223> OTHER INFORMATION: oligonucleotide primer for MDV-A mutation correction

<400> SEQUENCE: 30
ccctcaatgt agccgttcgg ttcg 24

<210> SEQ ID NO 31
<211> LENGTH: 24
<212> TYPE: DNA
<213> ORGANISM: Artificial
<220> FEATURE:
<223> OTHER INFORMATION: oligonucleotide primer for MDV-A mutation -continued correction

<400> SEQUENCE: 31
cagagaaggt agatttgacg actg 24

<210> SEQ ID NO 32
<211> LENGTH: 25
<212> TYPE: DNA
<213> ORGANISM: Artificial
<220> FEATURE:
<223> OTHER INFORMATION: oligonucleotide primer for MDV-A mutation correction

<400> SEQUENCE: 32
cagtcgtcaa agtctacctt ctctg 25

<210> SEQ ID NO 33
<211> LENGTH: 23
<212> TYPE: DNA
<213> ORGANISM: Artificial
<220> FEATURE:
<223> OTHER INFORMATION: oligonucleotide primer for MDV-A mutation correction

<400> SEQUENCE: 33
cactgaccca agacttgagc cac 23

<210> SEQ ID NO 34
<211> LENGTH: 23
<212> TYPE: DNA
<213> ORGANISM: Artificial
<220> FEATURE:
<223> OTHER INFORMATION: oligonucleotide primer for MDV-A mutation correction

<400> SEQUENCE: 34
gtggctcaag tcttgggtca gtg 23

<210> SEQ ID NO 35
<211> LENGTH: 26
<212> TYPE: DNA
<213> ORGANISM: Artificial
<220> FEATURE:
<223> OTHER INFORMATION: oligonucleotide primer for MDV-A mutation correction

<400> SEQUENCE: 35
caaagattaa aatgaaatgg ggaatg 26

<210> SEQ ID NO 36
<211> LENGTH: 26
<212> TYPE: DNA
<213> ORGANISM: Artificial
<220> FEATURE:
<223> OTHER INFORMATION: oligonucleotide primer for MDV-A mutation correction

<400> SEQUENCE: 36
cattccccat ttcattttaa tctttg 26

<210> SEQ ID NO 37
<211> LENGTH: 26
<212> TYPE: DNA
<213> ORGANISM: Artificial
<220> FEATURE:
<223> OTHER INFORMATION: oligonucleotide primer for MDV-A mutation correction -continued

<400> SEQUENCE: 37
gtaccttgtt tctactaata acccgg 26

<210> SEQ ID NO 38
<211> LENGTH: 26
<212> TYPE: DNA
<213> ORGANISM: Artificial
<220> FEATURE:
<223> OTHER INFORMATION: oligonucleotide primer for MDV-A mutation correction

<400> SEQUENCE: 38
ccgggttatt agtagaaaca aggtac 26

<210> SEQ ID NO 39
<211> LENGTH: 24
<212> TYPE: DNA
<213> ORGANISM: Artificial
<220> FEATURE:
<223> OTHER INFORMATION: oligonucleotide primer for MDV-A mutation correction

<400> SEQUENCE: 39
ggaacacttg agaactgtga gacc 24

<210> SEQ ID NO 40
<211> LENGTH: 24
<212> TYPE: DNA
<213> ORGANISM: Artificial
<220> FEATURE:
<223> OTHER INFORMATION: oligonucleotide primer for MDV-A mutation correction

<400> SEQUENCE: 40
ggtctcacag ttctcaagtg ttcc 24

<210> SEQ ID NO 41
<211> LENGTH: 29
<212> TYPE: DNA
<213> ORGANISM: Artificial
<220> FEATURE:
<223> OTHER INFORMATION: oligonucleotide primer for MDV-A mutation correction

<400> SEQUENCE: 41
gaattttatc acaaatgtga tgatgaatg 29

<210> SEQ ID NO 42
<211> LENGTH: 29
<212> TYPE: DNA
<213> ORGANISM: Artificial
<220> FEATURE:
<223> OTHER INFORMATION: oligonucleotide primer for MDV-A mutation correction

<400> SEQUENCE: 42
cattcatcat cacatttgtg ataaaattc 29

<210> SEQ ID NO 43
<211> LENGTH: 25
<212> TYPE: DNA
<213> ORGANISM: Artificial
<220> FEATURE:
<223> OTHER INFORMATION: oligonucleotide primer for MDV-A mutation correction -continued

<400> SEQUENCE: 43
gccagaatgc aactgaaatc agagc 25

<210> SEQ ID NO 44
<211> LENGTH: 25
<212> TYPE: DNA
<213> ORGANISM: Artificial
<220> FEATURE:
<223> OTHER INFORMATION: oligonucleotide primer for MDV-A mutation correction

<400> SEQUENCE: 44
gctctgattt cagtttcatt ctggc 25

<210> SEQ ID NO 45
<211> LENGTH: 24
<212> TYPE: DNA
<213> ORGANISM: Artificial
<220> FEATURE:
<223> OTHER INFORMATION: oligonucleotide primer for MDV-A mutation correction

<400> SEQUENCE: 45
ccgaatgaga atccagcaca caag 24

<210> SEQ ID NO 46
<211> LENGTH: 24
<212> TYPE: DNA
<213> ORGANISM: Artificial
<220> FEATURE:
<223> OTHER INFORMATION: oligonucleotide primer for MDV-A mutation correction

<400> SEQUENCE: 46
cttgtgtgct ggattctcat tcgg 24

<210> SEQ ID NO 47
<211> LENGTH: 28
<212> TYPE: DNA
<213> ORGANISM: Artificial
<220> FEATURE:
<223> OTHER INFORMATION: oligonucleotide primer for MDV-A mutation correction

<400> SEQUENCE: 47
catcaatttc atgcctatat aagctttc 28

<210> SEQ ID NO 48
<211> LENGTH: 28
<212> TYPE: DNA
<213> ORGANISM: Artificial
<220> FEATURE:
<223> OTHER INFORMATION: oligonucleotide primer for MDV-A mutation correction

<400> SEQUENCE: 48
gaaagcttat ataggcatga aattgatg 28

<210> SEQ ID NO 49
<211> LENGTH: 28
<212> TYPE: DNA
<213> ORGANISM: Artificial
<220> FEATURE:
<223> OTHER INFORMATION: oligonucleotide primer for MDV-A mutation correction

<400> SEQUENCE: 49

-continued cataatggat cctaacactg tgtcaagc 28

<210> SEQ ID NO 50
<211> LENGTH: 28
<212> TYPE: DNA
<213> ORGANISM: Artificial
<220> FEATURE:
<223> OTHER INFORMATION: oligonucleotide primer for MDV-A mutation correction

<400> SEQUENCE: 50
gcttgacaca gtgttaggat ccattatg 28

<210> SEQ ID NO 51
<211> LENGTH: 26
<212> TYPE: DNA
<213> ORGANISM: Artificial
<220> FEATURE:
<223> OTHER INFORMATION: oligonucleotide primer for MDV-A mutation correction

<400> SEQUENCE: 51
ggagaataga ttcatcgaga ttggag 26

<210> SEQ ID NO 52
<211> LENGTH: 26
<212> TYPE: DNA
<213> ORGANISM: Artificial
<220> FEATURE:
<223> OTHER INFORMATION: oligonucleotide primer for MDV-A mutation correction

<400> SEQUENCE: 52
ctccaatctc gatgaatcta ttctcc 26

<210> SEQ ID NO 53
<211> LENGTH: 38
<212> TYPE: DNA
<213> ORGANISM: Artificial
<220> FEATURE:
<223> OTHER INFORMATION: oligonucleotide primer for influenza ca B/Ann Arbor/1/66 RT-PCR

<400> SEQUENCE: 53
tattcgtctc agggagcaga agcggagcct ttaagatg 38

<210> SEQ ID NO 54
<211> LENGTH: 39
<212> TYPE: DNA
<213> ORGANISM: Artificial
<220> FEATURE:
<223> OTHER INFORMATION: oligonucleotide primer for influenza ca B/Ann Arbor/1/66 RT-PCR

<400> SEQUENCE: 54
tattcgtctc gatgccgttc cttcttcatt gaagaatgg 39

<210> SEQ ID NO 55
<211> LENGTH: 38
<212> TYPE: DNA
<213> ORGANISM: Artificial
<220> FEATURE:
<223> OTHER INFORMATION: oligonucleotide primer for influenza ca B/Ann Arbor/1/66 RT-PCR

<400> SEQUENCE: 55

-continued tattcgtctc ggcatctttg tcgcctggga tgatgatg 38

<210> SEQ ID NO 56
<211> LENGTH: 33
<212> TYPE: DNA
<213> ORGANISM: Artificial
<220> FEATURE:
<223> OTHER INFORMATION: oligonucleotide primer for influenza ca
B/Ann Arbor/1/66 RT-PCR

<400> SEQUENCE: 56
atatcgtctc gtattagtag aaacacgagc ctt 33

<210> SEQ ID NO 57
<211> LENGTH: 40
<212> TYPE: DNA
<213> ORGANISM: Artificial
<220> FEATURE:
<223> OTHER INFORMATION: oligonucleotide primer for influenza ca
B/Ann Arbor/1/66 RT-PCR

<400> SEQUENCE: 57
tattcgtctc agggagcaga agcggagcgt tttcaagatg 40

<210> SEQ ID NO 58
<211> LENGTH: 39
<212> TYPE: DNA
<213> ORGANISM: Artificial
<220> FEATURE:
<223> OTHER INFORMATION: oligonucleotide primer for influenza ca
B/Ann Arbor/1/66 RT-PCR

<400> SEQUENCE: 58
tattcgtctc tctcattttg ctcttttta atattcccc 39

<210> SEQ ID NO 59
<211> LENGTH: 42
<212> TYPE: DNA
<213> ORGANISM: Artificial
<220> FEATURE:
<223> OTHER INFORMATION: oligonucleotide primer for influenza ca
B/Ann Arbor/1/66 RT-PCR

<400> SEQUENCE: 59
tattcgtctc atgagaatgg aaaaactact aataaattca gc 42

<210> SEQ ID NO 60
<211> LENGTH: 33
<212> TYPE: DNA
<213> ORGANISM: Artificial
<220> FEATURE:
<223> OTHER INFORMATION: oligonucleotide primer for influenza ca
B/Ann Arbor/1/66 RT-PCR

<400> SEQUENCE: 60
atatcgtctc gtattagtag aaacacgagc att 33

<210> SEQ ID NO 61
<211> LENGTH: 34
<212> TYPE: DNA
<213> ORGANISM: Artificial
<220> FEATURE:
<223> OTHER INFORMATION: oligonucleotide primer for influenza ca
B/Ann Arbor/1/66 RT-PCR

<400> SEQUENCE: 61
tattcgtctc agggagcaga agcggtgcgt ttga 34

-continued

<210> SEQ ID NO 62
<211> LENGTH: 37
<212> TYPE: DNA
<213> ORGANISM: Artificial
<220> FEATURE:
<223> OTHER INFORMATION: oligonucleotide primer for influenza ca
B/Ann Arbor/1/66 RT-PCR

<400> SEQUENCE: 62
tattcgtctc ccagggccct tttacttgtc agagtgc 37

<210> SEQ ID NO 63
<211> LENGTH: 39
<212> TYPE: DNA
<213> ORGANISM: Artificial
<220> FEATURE:
<223> OTHER INFORMATION: oligonucleotide primer for influenza ca
B/Ann Arbor/1/66 RT-PCR

<400> SEQUENCE: 63
tattcgtctc tcctggatct accagaaata gggccagac 39

<210> SEQ ID NO 64
<211> LENGTH: 33
<212> TYPE: DNA
<213> ORGANISM: Artificial
<220> FEATURE:
<223> OTHER INFORMATION: oligonucleotide primer for influenza ca
B/Ann Arbor/1/66 RT-PCR

<400> SEQUENCE: 64
atatcgtctc gtattagtag aaacacgtgc att 33

<210> SEQ ID NO 65
<211> LENGTH: 41
<212> TYPE: DNA
<213> ORGANISM: Artificial
<220> FEATURE:
<223> OTHER INFORMATION: oligonucleotide primer for influenza ca
B/Ann Arbor/1/66 RT-PCR

<400> SEQUENCE: 65
tattcgtctc agggagcaga agcagagcat tttctaatat c 41

<210> SEQ ID NO 66
<211> LENGTH: 37
<212> TYPE: DNA
<213> ORGANISM: Artificial
<220> FEATURE:
<223> OTHER INFORMATION: oligonucleotide primer for influenza ca
B/Ann Arbor/1/66 RT-PCR

<400> SEQUENCE: 66
atatcgtctc gtattagtag taacaagagc atttttc 37

<210> SEQ ID NO 67
<211> LENGTH: 38
<212> TYPE: DNA
<213> ORGANISM: Artificial
<220> FEATURE:
<223> OTHER INFORMATION: oligonucleotide primer for influenza ca
B/Ann Arbor/1/66 RT-PCR

<400> SEQUENCE: 67
tattggtctc agggagcaga agcacagcat tttcttgt 38

-continued

<210> SEQ ID NO 68
<211> LENGTH: 36
<212> TYPE: DNA
<213> ORGANISM: Artificial
<220> FEATURE:
<223> OTHER INFORMATION: oligonucleotide primer for influenza ca
B/Ann Arbor/1/66 RT-PCR

<400> SEQUENCE: 68
atatggtctc gtattagtag aaacaacagc attttt 36

<210> SEQ ID NO 69
<211> LENGTH: 41
<212> TYPE: DNA
<213> ORGANISM: Artificial
<220> FEATURE:
<223> OTHER INFORMATION: oligonucleotide primer for influenza ca
B/Ann Arbor/1/66 RT-PCR

<400> SEQUENCE: 69
tattcgtctc agggagcaga agcagagcat cttctcaaaa c 41

<210> SEQ ID NO 70
<211> LENGTH: 39
<212> TYPE: DNA
<213> ORGANISM: Artificial
<220> FEATURE:
<223> OTHER INFORMATION: oligonucleotide primer for influenza ca
B/Ann Arbor/1/66 RT-PCR

<400> SEQUENCE: 70
atatcgtctc gtattagtag taacaagagc atttttcag 39

<210> SEQ ID NO 71
<211> LENGTH: 41
<212> TYPE: DNA
<213> ORGANISM: Artificial
<220> FEATURE:
<223> OTHER INFORMATION: oligonucleotide primer for influenza ca
B/Ann Arbor/1/66 RT-PCR

<400> SEQUENCE: 71
tattcgtctc agggagcaga agcacgcact ttcttaaaat g 41

<210> SEQ ID NO 72
<211> LENGTH: 40
<212> TYPE: DNA
<213> ORGANISM: Artificial
<220> FEATURE:
<223> OTHER INFORMATION: oligonucleotide primer for influenza ca
B/Ann Arbor/1/66 RT-PCR

<400> SEQUENCE: 72
atatcgtctc gtattagtag aaacaacgca ctttttccag 40

<210> SEQ ID NO 73
<211> LENGTH: 40
<212> TYPE: DNA
<213> ORGANISM: Artificial
<220> FEATURE:
<223> OTHER INFORMATION: oligonucleotide primer for influenza ca
B/Ann Arbor/1/66 RT-PCR

<400> SEQUENCE: 73
tattcgtctc agggagcaga agcagaggat ttgtttagtc 40

-continued

<210> SEQ ID NO 74
<211> LENGTH: 38
<212> TYPE: DNA
<213> ORGANISM: Artificial
<220> FEATURE:
<223> OTHER INFORMATION: oligonucleotide primer for influenza ca B/Ann Arbor/1/66 RT-PCR

<400> SEQUENCE: 74
atatcgtctc gtattagtag taacaagagg atttttat 38

<210> SEQ ID NO 75
<211> LENGTH: 39
<212> TYPE: DNA
<213> ORGANISM: Artificial
<220> FEATURE:
<223> OTHER INFORMATION: oligonucleotide primer for B/Yamanashi/166/98 NP amplification

<400> SEQUENCE: 75
tattcgtctc agggagcaga agcacagcat tttcttgtg 39

<210> SEQ ID NO 76
<211> LENGTH: 39
<212> TYPE: DNA
<213> ORGANISM: Artificial
<220> FEATURE:
<223> OTHER INFORMATION: oligonucleotide primer for B/Yamanashi/166/98 NP amplification

<400> SEQUENCE: 76
atatcgtctc gtattagtag aaacaacagc attttttac 39

<210> SEQ ID NO 77
<211> LENGTH: 29
<212> TYPE: DNA
<213> ORGANISM: Artificial
<220> FEATURE:
<223> OTHER INFORMATION: oligonucleotide primer for B/Yamanashi/166/98 NA amplification

<400> SEQUENCE: 77
tattcgtctc agggagcaga agcagagca 29

<210> SEQ ID NO 78
<211> LENGTH: 35
<212> TYPE: DNA
<213> ORGANISM: Artificial
<220> FEATURE:
<223> OTHER INFORMATION: oligonucleotide primer for B/Yamanashi/166/98 NA amplification

<400> SEQUENCE: 78
atatcgtctc gtattagtag taacaagagc atttt 35

<210> SEQ ID NO 79
<211> LENGTH: 29
<212> TYPE: DNA
<213> ORGANISM: Artificial
<220> FEATURE:
<223> OTHER INFORMATION: oligonucleotide primer for introducing ts mutations into PR8 PB1 and PB2 genes

<400> SEQUENCE: 79
gaaagaagat tgaagaaatc cgaccgctc 29

-continued

<210> SEQ ID NO 80
<211> LENGTH: 29
<212> TYPE: DNA
<213> ORGANISM: Artificial
<220> FEATURE:
<223> OTHER INFORMATION: oligonucleotide primer for introducing ts mutations into PR8 PB1 and PB2 genes

<400> SEQUENCE: 80
gagcggtcgg atttcttcaa tcttctttc 29

<210> SEQ ID NO 81
<211> LENGTH: 33
<212> TYPE: DNA
<213> ORGANISM: Artificial
<220> FEATURE:
<223> OTHER INFORMATION: oligonucleotide primer for introducing ts mutations into PR8 PB1 and PB2 genes

<400> SEQUENCE: 81
gaaataaaga aactgtgggg gcaaacccgt tcc 33

<210> SEQ ID NO 82
<211> LENGTH: 33
<212> TYPE: DNA
<213> ORGANISM: Artificial
<220> FEATURE:
<223> OTHER INFORMATION: oligonucleotide primer for introducing ts mutations into PR8 PB1 and PB2 genes

<400> SEQUENCE: 82
ggaacgggtt tgcccccaca gtttctttat ttc 33

<210> SEQ ID NO 83
<211> LENGTH: 28
<212> TYPE: DNA
<213> ORGANISM: Artificial
<220> FEATURE:
<223> OTHER INFORMATION: oligonucleotide primer for introducing ts mutations into PR8 PB1 and PB2 genes

<400> SEQUENCE: 83
gtatgatgct gttacaacaa cacactcc 28

<210> SEQ ID NO 84
<211> LENGTH: 28
<212> TYPE: DNA
<213> ORGANISM: Artificial
<220> FEATURE:
<223> OTHER INFORMATION: oligonucleotide primer for introducing ts mutations into PR8 PB1 and PB2 genes

<400> SEQUENCE: 84
ggagtgtgtt gttgtaacag catcatac 28

<210> SEQ ID NO 85
<211> LENGTH: 29
<212> TYPE: DNA
<213> ORGANISM: Artificial
<220> FEATURE:
<223> OTHER INFORMATION: oligonucleotide primer for introducing ts mutations into PR8 PB1 and PB2 genes -continued

<400> SEQUENCE: 85
attgctgcta ggagcatagt gagaagagc 29

<210> SEQ ID NO 86
<211> LENGTH: 29
<212> TYPE: DNA
<213> ORGANISM: Artificial
<220> FEATURE:
<223> OTHER INFORMATION: oligonucleotide primer for introducing ts mutations into PR8 PB1 and PB2 genes

<400> SEQUENCE: 86
gctcttctca ctatgctcct agcagcaat 29

<210> SEQ ID NO 87
<211> LENGTH: 29
<212> TYPE: DNA
<213> ORGANISM: Artificial
<220> FEATURE:
<223> OTHER INFORMATION: oligonucleotide primer for RT-PCR of HA and NA

<400> SEQUENCE: 87
tattcgtctc agggagcaga agcagagca 29

<210> SEQ ID NO 88
<211> LENGTH: 35
<212> TYPE: DNA
<213> ORGANISM: Artificial
<220> FEATURE:
<223> OTHER INFORMATION: oligonucleotide primer for RT-PCR of HA and NA

<400> SEQUENCE: 88
atatcgtctc gtattagtag taacaagagc atttt 35

<210> SEQ ID NO 89
<211> LENGTH: 23
<212> TYPE: DNA
<213> ORGANISM: Artificial
<220> FEATURE:
<223> OTHER INFORMATION: oligonucleotide primer for primer extension

<400> SEQUENCE: 89
atgttcttta cgatgcgatt ggg 23

<210> SEQ ID NO 90
<211> LENGTH: 38
<212> TYPE: DNA
<213> ORGANISM: Artificial
<220> FEATURE:
<223> OTHER INFORMATION: oligonucleotide primer for amplification of HA

<400> SEQUENCE: 90
cacttatatt cacctgcctc agggagcaaa agcagggg 38

<210> SEQ ID NO 91
<211> LENGTH: 43
<212> TYPE: DNA
<213> ORGANISM: Artificial
<220> FEATURE:
<223> OTHER INFORMATION: oligonucleotide primer for amplification of HA

<400> SEQUENCE: 91
cctaacatat cacctgcctc gtattagtag aaacaagggt gtt 43

-continued

<210> SEQ ID NO 92
<211> LENGTH: 39
<212> TYPE: DNA
<213> ORGANISM: Artificial
<220> FEATURE:
<223> OTHER INFORMATION: oligonucleotide primer for amplification of NA

<400> SEQUENCE: 92
cacttatatt cacctgcctc agggagcaaa agcaggagt 39

<210> SEQ ID NO 93
<211> LENGTH: 43
<212> TYPE: DNA
<213> ORGANISM: Artificial
<220> FEATURE:
<223> OTHER INFORMATION: oligonucleotide primer for amplification of NA

<400> SEQUENCE: 93
cctaacatat cacctgcctc gtattagtag aaacaaggag ttt 43

<210> SEQ ID NO 94
<211> LENGTH: 2836
<212> TYPE: DNA
<213> ORGANISM: Artificial
<220> FEATURE:
<223> OTHER INFORMATION: pAD3000

<400> SEQUENCE: 94
ctagcagtta accggagtac tggtcgacct ccgaagttgg gggggaggag acggtaccgt 60
ctccaataac ccggcggccc aaaatgccga ctcggagcga aagatatacc tcccccgggg 120
ccgggaggtc gcgtcaccga ccacgccgcc ggcccaggcg acgcgcgaca cggacacctg 180
tccccaaaaa cgccaccatc gcagccacac acggagcgcc cggggccctc tggtcaaccc 240
caggacacac gcgggagcag cgccgggccg gggacgccct cccggcggtc acctcagaca 300
tgataagata cattgatgag tttggacaaa ccacaactag aatgcagtga aaaaaatgct 360
ttatttgtga aatttgtgat gctattgctt tatttgtaac cattataagc tgcaataaac 420
aaggatctgc attaatgaat cggccaacgc gcggggagag gcggtttgcg tattgggcgc 480
tcttccgctt cctcgctcac tgactcgctg cgctcggtcg ttcggctgcg gcgagcggta 540
tcagctcact caaaggcggt aatacggtta tccacagaat caggggataa cgcaggaaag 600
aacatgtgag caaaaggcca gcaaaaggcc aggaaccgta aaaaggccgc gttgctggcg 660
tttttccata ggctccgccc ccctgacgag catcacaaaa atcgacgctc aagtcagagg 720
tggcgaaacc cgacaggact ataaagatac caggcgtttc cccctggaag ctccctcgtg 780
cgctctcctg ttccgaccct gccgcttacc ggatacctgt ccgcctttct cccttcggga 840
agcgtggcgc tttctcaatg ctcacgctgt aggtatctca gttcggtgta ggtcgttcgc 900
tccaagctgg gctgtgtgca cgaacccccc gttcagcccg accgctgcgc cttatccggt 960
aactatcgtc ttgagtccaa cccggtaaga cacgacttat cgccactggc agcagccact 1020
ggtaacagga ttagcagagc gaggtatgta ggcggtgcta cagagttctt gaagtggtgg 1080
cctaactacg gctacactag aaggacagta tttggtatct gcgctctgct gaagccagtt 1140
accttcggaa aaagagttgg tagctcttga tccggcaaac aaaccaccgc tggtagcggt 1200
ggtttttttg tttgcaagca gcagattacg cgcagaaaaa aaggatctca agaagatcct 1260
ttgatctttt ctacggggtc tgacgctcag tggaacgaaa actcacgtta agggattttg 1320
gtcatgagat tatcaaaaag gatcttcacc tagatccttt taaattaaaa atgaagtttt 1380

-continued

```
aaatcaatct aaagtatata tgagtaaact tggtctgaca gttaccaatg cttaatcagt   1440

gaggcaccta tctcagcgat ctgtctattt cgttcatcca tagttgcctg actccccgtc   1500

gtgtagataa ctacgatacg ggagggctta ccatctggcc ccagtgctgc aatgataccg   1560

cgagacccac gctcaccggc tccagattta tcagcaataa accagccagc cggaagggcc   1620

gagcgcagaa gtggtcctgc aactttatcc gcctccatcc agtctattaa ttgttgccgg   1680

gaagctagag taagtagttc gccagttaat agtttgcgca acgttgttgc cattgctaca   1740

ggcatcgtgg tgtcacgctc gtcgtttggt atggcttcat tcagctccgg ttcccaacga   1800

tcaaggcgag ttacatgatc ccccatgttg tgcaaaaaag cggttagctc cttcggtcct   1860

ccgatcgttg tcagaagtaa gttggccgca gtgttatcac tcatggttat ggcagcactg   1920

cataattctc ttactgtcat gccatccgta agatgctttt ctgtgactgg tgagtactca   1980

accaagtcat tctgagaata gtgtatgcgg cgaccgagtt gctcttgccc ggcgtcaata   2040

cgggataata ccgcgccaca tagcagaact ttaaaagtgc tcatcattgg aaaacgttct   2100

tcggggcgaa aactctcaag gatcttaccg ctgttgagat ccagttcgat gtaacccact   2160

cgtgcaccca actgatcttc agcatctttt actttcacca gcgtttctgg gtgagcaaaa   2220

acaggaaggc aaaatgccgc aaaaaaggga ataagggcga cacggaaatg ttgaatactc   2280

atactcttcc tttttcaata ttattgaagc atttatcagg gttattgtct catgagcgga   2340

tacatatttg aatgtattta gaaaaataaa caaatagggg ttccgcgcac atttccccga   2400

aaagtgccac ctgacgtcga tatgccaagt acgcccccta ttgacgtcaa tgacggtaaa   2460

tggcccgcct ggcattatgc ccagtacatg accttatggg actttcctac ttggcagtac   2520

atctacgtat tagtcatcgc tattaccatg gtgatgcggt tttggcagta catcaatggg   2580

cgtggatagc ggtttgactc acggggattt ccaagtctcc accccattga cgtcaatggg   2640

agtttgtttt ggcaccaaaa tcaacgggac tttccaaaat gtcgtaacaa ctccgcccca   2700

ttgacgcaaa tgggcggtag gcgtgtacgg tgggaggtct atataagcag agctctctgg   2760

ctaactagag aacccactgc ttactggctt atcgaaatta atacgactca ctatagggag   2820

acccaagctg ttaacg                                                   2836
```

<210> SEQ ID NO 95
<211> LENGTH: 2369
<212> TYPE: DNA
<213> ORGANISM: Influenza B virus

<400> SEQUENCE: 95

```
agcagaagcg gagcctttaa gatgaatata aatccttatt ttctcttcat agatgtaccc     60

atacaggcag caatttcaac aacattccca tacaccggtg ttccccctta ttcccatgga    120

acgggaacag gctacacaat agacaccgtg attagaacac atgagtactc aaacaaggga    180

aaacaataca tttctgatgt tacaggatgt gcaatggtag atccaacaaa tgggccatta    240

cccgaagata atgagccgag tgcctatgca caattggatt gcgttctgga ggctttggat    300

agaatggatg aagaacatcc aggtctgttt caagcagcct cacagaatgc catggaggca    360

ctaatggtca caactgtaga caaattaacc caggggagac agacttttga ttggacagtg    420

tgcagaaacc aacctgctgc aacggcactg aacacaacaa taacctcttt taggttgaat    480

gatttgaatg gagccgacaa gggtggatta gtaccctttt gccaagatat cattgattca    540

ttggacaaac ctgaaatgac tttcttctcg gtaaagaata taaagaaaaa attgcctgct    600

aaaaacagaa agggtttcct cataaagaga ataccaatga aggtaaaaga cagaataacc    660
```

-continued agagtggaat acatcaaaag agcattatca ttaaacacaa tgacaaaaga tgctgaaaga 720
ggcaaactaa aaagaagagc aattgccacc gctgggatac aaatcagagg gtttgtatta 780
gtagttgaaa acttggctaa aaatatctgt gaaaatctag aacaaagtgg tttgccagta 840
ggtgggaacg agaagaaggc caaactgtca aatgcagtgg ccaaaatgct cagtaactgc 900
ccaccaggag ggatcagcat gacagtgaca ggagacaata ctaaatggaa tgaatgctta 960
aatccaagaa tctttttggc tatgactgaa agaataacca gagacagccc aatttggttc 1020
cgggattttt gtagtatagc accggtcttg ttctccaata aaatagccag attgggaaaa 1080
gggttcatga taacaagcaa aacaaaaaga ctgaaggctc aaataccttg tcccgatctg 1140
tttaatatac cattagaaag atataatgaa gaaacaaggg caaaattaaa aaagctgaaa 1200
ccattcttca atgaagaagg aacggcatct ttgtcgcctg ggatgatgat gggaatgttt 1260
aatatgctat ctaccgtgtt gggagtagcc gcactaggga tcaaaaacat tggaaacaaa 1320
gaatacttat gggatggact gcaatcttct gatgattttg ctctgtttgt taatgcaaaa 1380
gatgaagaga catgtatgga aggaataaac gatttttacc gaacatgtaa gctattggga 1440
ataaacatga gcaaaaagaa aagttactgt aatgaaactg gaatgtttga atttacaagc 1500
atgttctaca gagatggatt tgtatctaat tttgcaatgg aacttccttc atttggagtt 1560
gctggagtaa atgaatcagc agatatggca ataggaatga caataataaa gaacaatatg 1620
atcaacaatg ggatgggtcc agcaacagca caaacagcca tacaattatt catagctgat 1680
tatagataca cctacaaatg ccacagggga gattccaaag tggaaggaaa gagaatgaaa 1740
attataaagg agctatggga aaacactaaa ggaagagatg gtctgttagt agcagatggt 1800
gggcctaaca tttacaattt gagaaacttg catatcccag aaatagtatt aaagtacaac 1860
ctaatggacc ctgaatacaa agggcggtta ctgcatcctc aaaatccctt tgtaggacat 1920
ttgtctattg agggcatcaa agaggcagat ataaccccag cacatggtcc agtaaagaaa 1980
atggactatg atgcggtatc tggaactcat agttggagaa ccaaaaggaa cagatctata 2040
ctaaacactg atcagaggaa catgattctt gaggaacaat gctacgctaa gtgttgcaac 2100
ctttttgagg cctgttttaa cagtgcatca tacaggaaac cagtaggtca gcacagcatg 2160
cttgaggcta tggcccacag attaagaatg gatgcacgac tagattatga atcaggaaga 2220
atgtcaaagg atgattttga gaaagcaatg gctcaccttg gtgagattgg gtacatataa 2280
gcttcgaaga tgtctatggg gttattggtc atcattgaat acatgcggta cacaaatgat 2340
taaaatgaaa aaaggctcgt gtttctact 2369

<210> SEQ ID NO 96
<211> LENGTH: 2396
<212> TYPE: DNA
<213> ORGANISM: Influenza B virus

<400> SEQUENCE: 96
agcagaagcg gagcgttttc aagatgacat tggccaaaat tgaattgtta aaacaactgt 60
taagggacaa tgaagccaaa acggtattga aacaaacaac ggtagaccaa tataacataa 120
taagaaaatt caatacatca agaattgaaa agaacccttc attaaggatg aagtgggcca 180
tgtgttctaa ttttcccttg gctctgacca agggtgatat ggcaaataga atccccttgg 240
aatacaaggg aatacaactt aaaacaaatg ctgaagacat aggaaccaaa ggccaaatgt 300
gctcaatagc agcagttacc tggtggaata catatggacc aataggagat actgaaggtt 360

-continued

```
tcgaaaaggt ctacgaaagc ttttttctca gaaagatgag acttgacaat gccacttggg    420

gccgaataac ttttggccca gttgaaagag tgagaaaaag ggtactgcta aaccctctca    480

ccaaggaaat gcctccagat gaagcgagca atgtgataat ggaaatattg ttccctaaag    540

aagcaggaat accaagagaa tctacttgga tacataggga actgataaaa gaaaaaagag    600

aaaaattgaa aggaacgatg ataactccca ttgtactggc atacatgctt gagagagaac    660

tggttgcccg aagaaggttc ctgccagtgg caggagcaac atcagccgag ttcatagaaa    720

tgctacactg cttacaaggt gaaaattgga gacaaatata tcacccagga gggaataaac    780

taactgaatc taggtctcaa tcaatgattg tagcttgtag aaaaataatc agaagatcaa    840

tagtcgcatc aaacccacta gagctagctg tagaaattgc aaacaagact gtgatagata    900

ctgaaccttt aaaatcatgt ctggcagcca tagacggagg tgatgtagcc tgtgacataa    960

taagagctgc attaggacta aagatcagac aaagacaaag atttggacgg cttgaactaa   1020

agagaatatc aggaagagga ttcaaaaatg atgaagaaat attaatcggg aacggaacaa   1080

tacagaaaat tggaatatgg gacggagaag aggagttcca tgtaagatgt ggtgaatgca   1140

ggggaatatt aaaaaagagc aaaatgagaa tggaaaaact actaataaat tcagccaaaa   1200

aggaggacat gaaagattta ataatcttgt gcatggtatt ttctcaagac actaggatgt   1260

tccaaggagt gagaggagaa ataaattttc ttaatcgagc aggccaactt ttatctccaa   1320

tgtaccaact ccagcgatat tttttgaata ggagcaacga ccttttttgat caatgggggt   1380

atgaggaatc acccaaagca agtgaactac atgggataaa tgaattaatg aatgcatctg   1440

actatacgtt gaaaggggtt gtagtaacaa aaaatgtgat tgatgacttt agttctactg   1500

aaacagaaaa agtatctata acaaaaaatc ttagtttaat aaaaaggact ggggaagtca   1560

taatgggggc taatgacgta agtgaattag aatcacaagc acagctaatg ataacatatg   1620

atacacctaa gatgtgggag atgggaacaa ccaaagaact ggtgcaaaac acctaccaat   1680

gggtgctaaa aaatttggta acactgaagg ctcagtttct tctgggaaaa gaagacatgt   1740

tccaatggga tgcatttgaa gcatttgaaa gcataatccc ccagaagatg gctggccagt   1800

acagtggatt tgcaagagca gtgctcaaac aaatgagaga ccaagaggtt atgaaaactg   1860

accagttcat aaagttgttg cctttctgtt tctcaccacc aaaattaagg agaaatgggg   1920

agccttatca attcttgagg cttatgttga agggaggagg ggaaaatttc atcgaagtaa   1980

ggaaagggtc ccctctattc tcctacaatc cacaaacaga agtcctaact atatgcggca   2040

gaatgatgtc attaaaagga aaaattgaag atgaagaaag gaatagatca atggggaatg   2100

cagtattggc aggctttctc gttagtggca agtatgaccc agatcttgga gatttcaaaa   2160

ctattgaaga acttgaaaag ctaaaaccgg gggaaaaagc aaacatctta ctttatcaag   2220

gaaagcccgt taaagtagtt aaaaggaaaa gatatagtgc tttatccaat gacatttcac   2280

aaggaattaa gagacaaaga atgacagttg agtccatggg gtgggccttg agctaatata   2340

aatttatcca ttaattcaat agacacaatt gagtgaaaaa tgctcgtgtt tctact       2396
```

<210> SEQ ID NO 97
<211> LENGTH: 2308
<212> TYPE: DNA
<213> ORGANISM: Influenza B virus

<400> SEQUENCE: 97

```
agcagaagcg gtgcgtttga tttgccataa tggatacttt tattacaaga aacttccaga     60

ctacaataat acaaaaggcc aaaaacacaa tggcagaatt tagtgaagat cctgaattac    120
```

-continued

```
aaccagcaat gctattcaac atctgcgtcc atctggaggt ctgctatgta ataagtgata    180
tgaattttct tgatgaagaa ggaaaaacat atacagcatt agaaggacaa ggaaaagaac    240
aaaacttgag accacaatat gaagtgattg agggaatgcc aagaaacata gcatggatgg    300
ttcaaagatc cttagcccaa gagcatggaa tagagactcc aaggtatctg gctgatttgt    360
tcgattataa aaccaagagg tttatagaag ttggaataac aaagggattg gctgacgatt    420
acttttggaa aaagaaagaa aagctgggga atagcatgga actgatgata ttcagctaca    480
atcaagacta ttcgttaagt aatgaatcct cattggatga ggaaggaaaa gggagagtgc    540
taagcagact cacagaactt caggctgagt taagtctgaa aaatctatgg caagttctca    600
taggagaaga agatattgaa aaaggaattg acttcaaact tggacaaaca atatctaaac    660
taagggatat atctgttcca gctggtttct ccaattttga aggaatgagg agctacatag    720
acaatataga tcctaaagga gcaatagaga gaaatctagc aaggatgtct cccttagtat    780
cagttacacc taaaaagttg aaatgggagg acctaagacc aatagggcct cacatttaca    840
accatgagct accagaagtt ccatataatg cctttcttct aatgtctgat gagttggggc    900
tggctaatat gactgaaggg aagtccaaga aaccgaagac cttagccaaa gaatgtctag    960
aaaagtactc aacactacgg gatcaaactg acccaatatt aataatgaaa agcgaaaaag   1020
ctaacgaaaa cttcttatgg aagctgtgga gggactgtgt aaatacaata agtaatgagg   1080
aaacaagtaa cgaattacag aaaaccaatt atgccaagtg ggccacagga gatggattaa   1140
cataccagaa aataatgaaa gaagtagcaa tagatgacga aacaatgtac caagaagagc   1200
ccaaaatacc taacaaatgt agagtggctg cttgggttca aacagagatg aatctattga   1260
gcactctgac aagtaaaagg gccctggatc taccagaaat agggccagac gtagcaccca   1320
tggagcatgt agggagtgaa agaaggaaat actttgttaa tgaaatcaac tactgtaagg   1380
cctctaccgt tatgatgaag tatgtacttt ttcacacttc attattaaat gaaagcaatg   1440
ccagcatggg aaaatataaa gtaataccaa taaccaacag agtagtaaat gaaaaaggag   1500
aaagttttga catgcttcat ggtctggcgg ttaaagggca atctcatctg aggggagata   1560
ctgatgttgt aacagttgtg actttcgaat ttagtagtac agatcccaga gtggactcag   1620
gaaagtggcc aaaatatact gtatttagaa ttggctcctt atttgtgagt ggaagggaaa   1680
aatctgtgta cctatattgc cgagtgaatg gtacaaataa gatccaaatg aaatggggaa   1740
tggaagctag aagatgtctg cttcaatcaa tgcaacaaat ggaagcaatt gttgaacaag   1800
aatcatcgat acaaggatat gacatgacca aagcttgttt caagggagac agagtgaata   1860
gtcccaaaac tttcagtatt gggactcaag aaggaaaact agtaaaagga tcctttggga   1920
aagcactaag agtaatattc accaaatgtt tgatgcacta tgtatttgga aatgcccaat   1980
tggaggggtt tagtgccgaa tctaggagac ttctactgtt aattcaggca ttaaaggaca   2040
gaaagggccc ttgggtattc gacttagagg gaatgtattc tggaatagaa gaatgtatta   2100
gtaacaaccc ttgggtaata cagagtgcat actggtttaa tgaatggttg ggctttgaaa   2160
aagaggggag taaagtatta gaatcaatag atgaaataat ggatgaatga aagaagggca   2220
tagcgctcaa tttggtacta ttttgttcat tatgtatcta aacatccaat aaaaagaatt   2280
gagaattaaa aatgcacgtg tttctact                                       2308
```

<210> SEQ ID NO 98
<211> LENGTH: 1884
<212> TYPE: DNA

<213> ORGANISM: Influenza B virus

<400> SEQUENCE: 98
agcagaagca gagcattttc taatatccac aaaatgaagg caataattgt actactcatg 60
gtagtaacat ccaatgcaga tcgaatctgc actgggataa catcgtcaaa ctcaccccat 120
gtggtcaaaa ctgctactca aggggaagtc aacgtgactg gtgtgatacc actgacaaca 180
acacctacca aatctcattt tgcaaatctc aaaggaacac agaccagagg gaaactatgc 240
ccaaactgtc tcaactgcac agatctggac gtggccttgg gcagaccaaa gtgtatgggg 300
accatacctt cggcaaaagc ttcaatactc cacgaagtca aacctgttac atctgggtgc 360
tttcctataa tgcacgacag aacaaaaatc agacagctac ccaatcttct cagaggatat 420
gaaaatatca ggttatcagc ccgtaacgtt atcaacgcag aaacggcacc aggaggaccc 480
tacatagttg gaacctcagg atcttgccct aacgttacca atgggaaagg attcttcgca 540
acaatggctt gggctgtccc aaaaaacaac aaaaccaaaa cagcaacgaa cccattaaca 600
gtagaagtac catacatttg tacaaaagga gaagaccaaa ttactgtttg gggttccat 660
tctgatgacg aaacccaaat ggtaacactc tatggagact cgaagcctca aaagttcacc 720
tcatctgcca acggagtaac cacacattat gtttctcaga ttggtggctt cccaaatcaa 780
acagaagacg aagggctacc acaaagcggc agaattgttg ttgattacat ggtgcaaaaa 840
cctggaaaaa caggaacaat tgtctatcaa agaggtgttt tattgcctca aaaagtgtgg 900
tgcgcaagtg gcaggagcaa ggtaataaaa ggggccttgc ctttaattgg tgaagcagat 960
tgcctccacg aaaaatacgg tggattaaac aaaagcaagc cttactacac aggagaacat 1020
gcaaaagcca taggaaattg cccaatatgg gtgaaaacac ccttgaagct ggccaatgga 1080
accaaatata gacctcctgc aaaactatta aaggaaaggg gtttcttcgg agctattgct 1140
ggtttcttgg aaggaggatg ggaaggaatg attgcaggtt ggcacggata cacatctcat 1200
ggagcacatg gagtggcagt ggcagcagac cttaagagta cgcaagaagc tataaacaag 1260
ataacaaaaa atctcaattc tttaagtgag ctagaagtaa agaatcttca aagactaagc 1320
ggtgcaatgg atgaactcca caacgaaata ctcgagctgg atgagaaagt ggatgatctc 1380
agagctgata caataagctc gcaaatagag cttgcagtct tgctttccaa cgaaggaata 1440
ataaacagtg aagatgagca tctcttggca cttgaaagaa aactgaagaa aatgctgggc 1500
ccctctgctg tagacatagg gaatggatgc ttcgaaacca aacacaaatg caaccagact 1560
tgcctagaca ggatagctgc tggcaccttt aatgcaggag aattttctct tcccactttt 1620
gattcactaa atattactgc tgcatcttta aatgatgatg gattggataa tcatactata 1680
ctgctctact actcaactgc tgcttctagt ttggctgtaa cattgatgat agctatcttt 1740
attgtttata tggtctccag agacaatgtt tcttgctcca tctgtctata aggaaaatta 1800
agccctgtat tttcctttat tgtagtgctt gtttgcttgt caccattaca aaaaacgtta 1860
ttgaaaaatg ctcttgttac tact 1884

<210> SEQ ID NO 99
<211> LENGTH: 1842
<212> TYPE: DNA
<213> ORGANISM: Influenza B virus

<400> SEQUENCE: 99
agcagaagca cagcattttc ttgtgaactt caagtaccaa caaaaactga aaatcaaaat 60
gtccaacatg gatattgacg gcatcaacac tggaacaatt gacaaaacac cagaagaaat 120

-continued aacttccgga accagtgggg caaccagacc aatcatcaaa ccagcaaccc ttgccccacc 180
aagcaacaaa cgaacccgaa acccatcccc ggaaagggca gccacaagca gtgaagctga 240
tgtcggaagg agaacccaaa agaaacaaac cccgacagag ataaagaaga gcgtctacaa 300
tatggtagtg aaactgggtg aattctacaa ccagatgatg gtcaaagctg gactcaacga 360
tgacatggag agaaacctaa tccaaaatgc acatgctgcg gaaagaattc tattggctgc 420
tactgatgac aagaaaactg aattccaaaa gaaaaagaat gccagagatg tcaaagaagg 480
gaaagaagaa atagaccaca acaaaacagg aggcaccttt tacaagatgg taagagatga 540
taaaaccatc tacttcagcc ctataagaat taccttttta aaagaagagg tgaaaacaat 600
gtacaaaacc accatgggga gtgatggttt cagtggacta aatcacatca tgattgggca 660
ttcacagatg aacgatgtct gtttccaaag atcaaaggca ctaaaaagag ttggacttga 720
cccttcatta atcagtactt ttgcaggaag cacactcccc agaagatcag gtgcaactgg 780
tgttgcgatc aaaggaggtg gaactttagt ggcagaagcc attcgattta taggaagagc 840
aatggcagac agagggctat tgagagacat cagagccaag acggcctatg aaaagattct 900
tctgaatctg aaaaacaagt gctctgcgcc ccaacaaaag gctctagttg atcaagtgat 960
cggaagtaga aatccaggga ttgcagacat agaagaccta accctgcttg cccgaagcat 1020
ggtcgttgtc aggccctctg tagcgagcaa agtggtgctt cccataagca tttatgccaa 1080
aatacctcaa ctagggttca atgttgaaga atactctatg gttgggtatg aagccatggc 1140
tctttataat atggcaacac ctgtttccat attaagaatg ggagacgatg caaaagataa 1200
atcacaatta ttcttcatgt cttgcttcgg agctgcctat gaagacctaa gagttttgtc 1260
tgcactaaca ggcacagaat tcaagcatag gtcagcatta aagtgcaagg gtttccacgt 1320
tccagcaaag gagcaagtgg aaggaatggg ggcagctctg atgtccatca agctccagtt 1380
ttgggctcca atgaccagat ctgggggga tgaagtaggt ggagacggag ggtctggtca 1440
aataagttgc agccccgtgt ttgcagtaga aagacctatt gctctaagca agcaagctgt 1500
aagaagaatg ctgtcaatga atattgaggg acgtgatgca gatgtcaaag gaaatctact 1560
caagatgatg aatgattcaa tgactaagaa aaccaatgga aatgctttca ttgggaagaa 1620
aatgtttcaa atatcagaca aaaacaaaac caatcccatt gagattccaa ttaagcagac 1680
catccccaat ttcttctttg ggagggacac agcagaggat tatgatgacc tcgattatta 1740
aagcaacaaa atagacacta tggctgtgac tgtttcagta cgtttggaat gtgggtgttt 1800
acttttattg aaataaatgt aaaaaatgct gttgtttcta ct 1842

<210> SEQ ID NO 100
<211> LENGTH: 1557
<212> TYPE: DNA
<213> ORGANISM: Influenza B virus

<400> SEQUENCE: 100
agcagaagca gagcatcttc tcaaaactga agcaaatagg ccaaaaatga acaatgctac 60
cttcaactat acaaacgtta accctatttc tcacatcagg gggagtgtta ttatcactat 120
atgtgtcagc ttcactgtca tacttattgt attcggatat attgctaaaa ttttcaccaa 180
caaaaataac tgcaccaaca atgtcattgg attgcgcgaa cgtatcaaat gttcaggctg 240
tgaaccgttc tgcaacaaaa gagatgacat ttcttctccc agagccggag tggacatacc 300
ctcgtttatc ttgccagggc tcaacctttc agaaagcact cctaattagc cctcataggt 360

-continued

```
tcggagaaac cagaggaaac tcagctccct tgataataag ggaacccttt gttgcttgtg    420

gaccaaagga atgcagacac tttgctctaa cccattatgc agctcaacca gggggatact    480

acaatggaac aagaaaggac agaaacaagc tgaggcatct gatttcagtc aaattaggca    540

aaatcccaac tgtagaaaac tccattttcc acatggcagc ttggagtggg tccgcatgcc    600

atgatggtag agaatggaca tatatcggag ttgatggccc tgacagtaat gcactgatca    660

aaataaaata tggagaagca tatactgaca cataccattc ctatgcaaac aacatcctaa    720

gaacacaaga aagtgcctgc aattgcatcg gggagattg ttatcttatg ataactgatg     780

gctcagcttc aggaattagt aaatgcagat ttcttaaaat tcgagagggt cgaataataa    840

aagaaatatt tccaacagga agagtagagc atactgaaga atgcacatgc gggttcgcca    900

gcaataaaac catagaatgt gcctgtagag ataacagtta cacagcaaaa agaccctttg    960

tcaaattaaa tgtggagact gatacagctg aaataagatt gatgtgcaca gagacttatt   1020

tggacacccc cagaccagat gatggaagca taacagggcc ttgcgaatct aatggggaca   1080

aagggcttgg aggcatcaaa ggaggatttg tccatcaaag aatggcatct aagattggaa   1140

gatggtactc ccgaacgatg tctaaaactg aaagaatggg gatggaactg tatgtcaagt   1200

atgatggaga cccatggact gacagtgacg cccttgctcc tagtggagta atggtttcaa   1260

tgaaagaacc tggttggtat tcttttggct tcgaaataaa agataagaaa tgtgatgtcc   1320

cctgtattgg gatagagatg gtacacgatg gtggaaaaga gacttggcac tcagcagcaa   1380

cagccattta ctgtttgatg ggctcaggac aattgctatg ggacactgtc acaggtgttg   1440

atatggctct gtaatggagg aatggttgaa tctgttctaa accctttgtt cctattttgt   1500

ttgaacaatt gtccttactg gacttaattg tttctgaaaa atgctcttgt tactact      1557
```

<210> SEQ ID NO 101
<211> LENGTH: 1190
<212> TYPE: DNA
<213> ORGANISM: Influenza B virus

<400> SEQUENCE: 101

```
agcagaagca cgcactttct taaaatgtcg ctgtttggag acacaattgc ctacctgctt     60

tcactaacag aagatggaga aggcaaagca gaactagcag aaaaattaca ctgttggttc    120

ggtgggaaag aatttgacct agactctgct ttggaatgga taaaaaacaa aagatgccta    180

actgatatac aaaaagcact aattggtgcc tctatctgct ttttaaaacc caaagaccaa    240

gaaagaaaaa gaagattcat cacagagccc ctgtcaggaa tgggaacaac agcaacaaaa    300

aagaaaggcc tgattctagc tgagagaaaa atgagaagat gtgtgagttt tcatgaagca    360

tttgaaatag cagaaggcca tgaaagctca gcactactat attgtctcat ggtcatgtac    420

ctgaaccctg gaaattattc aatgcaagta aaactaggaa cgctctgtgc tttatgcgag    480

aaacaagcat cacattcaca aagagctcat agcagagcag caagatcttc agtgcctgga    540

gtgaggcgag aaatgcagat ggtttcagct gtgaacacag caaaaacaat gaatggaatg    600

gggaagggag aagacgtcca aaaactggca gaagagctgc aaagcaacat tggagtattg    660

agatctctgg gggcaagtca aaagaatgga gaaggaattg caaaggatgt aatggaagtg    720

ctaaagcaga gctctatggg aaattcagct cttgtgaaga aatacctata atgctcgaac    780

catttcagat tctttcaatt tgttctttca ttttatcagc tctccatttc atggcttgga    840

caatagggca tttgaatcaa ataaaaagag gagtaaacct gaaaatacga ataagaaatc    900

caaataaaga gacaataaac agagaggtat caattttgag acacagttac caaaaagaaa    960
```

-continued tccaagccaa agaaacaatg aaggaagtac tctctgacaa catggagata ttgagtgacc 1020
acatagtaat tgaggggctt tctgctgaag agataataaa aatgggtgaa acagttttgg 1080
aggtagaaga attgcagtaa acccaatttt caccgtattt cttgctatgc atttaagcaa 1140
attgtaatca atgtcagcaa ataaactgga aaaagtgcgt tgtttctact 1190

<210> SEQ ID NO 102
<211> LENGTH: 1098
<212> TYPE: DNA
<213> ORGANISM: Influenza B virus

<400> SEQUENCE: 102
agcagaagca gaggatttgt ttagtcactg gcaaacggaa aaaaatggcg gacaacatga 60
ccacaacaca aattgaggta ggtccgggag caaccaatgc caccataaac tttgaagcag 120
gaattctgga gtgctatgaa aggctttcat ggcaaagagc ccttgactac cctggtcaag 180
accgcctaaa cagactaaag agaaaattag aatcaagaat aaagactcac aacaaaagtg 240
agcctgaaag taaaaggatg tctcttgaag agagaaaagc aattggggta aaaatgatga 300
aagtgctcct atttatgaat ccatctgctg gaattgaagg gtttgagcca tactgtatga 360
aaaattcctc aaatagcaac tgtccaaact gcaattggac cgattaccct ccaacaccag 420
gaaagtgcct tgatgacata gaagaagaac cggagaatgt tgatgaccca actgaaatag 480
tattgaggga catgaacaac aaagatgcaa ggcaaaagat aaaggaggaa gtaaacactc 540
agaaagaagg gaagttccgt ttgacaataa aaagggatat acgtaatgtg ttgtccttga 600
gagtgttggt aaacggaaca ttcctcaagc accctaatgg atacaagtcc ttatcaactc 660
tgcatagatt gaatgcatat gaccagagtg ggaggcttgt tgctaaactt gttgctactg 720
atgatcttac agtggaggat gaagaagatg gccatcggat cctcaactca ctcttcgagc 780
gttttaatga aggacattca aagccaattc gagcagctga aactgcggtg ggagtcttat 840
cccaatttgg tcaagagcac cgattatcac cagaggaggg agacaattag actggttacg 900
gaagaacttt atcttttaag taaaagaatt gatgataaca tattgttcca caaaacagta 960
atagctaaca gctccataat agctgacatg attgtatcat tatcattatt ggaaacattg 1020
tatgaaatga aggatgtggt tgaagtgtac agcaggcagt gcttgtgaat ttaaaataaa 1080
aatcctcttg ttactact 1098